(12) United States Patent
Gijsen et al.

(10) Patent No.: US 8,772,504 B2
(45) Date of Patent: Jul. 8, 2014

(54) SUBSTITUTED BENZOXAZOLE, BENZIMIDAZOLE, OXAZOLOPYRIDINE AND IMIDAZOPYRIDINE DERIVATIVES AS GAMMA SECRETASE MODULATORS

(75) Inventors: Henricus Jacobus Maria Gijsen, Breda (NL); François Paul Bischoff, Vosselaar (BE); Wei Zhuang, Antwerpen (BE); Sven Franciscus Anna Van Brandt, Nijlen (BE); Michel Surkyn, Merksplas (BE); Mirko Zaja, München (DE); Didier Jean-Claude Berthelot, Antwerpen (BE); Michel Anna Jozef De Cleyn, Lille (BE); Gregor James MacDonald, Zoersel (BE); Daniel Oehlrich, Malle (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 130 days.

(21) Appl. No.: 13/144,557

(22) PCT Filed: Feb. 15, 2010

(86) PCT No.: PCT/EP2010/051843
§ 371 (c)(1),
(2), (4) Date: Jul. 14, 2011

(87) PCT Pub. No.: WO2010/094647
PCT Pub. Date: Aug. 26, 2010

(65) Prior Publication Data
US 2012/0022090 A1    Jan. 26, 2012

(30) Foreign Application Priority Data

Feb. 19, 2009  (EP) ..................... 09153188
Jun. 22, 2009  (EP) ..................... 09163409

(51) Int. Cl.
*C07D 235/00* (2006.01)
*C07D 403/02* (2006.01)

(52) U.S. Cl.
USPC .................... 548/304.4; 548/306.1

(58) Field of Classification Search
USPC ............. 546/273.4; 514/338; 548/304.4, 30
See application file for complete search history.

(56) References Cited

U.S. PATENT DOCUMENTS

| | | | |
|---|---|---|---|
| 7,923,563 B2 | 4/2011 | Kushida et al. | |
| 2002/0128319 A1 | 9/2002 | Koo et al. | |
| 2008/0280948 A1 | 11/2008 | Baumann et al. | |
| 2009/0062529 A1 | 3/2009 | Kimura et al. | |
| 2010/0137320 A1 | 6/2010 | Huanag et al. | |

FOREIGN PATENT DOCUMENTS

| | | |
|---|---|---|
| EP | 1757591 A1 | 2/2007 |
| JP | 2003/502313 | 1/2003 |
| WO | WO 01/78721 A1 | 10/2001 |
| WO | WO 2004/017963 A1 | 3/2004 |
| WO | 2004/110350 A2 | 12/2004 |
| WO | WO 2004/110350 A2 | 12/2004 |
| WO | 2005/085245 A1 | 9/2005 |
| WO | WO 2005/115990 A1 | 12/2005 |
| WO | 2006/135667 A1 | 12/2006 |
| WO | WO 2007/038314 | 4/2007 |
| WO | WO 2007/044895 A2 | 4/2007 |
| WO | 2007/105053 A2 | 9/2007 |
| WO | 2007/113276 A1 | 10/2007 |
| WO | WO 2007/113276 A1 | 10/2007 |
| WO | 2007/131991 A1 | 11/2007 |
| WO | 2008/065199 A1 | 6/2008 |
| WO | WO 2008/082490 | 7/2008 |
| WO | WO 2008/097538 A1 | 8/2008 |
| WO | 2008/137139 A1 | 11/2008 |
| WO | WO 2008/156580 A1 | 12/2008 |
| WO | WO 2009/005729 A1 | 1/2009 |
| WO | 2009/005729 A1 | 3/2009 |
| WO | 2009/032277 A1 | 3/2009 |
| WO | 2009/073777 A1 | 6/2009 |

(Continued)

OTHER PUBLICATIONS

Garofalo, Albert, "Patents targeting gamma-secretase inhibition and modulation for the treatment of Alzheimer's disease: 2004-2008", Expert Opinion Ther. Patents (2008) 18 (7): 693-703.*

(Continued)

*Primary Examiner* — Nizal Chandrakumar
(74) *Attorney, Agent, or Firm* — Baker & Hostetler LLP

(57) ABSTRACT

The present invention is concerned with novel substituted benzoxazole, benzimidazole, oxazolopyridine and imidazopyridine derivatives of Formula (I)

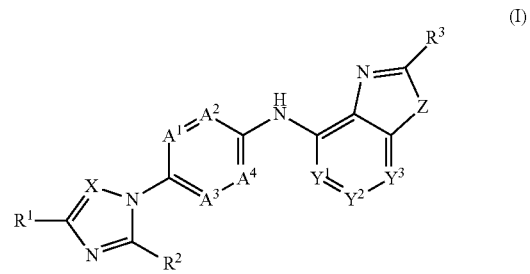

wherein $R^1$, $R^2$, $R^3$, $R^4$, X, $A^1$, $A^2$, $A^3$, $A^4$, $Y^1$, $Y^2$, $Y^3$ and Z have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

12 Claims, No Drawings

(56) References Cited

FOREIGN PATENT DOCUMENTS

| | | | |
|---|---|---|---|
| WO | 2009/076352 A1 | 6/2009 |
| WO | 2009/103652 A1 | 8/2009 |
| WO | 2010/010188 A1 | 1/2010 |
| WO | 2010/065310 A1 | 6/2010 |
| WO | 2010/070008 A1 | 6/2010 |
| WO | 2010/083141 A1 | 7/2010 |
| WO | 2010/089292 A1 | 8/2010 |
| WO | 2010/094647 A1 | 8/2010 |
| WO | 2010/098495 A1 | 9/2010 |
| WO | 2010/100606 A1 | 9/2010 |
| WO | 2010/126745 A1 | 11/2010 |
| WO | 2010/145883 A1 | 12/2010 |
| WO | 2011/006903 A1 | 1/2011 |
| WO | 2012/131539 A1 | 10/2012 |

OTHER PUBLICATIONS

Citron, M., et al. "Mutant Presenilins of Alzheimer's Disease Increase Production of 42-Residue Amyloid β-Protein in Both Transfected Cells and Transgenic Mice", Nature Medicine, vol. 3, No. 1, pp. 67-72 (1997).

Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.

Greene, T., et al. "Protective Groups in Organic Synthesis", John Wiley & Sons, Inc. (1999).

Larner, A., "Secretases as Therapeutic Targets in Alzheimer's Disease: Patents 2000-2004", Exp. Opinion Ther. Patents 14, p. 1403 (2004).

Marjaux, E., et al. "γ-Secretase Inhibitors: Still in the Running as Alzheimer's Therapeutics", Drug Discovery Today: Therapeutics Strategies 1, p. 1 (2004).

Moechars, D., et al., "Early Phenotypic Changes in Transgenic Mice That Overexpress Different Mutants of Amyloi Precursor Protein in Brain", Journal of Biological Chemistry, vol. 274, No. 10, pp. 6483-6492 (1999).

Morihara, T., et al. "Selective Inhibition of Aβ42 Production b NSAID R-Enantiomer", J., Neurochem. 83, p. 1009 (2002).

Peretto, D., et al. "Synthesis and Biological Activity of Fluriprofen Analogues as Selective Inhibitors of β-Amylid 1-42 Secretion", J. Med. Chem. 48 p. 5705 (2005).

Schweisguth, F., et al. Regulation of Notch Signaling Activity, Curr. Biol. 14, p. R129 (2004).

Steiner, H., "Uncovering γ-Sucretase", Curr. Alzheimer Research 1(3), p. 175 (2004).

Tanzi, R., et al. "Twenty Years of the Alzheimer's Disease Amyloid Hypothesis: A Genetic Perspective", Cell, vol. 120, (2005), p. 545-555.

Weggen, S., et al. "A Subset of NSAIDs Lower Amylidogenic Aβ42 Independently of Cyclooxygenase Activity", Nature 414, p. 212 (2001).

Jadhav, G., et al. "Amonium Metavanadate: A Novel Catalyst for Synthesis of 2-Substituted Benzimidazole Derivatives", Chinese Chemical Letters, vol. 20 (2009) pp. 292-295.

Matthews, D., et al. A Convenient Procedure for the Preparation of 4(5)-Cyanoimidazoles, Journal of Organic Chemistry, vol. 51 (1986), pp. 3228-3231.

Oumata, N., et al. "Roscovitine-Derived, Dual-Specificity Inhibitors of Cyclin-Dependent Kinases and Casein Kinases 1", Journal of Medicinal Chemistry, vol. 51, pp. 5229-5242 (2008).

European Search Report for Application No. EP12168186 dated Jul. 20, 2012.

European Search Report for Application No. EP09153188 dated Jun. 10, 2009.

International Search Report for Application No. PCT/EP2012/063667 dated Aug. 7, 2012.

International Search Report for application No. PCT/EP2011/050350 dated Feb. 23, 2011.

International Search Report for Application No. PCT/EP2011/050349 dated Feb. 23, 2011.

Sechi, M., et al., "Design and Synthesis of Novel Indole β-Diketo Acid Derivatives as HIV-1 Integrase Inhibitors", J. Medical Chemistry, vol. 47, pp. 5208-5319 (2004).

Zettl, H., et al., "Exploring the Chemical Space of γ-Secretase Modulators", Trends in Pharmacological Sciences, vol. 31, No. 9, pp. 402-410.

* cited by examiner

SUBSTITUTED BENZOXAZOLE, BENZIMIDAZOLE, OXAZOLOPYRIDINE AND IMIDAZOPYRIDINE DERIVATIVES AS GAMMA SECRETASE MODULATORS

CROSS-REFERENCE TO RELATED APPLICATIONS

The present application claims the benefits of the filing of Application Nos. EP 09153188.9 filed Feb. 19, 2009, EP 09163409.7 filed Jun. 22, 2009 and PCT/EP2010/051843 filed Feb. 15, 2010. The complete disclosures of the aforementioned related patent applications are hereby incorporated herein by reference for all purposes.

FIELD OF THE INVENTION

The present invention is concerned with novel substituted benzoxazole, benzimidazole, oxazolopyridine and imidazopyridine derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or A$\beta$) peptides of various lengths. A variant thereof, which is the A$\beta$1-42-peptide (Abeta-42), is believed to be the major causative agent for amyloid formation. Another variant is the A$\beta$1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the $\beta$-amyloid precursor protein ($\beta$-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (A$\beta$), specifically A$\beta$42, and have given strong support to the "amyloid cascade hypothesis" of AD (Tanzi and Bertram, 2005, Cell 120, 545). The likely link between A$\beta$ peptide generation and AD pathology emphasizes the need for a better understanding of the mechanisms of A$\beta$ production and strongly warrants a therapeutic approach at modulating A$\beta$ levels.

The release of A$\beta$ peptides is modulated by at least two proteolytic activities referred to as $\beta$- and $\gamma$-secretase cleavage at the N-terminus (Met-Asp bond) and the C-terminus (residues 37-42) of the A$\beta$ peptide, respectively. In the secretory pathway, there is evidence that $\beta$-secretase cleaves first, leading to the secretion of s-APP$\beta$ (s$\beta$) and the retention of a 11 kDa membrane-bound carboxy terminal fragment (CTF). The latter is believed to give rise to A$\beta$ peptides following cleavage by $\gamma$-secretase. The amount of the longer isoform, A$\beta$42, is selectively increased in patients carrying certain mutations in a particular protein (presenilin), and these mutations have been correlated with early-onset familial Alzheimer's disease. Therefore, A$\beta$42 is believed by many researchers to be the main culprit of the pathogenesis of Alzheimer's disease.

It has now become clear that the $\gamma$-secretase activity cannot be ascribed to a single protein, but is in fact associated with an assembly of different proteins.

The gamma ($\gamma$)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the $\gamma$-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420).

Indeed, this finding was recently supported by biochemical studies in which an effect of certain NSAIDs on $\gamma$-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of COX enzymes, which can lead to unwanted side effects, and their low CNS penetration (Peretto et al., 2005, J. Med. Chem. 48, 5705-5720).

US 2008/0280948 A1 relates to aminophenyl derivatives which are modulators for amyloid beta.

WO-2009/005729 relates to heterocyclic compounds and their use as gamma secretase modulators.

WO-2008/097538 encompasses 2-[4-imidazolyl)-phenyl] vinyl-heterocycle derivatives which selectively attenuate production of Abeta(1-42) and are useful in the treatment of Alzheimer's disease.

WO-2004/017963 discloses benzimidazoles as coagulation factor Xa inhibitors for the treatment of thromboembolic illnesses.

WO-2005/115990 discloses cinnamide compounds that are useful for the treatment of neurodegenerative diseases caused by amyloid β proteins such as Alzheimer's disease, senile dementia, Down's syndrome and amyloidosis.

WO-2007/044895 discloses diaromatic amines and their use in lubricating oil compositions and stabilizer-containing compositions.

WO-2008/156580 discloses triazole derivatives for treating diseases associated with deposition of Aβ in the brain, in particular Alzheimer's disease.

There is a strong need for novel compounds which modulate γ-secretase activity thereby opening new avenues for the treatment of Alzheimer's disease. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention are useful as gamma secretase modulators. The compounds according to the invention and the pharmaceutically acceptable compositions thereof, may be useful in the treatment or prevention of Alzheimer's disease.

The present invention concerns novel compounds of Formula (I):

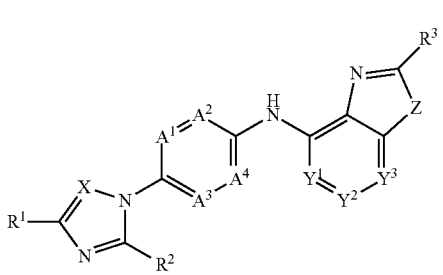

and stereoisomeric forms thereof, wherein
$R^1$ is hydrogen, cyano, $CF_3$, halo, or $C_{1-4}$alkyl optionally substituted with one or more substituents each independently selected from the group consisting of hydroxyl and $C_{1-4}$alkyloxy;
$R^2$ is hydrogen, $C_{1-4}$alkyl or halo;
X is $CR^5$ or N;
$R^5$ is hydrogen or halo;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$ or N;
$Y^3$ is CH or N;
provided that only one of $Y^1$, $Y^2$ and $Y^3$ may represent N;
$R^4$ is hydrogen, halo, $C_{1-4}$alkyloxy, cyano, cycloC$_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents;
$C_{1-6}$alkyl optionally substituted with one or more substituents each independently selected from the group consisting of piperidinyl, morpholinyl, pyrrolidinyl, Ar, $C_{1-6}$alkyloxy, tetrahydropyranyl, cycloC$_{3-7}$alkyloxy and cycloC$_{3-7}$alkyl; cycloC$_{3-7}$alkyl substituted with one or more phenyl substituents optionally substituted with one or more halo substituents;
cycloC$_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; NH—Ar; or 1,6-dihydro-1-methyl-6-oxo-3-pyridinyl;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is
phenyl optionally substituted with one or more substituents each independently selected from the group consisting of halo, $C_{1-4}$alkyloxy, cyano, $NR^7R^8$, morpholinyl, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl, $C_{1-4}$alkyloxy substituted with one or more halo substituents, and $C_{1-4}$alkyl substituted with one or more halo substituents;
each $R^7$ is selected independently from hydrogen or $C_{1-4}$alkyl;
each $R^8$ is selected independently from hydrogen, $C_{1-4}$alkyl or $C_{1-4}$alkylcarbonyl;
Z is O or $NR^9$;
$R^9$ is hydrogen, or $C_{1-6}$alkyl optionally substituted with one or more substituents each independently selected from the group consisting of halo, cyano, phenyl, cycloC$_{3-7}$alkyl and $C_{1-4}$alkyloxy;
and the pharmaceutically acceptable addition salts, and the solvates thereof.

The present invention also concerns methods for the preparation of compounds of Formula (I) and pharmaceutical compositions comprising them.

The present compounds surprisingly were found to modulate the γ-secretase activity in vitro and in vivo, and are therefore useful in the treatment or prevention of Alzheimer's disease, traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease and other disorders with Beta-amyloid pathology (eg glaucoma).

In view of the aforementioned pharmacology of the compounds of Formula (I), it follows that they are suitable for use as a medicament.

More especially the compounds are suitable in the treatment or prevention of Alzheimer's disease, cerebral amyloid angiopathy, multi-infarct dementia, dementia pugilistica or Down syndrome.

The present invention also concerns to the use of a compound according to the general Formula (I), the stereoisomeric forms thereof and the pharmaceutically acceptable acid or base addition salts and the solvates thereof, for the manufacture of a medicament for the modulation of γ-secretase activity.

Use of a compound of Formula (I) for the modulation of γ-secretase activity resulting in a decrease in the relative amount of Aβ42-peptides produced are preferred.

One advantage of the compounds or a part of the compounds of the present invention may lie in their enhanced CNS-penetration.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" or "halogen" as a group or part of a group is generic for fluoro, chloro, bromo, iodo unless otherwise is indicated.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{2-6}$alkyl" as a group or part of a group refers to a hydrocarbyl radical of Formula $C_nH_{2n+1}$ wherein n is a number ranging from 2 to 6. $C_{2-6}$alkyl groups comprise from 2 to 6 carbon atoms, in particular from 2 to 4 carbon atoms, more in particular from 2 to 3 carbon atoms. Alkyl groups may be linear or branched and may be substituted as indicated herein. Thus, for example, $C_{2-6}$alkyl includes all linear, or branched alkyl groups with between 2 and 6 carbon atoms, and thus includes such as for example ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. The term "$C_{1-3}$alkyl" as a group or part of a group refers to a hydrocarbyl radical of Formula $C_nH_{2n+1}$ wherein n is a number ranging from 1 to 3. Alkyl groups may be linear or branched and may be substituted as indicated herein. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-6}$alkyloxy" as a group or part of a group refers to a radical having the Formula —$OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula —$OR^c$ wherein $R^c$ is $C_{1-4}$alkyl. Non-limiting examples of suitable alkyloxy include methyloxy (also methoxy), ethyloxy (also ethoxy), propyloxy, isopropyloxy, butyloxy, isobutyloxy, sec-butyloxy and tert-butyloxy.

In the framework of this application, $C_{2-6}$alkenyl is a straight or branched hydrocarbon radical having from 2 to 6 carbon atoms containing a double bond such as ethenyl, propenyl, butenyl, pentenyl, 1-propen-2-yl, hexenyl and the like.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "cyclo$C_{3-7}$alkyloxy" alone or in combination, refers to a radical having the Formula —$OR^d$, wherein $R^d$ is cyclo$C_{3-7}$alkyl. Non-limiting examples of suitable cyclo $C_{3-7}$alkyloxy include cyclopropyloxy, cyclobutyloxy, cyclopentyloxy, cyclohexyloxy and cycloheptyloxy.

The term "thiophenyl" is equivalent to "thienyl".

The chemical names of the compounds of the present invention were generated according to the nomenclature rules agreed upon by the Chemical Abstracts Service.

In case of tautomeric forms, it should be clear that the other non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

When a specific regioisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^1$H, $^2$H, $^3$H and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

The present invention concerns novel compounds of Formula (I):

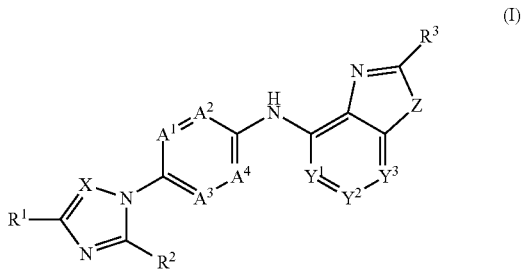

and stereoisomeric forms thereof, wherein
R$^1$ is hydrogen, cyano, CF$_3$, halo, or C$_{1-4}$alkyl optionally substituted with one or more substituents each independently selected from the group consisting of hydroxyl and C$_{1-4}$alkyloxy;
R$^2$ is hydrogen, C$_{1-4}$alkyl or halo;
X is CR$^5$ or N;
R$^5$ is hydrogen or halo;
A$^1$ is CR$^6$ or N;
R$^6$ is hydrogen, halo or C$_{1-4}$alkyloxy;

$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$ or N;
$Y^3$ is CH or N;
provided that only one of $Y^1$, $Y^2$ and $Y^3$ may represent N;
$R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents;
$C_{1-6}$alkyl optionally substituted with one or more substituents each independently selected from the group consisting of piperidinyl, morpholinyl, pyrrolidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl substituted with one or more phenyl substituents optionally substituted with one or more halo substituents;
cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; NH—Ar; or 1,6-dihydro-1-methyl-6-oxo-3-pyridinyl;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is
phenyl optionally substituted with one or more substituents each independently selected from the group consisting of halo, $C_{1-4}$alkyloxy, cyano, $NR^7R^8$, morpholinyl, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl, $C_{1-4}$alkyloxy substituted with one or more halo substituents, and $C_{1-4}$alkyl substituted with one or more halo substituents;
each $R^7$ is selected independently from hydrogen or $C_{1-4}$alkyl;
each $R^8$ is selected independently from hydrogen, $C_{1-4}$alkyl or $C_{1-4}$alkylcarbonyl;
Z is O or $NR^9$;
$R^9$ is hydrogen, or $C_{1-6}$alkyl optionally substituted with one or more substituents each independently selected from the group consisting of halo, cyano, phenyl, cyclo$C_{3-7}$alkyl and $C_{1-4}$alkyloxy;
and the pharmaceutically acceptable addition salts, and the solvates thereof.

In an embodiment, the invention relates to compounds of Formula (I) and stereoisomeric forms thereof, wherein
$R^1$ is hydrogen, cyano, $CF_3$, halo, or $C_{1-4}$alkyl optionally substituted with one or more substituents each independently selected from the group consisting of hydroxyl and $C_{1-4}$alkyloxy;
$R^2$ is hydrogen, $C_{1-4}$alkyl or halo;
X is $CR^5$ or N;
$R^5$ is hydrogen or halo;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$ or N;
$Y^3$ is CH or N;
provided that only one of $Y^1$, $Y^2$ and $Y^3$ may represent N;
$R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents;
$C_{1-6}$alkyl optionally substituted with one or more substituents each independently selected from the group consisting of piperidinyl, morpholinyl, pyrrolidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl substituted with one or more phenyl substituents optionally substituted with one or more halo substituents;
cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; NH—Ar; or 1,6-dihydro-1-methyl-6-oxo-3-pyridinyl;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is
phenyl optionally substituted with one or more substituents each independently selected from the group consisting of halo, $C_{1-4}$alkyloxy, cyano, $NR^7R^8$, morpholinyl, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl and $C_{1-4}$alkyl substituted with one or more halo substituents;
each $R^7$ is selected independently from hydrogen or $C_{1-4}$alkyl;
each $R^8$ is selected independently from hydrogen, $C_{1-4}$alkyl or $C_{1-4}$alkylcarbonyl;
Z is O or $NR^9$;
$R^9$ is hydrogen, or $C_{1-6}$alkyl optionally substituted with one or more substituents each independently selected from the group consisting of halo, phenyl and $C_{1-4}$alkyloxy;
and the pharmaceutically acceptable addition salts, and the solvates thereof.

In an embodiment, the invention relates to compounds of Formula (I) and stereoisomeric forms thereof, or any subgroup thereof as mentioned in any of the other embodiments, wherein one or more, preferably all, of the following restrictions apply:
(a) $R^1$ is hydrogen, cyano, halo, or $C_{1-4}$alkyl optionally substituted with one or more substituents each independently selected from the group consisting of hydroxyl and $C_{1-4}$alkyloxy;
(b) $R^5$ is hydrogen;
(c) $Y^1$ is CH or N; $Y^2$ is $CR^4$ or N; $Y^3$ is CH; provided that only one of $Y^1$ and $Y^2$ may represent N;
(d) $R^4$ is hydrogen, halo, $C_{1-4}$alkyloxy, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
(e) $R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl and cyclo$C_{3-7}$alkyl; cyclo$C_{3-7}$alkyl substituted with one or more phenyl substituents optionally substituted with one or more halo substituents; cyclo$C_{3-7}$alkyl; piperidinyl; morpholinyl; tetrahydropyranyl; O—Ar; $C_{1-6}$alkyloxy; $C_{1-6}$alkylthio; Ar; CH$_2$—O—Ar; NH—Ar; or 1,6-dihydro-1-methyl-6-oxo-3-pyridinyl;
wherein each piperidinyl and morpholinyl may be substituted with one or more substituents each independently selected from the group consisting of $C_{1-4}$alkyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy, cyano, NR$^7$R$^8$, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl and thiophenyl; wherein said 5- or 6-membered heteroaryl is optionally substituted with one or more substituents each independently selected from the group consisting of halo and $C_{1-4}$alkyl substituted with one or more halo substituents;
(f) each $R^8$ is selected independently from $C_{1-4}$alkyl or $C_{1-4}$alkylcarbonyl.

In an embodiment, the invention relates to compounds of Formula (I) and stereoisomeric forms thereof, or any subgroup thereof as mentioned in any of the other embodiments, wherein one or more, preferably all, of the following restrictions apply:
(a) $R^1$ is hydrogen, cyano, Br, or methyl optionally substituted with one or more substituents each independently selected from the group consisting of hydroxyl and methoxy;
(b) $R^2$ is hydrogen, methyl or I;
(c) X is CH or N;
(d) $R^6$ is hydrogen, F or methoxy;
(d) $Y^1$ is CH or N; $Y^2$ is CR$^4$ or N; $Y^3$ is CH; provided that only one of $Y^1$ and $Y^2$ may represent N;
(e) $R^4$ is hydrogen, F, methoxy, cyclopropyl, 1-propen-2-yl, or $C_{1-4}$alkyl optionally substituted with one or more substituents each independently selected from the group consisting of F and methoxy;
(f) $R^3$ is n-propyl substituted with one or more F substituents; $C_{1-4}$alkyl optionally substituted with one or more substituents each independently selected from the group consisting of piperidinyl, Ar, methoxy, tetrahydropyranyl and cyclopropyl; cyclopropyl substituted with one or more phenyl substituents optionally substituted with one or more Cl substituents; cyclopentyl; cyclohexyl; piperidinyl; morpholinyl; tetrahydropyranyl; O—Ar; $C_{1-4}$alkyloxy; $C_{1-4}$alkylthio; Ar; CH$_2$—O—Ar; NH—Ar; or 1,6-dihydro-1-methyl-6-oxo-3-pyridinyl;
wherein each piperidinyl and morpholinyl may be substituted with one or more substituents each independently selected from the group consisting of methyl, methylcarbonyl, F and tert-butyloxycarbonyl;
wherein each Ar independently is phenyl optionally substituted with one or more substituents each independently selected from the group consisting of halo, methoxy, ethoxy, isopropoxy, cyano, NR$^7$R$^8$, methyl, isopropyl, methoxy substituted with one or more F substituents, and $C_{1-4}$alkyl substituted with one or more F substituents; or
a 5- or 6-membered heteroaryl selected from the group consisting of pyridinyl and thiophenyl; wherein said 5- or 6-membered heteroaryl is optionally substituted with one or more substituents each independently selected from the group consisting of F and $C_{1-4}$alkyl substituted with one or more F substituents;
(g) each $R^7$ is selected independently from hydrogen or methyl;
(h) each $R^8$ is selected independently from methyl or methylcarbonyl;
(i) $R^9$ is hydrogen, or $C_{1-4}$alkyl optionally substituted with one or more substituents each independently selected from the group consisting of F, phenyl and methoxy.

In an embodiment, the invention relates to compounds of Formula (I) and stereoisomeric forms thereof, or any subgroup thereof as mentioned in any of the other embodiments, wherein one or more, preferably all, of the following restrictions apply:
(a) $R^1$ is $C_{1-4}$alkyl; in particular methyl;
(b) $R^2$ is hydrogen;
(c) X is CH or N;
(d) $A^1$ is CR$^6$;
(e) $R^6$ is hydrogen, methoxy or halo; in particular hydrogen, methoxy or F;
(f) $A^2$ is CH or N;
(g) $A^3$ and $A^4$ are CH;
(h) $Y^1$ is CH or N; $Y^2$ is CR$^4$; $Y^3$ is CH;
(i) $R^4$ is hydrogen, halo or $C_{1-4}$alkyl; in particular hydrogen, F, methyl or isopropyl;
(j) $R^3$ is phenyl optionally substituted with one or more substituents each independently selected from the group consisting of halo, $C_{1-4}$alkyloxy, NR$^7$R$^8$ and $C_{1-4}$alkyl substituted with one or more halo substituents; in particular phenyl substituted with one or more substituents each independently selected from the group consisting of F, Cl, methoxy, NR$^7$R$^8$ and CF$_3$;
(k) $R^7$ is hydrogen;
(l) $R^8$ is $C_{1-4}$alkylcarbonyl; in particular methylcarbonyl;
(m) Z is NR$^9$;
(n) $R^9$ is $C_{1-6}$alkyl; in particular $C_{1-4}$alkyl; more in particular methyl or isopropyl.

In an embodiment, the invention relates to compounds of Formula (I) and stereoisomeric forms thereof, wherein
$R^1$ is hydrogen, $C_{1-4}$alkyl, cyano, CF$_3$, or halo;
$R^2$ is hydrogen or $C_{1-4}$alkyl;
X is CR$^5$ or N;
$R^5$ is hydrogen or halo;
$A^1$ is CR$^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is CR$^4$ or N;
$Y^3$ is CH or N;
provided that only one of $Y^1$, $Y^2$ and $Y^3$ may represent N;
$R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl; piperidinyl; morpholinyl; pyrrolidinyl; tetrahydropyranyl;

O—Ar; NR$^7$R$^8$; C$_{1-6}$alkyloxy; C$_{1-6}$alkylthio; Ar; CH$_2$—O—Ar; S—Ar; NCH$_3$—Ar; or NH—Ar;
wherein each piperidinyl, morpholinyl and pyrrolidinyl may be substituted with one or more substituents each independently selected from the group consisting of C$_{1-4}$alkyl, C$_{2-6}$alkenyl, C$_{1-4}$alkylcarbonyl, halo and C$_{1-4}$alkyloxycarbonyl;
wherein each Ar independently is phenyl optionally substituted with one or more substituents each independently selected from the group consisting of halo, C$_{1-4}$alkyloxy, cyano, NR$^7$R$^8$, morpholinyl, C$_{1-4}$alkyl and C$_{1-4}$alkyl substituted with one or more halo substituents; or a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, C$_{1-4}$alkyloxy, cyano, C$_{1-4}$alkyl and
C$_{1-4}$alkyl substituted with one or more halo substituents;
each R$^7$ is selected independently from hydrogen or C$_{1-4}$alkyl;
each R$^8$ is selected independently from hydrogen or C$_{1-4}$alkyl;
Z is O or NR$^9$;
R$^9$ is hydrogen, or C$_{1-6}$alkyl optionally substituted with one or more substituents each independently selected from the group consisting of halo, phenyl and C$_{1-4}$alkyloxy; and the pharmaceutically acceptable addition salts, and the solvates thereof.

In an embodiment, the invention relates to compounds of Formula (I) and stereoisomeric forms thereof, wherein
R$^1$ is hydrogen, C$_{1-4}$alkyl, cyano, CF$_3$, or halo;
R$^2$ is hydrogen or C$_{1-4}$alkyl;
X is CR$^5$ or N; wherein R$^5$ is H or halo;
A$^1$ is CR$^6$ or N;
R$^6$ is hydrogen, halo or C$_{1-4}$alkyloxy;
A$^2$, A$^3$ and A$^4$ each independently are CH, CF or N; provided that no more than two of A$^1$, A$^2$, A$^3$ and A$^4$ are N;
Y$^1$ is CH or N;
Y$^2$ is CR$^4$ or N;
Y$^3$ is CH or N;
provided that only one of Y$^1$, Y$^2$ and Y$^3$ may represent N;
R$^3$ is C$_{2-6}$alkyl substituted with one or more substituents selected from halo; C$_{1-6}$alkyl optionally substituted with one or more substituents selected from piperidinyl, Ar, C$_{1-6}$alkyloxy, tetrahydropyranyl, cycloC$_{3-7}$alkyloxy and cycloC$_{3-7}$alkyl; cycloC$_{3-7}$alkyl; piperidinyl; morpholinyl; pyrrolidinyl; tetrahydropyranyl; O—Ar; NR$^7$R$^8$; C$_{1-6}$alkyloxy; C$_{1-6}$alkylthio; Ar; CH$_2$—O—Ar; S—Ar; NCH$_3$—Ar; or NH—Ar;
wherein each piperidinyl, morpholinyl and pyrrolidinyl may optionally be substituted with one or more substituents selected from C$_{1-4}$alkyl, C$_{2-6}$alkenyl, C$_{1-4}$alkylcarbonyl, halo and C$_{1-4}$alkyloxycarbonyl;
wherein each Ar independently is phenyl optionally substituted with one or more substituents each independently selected from halo, C$_{1-4}$alkyloxy, cyano, NR$^2$R$^8$, morpholinyl, C$_{1-4}$alkyl and C$_{1-4}$alkyl substituted with one or more substituents selected from halo; or a 5- or 6-membered heteroaryl selected from pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl, or pyrazinyl, wherein said 5- or 6-membered heteroaryl is optionally substituted with 1 or more substituents each independently selected from halo, C$_{1-4}$alkyloxy, cyano, C$_{1-4}$alkyl and C$_{1-4}$alkyl substituted with one or more substituents selected from halo;
wherein each R$^7$ is selected independently from hydrogen or C$_{1-4}$alkyl;
wherein each R$^8$ is selected independently from hydrogen or C$_{1-4}$alkyl;
R$^4$ is hydrogen, halo, C$_{1-4}$alkyloxy, cyano, cycloC$_{3-7}$alkyl, C$_{2-4}$alkenyl, or C$_{1-4}$alkyl optionally substituted with one or more substituents selected from halo or C$_{1-4}$alkyloxy; Z is O or NR$^9$; wherein R$^9$ is hydrogen, C$_{1-6}$alkyl optionally substituted with one or more substituents selected from halo, phenyl and C$_{1-4}$alkyloxy;
and the pharmaceutically acceptable addition salts, and the solvates thereof.

In an embodiment, the invention relates to compounds of Formula (I) and stereoisomeric forms thereof, wherein
R$^1$ is hydrogen, C$_{1-4}$alkyl, cyano, CF$_3$, or halo;
R$^2$ is hydrogen or C$_{1-4}$alkyl;
X is CR$^5$ or N;
R$^5$ is hydrogen or halo;
A$^1$ is CR$^6$ or N;
R$^6$ is hydrogen, halo or C$_{1-4}$alkyloxy;
A$^2$, A$^3$ and A$^4$ each independently are CH, CF or N;
provided that no more than two of A$^1$, A$^2$, A$^3$ and A$^4$ are N;
Y$^1$ is CH or N;
Y$^2$ is CR$^4$;
Y$^3$ is CH;
R$^4$ is hydrogen, halo, C$_{1-4}$alkyloxy, cyano, or C$_{1-4}$alkyl optionally substituted with one or more halo substituents;
R$^3$ is C$_{2-6}$alkyl substituted with one or more halo substituents; C$_{1-6}$alkyl optionally substituted with one or more substituents each independently selected from the group consisting of piperidinyl, Ar, C$_{1-6}$alkyloxy, tetrahydropyranyl, cycloC$_{3-7}$alkyloxy and cycloC$_{3-7}$alkyl; cycloC$_{3-7}$alkyl; piperidinyl; morpholinyl; pyrrolidinyl; tetrahydropyranyl; O—Ar; NR$^7$R$^8$; C$_{1-6}$alkyloxy; C$_{1-6}$alkylthio; Ar; CH$_2$—O—Ar; S—Ar; NCH$_3$—Ar; or NH—Ar;
wherein each piperidinyl, morpholinyl and pyrrolidinyl may be substituted with one or more substituents each independently selected from the group consisting of C$_{1-4}$alkyl, C$_{2-6}$alkenyl, C$_{1-4}$alkylcarbonyl, halo and C$_{1-4}$alkyloxycarbonyl;
wherein each Ar independently is phenyl optionally substituted with one or more substituents each independently selected from the group consisting of halo, C$_{1-4}$alkyloxy, cyano, NR$^7$R$^8$, morpholinyl, C$_{1-4}$alkyl and C$_{1-4}$alkyl substituted with one or more halo substituents; or a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, C$_{1-4}$alkyloxy, cyano, C$_{1-4}$alkyl and C$_{1-4}$alkyl substituted with one or more halo substituents;
each R$^7$ is selected independently from hydrogen or C$_{1-4}$alkyl;
each R$^8$ is selected independently from hydrogen or C$_{1-4}$alkyl;
Z is O or NR$^9$;
R$^9$ is hydrogen, or C$_{1-6}$alkyl optionally substituted with one or more substituents each independently selected from the group consisting of halo, phenyl and C$_{1-4}$alkyloxy; and the pharmaceutically acceptable addition salts, and the solvates thereof.

In an embodiment, the invention relates to compounds of Formula (I) and stereoisomeric forms thereof, wherein
$R^1$ is hydrogen, $C_{1-4}$alkyl, cyano, $CF_3$, or halo;
$R^2$ is hydrogen or $C_{1-4}$alkyl;
X is $CR^5$ or N; wherein $R^5$ is H or halo;
$A^1$ is $CR^6$ or N;
$R^6$ is hydrogen, halo or $C_{1-4}$alkyloxy;
$A^2$, $A^3$ and $A^4$ each independently are CH, CF or N; provided that no more than two of $A^1$, $A^2$, $A^3$ and $A^4$ are N;
$Y^1$ is CH or N; $Y^2$ is $CR^4$; $Y^3$ is CH;
$R^3$ is $C_{2-6}$alkyl substituted with one or more substituents selected from halo; $C_{1-6}$alkyl optionally substituted with one or more substituents selected from piperidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar, or NH—Ar;
wherein each piperidinyl, morpholinyl and pyrrolidinyl may optionally be substituted with one or more substituents selected from $C_{1-4}$alkyl, $C_{2-6}$alkenyl, $C_{1-4}$alkylcarbonyl, halo and $C_{1-4}$alkyloxycarbonyl;
wherein each Ar independently is phenyl optionally substituted with one or more substituents each independently selected from halo, $C_{1-4}$alkyloxy, cyano, $NR^7R^8$, morpholinyl, $C_{1-4}$alkyl and $C_{1-4}$alkyl substituted with one or more substituents selected from halo; or a 5- or 6-membered heteroaryl selected from pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl, or pyrazinyl, wherein said 5- or 6-membered heteroaryl is optionally substituted with 1 or more substituents each independently selected from halo, $C_{1-4}$alkyloxy, cyano, $C_{1-4}$alkyl and $C_{1-4}$alkyl substituted with one or more substituents selected from halo;
wherein $R^7$ is hydrogen or $C_{1-4}$alkyl;
wherein $R^8$ is hydrogen or $C_{1-4}$alkyl;
$R^4$ is hydrogen, halo, $C_{1-4}$alkyloxy, cyano, or $C_{1-4}$alkyl optionally substituted with one or more substituents selected from halo;
Z is O or $NR^9$; wherein $R^9$ is hydrogen, $C_{1-6}$alkyl optionally substituted with one or more substituents selected from halo, phenyl and $C_{1-4}$alkyloxy;
and the pharmaceutically acceptable addition salts, and the solvates thereof.

In an embodiment, the invention relates to compounds of Formula (I) and stereoisomeric forms thereof, wherein
$R^1$ is hydrogen, $C_{1-4}$alkyl, cyano or halo;
$R^2$ is hydrogen or $C_{1-4}$alkyl;
X is CH or N;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$;
$Y^3$ is CH or N;
provided that only one of $Y^1$ and $Y^3$ may represent N;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl and cyclo$C_{3-7}$alkyl; cyclo$C_{3-7}$alkyl; piperidinyl; morpholinyl; O—Ar; $C_{1-6}$alkyloxy; $C_{1-6}$alkylthio; Ar; or NH—Ar;
wherein each piperidinyl and morpholinyl may be substituted with one or more substituents each independently selected from the group consisting of $C_{1-4}$alkyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy and $C_{1-4}$alkyl; or pyridinyl;
$R^4$ is hydrogen, halo, cyano, or $C_{1-4}$alkyl optionally substituted with one or more halo substituents;
Z is O or $NR^9$;
$R^9$ is hydrogen, or $C_{1-6}$alkyl optionally substituted with one or more substituents each independently selected from the group consisting of halo, phenyl and $C_{1-4}$alkyloxy;
and the pharmaceutically acceptable addition salts, and the solvates thereof.

In an embodiment, the invention relates to compounds of Formula (I) and stereoisomeric forms thereof, wherein
$R^1$ is hydrogen, $C_{1-4}$alkyl, cyano or halo;
$R^2$ is hydrogen or $C_{1-4}$alkyl;
X is CH or N;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$;
$Y^3$ is CH;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl and cyclo$C_{3-7}$alkyl; cyclo$C_{3-7}$alkyl; piperidinyl; morpholinyl; O—Ar; $C_{1-6}$alkyloxy; $C_{1-6}$alkylthio; Ar; or NH—Ar;
wherein each piperidinyl and morpholinyl may be substituted with one or more substituents each independently selected from the group consisting of $C_{1-4}$alkyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy and $C_{1-4}$alkyl; or pyridinyl;
$R^4$ is hydrogen, halo, cyano, or $C_{1-4}$alkyl optionally substituted with one or more halo substituents;
Z is O or $NR^9$;
$R^9$ is hydrogen, or $C_{1-6}$alkyl optionally substituted with one or more substituents each independently selected from the group consisting of halo, phenyl and $C_{1-4}$alkyloxy; and the pharmaceutically acceptable addition salts, and the solvates thereof.

In another embodiment, the invention relates to compounds of Formula (I) and stereoisomeric forms thereof, wherein
$R^1$ is hydrogen, methyl, cyano or bromo;
$R^2$ is hydrogen or methyl;
X is CH or N;
$A^1$ is $CR^6$ or N;
$R^6$ is hydrogen, F or methoxy;
$A^2$, $A^3$ and $A^4$ each independently are CH, CF or N;
provided that no more than two of $A^1$, $A^2$, $A^3$ and $A^4$ are N;
$Y^1$ is CH or N;
$Y^2$ is $CR^4$;
$Y^3$ is CH;
$R^3$ is 3,3,3-trifluoropropyl; $C_{1-6}$alkyl optionally substituted with one or more substituents each independently selected from the group consisting of piperidinyl, Ar, methoxy, tetrahydropyranyl and cyclopropyl; hexyl; pentyl; piperidinyl; morpholinyl; O—Ar; isopropyloxy; isobutylthio; Ar; or NH—Ar;

wherein each piperidinyl and morpholinyl may be substituted with one or more substituents each independently selected from the group consisting of methyl, methylcarbonyl, F and tert-butyloxycarbonyl;

wherein each Ar independently is phenyl optionally substituted with one or more substituents each independently selected from the group consisting of Cl, F, methyloxy, ethyloxy, methyl and isobutyl; or pyridinyl;

$R^4$ is hydrogen, F, methyl, cyano or $CF_3$;

Z is O or $NR^9$;

$R^9$ is hydrogen, or $C_{1-4}$alkyl optionally substituted with one or more substituents each independently selected from the group consisting of F, phenyl and methoxy;

and the pharmaceutically acceptable addition salts, and the solvates thereof.

In an embodiment, the invention relates to compounds of Formula (I) and stereoisomeric forms thereof, or any subgroup thereof as mentioned in any of the other embodiments, wherein one or more, preferably all, of the following restrictions apply:

(a) $R^1$ is $C_{1-4}$alkyl; in particular methyl;
(b) $R^2$ is hydrogen;
(c) X is CH;
(d) $A^1$ is $CR^6$;
(e) $R^6$ is F or methoxy; in particular methoxy;
(f) $A^2$ is N or CH; in particular N;
(g) $A^3$ and $A^4$ are CH;
(h) $Y^1$ is CH or N;
(i) $Y^2$ is $CR^4$;
(j) $Y^3$ is CH;
(k) $R^4$ is hydrogen or methyl;
(l) $R^3$ is phenyl optionally substituted with one or more substituents each independently selected from the group consisting of halo and methoxy; in particular $R^3$ is phenyl substituted with one or more substituents each independently selected from the group consisting of halo and methoxy; more in particular $R^3$ is phenyl substituted with one or two substituents each independently selected from the group consisting of halo and methoxy; even more in particular $R^3$ is phenyl substituted with one or two substituents each independently selected from the group consisting of F and methoxy;
(m) Z is $NR^9$;
(n) $R^9$ is $C_{1-6}$alkyl; in particular $C_{1-4}$alkyl; more in particular methyl.

In an embodiment, the invention relates to compounds of Formula (I) and stereoisomeric forms thereof, or any subgroup thereof as mentioned in any of the other embodiments, wherein one or more, preferably all, of the following restrictions apply:

(a) $R^1$ is $C_{1-4}$alkyl; in particular methyl;
(b) $R^2$ is hydrogen;
(c) X is CH;
(d) $A^1$ is $COCH_3$; $A^2$ is N; $A^3$ is CH; $A^4$ is CH;
(e) $Y^1$, $Y^2$ and $Y^3$ are CH;
(f) $R^3$ is phenyl optionally substituted with one or more halo substituents; in particular phenyl substituted with one or more halo substituents; more in particular phenyl substituted with one halo substituent; even more in particular phenyl substituted with one fluoro substituent;
(g) Z is $NR^9$;
(h) $R^9$ is $C_{1-6}$alkyl; in particular $C_{1-4}$alkyl; more in particular methyl.

In a further embodiment, the invention relates to compounds according to any of the other embodiments, wherein $R^1$ is methyl and wherein $R^2$ is hydrogen.

In a further embodiment, the invention relates to compounds according to any of the other embodiments, wherein $R^1$ is hydrogen and wherein $R^2$ is methyl.

In a further embodiment, the invention relates to compounds according to any of the other embodiments, wherein $R^1$ is hydrogen, wherein $R^2$ is methyl and wherein X is N.

In a further embodiment, the invention relates to compounds according to any of the other embodiments, wherein $R^1$ is hydrogen, $C_{1-4}$alkyl, cyano or halo.

In a further embodiment, the invention relates to compounds according to any of the other embodiments, wherein X is $CR^5$.

In a further embodiment, the invention relates to compounds according to any of the other embodiments, wherein X is N.

In a further embodiment, the invention relates to compounds according to any of the other embodiments, wherein X is N or CH.

In a further embodiment, the invention relates to compounds according to any of the other embodiments, wherein X is CH.

In a further embodiment, the invention relates to compounds according to any of the other embodiments, wherein $Y^1$ is CH or N; $Y^2$ is $CR^4$; and $Y^3$ is CH or N;
provided that only one of $Y^1$ and $Y^3$ may represent N.

In a further embodiment, the invention relates to compounds according to any of the other embodiments, wherein $Y^1$ is CH; $Y^2$ is $CR^4$; and $Y^3$ is CH.

In a further embodiment, the invention relates to compounds according to any of the other embodiments, wherein $Y^1$ is N; $Y^2$ is $CR^4$; and $Y^3$ is CH.

In a further embodiment, the invention relates to compounds according to any of the other embodiments, wherein $Y^1$ is CH; $Y^2$ is N; and $Y^3$ is CH.

In a further embodiment, the invention relates to compounds according to any of the other embodiments, wherein $Y^1$ is CH; $Y^2$ is $CR^4$; and $Y^3$ is N.

In a further embodiment, the invention relates to compounds according to any of the other embodiments, wherein $R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl substituted with one or more phenyl substituents optionally substituted with one or more halo substituents; cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; NH—Ar; or 1,6-dihydro-1-methyl-6-oxo-3-pyridinyl.

In a further embodiment, the invention relates to compounds according to any of the other embodiments, wherein $R^3$ is $C_{2-6}$alkyl substituted with one or more halo substituents;
$C_{1-6}$alkyl optionally substituted with one or more substituents each independently selected from the group consisting of Ar, $C_{1-6}$alkyloxy, cyclo$C_{3-7}$alkyloxy and cyclo$C_{3-7}$alkyl; Ar; or $CH_2$—O—Ar; wherein each Ar independently is phenyl optionally substituted with one or more substituents each independently selected from the group consisting of halo, $C_{1-4}$alkyloxy, cyano, $C_{1-4}$alkyl and $C_{1-4}$alkyl substituted with one or more halo substituents.

In a further embodiment, the invention relates to compounds according to any of the other embodiments, wherein $R^3$ is isobutyl; cyclopropylmethyl; 3,3,3-trifluoropropyl; $C_{2-4}$alkyl substituted with methoxy; $CH_2$—O—Ar; or Ar.

In a further embodiment, the invention relates to compounds according to any of the other embodiments, wherein $R^3$ is Ar.

In a further embodiment, the invention relates to compounds according to any of the other embodiments, wherein each Ar independently is phenyl optionally substituted with one or more substituents each independently selected from the group consisting of halo, $C_{1-4}$alkyloxy, cyano, $NR^7R^8$, morpholinyl, $C_{1-4}$alkyl and $C_{1-4}$alkyl substituted with one or more halo substituents; or a 5- or 6-membered heteroaryl selected from the group consisting of pyridinyl, oxazolyl, thiophenyl, thiazolyl and oxadiazolyl; wherein said 5- or 6-membered heteroaryl is optionally substituted with one or more substituents each independently selected from the group consisting of halo, $C_{1-4}$alkyloxy, cyano, $C_{1-4}$alkyl and $C_{1-4}$alkyl substituted with one or more halo substituents.

In a further embodiment, the invention relates to compounds according to any of the other embodiments, wherein each Ar independently is phenyl optionally substituted with one or more substituents each independently selected from the group consisting of halo, $C_{1-4}$alkyloxy, cyano, $NR^7R^8$, morpholinyl, $C_{1-4}$alkyl and $C_{1-4}$alkyl substituted with one or more halo substituents; or pyridinyl optionally substituted with one or more substituents each independently selected from the group consisting of halo, $C_{1-4}$alkyloxy, cyano, $C_{1-4}$alkyl and $C_{1-4}$alkyl substituted with one or more halo substituents.

In a further embodiment, the invention relates to compounds according to any of the other embodiments, wherein each Ar independently is phenyl optionally substituted with one or more substituents each independently selected from the group consisting of halo, $C_{1-4}$alkyloxy, cyano, $NR^7R^8$, morpholinyl, $C_{1-4}$alkyl and $C_{1-4}$alkyl substituted with one or more halo substituents; or a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl and $C_{1-4}$alkyl substituted with one or more halo substituents.

In a further embodiment, the invention relates to compounds according to any of the other embodiments, wherein $R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy.

In a further embodiment, the invention relates to compounds according to any of the other embodiments, wherein $R^4$ is hydrogen, halo, $C_{1-4}$alkyloxy, cyano, or $C_{1-4}$alkyl optionally substituted with one or more halo substituents.

In a further embodiment, the invention relates to compounds according to any of the other embodiments, wherein $R^4$ is hydrogen, halo, or $C_{1-4}$alkyl optionally substituted with one or more halo substituents.

In a further embodiment, the invention relates to compounds according to any of the other embodiments, wherein $R^4$ is hydrogen, halo, methyl, cyano or $CF_3$.

In a further embodiment, the invention relates to compounds according to any of the other embodiments, wherein $R^4$ is hydrogen, F or $CF_3$.

In a further embodiment, the invention relates to compounds according to any of the other embodiments, wherein Z is O.

In a further embodiment, the invention relates to compounds according to any of the other embodiments, wherein Z is $NR^9$.

In a further embodiment, the invention relates to compounds according to any of the other embodiments, wherein Z is $NR^9$ and wherein $R^9$ is $C_{1-6}$alkyl optionally substituted with one or more substituents each independently selected from the group consisting of $C_{1-4}$alkyloxy and $CF_3$.

In a further embodiment, the invention relates to compounds according to any of the other embodiments, wherein $R^9$ is $C_{1-3}$alkyl.

In a further embodiment, the invention relates to compounds according to any of the other embodiments or any combination of the other embodiments, wherein each $R^8$ is selected independently from hydrogen or $C_{1-4}$alkyl.

In a further embodiment, the invention relates to compounds according to any of the other embodiments, wherein $A^1$ is N, CH, CF or $COCH_3$.

In a further embodiment, the invention relates to compounds according to any of the other embodiments, wherein $A^2$ is CH.

In a further embodiment, the invention relates to compounds according to any of the other embodiments, wherein $A^3$ is CH or N.

In a further embodiment, the invention relates to compounds according to any of the other embodiments, wherein $A^4$ is CH.

In a further embodiment, the invention relates to compounds according to any of the other embodiments, wherein $A^2$, $A^3$ and $A^4$ each independently are CH or N; provided that no more than two of $A^1$, $A^2$, $A^3$ and $A^4$ are N.

In a further embodiment, the invention relates to compounds according to any of the other embodiments, wherein $A^3$ and $A^4$ are CH.

In a further embodiment, the invention relates to compounds according to any of the other embodiments, wherein
$A^2$ is CH, CF or N; and
$A^3$ and $A^4$ each independently are CH or N; provided that no more than two of $A^1$, $A^2$, $A^3$ and $A^4$ are N;

In a further embodiment, the invention relates to compounds according to any of the other embodiments, wherein
$A^1$ is N, CH, CF or $COCH_3$;
$A^2$ is CH;
$A^3$ is CH or N; and
$A^4$ is CH.

In a further embodiment, the invention relates to compounds according to any of the other embodiments, wherein $C_{1-6}$alkyl is restricted to $C_{1-4}$alkyl.

In an embodiment the compound of Formula (I) is selected from the group comprising:

2-(4-fluorophenyl)-N-[3-methoxy-4-(4-methyl-1H-imidazol-1-yl)phenyl]-4-benzoxazolamine, 2-cyclohexyl-N-[3-methoxy-4-(4-methyl-1H-imidazol-1-yl)phenyl]-4-benzoxazolamine, 2-(4-fluorophenyl)-N-[3-methoxy-4-(4-methyl-1H-imidazol-1-yl)phenyl]-1-methyl-1H-benzimidazol-4-amine, 2-cyclopentyl-N-[3-methoxy-4-(4-methyl-1H-imidazol-1-yl)phenyl]-4-benzoxazolamine, N-[3-methoxy-4-(4-methyl-1H-imidazol-1-yl)phenyl]-2-(2-methylpropyl)-4-benzoxazolamine, N-[3-methoxy-4-(4-methyl-1H-imidazol-1-yl)phenyl]-2-(3-pyridinyl)-4-benzoxazolamine, 2-(4-fluorophenyl)-N-[3-methoxy-4-(4-methyl-1H-imidazol-1-yl)phenyl]-1-(1-methylethyl)-1H-benzimidazol-4-amine, 4-[4-[[3-methoxy-4-(4-methyl-1H-imidazol-1-yl)phenyl]
amino]-2-benzoxazolyl]-1-piperidinecarboxylic acid, 1,1-
dimethylethyl ester 2-(2-chlorophenyl)-N-[3-methoxy-4-(4-methyl-1H-imida-
zol-1-yl)phenyl]-4-benzoxazolamine, 2-(4-fluorophenyl)-N-[3-methoxy-4-(4-methyl-1H-imida-
zol-1-yl)phenyl]-1-(phenylmethyl)-1H-benzimidazol-4-
amine, 2-cyclohexyl-N-[3-methoxy-4-(4-methyl-1H-imidazol-1-
yl)phenyl]-1-methyl-1H-benzimidazol-4-amine, 2-(4-fluorophenyl)-N-[3-methoxy-4-(4-methyl-1H-imida-
zol-1-yl)phenyl]-1H-benzimidazol-4-amine, N-[3-methoxy-4-(4-methyl-1H-imidazol-1-yl)phenyl]-2-(4-
methoxyphenyl)-1-methyl-1H-benzimidazol-4-amine, 2-(2,4-difluorophenyl)-N-[3-methoxy-4-(4-methyl-1H-imi-
dazol-1-yl)phenyl]-1-methyl-1H-benzimidazol-4-amine, 2-(2,6-dimethyl-4-morpholinyl)-N-[3-methoxy-4-(4-me-
thyl-1H-imidazol-1-yl)-phenyl]-1-methyl-1H-benzimida-
zol-4-amine, 2-(2-fluorophenyl)-N-[3-methoxy-4-(4-methyl-1H-imida-
zol-1-yl)phenyl]-1-methyl-1H-benzimidazol-4-amine, N-[3-methoxy-4-(4-methyl-1H-imidazol-1-yl)phenyl]-2-(2-
methoxyphenyl)-4-benzoxazolamine, 1-acetyl-4-[4-[[3-methoxy-4-(4-methyl-1H-imidazol-1-yl)
phenyl]amino]-2-benzoxazolyl]-piperidine, 2-[(4-fluorophenyl)methyl]-N-[3-methoxy-4-(4-methyl-1H-
imidazol-1-yl)phenyl]-4-benzoxazolamine, N-[4-(4-bromo-1H-imidazol-1-yl)-3-methoxyphenyl]-2-(4-
fluorophenyl)-1-methyl-1H-benzimidazol-4-amine, N-[3-methoxy-4-(4-methyl-1H-imidazol-1-yl)phenyl]-2-(1-
methyl-4-piperidinyl)-4-benzoxazolamine, N-[3-methoxy-4-(4-methyl-1H-imidazol-1-yl)phenyl]-1-
methyl-2-(2-methyl-propyl)-1H-benzimidazol-4-amine, 2-(4-fluorophenyl)-N-[5-methoxy-6-(4-methyl-1H-imida-
zol-1-yl)-3-pyridinyl]-1-methyl-1H-benzimidazol-4-
amine, 2-(4-fluorophenyl)-N-[3-methoxy-4-(3-methyl-1H-1,2,4-
triazol-1-yl)phenyl]-1-methyl-1H-benzimidazol-4-amine, 1-[4-[[2-(4-fluorophenyl)-1-methyl-1H-benzimidazol-4-yl]
amino]-2-methoxy-phenyl]-1H-imidazole-4-carbonitrile, 2-(4-fluorophenyl)-N-[4-(1H-imidazol-1-yl)-3-methox-
yphenyl]-1-methyl-1H-benzimidazol-4-amine, N-[3-methoxy-4-(4-methyl-1H-imidazol-1-yl)phenyl]-2-(2-
methylphenyl)-1-(phenylmethyl)-1H-benzimidazol-4-
amine, 2-(1,1-dimethylethyl)-N-[3-methoxy-4-(4-methyl-1H-imi-
dazol-1-yl)phenyl]-4-benzoxazolamine, 2-(4-fluorophenyl)-1-methyl-N-[5-(4-methyl-1H-imidazol-
1-yl)-2-pyridinyl]-1H-benzimidazol-4-amine, 2-(4-fluorophenyl)-N-[3-methoxy-4-(1H-1,2,4-triazol-1-yl)
phenyl]-1-methyl-1H-benzimidazol-4-amine, N-[3-methoxy-4-(4-methyl-1H-imidazol-1-yl)phenyl]-1-
methyl-2-[(tetrahydro-2H-pyran-4-yl)methyl]-1H-benz-
imidazol-4-amine, 2-[(4-fluorophenyl)methyl]-N-[3-methoxy-4-(4-methyl-1H-
imidazol-1-yl)phenyl]-1-methyl-1H-benzimidazol-4-
amine, 2-(4-fluorophenyl)-N-[4-methoxy-5-(4-methyl-1H-imida-
zol-1-yl)-2-pyridinyl]-1-methyl-1H-benzimidazol-4-
amine, 2-(4-fluorophenyl)-1-methyl-N-[4-(4-methyl-1H-imidazol-
1-yl)phenyl]-1H-benzimidazol-4-amine, 2-(4-fluorophenyl)-1-methyl-N-[2-(4-methyl-1H-imidazol-
1-yl)-5-pyrimidinyl]-1H-benzimidazol-4-amine, N-[3-methoxy-4-(4-methyl-1H-imidazol-1-yl)phenyl]-2-(2-
methylphenyl)-1H-benzimidazol-4-amine, 2-(4,4-difluoro-1-piperidinyl)-N-[3-methoxy-4-(4-methyl-
1H-imidazol-1-yl)phenyl]-1-methyl-1H-benzimidazol-4-
amine, N-[3-methoxy-4-(4-methyl-1H-imidazol-1-yl)phenyl]-1-
methyl-2-phenoxy-1H-benzimidazol-4-amine, N-[3-methoxy-4-(4-methyl-1H-imidazol-1-yl)phenyl]-1-
methyl-2-(1-piperidinyl)-1H-benzimidazol-4-amine, 2-(4-fluorophenyl)-N-[3-methoxy-4-(4-methyl-1H-imida-
zol-1-yl)phenyl]-1H-imidazo[4,5-c]pyridin-4-amine, 1-(2-methoxyethyl)-N-[3-methoxy-4-(4-methyl-1H-imida-
zol-1-yl)phenyl]-2-(3-methoxyphenyl)-1H-benzimida-
zol-4-amine, 2-(4-fluorophenyl)-N-[3-methoxy-4-(5-methyl-1H-1,2,4-
triazol-1-yl)phenyl]-1-methyl-1H-benzimidazol-4-amine, N-[3-fluoro-4-(4-methyl-1H-imidazol-1-yl)phenyl]-2-(4-
fluorophenyl)-1-methyl-1H-benzimidazol-4-amine, 2-(4-fluorophenyl)-N-[3-methoxy-4-(4-methyl-1H-imida-
zol-1-yl)phenyl]-1-methyl-1H-imidazo[4,5-c]pyridin-4-
amine, 2-(4-fluorophenyl)-N-[3-fluoro-4-(1H-1,2,4-triazol-1-yl)
phenyl]-1-methyl-1H-benzimidazol-4-amine, N-[3-methoxy-4-(4-methyl-1H-imidazol-1-yl)phenyl]-1-
methyl-2-(1-methyl-ethoxy)-1H-benzimidazol-4-amine, N-[3-methoxy-4-(4-methyl-1H-imidazol-1-yl)phenyl]-1-
methyl-2-[(2-methyl-propyl)thio]-1H-benzimidazol-4-
amine, N-[3-methoxy-4-(4-methyl-1H-imidazol-1-yl)phenyl]-1-
methyl-2-(3,3,3-trifluoropropyl)-1H-benzimidazol-4-
amine, N-[3-methoxy-4-(4-methyl-1H-imidazol-1-yl)phenyl]-1-
methyl-2-(4-piperidinyl-methyl)-1H-benzimidazol-4-
amine, 1-acetyl-4-[[4-[[3-methoxy-4-(4-methyl-1H-imidazol-1-yl)
phenyl]amino]-1-methyl-1H-benzimidazol-2-yl]methyl]-
piperidine, N-[3-methoxy-4-(4-methyl-1H-imidazol-1-yl)phenyl]-1-
methyl-2-[(1-methyl-4-piperidinyl)methyl]-1H-benzimi-
dazol-4-amine, 2-(4-fluorophenyl)-1-methyl-N-[6-(4-methyl-1H-imidazol-
1-yl)-3-pyridinyl]-1H-benzimidazol-4-amine, 2-(4-fluorophenyl)-1-methyl-N-[6-(3-methyl-1H-1,2,4-tria-
zol-1-yl)-3-pyridinyl]-1H-benzimidazol-4-amine, N-[3-methoxy-4-(4-methyl-1H-imidazol-1-yl)phenyl]-2-(3-
methoxyphenyl)-1-methyl-1H-benzimidazol-4-amine, N-[3-methoxy-4-(3-methyl-1H-1,2,4-triazol-1-yl)phenyl]-
2-(2-methylpropyl)-4-benzoxazolamine, 2-[4-ethoxy-2-methyl-5-(1-methylethyl)phenyl]-N-[3-
methoxy-4-(3-methyl-1H-1,2,4-triazol-1-yl)phenyl]-1-
methyl-1H-benzimidazol-4-amine, 2-[4-ethoxy-2-methyl-5-(1-methylethyl)phenyl]-N-[3-
methoxy-4-(3-methyl-1H-1,2,4-triazol-1-yl)phenyl]-4-
benzoxazolamine, N-[3-methoxy-4-(4-methyl-1H-imidazol-1-yl)phenyl]-2-
methyl-1-(phenylmethyl)-1H-benzimidazol-4-amine, 2-(cyclopropylmethyl)-1-ethyl-N-[3-methoxy-4-(4-methyl-
1H-imidazol-1-yl)-phenyl]-1H-benzimidazol-4-amine, 2-(4-chloro-3-methoxyphenyl)-N-[3-fluoro-4-(1H-1,2,4-
triazol-1-yl)phenyl]-1-methyl-1H-benzimidazol-4-amine, 2-(4-fluorophenyl)-1-(1-methylethyl)-N-[4-(3-methyl-1H-
1,2,4-triazol-1-yl)-phenyl]-1H-benzimidazol-4-amine, 2-(4-fluorophenyl)-N-[3-methoxy-4-(3-methyl-1H-1,2,4-
triazol-1-yl)phenyl]-1-(1-methylethyl)-1H-benzimidazol-
4-amine, 2-(4-fluorophenyl)-N-[3-methoxy-4-(3-methyl-1H-1,2,4-
triazol-1-yl)phenyl]-1-(1-methylethyl)-1H-benzimidazol-
4-amine0.2HCl, 1-(1,1-dimethylethyl)-2-(4-fluorophenyl)-N-[4-(3-methyl-1H-1,2,4-triazol-1-yl)-phenyl]-1H-benzimidazol-4-amine, 1-(1,1-dimethylethyl)-2-(4-fluorophenyl)-N-[3-methoxy-4-(3-methyl-1H-1,2,4-triazol-1-yl)phenyl]-1H-benzimidazol-4-amine, $N^2$-[4-ethoxy-2-methyl-5-(1-methylethyl)phenyl]-$N^4$-[3-methoxy-4-(4-methyl-1H-imidazol-1-yl)phenyl]-1-methyl-1H-benzimidazole-2,4-diamine, 2-methyl-N-[4-(3-methyl-1H-1,2,4-triazol-1-yl)phenyl]-1-(phenylmethyl)-1H-benzimidazol-4-amine, 1,2-bis(2-methylpropyl)-N-[4-(3-methyl-1H-1,2,4-triazol-1-yl)phenyl]-1H-benzimidazol-4-amine, 1-(2-methoxyethyl)-2-(2-methylpropyl)-N-[4-(3-methyl-1H-1,2,4-triazol-1-yl)-phenyl]-1H-benzimidazol-4-amine, 2-(2-methylpropyl)-N-[5-(3-methyl-1H-1,2,4-triazol-1-yl)-2-pyridinyl]-4-benzoxazolamine, 2-(4-fluorophenyl)-1-(1-methylethyl)-N-[6-(3-methyl-1H-1,2,4-triazol-1-yl)-3-pyridinyl]-1H-benzimidazol-4-amine, N-[3-methoxy-4-(3-methyl-1H-1,2,4-triazol-1-yl)phenyl]-2-methyl-1-(1-methyl-ethyl)-1H-benzimidazol-4-amine, 2-(4-fluorophenyl)-1-methyl-N-[4-(3-methyl-1H-1,2,4-triazol-1-yl)phenyl]-6-(trifluoromethyl)-1H-benzimidazol-4-amine, N-[3-methoxy-4-(4-methyl-1H-imidazol-1-yl)phenyl]-2-(3-methoxypropyl)-1-methyl-1H-benzimidazol-4-amine, 1-ethyl-N-[3-methoxy-4-(4-methyl-1H-imidazol-1-yl)phenyl]-2-(3,3,3-trifluoro-propyl)-1H-benzimidazol-4-amine, N-[3-methoxy-4-(3-methyl-1H-1,2,4-triazol-1-yl)phenyl]-2-(3-methoxyphenyl)-1-methyl-1H-benzimidazol-4-amine, 2-(3-methoxyphenyl)-1-methyl-N-[4-(3-methyl-1H-1,2,4-triazol-1-yl)phenyl]-1H-benzimidazol-4-amine, 2-(4-fluorophenyl)-1-(1-methylethyl)-N-[5-(3-methyl-1H-1,2,4-triazol-1-yl)-2-pyridinyl]-1H-benzimidazol-4-amine, 2-methyl-1-(1-methylethyl)-N-[4-(3-methyl-1H-1,2,4-triazol-1-yl)phenyl]-1H-benzimidazol-4-amine, 2-(4-fluorophenyl)-1-(1-methylethyl)-N-[4-(5-methyl-1H-1,2,4-triazol-1-yl)-phenyl]-1H-benzimidazol-4-amine, N-[3-fluoro-4-(3-methyl-1H-1,2,4-triazol-1-yl)phenyl]-2-(4-fluorophenyl)-1-(1-methylethyl)-1H-benzimidazol-4-amine, N-[3-methoxy-4-(3-methyl-1H-1,2,4-triazol-1-yl)phenyl]-2-(3-methoxyphenyl)-1-(1-methylethyl)-1H-benzimidazol-4-amine, 2-(1,1-dimethylethyl)-N-[3-methoxy-4-(4-methyl-1H-imidazol-1-yl)phenyl]-1-methyl-1H-benzimidazol-4-amine, 2-(3-chlorophenyl)-N-[3-methoxy-4-(5-methyl-1H-1,2,4-triazol-1-yl)phenyl]-1-methyl-1H-benzimidazol-4-amine, 2-(2-chloro-3-methoxyphenyl)-N-[3-methoxy-4-(3-methyl-1H-1,2,4-triazol-1-yl)-phenyl]-1-methyl-1H-benzimidazol-4-amine, 2-(3-methoxyphenyl)-1-(1-methylethyl)-N-[4-(3-methyl-1H-1,2,4-triazol-1-yl)-phenyl]-1H-benzimidazol-4-amine, 2-(4-chloro-3-methoxyphenyl)-N-[3-methoxy-4-(3-methyl-1H-1,2,4-triazol-1-yl)-phenyl]-1-methyl-1H-benzimidazol-4-amine, 2-butyl-N-[3-fluoro-4-(3-methyl-1H-1,2,4-triazol-1-yl)phenyl]-1-methyl-1H-benzimidazol-4-amine, 2-(4-fluorophenyl)-1-methyl-N-[6-(4-methyl-1H-imidazol-1-yl)-3-pyridazinyl]-1H-benzimidazol-4-amine, 2-(4-fluorophenyl)-N-[6-methoxy-5-(4-methyl-1H-imidazol-1-yl)-2-pyridinyl]-1-methyl-1H-benzimidazol-4-amine, 6-fluoro-N-[3-methoxy-4-(3-methyl-1H-1,2,4-triazol-1-yl)phenyl]-2-(3-methoxy-phenyl)-1-methyl-1H-benzimidazol-4-amine, 6-fluoro-N-[3-fluoro-4-(3-methyl-1H-1,2,4-triazol-1-yl)phenyl]-2-(3-methoxy-phenyl)-1-methyl-1H-benzimidazol-4-amine, 6-fluoro-2-(3-methoxyphenyl)-1-methyl-N-[4-(3-methyl-1H-1,2,4-triazol-1-yl)-phenyl]-1H-benzimidazol-4-amine, 2-(4-fluorophenyl)-N-[3-methoxy-4-(3-methyl-1H-1,2,4-triazol-1-yl)phenyl]-1-methyl-1H-imidazo[4,5-c]pyridin-4-amine, 2-(4-fluorophenyl)-1-methyl-N-[6-(3-methyl-1H-1,2,4-triazol-1-yl)-3-pyridinyl]-6-(trifluoromethyl)-1H-benzimidazol-4-amine, N-[3-methoxy-4-(4-methyl-1H-imidazol-1-yl)phenyl]-1,2-dimethyl-1H-benzimidazol-4-amine, N-[3-fluoro-4-(5-methyl-1H-1,2,4-triazol-1-yl)phenyl]-2-(4-fluorophenyl)-1-(1-methylethyl)-1H-imidazo[4,5-c]pyridin-4-amine, N-[3-fluoro-4-(5-methyl-1H-1,2,4-triazol-1-yl)phenyl]-2-(4-fluorophenyl)-1-methyl-1H-imidazo[4,5-c]pyridin-4-amine, 2-(2,4-difluorophenyl)-N-[3-methoxy-4-(3-methyl-1H-1,2,4-triazol-1-yl)phenyl]-1-methyl-1H-imidazo[4,5-c]pyridin-4-amine, N-[3-methoxy-4-(5-methyl-1H-1,2,4-triazol-1-yl)phenyl]-1-methyl-2-(phenoxy-methyl)-1H-benzimidazol-4-amine, N-[3-fluoro-4-(5-methyl-1H-1,2,4-triazol-1-yl)phenyl]-2-(4-fluorophenyl)-1,6-dimethyl-1H-imidazo[4,5-c]pyridin-4-amine, 2-(cyclopropylmethyl)-N-[3-methoxy-4-(5-methyl-1H-1,2,4-triazol-1-yl)phenyl]-1-methyl-1H-imidazo[4,5-c]pyridin-4-amine, N-[3,5-difluoro-4-(3-methyl-1H-1,2,4-triazol-1-yl)phenyl]-2-(4-fluorophenyl)-1-methyl-1H-benzimidazol-4-amine, 2-(4-fluorophenyl)-1-methyl-N-[4-(3-methyl-1H-1,2,4-triazol-1-yl)phenyl]-1H-benzimidazol-4-amine, 2-(2,4-difluorophenyl)-N-[3-fluoro-4-(4-methyl-1H-imidazol-1-yl)phenyl]-1-methyl-1H-imidazo[4,5-c]pyridin-4-amine, N-[3-methoxy-4-(3-methyl-1H-1,2,4-triazol-1-yl)phenyl]-2-(2-methylpropyl)-1-(2,2,2-trifluoroethyl)-1H-benzimidazol-4-amine, N-[3-fluoro-4-(4-methyl-1H-imidazol-1-yl)phenyl]-2-(4-fluorophenyl)-1,6-dimethyl-1H-imidazo[4,5-c]pyridin-4-amine, 2-(4-fluorophenyl)-N-[3-methoxy-4-(3-methyl-1H-1,2,4-triazol-1-yl)phenyl]-3-methyl-5-(1-methylethyl)-3H-imidazo[4,5-b]pyridin-7-amine, 2-(4-chloro-3-methoxyphenyl)-N-[3-methoxy-4-(3-methyl-1H-1,2,4-triazol-1-yl)phenyl]-1-methyl-1H-imidazo[4,5-c]pyridin-4-amine, 2-(4-fluorophenyl)-N-[6-methoxy-5-(4-methyl-1H-imidazol-1-yl)-2-pyridinyl]-3-methyl-5-(1-methylethyl)-3H-imidazo[4,5-b]pyridin-7-amine, 2-(4-fluorophenyl)-N-[3-methoxy-4-(3-methyl-1H-1,2,4-triazol-1-yl)phenyl]-1-methyl-6-(1-methylethyl)-1H-imidazo[4,5-c]pyridin-4-amine, 6-fluoro-2-(4-fluorophenyl)-N-[6-methoxy-5-(4-methyl-1H-imidazol-1-yl)-2-pyridinyl]-1-methyl-1H-benzimidazol-4-amine, 6-fluoro-2-(4-fluorophenyl)-N-[6-methoxy-5-(4-methyl-1H-imidazol-1-yl)-2-pyridinyl]-1-(1-methylethyl)-1H-benzimidazol-4-amine, 2-(4-fluorophenyl)-N-[6-methoxy-5-(4-methyl-1H-imidazol-1-yl)-2-pyridinyl]-1-(1-methylethyl)-1H-benzimidazol-4-amine, N-[3-fluoro-4-(4-methyl-1H-imidazol-1-yl)phenyl]-2-(4-fluorophenyl)-3,5-dimethyl-3H-imidazo[4,5-b]pyridin-7-amine, 2-(4-fluorophenyl)-N-[3-methoxy-4-(3-methyl-1H-1,2,4-triazol-1-yl)phenyl]-3,5-dimethyl-3H-imidazo[4,5-b]pyridin-7-amine, 2-(4-fluorophenyl)-N-[3-methoxy-4-(3-methyl-1H-1,2,4-triazol-1-yl)phenyl]-3-methyl-5-(1-methylethenyl)-3H-imidazo[4,5-b]pyridin-7-amine, 1-[4-[[2-(4-fluorophenyl)-1-methyl-1H-benzimidazol-4-yl]amino]-2-methoxyphenyl]-1H-imidazole-4-methanol, 2-(4-fluorophenyl)-N-[3-methoxy-4-(3-methyl-1H-1,2,4-triazol-1-yl)phenyl]-1,6-dimethyl-1H-imidazo[4,5-c]pyridin-4-amine, 2-(2,4-difluorophenyl)-N-[2-fluoro-4-(3-methyl-1H-1,2,4-triazol-1-yl)phenyl]-1-methyl-1H-imidazo[4,5-c]pyridin-4-amine, N-[3-methoxy-4-(3-methyl-1H-1,2,4-triazol-1-yl)phenyl]-2-(3-methoxyphenyl)-1,6-dimethyl-1H-imidazo[4,5-c]pyridin-4-amine, N-[3-methoxy-4-(3-methyl-1H-1,2,4-triazol-1-yl)phenyl]-1-(1-methylethyl)-2-(tetrahydro-2H-pyran-4-yl)-1H-benzimidazol-4-amine, N-[3-methoxy-4-(4-methyl-1H-imidazol-1-yl)phenyl]-1-(1-methylethyl)-2-[6-(trifluoromethyl)-3-pyridinyl]-1H-benzimidazol-4-amine, N-[3-methoxy-4-(3-methyl-1H-1,2,4-triazol-1-yl)phenyl]-2-(3-methoxyphenyl)-1-methyl-1H-imidazo[4,5-c]pyridin-4-amine, N-[3-methoxy-4-(3-methyl-1H-1,2,4-triazol-1-yl)phenyl]-1-methyl-2-[2-(trifluoromethyl)phenyl]-1H-imidazo[4,5-c]pyridin-4-amine, 2-(2,5-difluorophenyl)-1-ethyl-6-fluoro-N-[3-methoxy-4-(3-methyl-1H-1,2,4-triazol-1-yl)phenyl]-1H-benzimidazol-4-amine, N-[3-methoxy-4-(3-methyl-1H-1,2,4-triazol-1-yl)phenyl]-2-(3-methoxyphenyl)-1-(1-methylethyl)-1H-imidazo[4,5-c]pyridin-4-amine, 2-(2-chlorophenyl)-6-fluoro-N-[3-methoxy-4-(3-methyl-1H-1,2,4-triazol-1-yl)phenyl]-1-methyl-1H-benzimidazol-4-amine, 2-(2-chlorophenyl)-N-[3-methoxy-4-(3-methyl-1H-1,2,4-triazol-1-yl)phenyl]-1-methyl-1H-imidazo[4,5-c]pyridin-4-amine, 2-(4-fluorophenyl)-N-[3-methoxy-4-(3-methyl-1H-1,2,4-triazol-1-yl)phenyl]-5-(3-methoxypropyl)-3-methyl-3H-imidazo[4,5-b]pyridin-7-amine, 2-(2-chlorophenyl)-N-[3-methoxy-4-(3-methyl-1H-1,2,4-triazol-1-yl)phenyl]-1-(1-methylethyl)-1H-imidazo[4,5-c]pyridin-4-amine, 2-(4-fluorophenyl)-N-[3-methoxy-4-[4-(methoxymethyl)-1H-imidazol-1-yl]phenyl]-1-methyl-1H-benzimidazol-4-amine, 2-(5-chloro-2-thienyl)-N-[3-methoxy-4-(3-methyl-1H-1,2,4-triazol-1-yl)phenyl]-1-(1-methylethyl)-1H-benzimidazol-4-amine, 2-(4-fluorophenyl)-N-[3-methoxy-4-(3-methyl-1H-1,2,4-triazol-1-yl)phenyl]-3-methyl-3H-imidazo[4,5-c]pyridin-7-amine, 2-(3-chlorophenyl)-N-[3-methoxy-4-(3-methyl-1H-1,2,4-triazol-1-yl)phenyl]-1-(1-methylethyl)-1H-benzimidazol-4-amine, 2-[1-(4-chlorophenyl)ethyl]-N-[3-methoxy-4-(3-methyl-1H-1,2,4-triazol-1-yl)phenyl]-1-methyl-1H-benzimidazol-4-amine, 2-[1-(4-chlorophenyl)cyclopropyl]-N-[3-methoxy-4-(3-methyl-1H-1,2,4-triazol-1-yl)phenyl]-1-methyl-1H-benzimidazol-4-amine, 2-(2-chlorophenyl)-6-fluoro-N-[6-methoxy-5-(4-methyl-1H-imidazol-1-yl)-2-pyridinyl]-1-methyl-1H-benzimidazol-4-amine, 2-(4-fluorophenyl)-N-[6-methoxy-5-(4-methyl-1H-imidazol-1-yl)-2-pyridinyl]-1,6-dimethyl-1H-imidazo[4,5-c]pyridin-4-amine, 2-(2-chlorophenyl)-N-[6-methoxy-5-(4-methyl-1H-imidazol-1-yl)-2-pyridinyl]-1,6-dimethyl-1H-imidazo[4,5-c]pyridin-4-amine, 2-(2-chlorophenyl)-N-[3-methoxy-4-(3-methyl-1H-1,2,4-triazol-1-yl)phenyl]-1,6-dimethyl-1H-imidazo[4,5-c]pyridin-4-amine, 2-(2-chlorophenyl)-N-[3-fluoro-4-(4-methyl-1H-imidazol-1-yl)phenyl]-1,6-dimethyl-1H-imidazo[4,5-c]pyridin-4-amine, N-[3-fluoro-4-(4-methyl-1H-imidazol-1-yl)phenyl]-2-(4-fluorophenyl)-1-methyl-1H-imidazo[4,5-c]pyridin-4-amine, 5-cyclopropyl-N-[3-fluoro-4-(4-methyl-1H-imidazol-1-yl)phenyl]-2-(4-fluorophenyl)-3-methyl-3H-imidazo[4,5-b]pyridin-7-amine, 6-chloro-2-(4-fluorophenyl)-N-[3-methoxy-4-(3-methyl-1H-1,2,4-triazol-1-yl)phenyl]-1-methyl-1H-imidazo[4,5-c]pyridin-4-amine, 4-[[4-[[3-methoxy-4-(4-methyl-1H-imidazol-1-yl)phenyl]amino]-1-methyl-1H-benzimidazol-2-yl]methyl]-1-piperidinecarboxylic acid 1,1-dimethylethyl ester, 5-cyclopropyl-2-(4-fluorophenyl)-N-[3-methoxy-4-(3-methyl-1H-1,2,4-triazol-1-yl)phenyl]-3-methyl-3H-imidazo[4,5-b]pyridin-7-amine, N-[3-fluoro-4-(4-methyl-1H-imidazol-1-yl)phenyl]-2-(4-fluorophenyl)-3-methyl-5-(1-methylethyl)-3H-imidazo[4,5-b]pyridin-7-amine, N-[3-fluoro-4-(4-methyl-1H-imidazol-1-yl)phenyl]-2-(4-fluorophenyl)-1-methyl-6-(1-methylethyl)-1H-imidazo[4,5-c]pyridin-4-amine, N-[3-fluoro-4-(4-methyl-1H-imidazol-1-yl)phenyl]-2-(4-fluorophenyl)-3-methyl-3H-imidazo[4,5-b]pyridin-7-amine, 2-(4-fluorophenyl)-N-[3-methoxy-4-(3-methyl-1H-1,2,4-triazol-1-yl)phenyl]-3-methyl-3H-imidazo[4,5-b]pyridin-7-amine, N-[3-fluoro-4-(4-methyl-1H-imidazol-1-yl)phenyl]-2-(4-fluorophenyl)-5-methoxy-3-methyl-3H-imidazo[4,5-b]pyridin-7-amine, 2-(4-fluorophenyl)-5-methoxy-N-[6-methoxy-5-(4-methyl-1H-imidazol-1-yl)-2-pyridinyl]-3-methyl-3H-imidazo[4,5-b]pyridin-7-amine, N-[6-methoxy-5-(4-methyl-1H-imidazol-1-yl)-2-pyridinyl]-2-(3-methoxyphenyl)-4-benzoxazolamine, 2-(3-bromo-4-fluorophenyl)-N-[3-fluoro-4-(4-methyl-1H-imidazol-1-yl)phenyl]-1,6-dimethyl-1H-imidazo[4,5-c]pyridin-4-amine, N-[3-fluoro-4-(2-iodo-4-methyl-1H-imidazol-1-yl)phenyl]-2-(4-fluorophenyl)-1,6-dimethyl-1H-imidazo[4,5-c]pyridin-4-amine, 2-(3-ethoxyphenyl)-N-[3-fluoro-4-(4-methyl-1H-imidazol-1-yl)phenyl]-1,6-dimethyl-1H-imidazo[4,5-c]pyridin-4-amine, 5-[4-[[3-fluoro-4-(4-methyl-1H-imidazol-1-yl)phenyl]amino]-1-methyl-1H-benzimidazol-2-yl]-1-methyl-2(1H)-pyridinone, 5-[4-[[6-methoxy-5-(4-methyl-1H-imidazol-1-yl)-2-pyridinyl]amino]-1-methyl-1H-benzimidazol-2-yl]-1-methyl-2(1H)-pyridinone, N-[3-fluoro-4-(4-methyl-1H-imidazol-1-yl)phenyl]-2-(2-methoxyphenyl)-1,6-dimethyl-1H-imidazo[4,5-c]pyridin-4-amine, 2-(2-fluoro-4-methoxyphenyl)-N-[3-fluoro-4-(4-methyl-1H-imidazol-1-yl)phenyl]-1,6-dimethyl-1H-imidazo[4,5-c]pyridin-4-amine, N-[3-fluoro-4-(4-methyl-1H-imidazol-1-yl)phenyl]-1,6-dimethyl-2-(3-pyridinyl)-1H-imidazo[4,5-c]pyridin-4-amine, 2-[3-(dimethylamino)phenyl]-N-[3-fluoro-4-(4-methyl-1H-imidazol-1-yl)phenyl]-1,6-dimethyl-1H-imidazo[4,5-c]pyridin-4-amine, N-[3-[4-[[3-fluoro-4-(4-methyl-1H-imidazol-1-yl)phenyl]amino]-1,6-dimethyl-1H-imidazo[4,5-c]pyridin-2-yl]phenyl]-acetamide, 2-(4-chloro-3-methoxyphenyl)-6-fluoro-N-[6-methoxy-5-(4-methyl-1H-imidazol-1-yl)-2-pyridinyl]-1-methyl-1H-benzimidazol-4-amine, 2-(4-chloro-3-methoxyphenyl)-N-[3-fluoro-4-(4-methyl-1H-imidazol-1-yl)phenyl]-1,6-dimethyl-1H-imidazo[4,5-c]pyridin-4-amine, 2-(4-chloro-3-methoxyphenyl)-N-[3-methoxy-4-(3-methyl-1H-1,2,4-triazol-1-yl)phenyl]-1,6-dimethyl-1H-imidazo[4,5-c]pyridin-4-amine, 2-(4-chloro-3-methoxyphenyl)-N-[6-methoxy-5-(4-methyl-1H-imidazol-1-yl)-2-pyridinyl]-1-methyl-1H-benzimidazol-4-amine, 2-(4-chloro-3-methoxyphenyl)-N-[6-methoxy-5-(4-methyl-1H-imidazol-1-yl)-2-pyridinyl]-1-(1-methylethyl)-1H-benzimidazol-4-amine, 6-fluoro-N-[3-fluoro-4-(4-methyl-1H-imidazol-1-yl)phenyl]-2-(4-fluorophenyl)-1-(1-methylethyl)-1H-benzimidazol-4-amine, 2-(4-fluorophenyl)-N-[6-methoxy-5-(4-methyl-1H-imidazol-1-yl)-2-pyridinyl]-3-methyl-3H-imidazo[4,5-b]pyridin-7-amine, 2-(4-fluorophenyl)-N-[6-methoxy-5-(3-methyl-1H-1,2,4-triazol-1-yl)-2-pyridinyl]-1-(1-methylethyl)-1H-benzimidazol-4-amine, 2-(4-fluorophenyl)-N-[6-methoxy-5-(3-methyl-1H-1,2,4-triazol-1-yl)-2-pyridinyl]-1-methyl-1H-benzimidazol-4-amine, 2-(4-fluorophenyl)-N-[6-methoxy-5-(4-methyl-1H-imidazol-1-yl)-2-pyridinyl]-3,5-dimethyl-3H-imidazo[4,5-b]pyridin-7-amine, 2-(4-fluorophenyl)-6-methoxy-N-[6-methoxy-5-(4-methyl-1H-imidazol-1-yl)-2-pyridinyl]-1-methyl-1H-benzimidazol-4-amine, 2-(3-bromo-4-fluorophenyl)-N-[6-methoxy-5-(4-methyl-1H-imidazol-1-yl)-2-pyridinyl]-1-methyl-1H-benzimidazol-4-amine, 2-[3-fluoro-5-(trifluoromethyl)phenyl]-N-[6-methoxy-5-(4-methyl-1H-imidazol-1-yl)-2-pyridinyl]-1-methyl-1H-benzimidazol-4-amine, 2-(3,5-difluorophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[3-(trifluoromethyl)phenyl]-1H-benzimidazol-4-amine, N-[6-methoxy-5-(4-methyl-1H-imidazol-1-yl)-2-pyridinyl]-1-methyl-2-[4-(trifluoromethyl)phenyl]-1H-benzimidazol-4-amine, 2-(4-fluoro-3-iodophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[2-(trifluoromethoxy)phenyl]-1H-benzimidazol-4-amine, 2-(3-fluorophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[2-(trifluoromethyl)phenyl]-1H-benzimidazol-4-amine, 2-[3-(dimethylamino)phenyl]-N-[6-methoxy-5-(4-methyl-1H-imidazol-1-yl)-2-pyridinyl]-1-methyl-1H-benzimidazol-4-amine, N-[3-[4-[[6-methoxy-5-(4-methyl-1H-imidazol-1-yl)-2-pyridinyl]amino]-1-methyl-1H-benzimidazol-2-yl]phenyl]-acetamide, 2-(3,4-difluorophenyl)-N-[6-methoxy-5-(4-methyl-1H-imidazol-1-yl)-2-pyridinyl]-1-methyl-1H-benzimidazol-4-amine, 2-(2,3-difluorophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-2-(3-methoxyphenyl)-1-methyl-1H-benzimidazol-4-amine, N-[6-methoxy-5-(4-methyl-1H-imidazol-1-yl)-2-pyridinyl]-2-(4-methoxyphenyl)-1-methyl-1H-benzimidazol-4-amine, 2-(3-ethoxyphenyl)-N-[6-methoxy-5-(4-methyl-1H-imidazol-1-yl)-2-pyridinyl]-1-methyl-1H-benzimidazol-4-amine, 2-(2-fluoro-5-methoxyphenyl)-N-[6-methoxy-5-(4-methyl-1H-imidazol-1-yl)-2-pyridinyl]-1-methyl-1H-benzimidazol-4-amine.2HCl.H$_2$O, 2-(2-fluoro-5-methoxyphenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[3-(1-methylethoxy)phenyl]-1H-benzimidazol-4-amine, 2-(2-fluoro-4-methoxyphenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-2-[3-methoxy-5-(trifluoromethyl)phenyl]-1-methyl-1H-benzimidazol-4-amine, 2-(4-fluoro-3-methoxyphenyl)-N-[6-methoxy-5-(4-methyl-1H-imidazol-1-yl)-2-pyridinyl]-1-methyl-1H-benzimidazol-4-amine, 2-(4-fluoro-3-methoxyphenyl)-N-[6-methoxy-5-(4-methyl-1H-imidazol-1-yl)-2-pyridinyl]-1-methyl-1H-benzimidazol-4-amine.2HCl.H$_2$O, 2-(4-fluoro-2-methylphenyl)-N-[6-methoxy-5-(4-methyl-1H-imidazol-1-yl)-2-pyridinyl]-1-methyl-1H-benzimidazol-4-amine, 2-(3,5-dimethoxyphenyl)-N-[6-methoxy-5-(4-methyl-1H-imidazol-1-yl)-2-pyridinyl]-1-methyl-1H-benzimidazol-4-amine, 2-[2-fluoro-5-(trifluoromethyl)phenyl]-N-[6-methoxy-5-(4-methyl-1H-imidazol-1-yl)-2-pyridinyl]-1-methyl-1H-benzimidazol-4-amine, 2-(3-fluoro-5-methoxyphenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[3-(trifluoromethoxy)phenyl]-1H-benzimidazol-4-amine, 2-(2,4-difluorophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-1-methyl-2-[4-(trifluoromethoxy)phenyl]-1H-benzimidazol-4-amine, 2-[4-fluoro-3-(trifluoromethyl)phenyl]-N-[6-methoxy-5-(4-methyl-1H-imidazol-1-yl)-2-pyridinyl]-1-methyl-1H-benzimidazol-4-amine, 2-(2-fluorophenyl)-N-[6-methoxy-5-(4-methyl-1H-imidazol-1-yl)-2-pyridinyl]-1-methyl-1H-benzimidazol-4-amine, N-[6-methoxy-5-(4-methyl-1H-imidazol-1-yl)-2-pyridinyl]-2-(4-methoxy-2-methylphenyl)-1-methyl-1H-benzimidazol-4-amine, N-[6-methoxy-5-(4-methyl-1H-imidazol-1-yl)-2-pyridinyl]-1-methyl-2-[2-methyl-5-(trifluoromethyl)phenyl]-1H-benzimidazol-4-amine, N-[6-methoxy-5-(4-methyl-1H-imidazol-1-yl)-2-pyridinyl]-1-methyl-2-phenyl-1H-benzimidazol-4-amine, 2-[4-(dimethylamino)phenyl]-N-[6-methoxy-5-(4-methyl-1H-imidazol-1-yl)-2-pyridinyl]-1-methyl-1H-benzimidazol-4-amine, and 3-[4-[[6-methoxy-5-(4-methyl-1H-imidazol-1-yl)-2-pyridinyl]amino]-1-methyl-1H-benzimidazol-2-yl]-benzonitrile, including any stereochemically isomeric form thereof, and the pharmaceutically acceptable addition salts and the solvates thereof.

In an embodiment the compound of Formula (I) is selected from the group comprising:

N-[3-fluoro-4-(4-methyl-1H-imidazol-1-yl)phenyl]-2-(4-fluorophenyl)-1,6-dimethyl-1H-imidazo[4,5-c]pyridin-4-amine, N-[3-fluoro-4-(4-methyl-1H-imidazol-1-yl)phenyl]-2-(4-fluorophenyl)-1,6-dimethyl-1H-imidazo[4,5-c]pyridin-4-amine.2CH$_3$SO$_3$H, N-[3-fluoro-4-(4-methyl-1H-imidazol-1-yl)phenyl]-2-(4-fluorophenyl)-1,6-dimethyl-1H-imidazo[4,5-c]pyridin-4-amine.2HCl, 2-(4-fluorophenyl)-N-[6-methoxy-5-(4-methyl-1H-imidazol-1-yl)-2-pyridinyl]-1-methyl-1H-benzimidazol-4-amine, 2-(4-fluorophenyl)-N-[6-methoxy-5-(4-methyl-1H-imidazol-1-yl)-2-pyridinyl]-1-methyl-1H-benzimidazol-4-amine.2HCl, 2-(2,3-difluorophenyl)-N-[6-methoxy-5-(4-methyl-1H-imidazol-1-yl)-2-pyridinyl]-1-methyl-1H-benzimidazol-4-amine.2HCl.H$_2$O, 2-(2,3-difluorophenyl)-N-[6-methoxy-5-(4-methyl-1H-imidazol-1-yl)-2-pyridinyl]-1-methyl-1H-benzimidazol-4-amine, 2-(4-fluoro-3-methoxyphenyl)-N-[6-methoxy-5-(4-methyl-1H-imidazol-1-yl)-2-pyridinyl]-1-methyl-1H-benzimidazol-4-amine.2HCl.H$_2$O, 2-(4-fluoro-3-methoxyphenyl)-N-[6-methoxy-5-(4-methyl-1H-imidazol-1-yl)-2-pyridinyl]-1-methyl-1H-benzimidazol-4-amine, 2-(3,5-dimethoxyphenyl)-N-[6-methoxy-5-(4-methyl-1H-imidazol-1-yl)-2-pyridinyl]-1-methyl-1H-benzimidazol-4-amine..2HCl.H$_2$O, and 2-(3,5-dimethoxyphenyl)-N-[6-methoxy-5-(4-methyl-1H-imidazol-1-yl)-2-pyridinyl]-1-methyl-1H-benzimidazol-4-amine, including any stereochemically isomeric form thereof, and the pharmaceutically acceptable addition salts and the solvates thereof.

In an embodiment the compound of Formula (I) is selected from the group comprising:

N-[3-fluoro-4-(4-methyl-1H-imidazol-1-yl)phenyl]-2-(4-fluorophenyl)-1,6-dimethyl-1H-imidazo[4,5-c]pyridin-4-amine, 2-(4-fluorophenyl)-N-[6-methoxy-5-(4-methyl-1H-imidazol-1-yl)-2-pyridinyl]-1-methyl-1H-benzimidazol-4-amine, 2-(4-fluoro-3-methoxyphenyl)-N-[6-methoxy-5-(4-methyl-1H-imidazol-1-yl)-2-pyridinyl]-1-methyl-1H-benzimidazol-4-amine.2HCl.H$_2$O, 2-(2,3-difluorophenyl)-N-[6-methoxy-5-(4-methyl-1H-imidazol-1-yl)-2-pyridinyl]-1-methyl-1H-benzimidazol-4-amine.2HCl.H$_2$O, and 2-(3,5-dimethoxyphenyl)-N-[6-methoxy-5-(4-methyl-1H-imidazol-1-yl)-2-pyridinyl]-1-methyl-1H-benzimidazol-4-amine.2HCl.H$_2$O.

In an embodiment the compound of Formula (I) is 2-(4-fluorophenyl)-N-[6-methoxy-5-(4-methyl-1H-imidazol-1-yl)-2-pyridinyl]-1-methyl-1H-benzimidazol-4-amine, including the pharmaceutically acceptable addition salts and the solvates thereof.

In an embodiment the compound of Formula (I) is 2-(4-fluorophenyl)-N-[6-methoxy-5-(4-methyl-1H-imidazol-1-yl)-2-pyridinyl]-1-methyl-1H-benzimidazol-4-amine.

In an embodiment the compound of Formula (I) is 2-(4-fluoro-3-methoxyphenyl)-N-[6-methoxy-5-(4-methyl-1H-imidazol-1-yl)-2-pyridinyl]-1-methyl-1H-benzimidazol-4-amine.2HCl.H$_2$O.

In an embodiment the compound of Formula (I) is 2-(4-fluoro-3-methoxyphenyl)-N-[6-methoxy-5-(4-methyl-1H-imidazol-1-yl)-2-pyridinyl]-1-methyl-1H-benzimidazol-4-amine, including the pharmaceutically acceptable addition salts and the solvates thereof.

All possible combinations of the above-indicated interesting embodiments are considered to be embraced within the scope of this invention.

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below:

Experimental Procedure 1

In general, compounds of formula (I) can be prepared as set out below in Scheme 1 wherein all variables are defined as hereinbefore:

$R^3$ groups containing suitable functional groups such as, for example, halo, (protected) amines, alcohols, or ketones, can be used to incorporate further substitution patterns in compounds of formula (I).

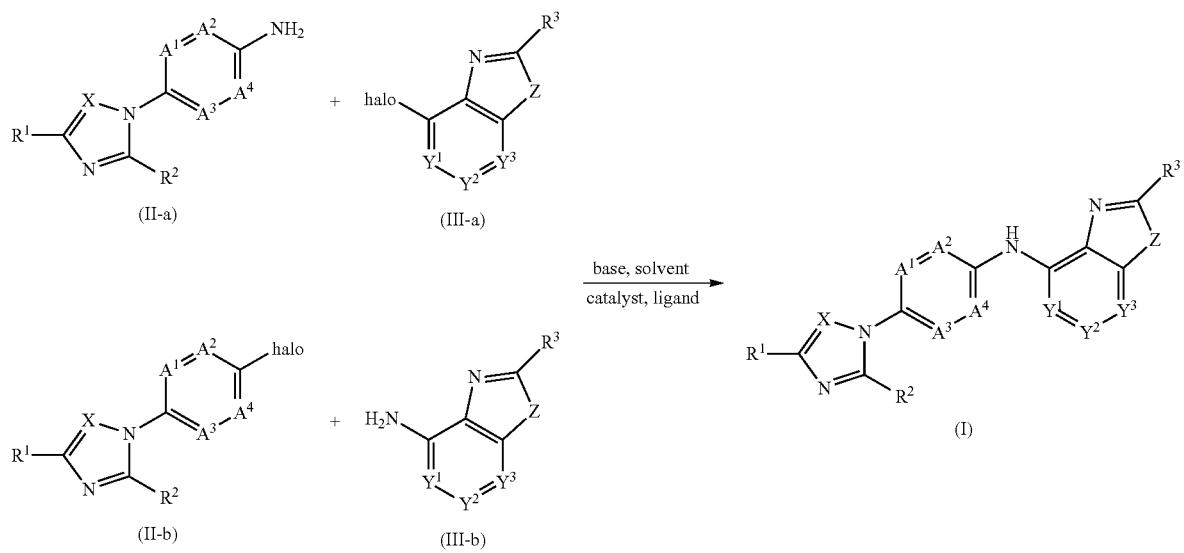

Scheme 1

A compound of formula (I) can be prepared via a coupling reaction between an intermediate of formula (II-a) and an intermediate of formula (III-a), or via a coupling reaction between an intermediate of formula (II-b) and an intermediate of formula (III-b). In Scheme 1, halo is defined as Cl, Br or I. This reaction may be performed in the presence of a suitable base such as, for example, $Cs_2CO_3$ or sodium tert-butoxide. The reaction can be performed in a reaction-inert solvent such as, for example, toluene, N,N-dimethylformamide (DMF), 1,2-dimethoxyethane (DME), tert-butanol or dioxane. The reaction typically is performed in the presence of a catalyst system comprising of a suitable catalyst such as tris(dibenzylideneacetone)dipalladium $(Pd_2(dba)_3)$, palladium(II) acetate $(Pd(OAc)_2)$ and a ligand such as (9,9-dimethyl-9H-xanthene-4,5-diyl)bis[diphenylphosphine] (Xantphos), [1,1'-binaphthalene]-2,2'-diylbis[diphenylphosphine] (BINAP), bis(2-diphenylphosphinophenyl)ether (DPEphos), or dicyclohexyl[2',4',6'-tris(1-methylethyl)[1,1'-biphenyl]-2-yl]-phosphine (X-phos). Preferably this reaction is carried out under an inert atmosphere, such as a nitrogen or an argon atmosphere. Reaction rate and yield may be enhanced by microwave assisted heating.

Palladium traces present after work-up of the reaction can optionally be removed by treatment of a solution of the compound of formula (I) in a suitable solvent or in a mixture of solvents, such as, for example DCM and MeOH, with N-acetyl-L-cysteine or thiol-functionalized silica.

In an alternative procedure, only valid when $Y^1$ or $Y^3$ is N in the definition of (III-a), a compound of formula (I) wherein $Y^1$ or $Y^3$ is N, can be prepared via an aromatic nucleophilic substitution between intermediates of formula (II-a) and (III-a). This reaction may be performed under basic or acidic conditions, e.g., in the presence of HCl or methanesulfonic acid in a reaction-inert solvent such as, for example, 2-propanol. Reaction rate and yield may be enhanced by microwave assisted heating.

Experimental Procedure 2

An intermediate of formula (II-a) can be prepared by a reduction of an intermediate of formula (IV) as shown in Scheme 2 below, wherein all variables are as defined before. The reduction of (IV) to (II-a) can be conducted by a conventional method such as, for example, a reductive hydrogenation or reduction with a metal or a metal salt and an acid [for example a metal such as iron, or a metal salt such as $SnCl_2$ and acid such as an inorganic acid (HCl, $H_2SO_4$ or the like) or an organic acid (acetic acid or the like)], or other well-known methods for converting a nitro-group to the corresponding amine

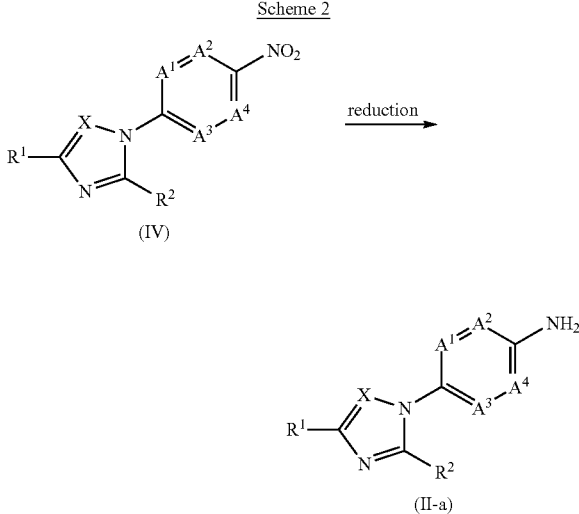

Scheme 2

Experimental Procedure 3

An intermediate of formula (II-a) can also be prepared by a copper catalysed reaction of an intermediate of formula (V) with a (un)substituted imidazole or triazole of formula (VI) according to Scheme 3, wherein halo is defined as Br or I and wherein all other variables are defined as mentioned hereabove. The reaction may be performed under a protecting atmosphere such as, for example, $N_2$ atmosphere. Stirring, elevated temperatures (for example between 70-200° C.) and/or pressure may enhance the rate of the reaction. The reaction typically is performed in an organic solvent such as, for example, dimethylsulfoxide (DMSO) or dimethylformamide (DMF). Optionally, the reaction is performed in the presence of a base such as, for example $K_2CO_3$, $Cs_2CO_3$, or triethylamine ($Et_3N$), and/or a ligand such as N,N'-dimethylethylenediamine or 1,10-phenanthroline. A copper catalyst such as copper salts, for example, copper(I)oxide, copper(I)iodide, or copper(I)bromide, can be used in catalytic or stoichiometric amounts. The amino-group in intermediate (V) can be protected before the reaction, and can be deprotected after reaction via the use of a suitable amino-protecting group in accordance with standard practice, for example, see T. W. Greene and P. G. M. Wuts in "Protective Groups in Organic Chemistry", John Wiley and Sons, 1999.

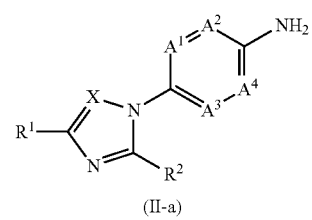

Experimental Procedure 5

An intermediate of formula (IV) can be prepared via a nucleophilic aromatic substitution of an intermediate of formula (VII) with a (un)substituted imidazole or triazole of formula (VI) according to Scheme 5, wherein halo is defined as F, Cl, or Br and wherein all other variables are defined as mentioned hereabove. The reaction may be performed under a protecting atmosphere such as, for example, $N_2$ atmosphere. Stirring, elevated temperatures (for example between 70-170° C.) and/or pressure may enhance the rate of the reaction. The reaction typically is performed in an organic solvent such as, for example, DMSO, DMF, or N-methylpyrolidinone (NMP) in the presence of a base such as, for example $K_2CO_3$, $Cs_2CO_3$, or $Et_3N$.

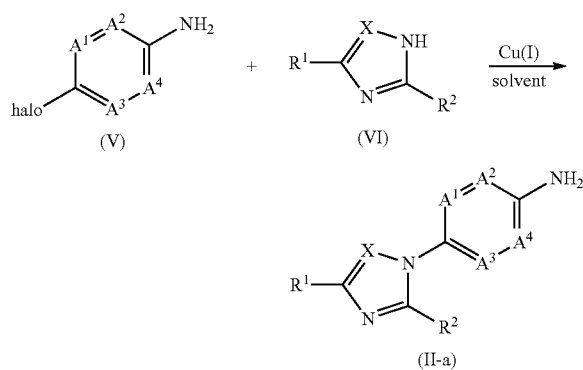

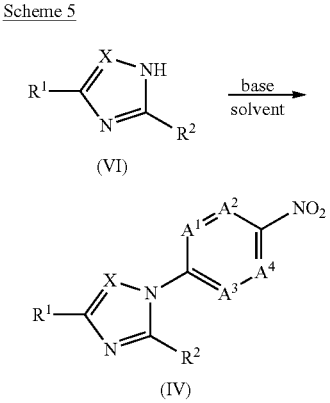

Experimental Procedure 4

An intermediate of formula (II-a) can also be prepared by conversion of the halo-substitutent in intermediate (II-b) into an amino-group or a masked amino functionality, which can subsequently be converted into an amino-group, according to Scheme 4. In Scheme 4, typical reaction conditions known to those skilled in the art can be used. In Scheme 4, halo is defined as Cl, Br or I, and all other variables are defined as mentioned hereabove.

Experimental Procedure 6

An intermediate of formula (II-b) can be prepared from intermediate of formula (II-a) via a Sandmeyer reaction according to Scheme 6 by conversion of (II-a) into the corresponding diazonium salt followed by treatment with a reagent such as, for example, KI, CuBr, or CuCl. Typical reaction conditions known to those skilled in the art can be used in Scheme 6. All variables in Scheme 6 are defined as before

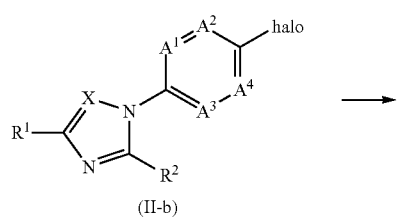

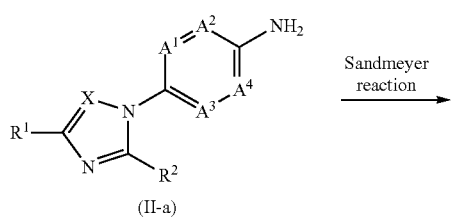

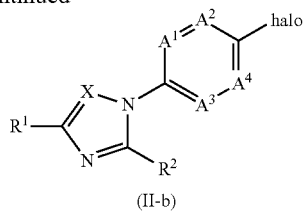

(II-b)

Experimental Procedure 7

An intermediate of formula (II-b) wherein $A^1$ and/or $A^3$ are N, hereby named an intermediate of formula (II-b1), can be prepared via a nucleophilic aromatic substitution of an intermediate (VIII) wherein $A^1$ and/or $A^3$ are N, with a (un)substituted imidazole or triazole of formula (VI) according to Scheme 7, wherein LG is defined as F, Cl, Br, or $NO_2$, wherein halo is defined as Br or I, and wherein all other variables are defined as hereinbefore. The reaction may be performed under similar conditions as described for experimental procedure 5.

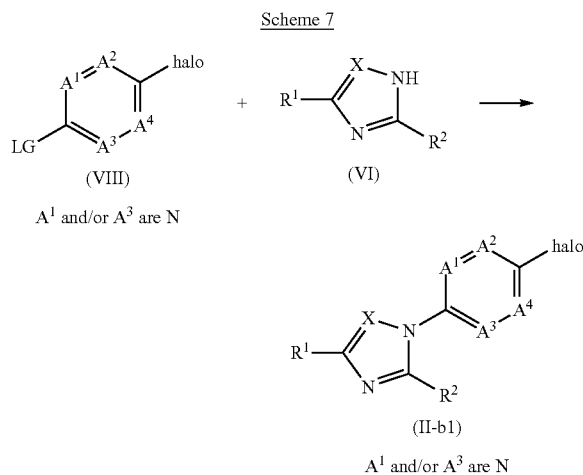

Scheme 7

(VIII)    (VI)

$A^1$ and/or $A^3$ are N (II-b1)

$A^1$ and/or $A^3$ are N

Experimental Procedure 8

An intermediate of formula (II-b) wherein X represents CH, hereby named an intermediate of formula (II-b2), can also be prepared via acylation of intermediate (IX) to yield intermediate (X) in the presence of a reaction inert solvent, such as THF, and optionally a suitable base, such as $Et_3N$, according to Scheme 8. An intermediate of formula (XII), can subsequently be prepared via alkylation of an intermediate of formula (X) with an intermediate of formula (XI), in the presence of a reaction inert solvent such as, for example, DMF, and a suitable base such as, for example, $Cs_2CO_3$ or $K_2CO_3$, and optionally in the presence of a catalytic amount of a iodide salt such as, for example, KI or NaI. A condensation reaction of intermediate (XII) with an ammonia source such as, for example, ammonium acetate ($NH_4OAc$) subsequently yields a compound of formula (II-b2). In Scheme 8, halo is defined as Cl, Br, or I, halo2 is defined as Cl or Br, and all other variables are defined as mentioned hereinbefore.

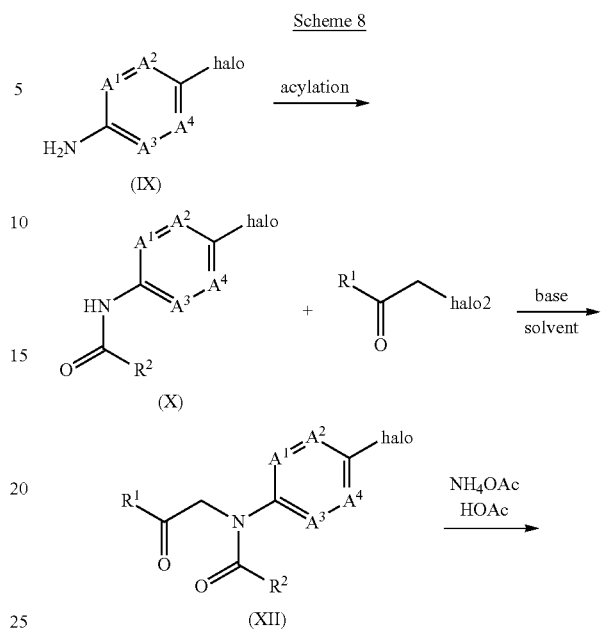

Scheme 8

(IX)

(X)

(XII)

(II-b2)

For the construction of the imidazole ring in an intermediate of formula (II-b2), the order of introduction of $R^2$ and $R^1$ can be reversed. This type of reaction is described in US2006/0004013 for 1-(4-bromo-2-methoxyphenyl)-4-methyl-1H-Imidazole.

Experimental Procedure 9

An intermediate of formula (III-a), wherein $R^3$ is carbon-linked to the heterocycle, and wherein Z is $N—R^9$, hereby named an intermediate of formula (III-a1), can be prepared by an acylation of an intermediate (XIII) with an intermediate of formula (XIV) followed by a condensation, according to Scheme 9. The acylation reaction can be carried out in a solvent such as, for example, pyridine or a reaction inert solvent such as, for example, DMF. The reaction may be performed in the presence of a base such as, for example, $Et_3N$. The subsequent condensation reaction can be carried out by heating the crude acylated product in a solvent such as, for example, acetic acid. In Scheme 9, halo is defined as Cl, Br or I, and all other variables are defined as before.

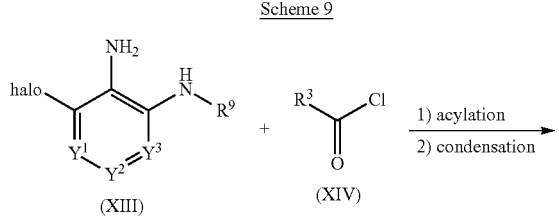

Scheme 9

(XIII)    (XIV)

1) acylation
2) condensation

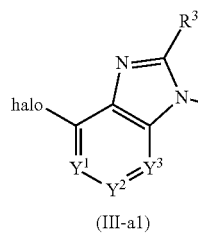

(III-a1)

Scheme 11

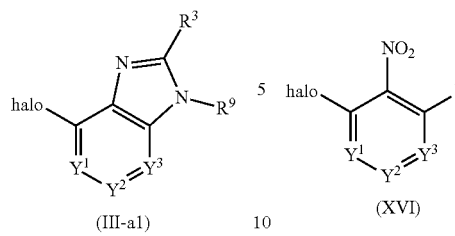

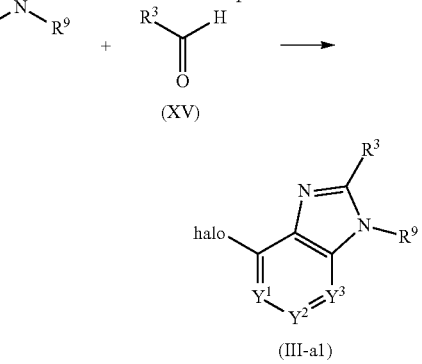

(III-a1)

In a similar condensation procedure, intermediate (XIII) can be condensed to intermediate (III-a1) directly by using a carboxylic acid of formula $R^3$—COOH. This reaction may be performed under dehydrating conditions such as, for example, heating in a solvent such as, for example, polyphosphoric acid.

Experimental Procedure 10

An intermediate of formula (III-a1), can also be prepared by treatment of an intermediate of formula (XIII) with an aldehyde of formula (XV). The reaction typically can be performed in the presence of a reducing agent such as, for example, sodium metabisulfite. The reaction typically may be performed in a reaction inert solvent such as, for example, N,N-dimethylacetamide (DMA), according to Scheme 10. In Scheme 10, halo is defined as Cl or Br and all other variables are defined as mentioned before.

Experimental Procedure 12

Alternatively, an intermediate of formula (III-a1) wherein $R^9$ is different from H, hereby named an intermediate of formula (III-a2), can also be prepared from an intermediate of formula (IIIa1) wherein $R^9$ is H, hereby named an intermediate of formula (III-a3). The group $R^{9a}$ can be introduced via N-alkylation, leading predominantly to an intermediate of formula (III-a2) wherein $R^{9a}$ is a substituent as defined before, except hydrogen, as described in Scheme 12.

Scheme 10

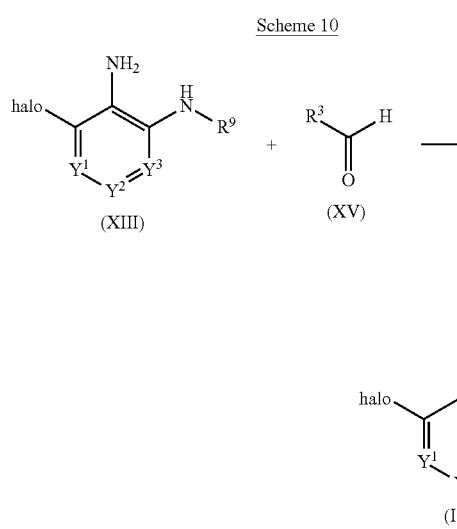

Scheme 12

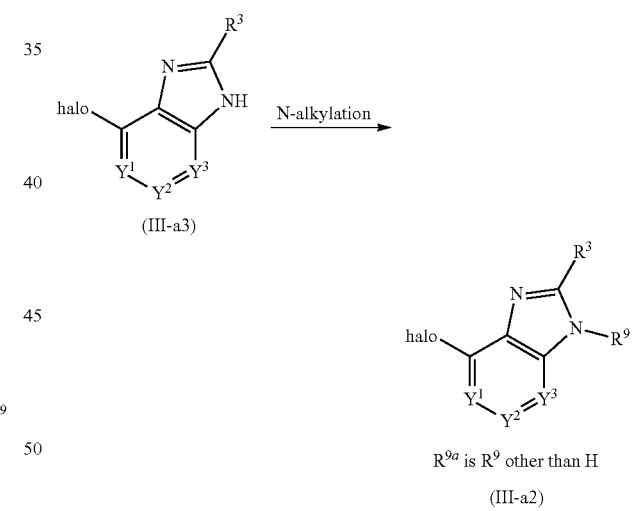

$R^{9a}$ is $R^9$ other than H (III-a2)

Experimental Procedure 11

An intermediate of formula (III-a1), can also be prepared by treatment of an intermediate of formula (XVI) with an aldehyde of formula (XV). This reaction may be performed in the presence of a reducing agent such as, for example, sodium dithionite. The reaction typically can be performed in a reaction inert solvent such as, for example, ethanol. In Scheme 11, halo is defined as Cl or Br and all other variables are defined as mentioned hereinbefore.

Experimental Procedure 13

An intermediate of formula (XIII) can be prepared via reduction of an intermediate of formula (XVI) as is shown in Scheme 13, wherein halo is defined as Br or Cl, and wherein all other variables are as defined before. The reduction of (XVI) to (XIII) can be conducted by a conventional method such as, for example, a reductive hydrogenation or reduction with a metal or a metal salt and an acid [for example a metal such as iron, or a metal salt such as $SnCl_2$ and acid such as an inorganic acid (hydrochloric acid, sulfuric acid or the like) or an organic acid (acetic acid or the like)], or other well-known methods for converting a nitro-group to the corresponding amine Scheme 13

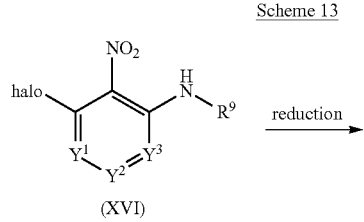

Experimental Procedure 14

An intermediate of formula (XVI) can be prepared via a substitution reaction of an intermediate of formula (XVII) with an amine of formula R$^9$—NH$_2$ as is shown in Scheme 14 below, wherein halo is defined as Br, I or Cl, wherein halo2 is defined as F, Cl or Br, and wherein all other variables are as defined before.

Scheme 14

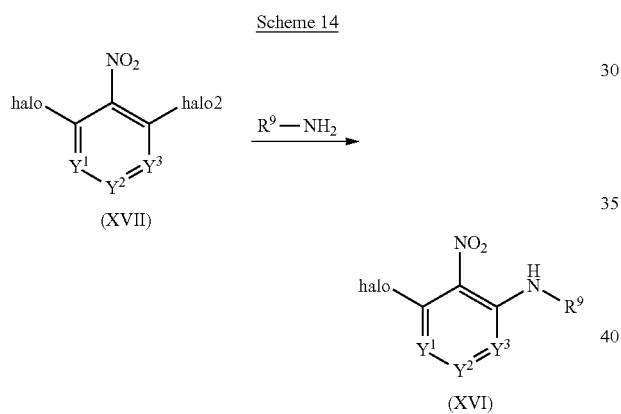

Experimental Procedure 15

An Intermediate of formula (III-b), wherein R$^3$ is carbon-linked to the heterocycle and Z is N—R$^9$, hereby named an intermediate of formula (III-b1), can be prepared as shown in Scheme 15. In a first step, acylation of intermediate (XVIII) with an activated carboxylic acid derivative such as, for example, a carboxylic acid chloride, yields intermediate (XIX) which can be condensed to a intermediate of formula (XX). Alternatively, a one step preparation of intermediate (XX) can also be performed via condensation of an intermediate of formula (XVIII) with a carboxylic acid of formula R$^9$—COOH under dehydrating conditions, such as heating in a solvent such as, for example, polyphosphoric acid.

Deprotonation of an intermediate of formula (XX) with a base such, for example, lithium hexamethyldisilazide, in a reaction-inert solvent such as, for example, toluene or (methyl)tetrahydrofuran, followed by treatment with an alkylating agent such as, for example, CH$_3$I, leads to an intermediate of formula (XXI).

Reduction of an intermediate of formula (XXI) via reductive hydrogenation, or treatment of (XXI) with a reducing agent such as, for example, iron in acetic acid, or other well-known methods for converting a nitro-group into the corresponding amine yields the required intermediate of formula (III-b1).

In scheme 15, all variables are defined as mentioned before.

Scheme 15

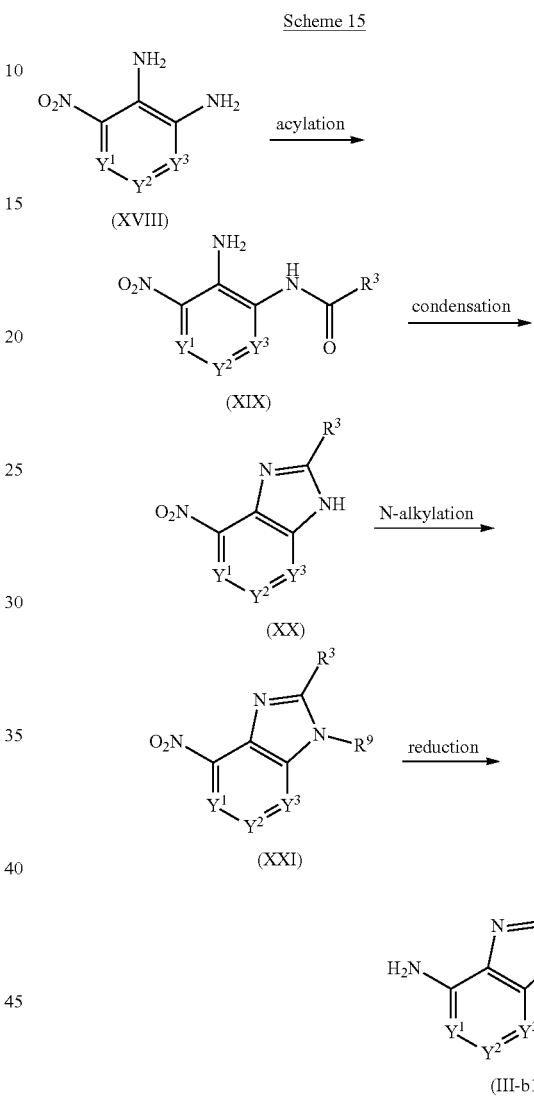

Experimental Procedure 16

Alternatively, an intermediates of formula (III-b1) can be prepared as set out below in Scheme 16. Deprotonation of an intermediate of formula (XXII) with a base such as, for example, lithium hexamethyldisilazide, typically in a reaction-inert solvent such as, for example, toluene or (methyl) tetrahydrofuran, followed by treatment with an alkylating agent such as, for example, CH$_3$I, leads to an intermediate of formula (XXIII). Treatment of an intermediate of formula (XXIII) with a halogenating agent such as, for example, phosphoroxychloride (POCl$_3$) gives an intermediate of formula (XXIV). This intermediate can be converted to an intermediate of formula (XXV) via reaction with amines, alcohols, thiols, or via Suzuki reactions with aryl- or alkyl-boronates. As in Scheme 15, reduction of an intermediate of formula (XXV) via reductive hydrogenation, or treatment of an intermediate of formula (XXV) with a reducing agent such as, for example, iron in acetic acid, or other known methods for converting a nitro-group into the corresponding amine, gives the required intermediate of formula (III-b1). In scheme 16, all variables are defined as mentioned before.

Scheme 16

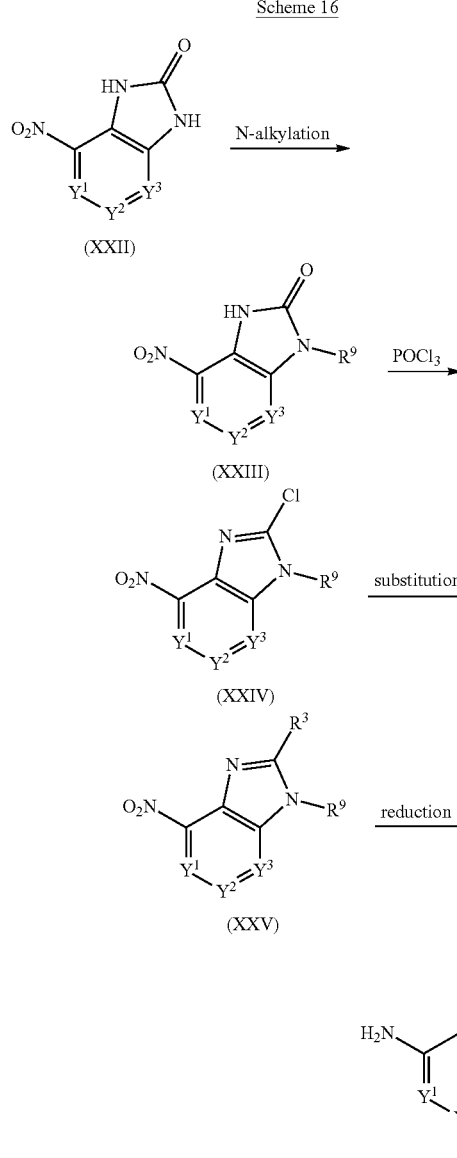

Experimental Procedure 17

An intermediate of formula (III-a1), can also be prepared as set out in Scheme 17. Condensation of an intermediate of formula (XIII) with urea, carbonyldiimidazole, phosgene or a phosgene equivalent such as e.g. diphosgene or triphosgene, gives an intermediate of formula (XXVI). Treatment of an intermediate of formula (XXVI) with a halogenating agent such as, for example, POCl$_3$, gives an intermediate of formula (XXVII). An intermediate of formula (XXVII) can be converted to an intermediate of formula (III-a1) via reaction with amines, alcohols, thiols, or via Suzuki reactions with aryl- or alkyl-boronates. In scheme 17, halo is defined as Br, I or Cl, and all other variables are defined as mentioned before. All reaction steps in Scheme 17, can be performed by using typical reaction conditions known to those skilled in the art.

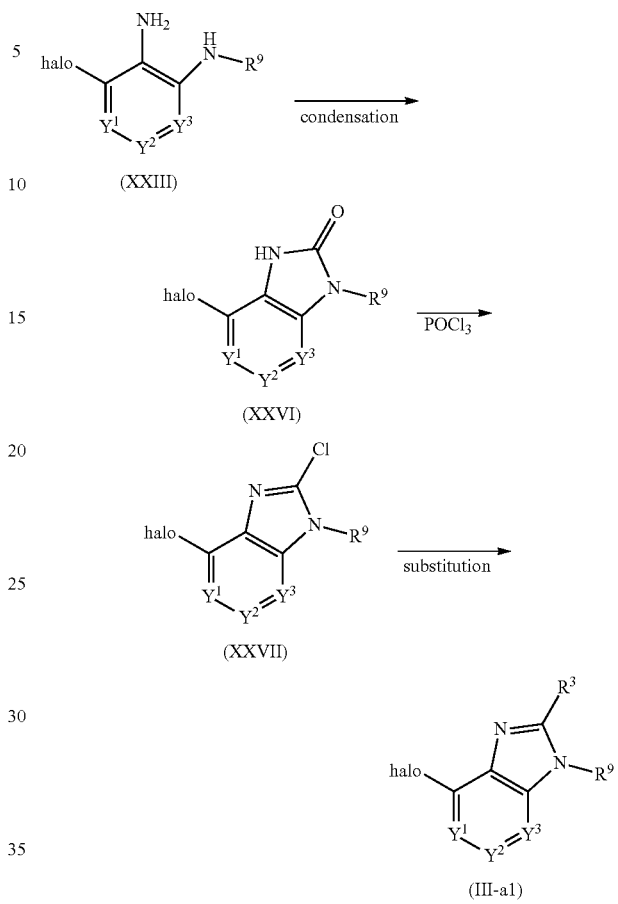

Experimental Procedure 18

Intermediates of formula (III-a), wherein R$^3$ is restricted to C$_{1-6}$alkylthio and wherein Z is N—R$^9$, hereby named an intermediate of formula (III-a3), can be prepared as set out below in Scheme 18. Condensation of an intermediate of formula (XIII) with thiourea or 1,1'-thiocarbonyldiimidazole via heating in a reaction inert solvent, such as, for example THF, yields an intermediate of formula (XXVIII). Subsequently, an intermediate of formula (XXVIII) may be alkylated, for example by a C$_{1-6}$alkyl-iodide, in the presence of a base such as, for example, K$_2$CO$_3$. This reaction step typically can be performed in a reaction inert solvent such as, for example, acetone, to give an intermediate of formula (III-a3). In Scheme 18, halo is defined as Br, I or Cl, R$^{3a}$ is defined as C$_{1-6}$alkylthio, and all other substituents are defined as mentioned hereinbefore.

Scheme 18

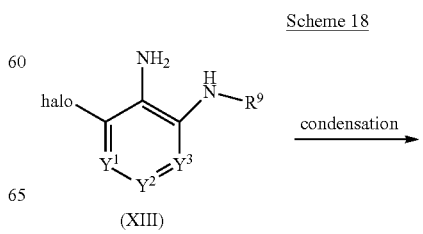

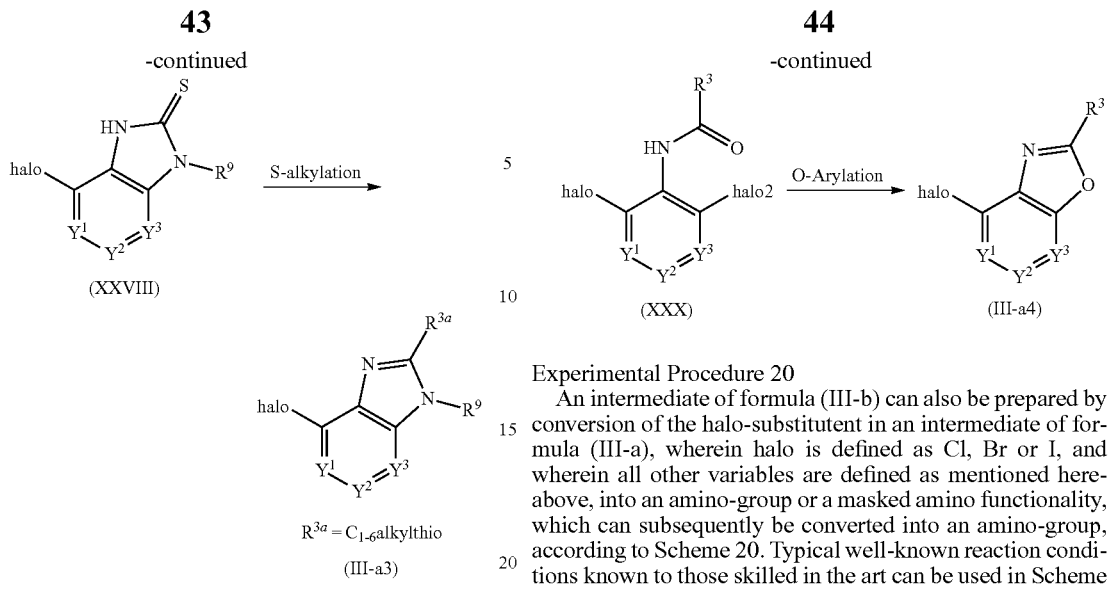

Experimental Procedure 19

Intermediates of formula (III-a), wherein $R^3$ is carbon-linked to the heterocycle and wherein Z is O, hereby named an intermediate of formula (III-a4), can be prepared as set out below in Scheme 19. Acylation of an intermediate of formula (XXIX) with an activated carboxylic acid derivative such as, for example, a carboxylic acid chloride with formula $R^3$—COCl gives an intermediate of formula (XXX). Subsequently, an intermediate of formula (XXX) can be O-arylated to a benzoxazole intermediate of formula (III-a4). In scheme 19, halo is defined as Br, I or Cl, halo2 is defined as Cl, Br or I, and all other variables are as defined before.

Scheme 19

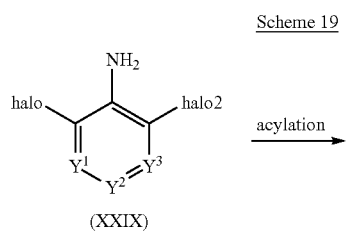

Experimental Procedure 20

An intermediate of formula (III-b) can also be prepared by conversion of the halo-substitutent in an intermediate of formula (III-a), wherein halo is defined as Cl, Br or I, and wherein all other variables are defined as mentioned hereabove, into an amino-group or a masked amino functionality, which can subsequently be converted into an amino-group, according to Scheme 20. Typical well-known reaction conditions known to those skilled in the art can be used in Scheme 20.

Scheme 20

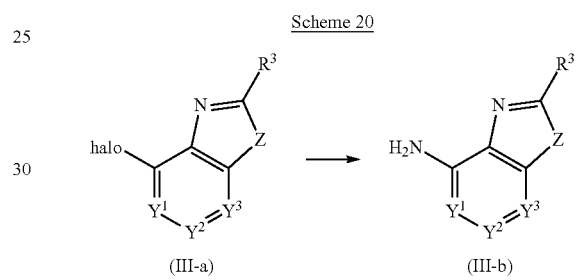

Experimental Procedure 21

A compound of formula (I), wherein Z is N—$R^9$, hereby named a compound of formula (I-a), can be prepared, starting from a coupling reaction between an intermediate of formula (XXVII) with an intermediate of formula (II-a) according to the conditions described under experimental procedure 1, to give an intermediate of formula (XXXI), followed by conversion of (XXXI) to a compound of formula (I-a) via reaction with amines, alcohols, thiols, or via Suzuki reactions with aryl- or alkyl-boronates. This last reaction in Scheme 21, can be performed by using typical reaction conditions known to those skilled in the art.

Scheme 21

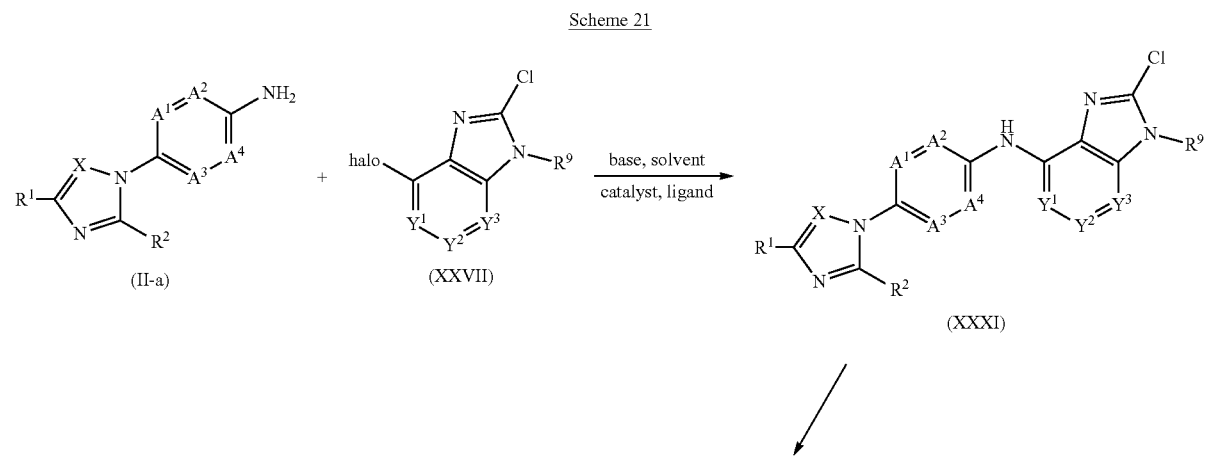

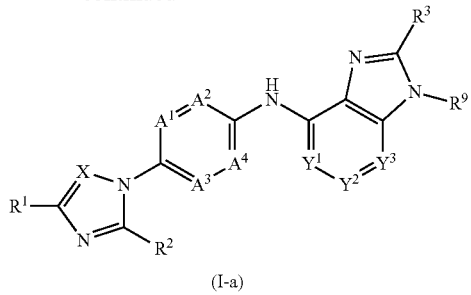

(I-a)

Experimental Procedure 22

A compound of formula (I), wherein $R^3$ is carbon-linked to the heterocycle, and wherein Z is N—$R^9$, hereby named a compound of formula (I-b), can be prepared, starting from a coupling reaction between an intermediate of formula (XVI) with an intermediate of formula (II-a) according to the conditions described under experimental procedure 1, to give an intermediate of formula (XXXII). The intermediate of formula (XXXII) can either be directly converted into a compound of formula (I-b) according to the conditions described under experimental procedure 11, or (XXXII) can first be reduced to an intermediate of formula (XXXIII) according to the conditions described under experimental procedure 13, followed by the conversion of (XXXIII) to a compound of formula (I-b) according to the conditions described under experimental procedure 10.

Intermediates of formula (III-a) or (III-b) and compounds of formula (I), any subgroup thereof, addition salts, solvates, and stereochemical isomeric forms thereof can be converted into further intermediates and compounds according to the invention using procedures known in the art.

In order to obtain the HCl salt forms of the compounds, several procedures known to those skilled in the art can be used. In a typical procedure, for example, the free base can be dissolved in DIPE or $Et_2O$ and subsequently, a 6 N HCl solution in 2-propanol or a 1 N HCl solution in $Et_2O$ can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting Scheme 22

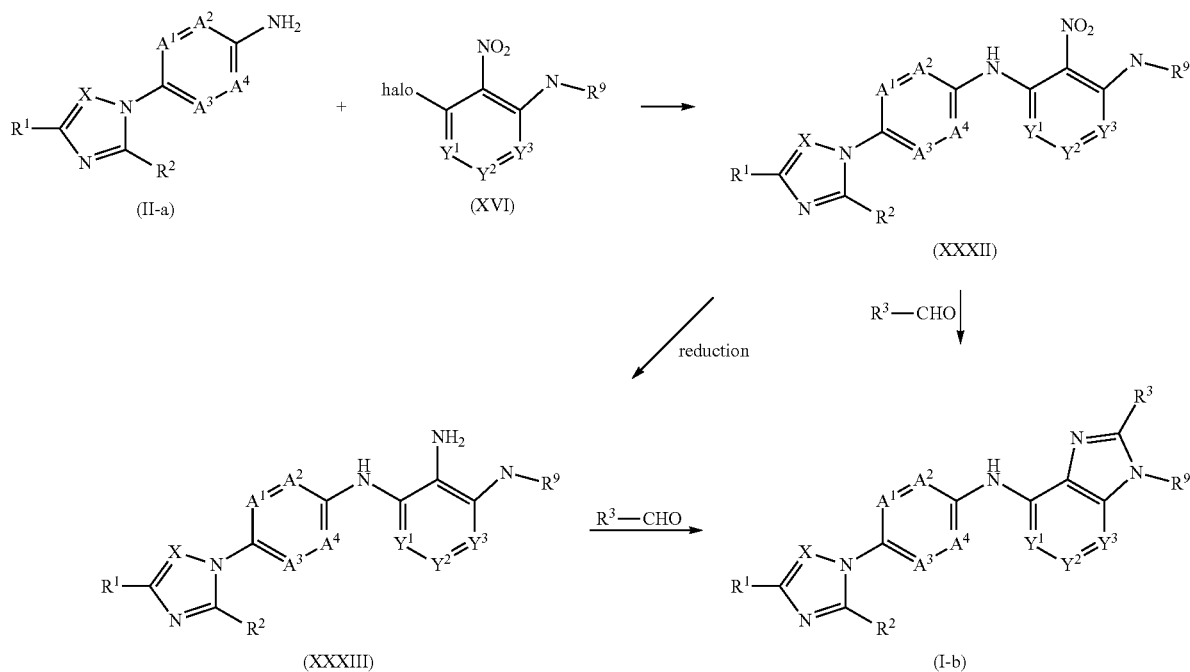

Intermediates of formula (V), (VI), (VII), (VIII), (IX), (XI), (XIV), (XV), (XVII), (XXII) and formula (XXIX) are commercially available or can be easily prepared by those skilled in the art.

Where necessary or desired, any one or more of the following further steps in any order may be performed:

groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof are therefore useful in the treatment or prevention of Alzheimer's disease (AD), traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of diseases or conditions selected from Alzheimer's disease, traumatic brain injury, mild cognitive impairment, senility, dementia, dementia with Lewy bodies, cerebral amyloid angiopathy, multi-infarct dementia, or Down's syndrome.

The invention also relates to a compound according to the general Formula (I), the stereoisomeric forms thereof and the pharmaceutically acceptable acid or base addition salts and the solvates thereof, for the treatment or prevention of diseases or conditions selected from AD, MCI, senility, dementia, dementia with Lewy bodies, cerebral amyloid angiopathy, multi-infarct dementia, or Down's syndrome.

In an embodiment, said disease or condition is preferably Alzheimer's disease.

The invention also relates to a compound according to the general Formula (I), the stereoisomeric forms thereof and the pharmaceutically acceptable acid or base addition salts and the solvates thereof, for the treatment of said diseases.

The invention also relates to a compound according to the general Formula (I), the stereoisomeric forms thereof and the pharmaceutically acceptable acid or base addition salts and the solvates thereof, for use in treating said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assays used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that are suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin or sulfobutyl-$\beta$-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "LCMS" means Liquid Chromatography/Mass spectrometry; "HPLC" means high-performance liquid chromatography; "sol." means solution; "sat." means saturated; "aq." means aqueous; "r.t." means room temperature; "AcOH" means acetic acid; "m.p." means melting point; "RP" means reversed phase; "BDS" means base deactivated silica; "min" means minute(s); "h" means hour(s); "I.D." means internal diameter; "EtOAc" means ethyl acetate; "Et$_3$N" means triethylamine; "BINAP" means [1,1'-binaphthalene]-2,2'-diylbis[diphenylphosphine] (racemic); "EtOH" means ethanol; "eq" means equivalent; "r.m." means reaction mixture(s); "DIPE" means diisopropyl ether; "q.s." quantum sufficit; "DMA" means N,N-dimethylacetamide; "NMP" means N-methyl-2-pyrrolidinone; "TFA" means trifluoroacetic acid; "THF" means tetrahydrofuran; "DMSO" means dimethyl sulfoxide; "mCPBA" means 3-chlorobenzenecarboperoxoic acid; "DMF" means N,N-dimethyl formamide; "LiHMDS" means lithium hexamethyldisilazane; "X-Phos" means dicyclohexyl[2',4',6'-tris(1-methylethyl)[1,1'-biphenyl]-2-yl]phosphine; "DCE" means 1,2-dichloroethane; "HBTU" means 1-[bis(dimethylamino)methylene]-1H-benzotriazol-1-ium 3-oxide hexafluorophosphate; "Pd(PPh$_3$)$_4$" means tetrakis(triphenylphosphine)palladium, "Pd(OAc)$_2$" means palladium(2+) diacetate; "PdCl$_2$(PPh$_3$)$_2$" means dichlorobis(triphenylphosphine)palladium; and "Pd$_2$(dba)$_3$" means tris[μ-[(1,2-η:4,5-η)-(1E,4E)-1,5-diphenyl-1,4-pentadien-3-one]]dipalladium.

A. Preparation of the Intermediates

Example A1 a) Preparation of Intermediate 1

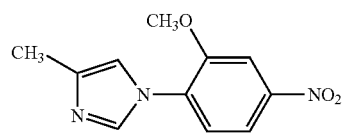

A mixture of 1-chloro-2-methoxy-4-nitrobenzene (50 g, 0.26 mol), 4-methyl-1H-imidazole (43.77 g, 0.53 mol) and K$_2$CO$_3$ (36.84 g, 0.26 mol) in DMSO (500 ml) was reacted in an autoclave under N$_2$ atmosphere for 6 h at 150° C. This reaction was repeated twice with 50 g of 1-chloro-2-methoxy-4-nitrobenzene each. Subsequently, the 3 r.m. (150g of 1-chloro-2-methoxy-4-nitrobenzene in total) were worked up together. The mixture was poured out into 6l of ice-water. The solid was filtered off and washed with H$_2$O. The solid was dissolved in DCM and this sol. was washed with H$_2$O. The separated organic layer was dried (MgSO$_4$), filtered and the solvent was evaporated. The residue was purified over silica gel on a glass filter (eluent: DCM/MeOH from 100/0 to 97/3). The product fractions were collected and the solvent was evaporated. The residue was suspended in DIPE, filtered off and dried in the oven. Yield: 48.54 g of intermediate 1 (26%).

b) Preparation of Intermediate 2a and Intermediate 2

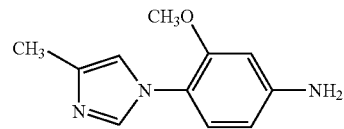

intermediate 2a: free base
intermediate 2: HCl salt (•HCl)

Intermediate 1 (13.2 g, 56.6 mmol) was dissolved in MeOH (250 ml). Pd/C (0.5 g) was added to the sol. and the resulting suspension was stirred overnight at 50° C. under H$_2$ (atmospheric pressure). After uptake of H$_2$ (1 eq), the catalyst was filtered off. The organic layer was evaporated, yielding intermediate 2a (free base). Intermediate 2a was dissolved in a sol. of HCl/EtOH and stirred for 30 min. The solvent was removed in vacuo. The residue was crystallized from EtOH with a small amount of petroleum ether to yield the desired product. Yield: 4.7 g of intermediate 2 (41%).

Example A2 a) Preparation of Intermediate 3 and Intermediate 4 (Regioisomers)

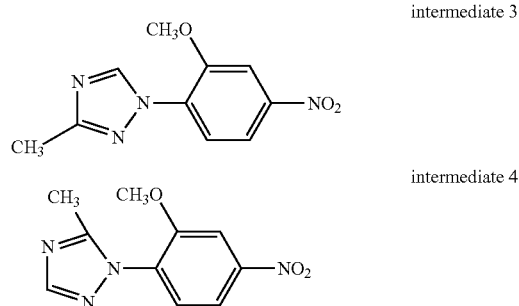

A mixture of 1-fluoro-2-methoxy-4-nitrobenzene (821 mg, 4 8 mmol), 5-methyl-1H-1,2,4-triazole (800 mg, 9.63 mmol), K$_2$CO$_3$ (4 8 mmol) and DMSO (8 ml) was stirred at 120° C. for 1 h. After cooling, the r.m. was poured into ice water. The solid was filtered off, washed with water and dried in vacuo at 50° C. Yield: 0.554 g of intermediate 3 (49%). The aq. layer was saturated with NaCl, extracted with DCM and the organic layer was dried (MgSO$_4$), filtered and the solvent was evaporated. The residue was purified by column chromatography over silica gel (eluent: DCM). The desired fraction was collected and the solvent was evaporated. Yield: 0.147 g of intermediate 4 (13%).

b) Preparation of Intermediate 5

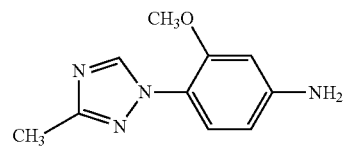

MeOH (50 ml) was added to Pd/C 10% (150 mg) under N$_2$ atmosphere. Subsequently, a 0.4% thiophene sol. in DIPE (1 ml) and intermediate 3 (550 mg, 2.348 mmol) were added. The r.m. was stirred at 25° C. under H$_2$ atmosphere until 3 eq of H$_2$ was absorbed. The catalyst was filtered off over diatomaceous earth. The filtrate was evaporated and the residue was suspended in DIPE, filtered off and dried in vacuo. Yield: 0.350 g of intermediate 5 (73%).

Example A3 a) Preparation of Intermediate 6 and Intermediate 7 (Regioisomers)

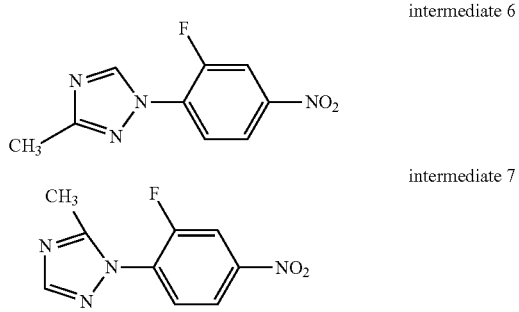

intermediate 6 intermediate 7

A mixture of 3,4-difluoro-nitrobenzene (15.7 g, 96 7 mmol), 5-methyl-1H-1,2,4-triazole (9.94 g, 116 mmol), $K_2CO_3$ (20 g, 145 mmol) and DMF (150 ml) was stirred at 75° C. for 2 h. After cooling, the r.m. was poured into ice water. The precipitate was filtered off, and washed with water. The resulting solid was recrystallized from $H_2O$/MeOH to yield intermediate 6 as a monohydrate solid (yield: 9.2 g, 43%), and a mother liquor. The mother liquor was concentrated in vacuo to yield 3.1 g of a residue containing 44% of intermediate 6 and 55% of intermediate 7.

b) Preparation of Intermediate 8

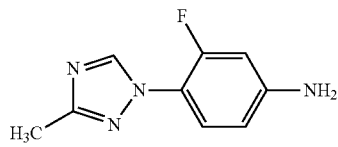

MeOH (150 ml) was added to Pd/C 10% (2g) under $N_2$ atmosphere. Subsequently, a 0.4% thiophene sol. in DIPE (1 ml) and intermediate 6 (9.1 g, 37.9 mmol) were added. The r.m. was stirred at 50° C. under $H_2$ atmosphere until 3 eq of $H_2$ was absorbed. The catalyst was filtered off over diatomaceous earth and the filtrate was evaporated. The residue was partitioned between DCM and $H_2O$. The combined organic layers were dried ($MgSO_4$), filtered and concentrated in vacuo. Yield: 7.23 g of intermediate 8 (99%).

c) Preparation of Intermediate 9

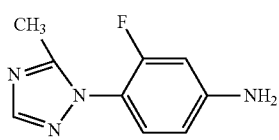

MeOH (150 ml) was added to Pd/C 10% (1 g) under $N_2$ atmosphere. Subsequently, a 0.4% thiophene sol. in DIPE (0.5 ml) and a mixture of intermediate 6 and intermediate 7 in a 4/5 ratio (3.1 g, 12.9 mmol) were added. The r.m. was stirred at 50° C. under $H_2$ atmosphere until 3 eq of $H_2$ was absorbed. The catalyst was filtered off over diatomaceous earth and the filtrate was evaporated. The residue was purified by RP preparative HPLC [RP Shandon Hyperprep® C18 BDS (8 μm, 250 g, I.D. 5 cm); mobile phase: a gradient of (0.25% $NH_4HCO_3$ sol. in water)/MeOH]. The product fractions were collected and worked up. Yield: 1.2 g of intermediate 9 (48%).

Example A4 a) Preparation of Intermediate 10

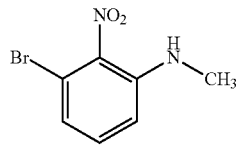

A 8 M methylamine sol. in EtOH (100 ml, 0.8 mol) was added to 1-bromo-3-fluoro-2-nitro-benzene (19.8 g, 90 mmol), cooled on a water bath. The r.m. was stirred at r.t. overnight. Then, the solvent was evaporated and the residue was partitioned between water and DCM. The combined organic layers were dried ($MgSO_4$), filtered and concentrated in vacuo. Yield: 20 g of intermediate 10 (96%), which was used as such in the next reaction step.

b) Preparation of Intermediate 11

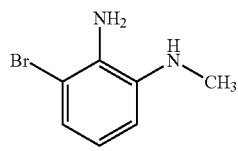

Intermediate 10 (20 g, 86 6 mmol) and iron powder (15 g, 269 mmol) were added to AcOH (150 ml), and the resulting suspension was stirred and heated at 60° C. for 1 h. The r.m. was concentrated in vacuo and the residue was partitioned between DCM and a sat. aq. $NaHCO_3$ sol. The organic layer was dried ($MgSO_4$), filtered and concentrated in vacuo. Yield: 14 g of intermediate 11 (80%), which was used as such in the next reaction step.

c) Preparation of Intermediate 12

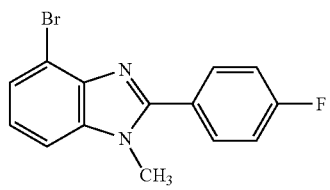

$Et_3N$ (8.1 g, 80 mmol) was added to a sol. of intermediate 11 (10 g, 39 8 mmol) in DCM (250 ml). Then 4-fluoro-benzoylchloride (5.5 g, 34 7 mmol) was added dropwise at r.t., and the r.m. was stirred at r.t. overnight. The r.m. was washed with water, and the organic layer was dried ($MgSO_4$), filtered and concentrated in vacuo. The residue was dissolved in AcOH (100 ml), and a concentrated aq. HCl sol. (3 ml) was added. The r.m. was stirred at 100° C. for 2 h. The r.m. was concentrated in vacuo and the residue was dissolved in DCM and washed with a saturated aq. $NaHCO_3$ sol. and water. The organic layer was dried (MgSO$_4$), filtered and concentrated in vacuo. Yield: 12 g of intermediate 12, which was used as such in the next reaction step.

Example A5 a) Preparation of Intermediate 13

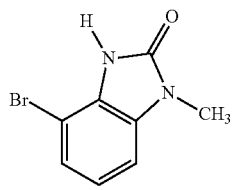

A mixture of intermediate 11 (3 g, 14.9 mmol) and urea (1 g, 17.9 mmol) in THF (30 ml) was stirred at 60° C. for 3 h. Subsequently, the r.m. was concentrated in vacuo and the residue was purified by flash chromatography over silica gel (eluent: DCM/MeOH from 99.5/0.5 to 99/1). The desired fraction was collected and the solvent was evaporated. Yield: 3.4 g of intermediate 13 (100%).

b) Preparation of Intermediate 14

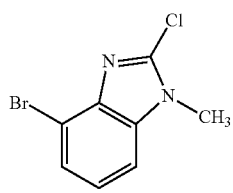

POCl$_3$ (27.9 ml, 299 mmol) was added slowly to intermediate 13 (3.4 g, 14.9 mmol) while cooling on ice and stirring. Then the r.m. was heated at 100° C. for 3 h. The r.m. was concentrated in vacuo. Yield: 3.1 g of crude intermediate 14, which was used as such in the next reaction step.

c) Preparation of Intermediate 15

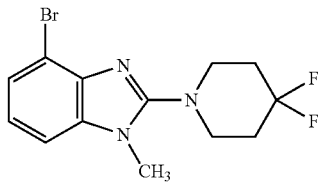

A mixture of intermediate 14 (800 mg), NaOH (391 mg, 9.78 mmol), and 4,4-difluoropiperidine, HCl salt (616 mg, 3.91 mmol) in THF (10 ml) was heated at 150° C. under microwave irradiation for 4 h. The r.m. was cooled to r.t., and a sat. aq. NH$_4$Cl sol. was added. The mixture was extracted with DCM. The organic layers were dried (Na$_2$SO$_4$), filtered and concentrated in vacuo. The residue was purified by flash chromatography over silica gel (eluent: EtOAc/heptane from 10/90 to 50/50). The desired fraction was collected and the solvent was evaporated. Yield: 0.2 g of intermediate 15.

Example A6

Preparation of Intermediate 16

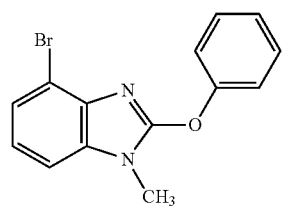 [SMILES: Cn1c(Oc2ccccc2)nc2c(Br)cccc21]

A mixture of intermediate 14 (1 g), NaOH (489 mg, 12 2 mmol), and phenol (460 mg, 4.89 mmol) in THF (10 ml) was heated at 110° C. under microwave irradiation for 4 h. The r.m. was cooled to r.t., and a saturated aq. NH$_4$Cl sol. was added. The mixture was extracted with DCM. The organic layers were dried (Na$_2$SO$_4$), filtered and concentrated in vacuo. The residue was purified by flash chromatography over silica gel (eluent: EtOAc/heptane from 10/90.5 to 50/50). The desired fraction was collected and the solvent was evaporated. Yield: 0.2 g of intermediate 16.

Example A7

Preparation of Intermediate 17

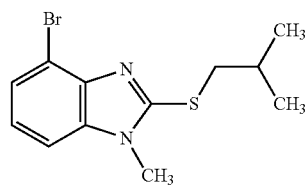 [SMILES: CC(C)CSc1nc2c(Br)cccc2n1C]

A mixture of intermediate 11 (1 g, 4.97 mmol) and 1.1'-thiocarbonyldiimidazole (1.15 g, 6.47 mmol) in THF (20 ml) was heated at 125° C. under microwave irradiation for 1.5 h. The r.m. was cooled to r.t., and the solvent was evaporated. The residue was dissolved in acetone (30 ml), and 1-iodo-2-methyl-propane (1.83 g, 9.95 mmol), and K$_2$CO$_3$ (1.37 g, 9.95 mmol) were added. The r.m. was heated at 100° C. under microwave irradiation for 0.5 h. The r.m. was cooled and partitioned between DCM and water. The organic layer was dried (MgSO$_4$), filtered and concentrated in vacuo. The residue was purified by flash chromatography over silica gel (eluent: DCM). The desired fraction was collected and the solvent was evaporated. Yield: 0.6 g of intermediate 17 (33%).

Example A8 a) Preparation of Intermediate 18

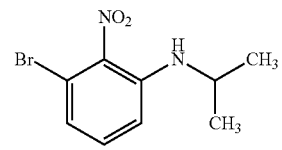

Isopropylamine (12.9 g, 218 mmol) was added to a sol. of 1-bromo-3-fluoro-2-nitro-benzene (8.0 g, 36 mmol) in EtOH (40 ml). The r.m. was stirred at r.t. overnight. Then, the solvent was evaporated and the residue was partitioned between water and DCM. The combined organic layers were dried (MgSO$_4$), filtered and concentrated in vacuo. Yield: 8.3 g of intermediate 18 (88%), which was used as such in the next reaction step.

b) Preparation of Intermediate 19

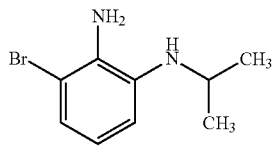

Intermediate 18 (8.3 g, 32 mmol) and iron powder (8.95 g, 160 mmol) were added to AcOH (50 ml), and the resulting suspension was stirred and heated at 60° C. for 1 h. The r.m. was concentrated in vacuo and the residue was partitioned between DCM and a saturated aq. NaHCO$_3$ sol. The organic layer was dried (MgSO$_4$), filtered and concentrated in vacuo. Yield: 7.5 g of intermediate 19 (100%), which was used as such in the next reaction step.

c) Preparation of Intermediate 20

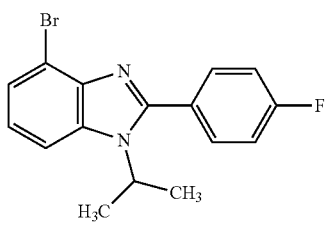

4-Fluoro-benzaldehyde (2.28 g, 18.3 mmol) and Na$_2$S$_2$O$_5$ (3.73 g, 19.6 mmol) were added to a sol. of intermediate 19 (3 g, 13.1 mmol) in DMA (50 ml). The r.m. was stirred at r.t. overnight. Then, the r.m. was poured into water, which resulted in the precipitation of a solid. The solid was filtered off, washed with water, and suspended in DIPE. The resulting solid was filtered off, washed with DIPE, and dried. Yield: 2.3 g of intermediate 20 (53%).

Example A9 a) Preparation of Intermediate 21

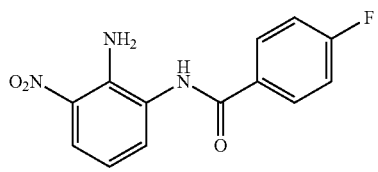 [SMILES: Nc1c(NC(=O)c2ccc(F)cc2)cccc1[N+](=O)[O-]]

Et$_3$N (2.02 g, 20 mmol) and 4-fluoro-benzoylchloride (1.58 g, 10 mmol) were added to a sol. of 3-nitro-benzene-1,2-diamine (1.53 g, 10 mmol) in DCM (50 ml) and CH$_3$CN (25 ml), and the r.m. was stirred at r.t. for 2 h. The r.m. was diluted with DCM and washed with water. The organic layer was dried (MgSO$_4$), filtered and concentrated in vacuo. The residue was suspended in DIPE, and the resulting solid was filtered off and dried in vacuo. Yield: 2.3 g of intermediate 21 (84%).

b) Preparation of Intermediate 22

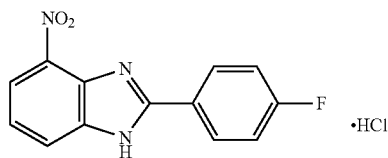 [SMILES: O=[N+]([O-])c1cccc2[nH]c(-c3ccc(F)cc3)nc12 ; Cl]

Intermediate 21 (1.35 g, 4.9 mmol) and a concentrated aq. HCl sol. (0.5 ml) were added to AcOH (15 ml), and the resulting mixture was stirred and heated at 150° C. for 0.5 h under microwave irradiation. The r.m. was cooled to r.t., resulting in the formation of a precipitate. The precipitate was filtered off, washed with AcOH, followed by DIPE, and then dried in vacuo. Yield: 1 g of intermediate 22 (69%).

c) Preparation of Intermediate 23

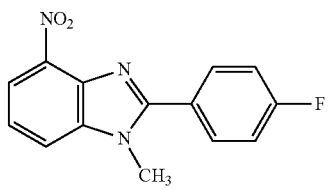 [SMILES: Cn1c(-c2ccc(F)cc2)nc2c([N+](=O)[O-])cccc21]

To a sol. of intermediate 22 (290 mg, 0.99 mmol) in THF (10 ml) was added a 1 M sol. of LiHMDS in THF (2.96 ml, 2.96 mmol) dropwise at 0° C. under a N$_2$ atmosphere. The r.m. was stirred at 0° C. for 30 min, and then CH$_3$I (210 mg, 1.48 mmol) was added. The r.m. was stirred overnight at 55° C. The mixture was cooled, then washed with brine, and the organic phase was separated, dried (MgSO$_4$), filtered and the solvent was evaporated in vacuo. The residue was suspended in DIPE. The resulting solid was filtered off, washed with DIPE, and dried. Yield: 160 mg of intermediate 23 (60%).

d) Preparation of Intermediate 24

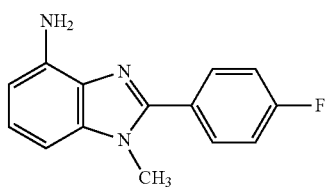 [SMILES: Cn1c(-c2ccc(F)cc2)nc2c(N)cccc21]

Intermediate 23 (150 mg, 0.55 mmol) and iron powder (162 mg, 2.9 mmol) were added to AcOH (10 ml), and the resulting suspension was stirred and heated at 60° C. for 1 h. The r.m. was concentrated in vacuo and the residue was partitioned between DCM and a saturated aq. NaHCO$_3$ sol. The organic layer was dried (MgSO$_4$), filtered and concentrated in vacuo. Yield: 120 mg of intermediate 24 (90%), which was used as such in the next reaction step.

e) Preparation of Intermediate 52

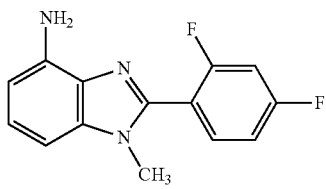 [SMILES: Cn1c(-c2ccc(F)cc2F)nc2c(N)cccc21]

Starting from 3-nitro-benzene-1,2-diamine and 2,4-difluoro-benzoylchloride, intermediate 46 was prepared according to the procedures as described in example A9.

Example A10

Preparation of Intermediate 24

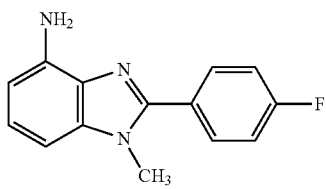

A stainless steel autoclave was loaded with intermediate 12 (370 mg, 1.21 mmol), copper(I)oxide (10 mg), and a 0.5 M sol. of $NH_3$ in dioxane (30 ml, 15 mmol). The autoclave was closed and the r.m. was heated at 150° C. for 18 h. Then, the r.m. was cooled, a sat. aq. $NH_4OH$ sol. (5 ml) was added, and the r.m. was heated at 150° C. for another 18 h The r.m. was cooled and concentrated in vacuo. The residue was partitioned between DCM and a saturated aq. $NH_4Cl$ sol. The organic layer was dried ($MgSO_4$), filtered and concentrated in vacuo. Yield: 240 mg of intermediate 24 (82%), which was used as such in the next reaction step.

Example A11 a) Preparation of Intermediate 25

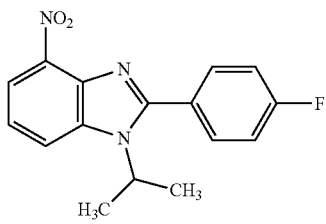

A 1 M sol. of LiHMDS in THF (4.94 ml, 4.94 mmol) was added dropwise at 0° C. under a $N_2$ atmosphere to a sol. of intermediate 22 (290 mg, 0.99 mmol) in THF (15 ml). The r.m. was stirred at 0° C. for 30 min, and then 2-iodopropane (1.68 g, 9.9 mmol) was added. The r.m. was stirred overnight at 55° C. The r.m. was transferred to a microwave vial, and additional amounts of a 1 M sol. of LiHMDS in THF (2 ml, 2 mmol) and 2-iodopropane (0.84 g, 5 mmol)was added. The r.m was stirred and heated at 150° C. for 4 h under microwave irradiation. The mixture was cooled, then washed with brine, and the organic phase was separated, dried ($MgSO_4$), filtered and the solvent was evaporated in vacuo. The residue was purified by RP preparative HPLC [RP Shandon Hyperprep® C18 BDS (8 μm, 250 g, I.D. 5 cm); mobile phase: a gradient of (0.25% $NH_4HCO_3$ sol. in water)/$CH_3CN$]. The product fractions were collected and worked up. Yield: 50 mg of intermediate 25 (17%).

b) Preparation of Intermediate 26

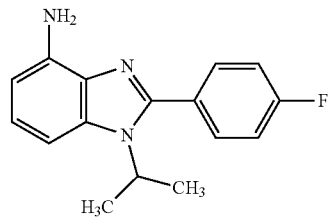 [SMILES: CC(C)n1c(-c2ccc(F)cc2)nc2c([N+](=O)[O-])cccc21]

Intermediate 25 (50 mg, 0.167 mmol) and iron powder (49 mg, 0.88 mmol) were added to AcOH (4 ml), and the resulting suspension was stirred and heated at 60° C. for 1 h. The r.m. was concentrated in vacuo and the residue was partitioned between DCM and a sat. aq. $NaHCO_3$ sol. The organic layer was dried ($MgSO_4$), filtered and concentrated in vacuo. Yield: 40 mg of intermediate 26 (89%), which was used as such in the next reaction step.

Example A12 a) Preparation of Intermediate 27

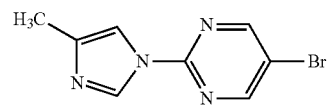

4-Bromo-2-chloropyrimidine (5 g, 25.8 mmol), 4-methyl-1H-imidazole (4.25 g, 51.7 mmol) and $K_2CO_3$ (10.72 g, 77.5 mmol) in NMP (100 ml) were heated overnight at 85° C. The mixture was separated between DCM and water. The organic layer was dried ($MgSO_4$), filtered and the solvent was evaporated. Water was added to the residue and the resulting precipitate was collected by filtration and dried in vacuo. Yield 4.7 g of intermediate 27 (76%).

b) Preparation of Intermediate 28

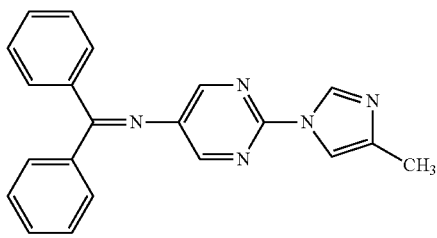 [SMILES: Cc1cn(-c2ncc(N=C(c3ccccc3)c3ccccc3)cn2)cn1]

2-Methyl-2-propanol, sodium salt (1.69 g, 17.6 mmol), BINAP (195 mg, 0.314 mmol), $Pd_2(dba)_3$ (287 mg, 0.31 mmol), intermediate 27 (3 g, 12.5 mmol) and benzophenone imine (2.27 g, 12.5 mmol) in toluene (40 ml; previously deoxygenated) were stirred and heated for 4 h at 120° C. The mixture was separated between DCM and water. The organic phase was separated, dried ($MgSO_4$), filtered and the solvent was evaporated in vacuo. Yield: 3.4 g of crude intermediate 28.

c) Preparation of Intermediate 29

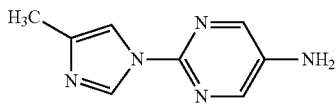

A 1 N aq. HCl sol. (11 ml, 11 mmol) was added to a sol. of intermediate 28 (3.4 g, 4.1 mmol) in THF (10 ml). The r.m. was stirred at r.t. for 2 h. The solvent was evaporated in vacuo and the residue was separated between DCM and water, basified with an aq. NH$_4$OH sol. till pH 10. The organic phase was separated, dried (MgSO$_4$), filtered and the solvent was evaporated in vacuo. The product was purified by flash column chromatography over silica gel (eluent: DCM/MeOH from 98/2 to 95/5). The product fractions were collected and the solvent was evaporated. Yield: 0.36 g of intermediate 29 (16% yield over 2 steps).

Example A13 a) Preparation of Intermediate 30

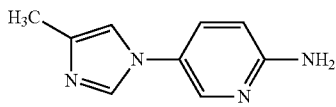

CuI (8.25 g, 43 mmol) was added under a N$_2$ flow to a sol. of 5-bromo-pyridin-2-ylamine (5 g, 28.9 mmol), 4-methyl-1H-imidazole (5.9 g, 72 mmol), and Cs$_2$CO$_3$ (9.4 g, 28.9 mmol) in DMSO (100 ml). The reaction mixture was heated for 2 nights at 130° C. and was then cooled. CH$_3$CN was added to form a blue precipitate which was removed by filtration. The filtrate was concentrated under reduced pressure, and the residue was separated between DCM and water. The organic phase was separated, dried (MgSO$_4$), filtered and the solvent was evaporated in vacuo. The residue was purified by flash column chromatography over silica gel (eluent: DCM/MeOH from 98/2 to 95/5). The product fractions were collected and the solvent was evaporated. Yield: 0.628 g of intermediate 30. The aq. layer was concentrated under reduced pressure, until some additional product precipitated, which was filtered off, and dried in vacuo, to give 0.16 g of intermediate 30.

Example A14 a) Preparation of Intermediate 31 and Intermediate 32 (Regioisomers)

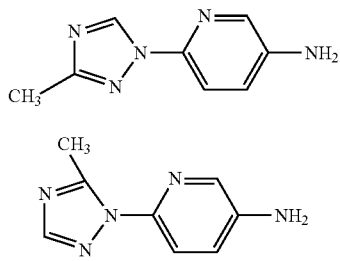

intermediate 31 intermediate 32

CuI (2.64 g, 13.9 mmol) was added under a N$_2$ flow to a sol. of 2-bromo-pyridin-5-ylamine (6 g, 34.7 mmol), 5-methyl-1H-1,2,4-triazole (4.03 g, 48.5 mmol), and Cs$_2$CO$_3$ (22.6 g, 69.4 mmol) in DMF (50 ml). The reaction mixture was heated for 2 nights at 120° C. and was then cooled and concentrated in vacuo. The residue was partitioned between DCM and water. The aq. phase was saturated with NaCl and extracted further with DCM and MeOH. The combined organic layers were dried (MgSO$_4$), filtered and the solvent was evaporated in vacuo. The residue was purified by RP preparative HPLC [RP Shandon Hyperprep® C18 BDS (8 µm, 250 g, I.D. 5 cm); mobile phase: a gradient of (0.25% NH$_4$HCO$_3$ sol. in water)/MeOH/CH$_3$CN]. The product fractions were collected and worked up. Yield: 1150 mg of intermediate 32 (19%) and 1500 mg of intermediate 31 (25%).

Example A15 a) Preparation of Intermediate 33

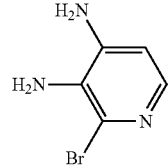

MeOH (100 ml) was added to Pt/C 5% (1 g) under N$_2$ atmosphere. Subsequently, a 0.4% thiophene sol. in DIPE (2 ml) and 4-amino-2-bromo-3-nitro-pyridine (3.5 g, 16 mmol) were added. The r.m. was stirred at 25° C. under H$_2$ atmosphere until 3 eq of H$_2$ was absorbed. The catalyst was filtered off over diatomaceous earth and the filtrate was concentrated in vacuo. Yield: 1.8 g of intermediate 33 (63%), which was used as such in the next reaction step.

b) Preparation of Intermediate 34

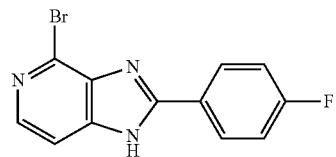 [SMILES: Fc1ccc(-c2nc3c(Br)nccc3[nH]2)cc1]

A mixture of intermediate 33 (1.8 g, 9.57 mmol) and 4-fluoro-benzoic acid (1.34 g, 9.57 mmol) in polyphosphoric acid (25 g) was stirred and heated for 1 h at 180° C. The r.m. was cooled to r.t, and water was added. The resulting sol. was neutralized with K$_2$CO$_3$, and the resulting precipitate was filtered off and washed with water. Yield: 1 g of crude intermediate 34, which was used as such in the next reaction step.

c) Preparation of Intermediate 35

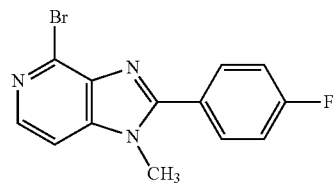

Intermediate 34 (825 mg, 2.8 mmol), CH$_3$I (400 mg, 2.8 mmol), and K$_2$CO$_3$ (830 mg, 6 mmol) were added to DMF (25 ml). The resulting mixture was stirred for 1 h at 50° C. The r.m. was cooled to r.t. and concentrated in vacuo. The residue was partitioned between DCM and water. The organic layer was dried (MgSO₄), filtered and concentrated in vacuo. The residue was purified by RP preparative HPLC [RP Shandon Hyperprep® C18 BDS (8 μm, 250 g, I.D. 5 cm); mobile phase: a gradient of (0.25% NH₄HCO₃ sol. in water)/MeOH]. The product fractions were collected and worked up. Yield: 180 mg of intermediate 35 (21%).

Example A16 a) Preparation of Intermediate 36

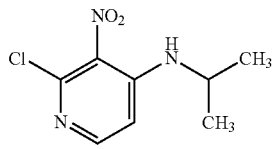

Et₃N (0.78 ml, 5.7 mmol) was added to a sol. of 2,4-dichloro-3-nitropyridine (cas 5975-12-2) (1 g, 5.2 mmol) in DMF (10 mL) at 0° C. Then, isopropylamine (0.444 ml, 5.2 mmol) was added, and the r.m. was stirred for 5 min. The r.m. was diluted with EtOAc and the resulting mixture was washed with water and brine. The organic layer was dried (MgSO₄), filtered and concentrated in vacuo. The residue was purified by flash column chromatography over silica gel (eluent: DCM/MeOH from 100/0 to 99/1). The product fractions were collected and the solvent was evaporated. Yield: 1.1 g of intermediate 36 (98%).

b) Preparation of Intermediate 37

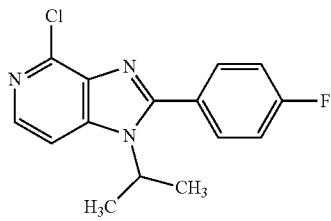 [SMILES: CC(C)n1c(-c2ccc(F)cc2)nc2c(Cl)nccc21]

4-Fluorobenzaldehyde (589 mg, 4.74 mmol) and Na₂S₂O₄ (3.0 g, 17.2 mmol) were added to a sol. of intermediate 36 (930 mg, 4.31 mmol) in EtOH (15 ml). The r.m. was heated under microwave conditions for 45 min at 160° C. The r.m. was cooled to r.t. and filtered through diatomaceous earth. The filtrate was evaporated and the residue was purified by flash column chromatography over silica gel (eluent: DCM/MeOH from 100/0 to 96/4). The product fractions were collected and the solvent was evaporated. Yield: 450 mg of intermediate 37 (36%).

Example A17 a) Preparation of Intermediate 38

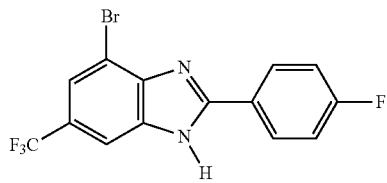 [SMILES: Fc1ccc(-c2nc3c(Br)cc(C(F)(F)F)cc3[nH]2)cc1]

Na₂S₂O₅ (1.64 g, 8.62 mmol) and 4-fluoro-benzaldehyde (891 mg, 7.18 mmol) were added to a sol. of 3-bromo-5-trifluoromethyl-1,2-diaminobenzene (1.65 g, 6.47 mmol) in DMA (40 ml). The r.m. was stirred overnight at 70° C. Then, the r.m. was cooled to r.t. and poured into water. The solid was filtered off, washed with water, and suspended in DIPE and drops of 2-propanol. The resulting solid was filtered off, washed with DIPE, and dried. Yield: 1.95 g of intermediate 38 (84%).

c) Preparation of Intermediate 39

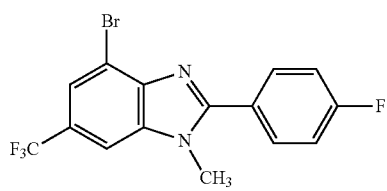

A 1 M sol. of LiHMDS in THF (9.2 ml, 9.2 mmol) was added dropwise at r.t. under a N₂ atmosphere to a sol. of intermediate 38 (1.65 g, 4.6 mmol) in THF (50 ml). The r.m. was stirred at r.t. for 30 min, and then CH₃I (3.26 g, 23 mmol) was added. The r.m. was stirred at r.t. for 1 h and then washed with a sat. aq. NaHCO₃ sol. and brine. The organic phase was separated, dried (MgSO₄), filtered and the solvent was evaporated in vacuo. The residue was purified by RP preparative HPLC [RP Shandon Hyperprep® C18 BDS (8 μm, 250 g, I.D. 5 cm); mobile phase: a gradient of (0.25% NH₄HCO₃ sol. in water)/MeOH/CH₃CN]. The product fractions were collected and worked up. Yield: 720 mg of intermediate 39 (42%).

Example A18

Preparation of Intermediate 40

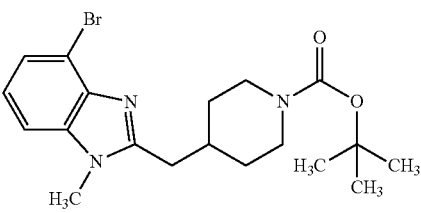 [SMILES: Cn1c(CC2CCN(C(=O)OC(C)(C)C)CC2)nc2c(Br)cccc21]

4-(2-Oxo-ethyl)-piperidine-1-carboxylic acid tert-butyl ester (682 mg, 3 mmol) and Na₂S₂O₅ (741 mg, 3.9 mmol) were added to a sol. of intermediate 11 (603 mg, 3 mmol) in DMA (15 ml). The r.m. was stirred overnight at r.t. Then, water was added and the mixture was extracted with EtOAc. The combined organic layers were dried (MgSO₄), filtered and concentrated in vacuo. The residue was purified by flash column chromatography over silica gel (eluent: DCM/MeOH from 100/0 to 98/2). The product fractions were collected and the solvent was evaporated. Yield: 840 mg of intermediate 40, which was used as such in the next reaction step.

Example A19 a) Preparation of Intermediate 42

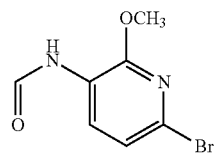 [SMILES: COc1nc(Br)ccc1NC=O]

A mixture of formic acid (12.8 ml, 340 mmol) and acetic acid anhydride (8.54 ml, (91 mmol) was stirred at r.t. for 40 min. Subsequently, a sol. of 3-amino-6-bromo-2-methoxy-pyridine (5 g, 24.6 mmol) in THF (30 ml) was added dropwise and the resulting r.m. was stirred overnight at 60° C. The r.m. was cooled and poured into ice-water, resulting in the precipitation of a solid. The solid was filtered off, washed with water, and dried. Yield: 5.2 g of intermediate 42 (76%).

b) Preparation of Intermediate 43

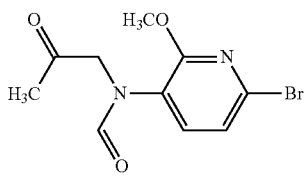 [SMILES: COc1nc(Br)ccc1N(C=O)CC(C)=O]

1-Chloro-propan-2-one (4.34 g, 46.9 mmol) was added dropwise to a mixture of intermediate 42 (5.2 g, 18.8 mmol), potassium iodide (0.343 g, 2.06 mmol), $Cs_2CO_3$ (21.4 g, 65.9 mmol) in DMF (50 ml). The r.m. was stirred at r.t. overnight. The r.m. was poured into ice-water and extracted with EtOAc. The combined organic layers were dried ($MgSO_4$), filtered and concentrated in vacuo. The residue was suspended in DIPE and the resulting solid was filtered off, washed with DIPE, and dried. Yield: 4.43 g of intermediate 43 (82%).

c) Preparation of Intermediate 44

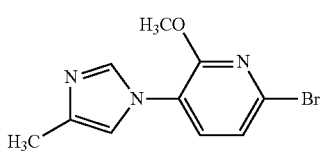

Intermediate 43 (4.4 g, 15.3 mmol) was added to a mixture of ammonium acetate (5.41 g, 70.2 mmol) in AcOH (10 ml). The r.m. was heated at reflux for 1 h. The r.m. was cooled to r.t. and poured into a mixture of ice-water and EtOAc. The mixture was basified with a 50% w/v (weight/volume percentage solution) aq. NaOH sol. to pH 9. The organic layer was separated, dried ($MgSO_4$), filtered and concentrated in vacuo. The resulting solid product was used as such in the next step. Yield: 3.78 g of crude intermediate 44.

d) Preparation of Intermediate 45

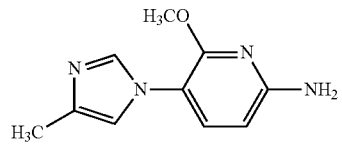

2-Methyl-2-propanol, sodium salt (0.717 g, 7.46 mmol), BINAP (464 mg, 0.75 mmol), $Pd_2(dba)_3$ (342 mg, 0.37 mmol), intermediate 44 (1.0 g, 3.73 mmol) and benzophenone imine (0.845 g, 4.66 mmol) in toluene (20 ml; previously deoxygenated) were stirred and heated at 100° C. for 2 h under microwave conditions. The mixture was cooled, and the solvent removed in vacuo. THF (50 ml) and a 1 N aq. HCl sol. (50 ml) were added to the residue, and the mixture was stirred at r.t. for 1 h. The r.m. was basified with a 10% aq. $Na_2CO_3$ sol. and extracted with EtOAc. The organic layers were dried ($MgSO_4$), filtered and the solvent was evaporated in vacuo. The product was purified by flash column chromatography over silica gel (eluent: DCM/MeOH from 100/0 to 95/5). The product fractions were collected and the solvent was evaporated. Yield: 0.6 g of intermediate 45 (52% yield over 2 reaction steps).

In an alternative procedure, $Cu_2O$ (320 mg, 2.24 mmol) and a 7 N $NH_3$ solution in MeOH (48 ml, 336 mmol) were added to a solution of intermediate 44 (6 g, 22.4 mmol) in ethylene glycol (50 ml). The r.m. was heated in a closed pressure vessel at 100° C. for 12 h. After cooling to r.t., the mixture was diluted with water, and extracted with EtOAc. The organic layer was dried ($MgSO_4$), filtered and the solvent was evaporated in vacuo. The residue was triturated with DIPE. Yield: 4 g of intermediate 45 (87%).

Example A20 a) Preparation of Intermediate 46

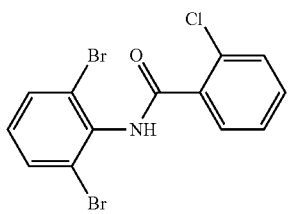 [SMILES: O=C(Nc1c(Br)cccc1Br)c1ccccc1Cl]

2-Chlorobenzoylchloride (1.46 g, 8.37 mmol) was added at r.t. to a sol. of 2,6-dibromoaniline (2.0 g, 7.97 mmol) in THF (24 ml). The r.m. was stirred at r.t. overnight. The mixture was diluted with EtOAc (30 ml) and the organic phase was washed with a sat. aq. $NaHCO_3$ sol., dried ($MgSO_4$), filtered and the solvent was evaporated. The residue was triturated in DIPE, filtered off, extensively washed with DIPE and dried in vacuo. Yield: 1.08 g of intermediate 46 (35%).

b) Preparation of Intermediate 47

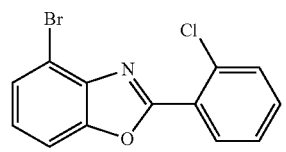 [SMILES: Clc1ccccc1-c1nc2c(Br)cccc2o1]

A mixture of intermediate 46 (0.5 g, 1.28 mmol), CuI (0.025 g, 0.13 mmol), Cs$_2$CO$_3$ (0.63 g, 1.93 mmol), 1,10-phenanthroline (0.046 g, 0.257 mmol) in DME (10 ml) was stirred at 90° C. in a sealed tube for 3 days. The mixture was diluted with H$_2$O (10 ml) and DCM (50 ml). The separated organic phase was dried (MgSO$_4$), filtered and the solvent was evaporated in vacuo. The residue was purified by flash column chromatography over silica gel (eluent: heptanes/DCM isocratic 1/2). The product fractions were collected and evaporated off. Yield: 0.18 g of intermediate 47 (46%).

Example A21 a) Preparation of Intermediate 48

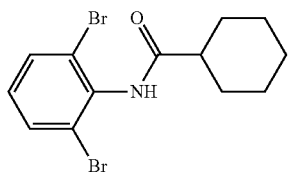 [SMILES: O=C(Nc1c(Br)cccc1Br)C1CCCCC1]

Cyclohexanecarboxylic acid chloride (0.61 g, 4.18 mmol) was added at r.t. to a sol. of 2,6-dibromoaniline (1.0 g, 3.98 mmol) in THF (12 ml). The r.m. was stirred at r.t. for 4 days. The mixture was diluted with EtOAc (30 ml) and the organic phase was washed with a saturated aq. NaHCO$_3$ sol., dried (MgSO$_4$), filtered and the solvent was evaporated. The residue was triturated in DIPE, filtered off, extensively washed with DIPE and dried in vacuo. Yield: 0.62 g of intermediate 48 (43%).

b) Preparation of Intermediate 49

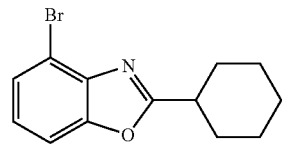 [SMILES: Brc1cccc2oc(C3CCCCC3)nc12]

A mixture of intermediate 48 (0.15 g, 0.41 mmol), CuI (0.008 g, 0.04 mmol), Cs$_2$CO$_3$ (0.203 g, 0.62 mmol) and 1,10-phenanthroline (0.015 g, 0.08 mmol) in DME (2 ml) was stirred overnight at 90° C. in a sealed tube. The mixture was diluted with H$_2$O (2 ml) and DCM (2 ml). The separated organic phase was passed through Extrelut® and the filtrate was evaporated in vacuo. The residue was purified by flash column chromatography over silica gel (eluent: heptane/DCM 30/70). The product fractions were collected and the solvent was evaporated. Yield: 0.095 g of intermediate 49 (77%).

Example A22 a) Preparation of Intermediate 50

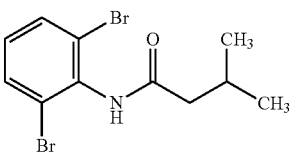

SOCl$_2$ (1.38 ml, 19.0 mmol) was added to a sol. of isopentanoic acid (1.87 g, 18.2 mmol) and pyridine (1.48 ml, 18.3 mmol) in DCM (15 ml) and the r.m. was stirred at r.t. for 2 h. A sol. of 2,6-dibromoaniline (0.92 g, 3.5 mmol) in DCM (5 ml) was added and the r.m. was stirred at r.t. for 2 days. Up to 5 extra equivalents of acyl chloride were prepared and added to the r.m. which was further stirred overnight. The mixture was diluted with DCM (20 ml) and the organic phase was washed with a 1 M HCl sol., then a saturated aq. NaHCO$_3$ sol., dried (MgSO$_4$), filtered and the solvent was evaporated. The crude product was recrystallized from DIPE/CH$_3$CN. Yield: 0.21 g of intermediate 50 (17%).

b) Preparation of Intermediate 51

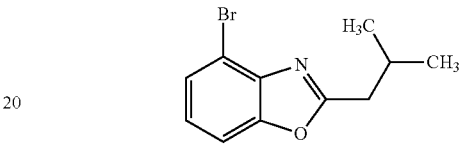

A mixture of intermediate 50 (0.21 g, 0.63 mmol), CuI (0.012 g, 0.063 mmol), Cs$_2$CO$_3$ (0.306 g, 0.94 mmol) and 1,10-phenanthroline (0.023 g, 0.125 mmol) in DME (3 ml) was stirred overnight at 90° C. in a sealed tube. The mixture was diluted with H$_2$O (20 ml) and DCM (20 ml). The separated organic phase was passed through Extrelut® and the filtrate was evaporated in vacuo. The residue was purified by flash column chromatography over silica gel (eluent: heptane/DCM 30/70). The product fractions were collected and evaporated off. Yield: 0.110 g of intermediate 51 (69%).

Example A23 a) Preparation of Intermediate 53

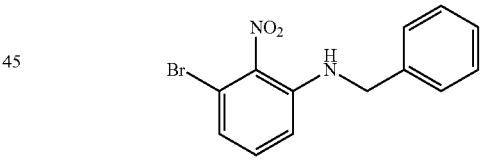

Benzylamine (17 g, 159 mmol) was added to a sol. of 1-bromo-3-fluoro-2-nitro-benzene (10 g, 45.5 mmol) in THF (100 ml). The r.m. was stirred at r.t. overnight. The formed precipitate was removed by filtration and the filtrate was concentrated under reduced pressure. The residue was dissolved in DCM and the resulting sol. was washed subsequently with an aq. AcOH sol., a saturated aq. NaHCO$_3$ sol., and water. The organic layer was dried (MgSO$_4$), filtered and concentrated in vacuo. The crude residue was dissolved in AcOH (100 mL) and iron powder (7.62 g, 136 mmol) was added. The resulting suspension was stirred and heated at 60° C. for 1 h. The r.m. was concentrated in vacuo and the residue was partitioned between DCM and a saturated aq. NaHCO$_3$ sol. The organic layer was dried (MgSO$_4$), filtered and concentrated in vacuo. Yield: 6.5 g of intermediate 53 (80% purity according to LC-MS analysis), which was used as such in the next reaction step.

b) Preparation of Intermediate 54

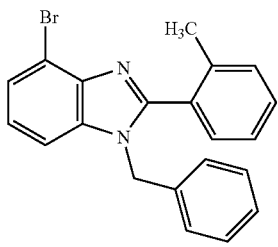 [SMILES: Cc1ccccc1-c1nc2c(Br)cccc2n1Cc1ccccc1]

Et₃N (1.21 g, 12 mmol) and 2-methyl-benzoylchloride (923 mg, 5.97 mmol) were added to a sol. of intermediate 53 (2.07 g, 5.97 mmol) in DCM (50 ml), and the r.m. was stirred at r.t. overnight. The r.m. was diluted with DCM and washed with water.

The organic layer was dried (MgSO₄), filtered and concentrated in vacuo. The residue was dissolved in AcOH (25 ml) and a concentrated aq. HCl sol. (0.5 ml) was added. The resulting mixture was stirred and heated at 100° C. for 18 h. The r.m. was cooled and concentrated in vacuo. The residue was partitioned between DCM and a saturated aq. NaHCO₃ sol. The organic layer was washed with water, dried (MgSO₄), filtered and concentrated in vacuo. Yield: 2.2 g of intermediate 54 (98%) which was used as such in the next reaction step.

Example A24 a) Preparation of Intermediate 55

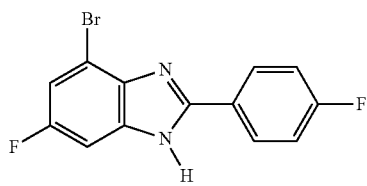 [SMILES: Fc1ccc(-c2nc3c(Br)cc(F)cc3[nH]2)cc1]

Na₂S₂O₅ (5.56 g, 29.2 mmol) and 4-fluoro-benzaldehyde (2.91 g, 23.4 mmol) were added to a sol. of 3-bromo-5-fluoro-1,2-diaminobenzene (4.0 g, 19.5 mmol) in DMA (80 ml). The r.m. was stirred overnight at 70° C. Then, the r.m. was cooled to r.t. and poured into water. The solid was filtered off, washed with water, and dried. Yield: 6 g of intermediate 55.

b) Preparation of Intermediate 56

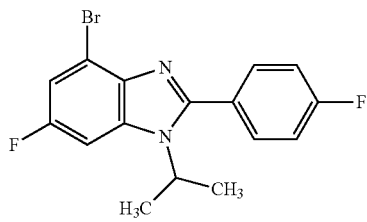 [SMILES: CC(C)n1c(-c2ccc(F)cc2)nc2c(Br)cc(F)cc21]

A suspension of NaH (60% in mineral oil; 233 mg, 5.82 mmol) was added under a N₂ atmosphere to a cooled (5° C.) sol. of intermediate 55 (900 mg, 2.91 mmol) in THF (5 ml). The r.m. was stirred at 5° C. for 30 min, and then isopropyliodide (1.98 g, 11.6 mmol) was added. The r.m. was stirred at 130° C. for 2 h under microwave irradiation. The r.m. was cooled, more THF (q.s.) was added and the mixture was washed with brine. The organic phase was separated, dried (MgSO₄), filtered and the solvent was evaporated. The residue was purified by flash column chromatography over silica gel (eluent: heptane/DCM 50/50 to 0/100). The product fractions were collected and the solvent was evaporated. Yield: 350 mg of intermediate 56 (34%).

Example A25 a) Preparation of Intermediate 57

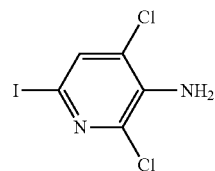

N-Iodosuccinimide (26.7 g, 119 mmol) and TFA (2.5 ml, 32.4 mmol) were added to a suspension of 2,4-dichloro-pyridin-3-ylamine (17.6 g, 108 mmol) in CH₃CN (150 ml). The reaction mixture was stirred at r.t. for 16 h., and then heated to 40° C. for 6 h. The r.m. was diluted with EtOAc and washed with a sat. aq. Na₂S₂O₃ sol. The aq. phase was extracted with EtOAc, and the combined organic layers were dried (MgSO₄), filtered and the solvent was evaporated in vacuo. The residue was purified by flash column chromatography over silica gel (eluent: DCM). The product fractions were collected and the solvent was evaporated. Yield: 22 g of intermediate 57 (71%).

b) Preparation of Intermediate 58 and Intermediate 59 (Regioisomers)

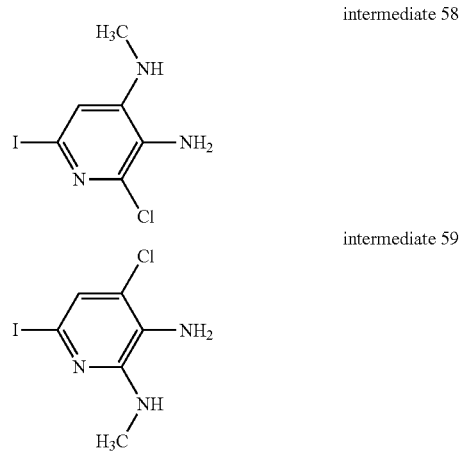

A sol. of methylamine in THF (2 M, 25 ml, 50 mmol) was added to a sol. of intermediate 57 (4.8 g, 16.6 mmol) in EtOH (20 ml). The r.m. was stirred at 160° C. under microwave irradiation for 8 h. Then, the solvent was evaporated and the residue was partitioned between aq. NaHCO₃ sol. and DCM. The combined organic layers were dried (Na₂SO₄), filtered and concentrated in vacuo. The residue was purified by flash column chromatography over silica gel (eluent: heptane/DCM 100/0 to 0/100). The product fractions were collected and the solvent was evaporated. Yield: 950 mg of intermediate 58 (20%) and 2900 mg of intermediate 59 (62%).

c) Preparation of Intermediate 60

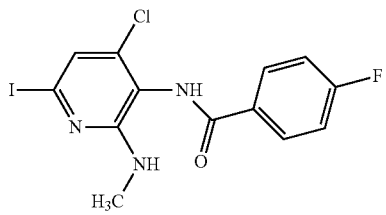 [SMILES: CNc1nc(I)cc(Cl)c1NC(=O)c1ccc(F)cc1]

Et₃N (3.61 ml, 26.5 mmol) and 4-fluoro-benzoylchloride (1.68 g, 10.6 mmol) were added to a sol. of intermediate 59 (2.5 g, 8.8 mmol) in DCM (100 ml), and the r.m. was stirred at r.t. for 4 h. The r.m. was concentrated in vacuo. Yield: 2.7 g of crude intermediate 60 (75%), which was used as such in the next reaction step.

d) Preparation of Intermediate 61

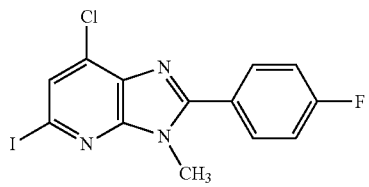 [SMILES: Cn1c(-c2ccc(F)cc2)nc2c(Cl)cc(I)nc21]

POCl₃ (907 mg, 5.9 mmol) was added to a sol. of intermediate 60 (2.0 g, 4.93 mmol) in DCE (15 ml), and the resulting mixture was stirred and heated at 150° C. for 15 min under microwave irradiation. The r.m. was concentrated in vacuo, and the residue was purified by flash column chromatography over silica gel (eluent: DCM/MeOH(NH₃) from 100/0 to 97/3). The product fractions were collected and the solvent was evaporated. Yield: 1.56 g of intermediate 61 (81%).

e) Preparation of Intermediate 62

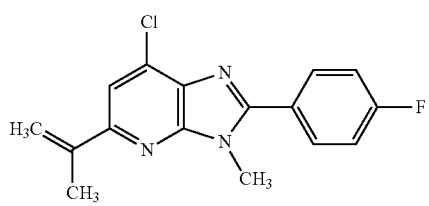 [SMILES: C=C(C)c1cc(Cl)c2nc(-c3ccc(F)cc3)n(C)c2n1]

Isopropenylboronic acid pinacol ester (867 mg, 5.16 mmol) and Pd(PPh₃)₄ (298 mg, 0.258 mmol) were added to a sol. of intermediate 61 (2.0 g, 5.16 mmol) in dioxane (8 ml) and an aq. NaHCO₃ sol. (4 ml). The r.m. was stirred and heated at 160° C. for 10 min. under microwave irradiation. The r.m. was cooled to r.t. and filtered over diatomaceous earth using EtOAc. The filtrate was evaporated. The residue was purified by flash column chromatography over silica gel (eluent: DCM/MeOH(NH₃) from 100/0 to 97/3). The product fractions were collected and the solvent was evaporated. Yield: 1.25 g of intermediate 62 (80%).

f) Preparation of Intermediate 63

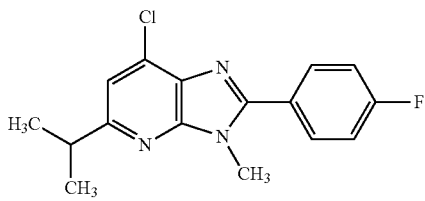 [SMILES: CC(C)c1cc(Cl)c2nc(-c3ccc(F)cc3)n(C)c2n1]

MeOH (40 ml) was added to Pt/C 5% (100 mg) under N₂ atmosphere. Subsequently, intermediate 62 (1.25 g, 4.14 mmol) was added. The r.m. was stirred at 25° C. under H₂ atmosphere until 1 eq of H₂ was absorbed. The catalyst was filtered off over diatomaceous earth and the filtrate was evaporated. Yield: 0.9 g of crude intermediate 63 (71%), which was used as such in the next reaction step.

g) Preparation of Intermediate 64

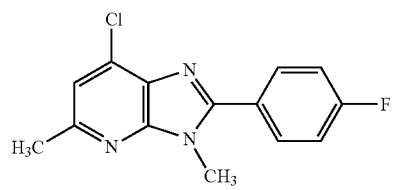 [SMILES: Cc1cc(Cl)c2nc(-c3ccc(F)cc3)n(C)c2n1]

Methylboronic acid (93 mg, 1.55 mmol) and Pd(PPh₃)₄ (71 mg, 0.062 mmol) were added to a sol. of intermediate 61 (600 mg, 0.31 mmol) in dioxane (10 ml) and an aq. NaHCO₃ sol. (5 ml). The resulting mixture was stirred and heated at 150° C. for 20 min. under microwave irradiation. The r.m. was cooled to r.t. and partitioned between water and DCM. The organic phase was separated, dried (MgSO₄), filtered and the solvent was evaporated in vacuo. Yield: 180 mg of crude intermediate 64 which was used as such in the next reaction step.

h) Preparation of Intermediate 74

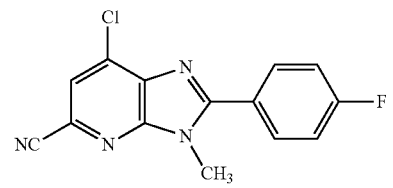 [SMILES: Cn1c(-c2ccc(F)cc2)nc2c(Cl)cc(C#N)nc21]

Zn(CN)₂ (36 mg, 0.31 mmol) and Pd(PPh₃)₄ (30 mg, 0.026 mmol) were added to a sol. of intermediate 61 (200 mg, 0.52 mmol) in DMF (5 ml). The resulting mixture was stirred and heated at 160° C. for 10 min. under microwave irradiation. The r.m. was cooled to r.t. and filtered through diatomaceous earth. The filtrate was concentrated in vacuo and the residue was purified by flash column chromatography over silica gel (eluent: DCM/MeOH(NH₃) 100/0 to 97/3). The product fractions were collected and the solvent was evaporated. Yield: 0.14 g of intermediate 74 (95%).

i) Preparation of Intermediate 75

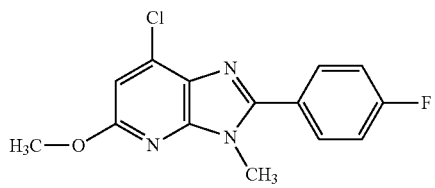 [SMILES: COc1cc(Cl)c2nc(-c3ccc(F)cc3)n(C)c2n1]

A mixture of intermediate 61 (200 mg, 0.52 mmol), 4,7-dimethoxy-[1,10]phenanthroline (25 mg, 0.1 mmol), and $Cs_2CO_3$ (336 mg, 1 mmol) in MeOH (1 ml) was degassed and stirred at 110° C. for 1 h under microwave irradiation. The r.m. was cooled to r.t. and concentrated in vacuo. The residue was partitioned between DCM and water. The organic phase was separated, dried ($MgSO_4$), filtered and the solvent was evaporated in vacuo. The residue was triturated with DIPE. Yield: 100 mg of intermediate 75 (66%).

j) Preparation of Intermediate 76

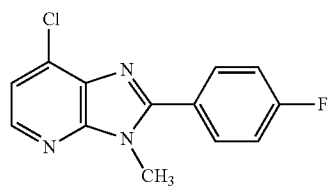 [SMILES: Cn1c(-c2ccc(F)cc2)nc2c(Cl)ccnc21]

THF (40 ml) was added to Pd/C 10% (0.1 g) under $N_2$ atmosphere. Subsequently, a 0.4% thiophene sol. in DIPE (1 ml) and intermediate 61 (800 mg, 2.06 mmol) were added. The r.m. was stirred at r.t. under $H_2$ atmosphere until 1 eq of $H_2$ was absorbed. The catalyst was filtered off over diatomaceous earth. The filtrate was evaporated and the residue was used as such in the next step. Yield: 0.45 g of intermediate 76 (83%).

Example A26 a) Preparation of Intermediate 65

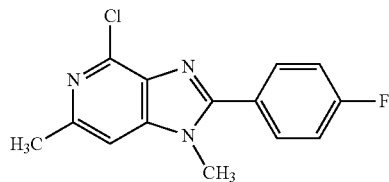

4-Fluorobenzaldehyde (1.11 g, 8.93 mmol) and $Na_2S_2O_4$ (3.89 g, 22.3 mmol) were added to a sol. of 2-chloro-N-6-dimethyl-3-nitro-pyridin-4-amine (1.5 g, 7.44 mmol) in EtOH (15 ml). The r.m. was heated under microwave conditions for 1 h at 160° C. The r.m. was cooled to r.t. and filtered through diatomaceous earth using EtOAc. This was repeated thrice. The combined filtrates were evaporated and the residue was purified by RP preparative HPLC [RP Vydec Denali C18 (10 μm, 250 g, I.D. 5 cm); mobile phase: a gradient of (0.25% $NH_4HCO_3$ sol. in water)/$CH_3CN$]. The product fractions were collected and worked up. Yield: 1.95 g of intermediate 65 (32%).

Example A27 a) Preparation of Intermediate 66

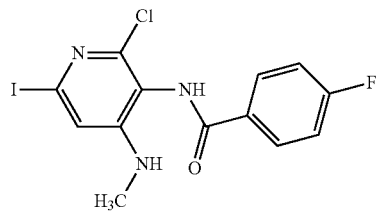 [SMILES: CNc1cc(I)nc(Cl)c1NC(=O)c1ccc(F)cc1]

$Et_3N$ (1.87 ml, 13.8 mmol) and 4-fluoro-benzoylchloride (873 mg, 5.5 mmol) were added to a sol. of intermediate 58 (1.3 g, 4.6 mmol) in DCM (80 ml, and the r.m. was stirred at r.t. for 4 h. The r.m. was concentrated in vacuo. Yield: 1.5 g of crude intermediate 66 (81%), which was used as such in the next reaction step.

b) Preparation of Intermediate 67

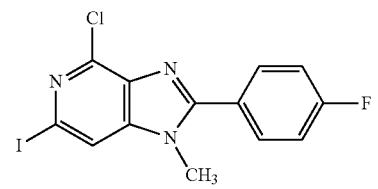

$POCl_3$ (121 mg, 0.79 mmol) was added to a sol. of intermediate 66 (267 mg, 0.66 mmol) in DCE (2 ml), and the resulting mixture was stirred and heated at 150° C. for 15 min under microwave irradiation. The r.m. was concentrated in vacuo, and the residue was purified by flash column chromatography over silica gel (eluent: DCM/MeOH($NH_3$) from 100/0 to 97/3). The product fractions were collected and the solvent was evaporated. Yield: 215 mg of intermediate 67 (84%).

c) Preparation of Intermediate 68

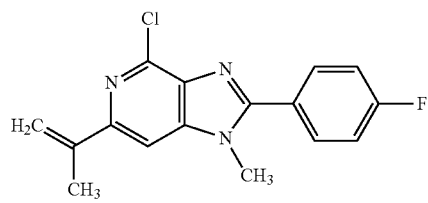

Isopropenylboronic acid pinacol ester (434 mg, 2.58 mmol) and $Pd(PPh_3)_4$ (149 mg, 0.129 mmol) was added to a sol. of intermediate 67 (1.0 g, 2.58 mmol) in dioxane (8 ml) and an aq. $NaHCO_3$ sol. (4 ml), and the resulting mixture was stirred and heated at 160° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH($NH_3$) from 100/0 to 97/3). The product fractions were collected and the solvent was evaporated. Yield: 0.72 g of intermediate 68 (92%).

d) Preparation of Intermediate 69

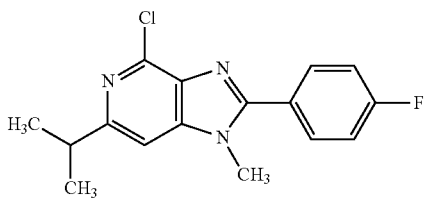 [SMILES: CC(C)c1cc2c(nc(-c3ccc(F)cc3)n2C)c(Cl)n1]

MeOH (40 ml) was added to Pt/C 5% (100 mg) under $N_2$ atmosphere. Subsequently, intermediate 68 (0.75 g, 2.49 mmol) was added. The r.m. was stirred at 25° C. under $H_2$ atmosphere until 1 eq of $H_2$ was absorbed. The catalyst was filtered off over diatomaceous earth and the filtrate was evaporated. Yield: 0.55 g of crude intermediate 69 (73%), which was used as such in the next reaction step.

e) Preparation of Intermediate 77

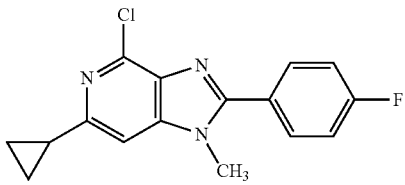 [SMILES: Cn1c(-c2ccc(F)cc2)nc2c(Cl)nc(C3CC3)cc21]

Cyclopropylboronic acid (86 mg, 1.0 mmol) and $Pd(PPh_3)_4$ (78 mg, 0.067 mmol) was added to a sol. of intermediate 67 (260 mg, 0.67 mmol) in dioxane (6 ml) and an aq. $NaHCO_3$ sol. (3 ml), and the resulting mixture was stirred and heated at 160° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH(NH$_3$) from 100/0 to 97/3). The product fractions were collected and the solvent was evaporated. Yield: 0.15 g of intermediate 77 (74%).

Example A28 a) Preparation of Intermediate 70

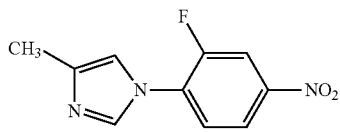 [SMILES: Cc1cn(-c2ccc([N+](=O)[O-])cc2F)cn1]

4-Methyl-1H-imidazole (37.2 g, 0.452 mol) and $K_2CO_3$ (62.5 g, 0.452 mol) were added to a sol. of 3,4-difluoronitrobenzene (60 g, 0.377 mol) in DMF (800 ml). The r.m. was heated at 125° C. for 4 h. The mixture was cooled and poured into ice-water. The solid was filtered off, washed ($H_2O$) and dried. Yield: 60.2 g of intermediate 70 (72%).

b) Preparation of Intermediate 71

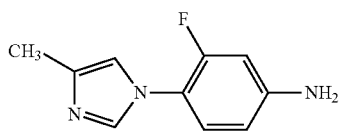

MeOH (250 ml) was added to Pd/C 10% (5 g) under $N_2$ atmosphere. Subsequently, a 0.4% thiophene sol. in DIPE (1 ml) and intermediate 71 (60.2 g, 272 mmol) were added. The r.m. was stirred at 50° C. under $H_2$ atmosphere until 3 eq of $H_2$ was absorbed. The catalyst was filtered off over diatomaceous earth. The filtrate was evaporated and the residue was purified by flash column chromatography over silica gel (eluent: DCM/MeOH(NH$_3$) from 100/0 to 95/5). The product fractions were collected and the solvent was evaporated. Yield: 36.5 g of intermediate 71 (70%).

Example A29 a) Preparation of Intermediate 72

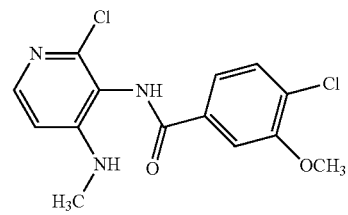 [SMILES: CNc1ccnc(Cl)c1NC(=O)c1ccc(Cl)c(OC)c1]

$Et_3N$ (2.65 ml, 19 mmol), and 3-amino-4-methylamino-2-chloropyridine (1500 mg, 9.52 mmol) were added to a sol. of HBTU (4.51 g, 11.9 mmol) and 4-chloro-3-methoxy-benzoic acid (1776 mg, 9.52 mmol) in DMF (30 ml). The r.m. was stirred at 70° C. for 16 h. The r.m. was diluted with DCM, and the mixture was washed with a sat. aq. $Na_2CO_3$.sol. and water. Yield: 1.8 g of crude intermediate 72 (58%), which was used as such in the next reaction step.

b) Preparation of Intermediate 73

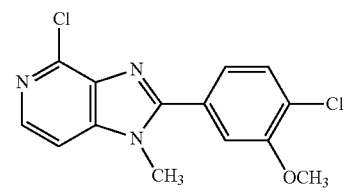

$POCl_3$ (1.05 ml, 11.5 mmol) was added to a sol. of intermediate 72 (1.7 g, 5.2 mmol) in DCE (16 ml). The r.m. was stirred and heated at 150° C. for 35 min. under microwave irradiation. The r.m. was diluted with DCM and washed with a sat. aq. $NaHCO_3$ sol. The organic phase was dried ($MgSO_4$), filtered and concentrated in vacuo. The residue was purified by flash column chromatography over silica gel (eluent: DCM/MeOH 100/0 to 90/10). The product fractions were collected and the solvent was evaporated. The residue was triturated with DIPE, then dissolved in DCM, and washed with a $Cs_2CO_3$ sol. The organic phase was dried ($MgSO_4$), filtered and concentrated in vacuo. Yield: 400 mg of intermediate 73 (25%).

Example A30 a) Preparation of Intermediate 78

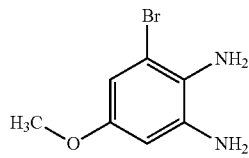

MeOH (150 ml) was added to Pt/C 5% (1 g) under $N_2$ atmosphere. Subsequently, a 0.4% thiophene sol. in DIPE (2 ml) and 2-bromo-4-methoxy-6-nitroaniline (5 g, 20.2 mmol) were added. The r.m. was stirred at 25° C. under $H_2$ atmosphere until 3 eq of $H_2$ was absorbed. The catalyst was filtered off over diatomaceous earth and the filtrate was concentrated in vacuo. Yield: 4.33 g of intermediate 78 (99%), which was used as such in the next reaction step.

b) Preparation of Intermediate 79

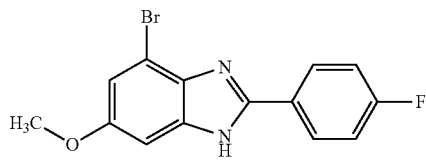 [SMILES: COc1cc(Br)c2nc(-c3ccc(F)cc3)[nH]c2c1]

4-Fluoro-benzaldehyde (1.17 ml, 11.1 mmol) and $Na_2S_2O_5$ (2.63 g, 13.8 mmol) were added to a sol. of intermediate 78 (2 g, 9.2 mmol) in DMA (40 ml). The r.m. was stirred at 90° C. overnight. Then, the r.m. was poured into water, resulting in the precipitation of a solid. The solid was filtered off, washed with water, and suspended in DIPE. The resulting solid was filtered off, washed with DIPE, and dried. Yield: 2.9 g of intermediate 79 (98%).

c) Preparation of Intermediate 80

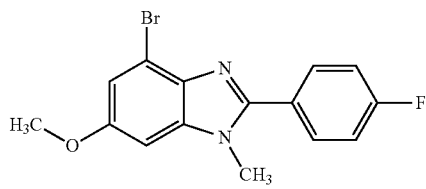 [SMILES: COc1cc(Br)c2nc(-c3ccc(F)cc3)n(C)c2c1]

A suspension of 60% NaH in mineral oil (486 mg, 12.1 mmol) was added under a $N_2$ atmosphere to a sol. of intermediate 79 (2.6 g, 8.1 mmol) in DMF (15 ml) at 5° C. The r.m. was stirred at 5° C. for 30 min, and then $CH_3I$ (1.26 ml, 20.2 mmol) was added. The r.m. was stirred at r.t. for 3 h., and partitioned between EtOAc and water. The organic phase was separated, dried ($MgSO_4$), filtered and the solvent was evaporated in vacuo. The residue was purified by flash column chromatography over silica gel (eluent: DCM/MeOH 100/0 to 99/1). The product fractions were collected and the solvent was evaporated. Yield: 1.25 g of intermediate 80 (46%).

Example A31 a) Preparation of Intermediate 81

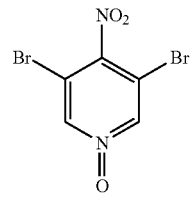

Concentrated $HNO_3$ (12.5 ml) was added to a sol. of 3,5-dibromo-pyridine N-oxide (4.5 g, 17.8 mmol) in concentrated $H_2SO_4$ (16 ml). The r.m. was refluxed for 4 h, then cooled and poured onto ice-water. The precipitate was collected by filtration and dried. Yield: 3.1 g of intermediate 81 (58%), which was used as such in the next step.

b) Preparation of Intermediate 82

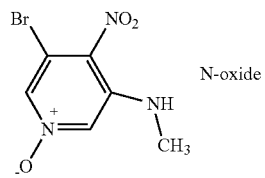

A 2 M sol. of methylamine in THF (7.15 ml, 14.3 mmol) was added to a mixture of intermediate 81 (2.66 g, 8.9 mmol) in THF (100 ml). The r.m. was stirred at 60° C. for 2 days and was then concentrated in vacuo. The residue was partitioned between DCM and an aq. $NaHCO_3$ sol. The organic phase was separated, dried ($Na_2SO_4$), filtered and the solvent was evaporated in vacuo. The residue was purified by flash column chromatography over silica gel (eluent: heptane/DCM/MeOH($NH_3$) 100/0/0 to 0/100/0 to 0/70/30). The product fractions were collected and the solvent was evaporated. Yield: 1.2 g of intermediate 82 (54%; N-oxide).

c) Preparation of Intermediate 83

4-Fluorobenzaldehyde (252 mg, 2.0 mmol) and $Na_2S_2O_4$ (1.18 g, 6.8 mmol) were added to a sol. of intermediate 82 (420 mg, 1.7 mmol) in EtOH (6 ml). The r.m. was heated under microwave conditions at 160° C. for 45 min. The r.m. was cooled to r.t. and diluted with EtOAc. The mixture was washed with an aq. NaHCO3 sol. and brine. The organic phase was separated, dried ($MgSO_4$), filtered and the solvent was evaporated in vacuo. The residue was purified by flash column chromatography over silica gel (eluent: DCM/MeOH ($NH_3$) 100/0 to 97/3). The product fractions were collected and the solvent was evaporated. Yield: 0.35 g of intermediate 83 (68%).

Example A32 a) Preparation of Intermediate 84

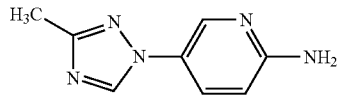

CuI (1.71 g, 8.9 mmol) and N,N'-dimethylethylenediamine (1.91 ml, 17.92 mmol) were added to a mixture of 2-amino-5-iodopyridine (5.03 g, 22.4 mmol), 3-methyl-1H-1,2,4-triazole (2.42 g, 29.1 mmol), and $Cs_2CO_3$ (14.60 g, 44.81 mmol) in DMF (40 ml). The r.m. was heated at 110° C. for 7 h., the r.m. was cooled, EtOAc was added and the mixture was washed with water. The water layer was extracted 5 times with EtOAc. The combined organic layers were dried ($MgSO_4$), filtered and the solvent was evaporated in vacuo. The residue was purified by RP preparative HPLC [RP Shandon Hyperprep® C18 BDS (8 µm, 250 g, I.D. 5 cm); mobile phase: a gradient of (0.25% $NH_4HCO_3$ solution in water)/MeOH/$CH_3CN$]. The product fractions were collected and the solvent was evaporated. Yield: 1.5 g of intermediate 84 (38%).

b) Preparation of Intermediate 85

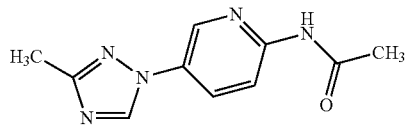 [SMILES: CC(=O)Nc1ccc(-n2cnc(C)n2)cn1]

Intermediate 84 (3.3 g, 18.8 mmol) was dissolved in THF (20 ml), $Et_3N$ (13.1 ml, 94.2 mmol) and acetic anhydride (17.8 ml, 188.4 mmol) were added. The r.m. was stirred at 65° C. for 18 h. The r.m. was cooled to r.t. and concentrated in vacuo. The residue was suspended in DIPE. The resulting solid was filtered off, washed with DIPE, and dried. Yield: 3.25 g of intermediate 85 (79%).

c) Preparation of Intermediate 86

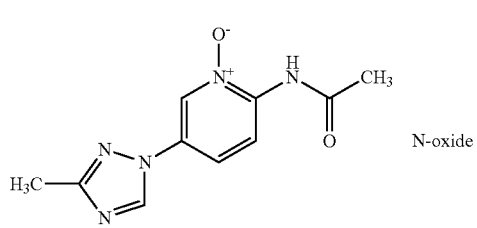 [SMILES: CC(=O)Nc1ccc(-n2cnc(C)n2)c[n+]1[O-]]

N-oxide

Intermediate 85 (10 g, 46.0 mmol) was dissolved in DCM (500 ml) and mCPBA (14.75 g, 59.84 mmol) was added. The r.m. was stirred at r.t. for 18 h. DCM and a sol. of 10% $NaHCO_3$ in water was added. The organic phase was separated, and washed twice with a solution of 10% $NaHCO_3$ in water. The combined water layers were extracted 10× with DCM. The combined organic layers were dried ($MgSO_4$), filtered and the solvent was evaporated in vacuo. Yield: 10.1 g of intermediate 86 (94%; N-oxide).

d) Preparation of Intermediate 87

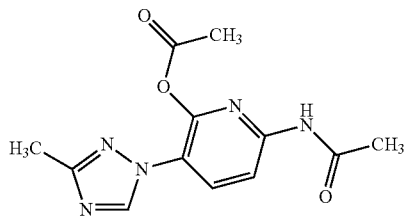 [SMILES: CC(=O)Nc1ccc(-n2cnc(C)n2)c(OC(C)=O)n1]

Intermediate 86 (10.1 g, 43.3 mmol) was dissolved in acetic anhydride (307 ml, 3.25 mol). The r.m. was stirred at 80° C. for 2 h. The r.m. was cooled to r.t. and concentrated in vacuo. The residue was suspended in DIPE. The resulting solid was filtered off. Yield: 10.5 g of crude intermediate 87, which was used as such in the next step.

e) Preparation of Intermediate 88

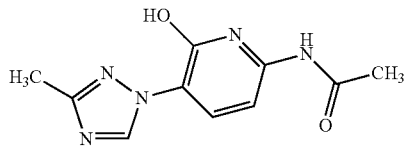 [SMILES: CC(=O)Nc1ccc(-n2cnc(C)n2)c(O)n1]

Intermediate 87 (2.5 g, 9.1 mmol) and $K_2CO_3$ (1.26 g, 9.1 mmol) were added to MeOH (30 ml). The r.m. was stirred at r.t. for 1 h. The residue was directly purified (without evaporation of the solvent) by flash column chromatography over silica gel (eluent: DCM/MeOH from 100/0 to 90/10). The product fractions were collected and the solvent was evaporated in vacuo. The residue was suspended in DIPE. The solid was filtered off, washed with DIPE, and dried. Yield: 1 g of intermediate 88 (47%).

f) Preparation of Intermediate 89

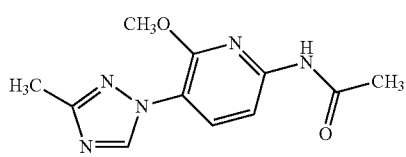

Intermediate 88 (1 g, 4.28 mmol), $CH_3I$ (0.4 ml, 6.43 mmol), and $Ag_2CO_3$ (1.18 g, 4.29 mmol) were added to DMF (50 ml). The resulting mixture was stirred at 60° C. for 4 h. The r.m. was cooled to r.t., and filtered through diatomaceous earth and concentrated in vacuo. The residue was purified by flash column chromatography over silica gel (eluent: DCM/EtOAc from 100/0 to 0/100). The product fractions were collected and the solvent was evaporated. Yield: 450 mg of intermediate 89 (42%).

g) Preparation of Intermediate 90

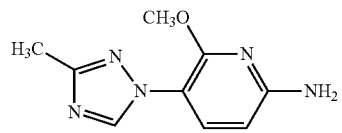

Intermediate 89 (1.1 g, 4.45 mmol) was dissolved in MeOH (120 ml) and NaOH 10% in water (30 ml) was added.

The r.m. was stirred at 80° C. for 3 h. The r.m. was cooled to r.t. and concentrated in vacuo. The residue was partitioned between DCM and water.

The organic layer was dried (MgSO$_4$), filtered and concentrated in vacuo. Yield: 870 mg of intermediate 90 (95%).

Example A33

Preparation of Intermediate 91

Intermediate 14 (14 g, 40.75 mmol) was partitioned between DCM and an aq. NH$_4$OH solution. The organic layer was dried (MgSO$_4$), filtered and concentrated in vacuo. The residue was dissolved in 2-methyl-2-propanol (750 ml), and intermediate 45 (8.32 g, 40.75 mmol), Pd$_2$(dba)$_3$ (3.73 g, 4.08 mmol), X-Phos (5.83 g, 12.2 mmol) and Cs$_2$CO$_3$ (40 g, 122 mmol) were added. The r.m. was purged with N$_2$, and subsequently heated at reflux for 16 h. The hot mixture was filtered, and the filtrate was concentrated in vacuo. The residue was suspended in DCM, and the resulting mixture filtered over diatomaceous earth. The filtrate was washed with a dilute aq. NaHCO$_3$ sol., followed by water. The organic layer was dried (MgSO$_4$), filtered and concentrated in vacuo. The residue was purified by flash column chromatography over silica gel (eluent: DCM/MeOH(NH$_3$) from 100/0 to 97/3). The product fractions were collected and the solvent was evaporated. The residue was triturated with a mixture of DIPE and 2-propanol. Yield: 4.5 g of intermediate 91 (30%).

Example A34 a) Preparation of Intermediate 92

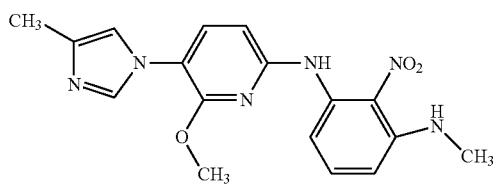

Intermediate 45 (2.02 g, 9.9 mmol), Pd$_2$(dba)$_3$ (635 mg, 0.7 mmol), X-Phos (992 mg, 2.08 mmol) and Cs$_2$CO$_3$ (9.7 g, 29.7 mmol) were added to a sol. of intermediate 10 (2.29 g, 9.9 mmol) in 2-methyl-2-propanol (100 ml) under a N$_2$ atmosphere. The r.m. was purged with N$_2$, and subsequently heated at reflux for 16 h. The hot mixture was filtered, and the filtrate was concentrated in vacuo. The residue was partitioned between DCM and a diluted aq. NaHCO$_3$ solution, followed by water. The organic layer was dried (MgSO$_4$), filtered and concentrated in vacuo. The residue was purified by flash column chromatography over silica gel (eluent: DCM/MeOH(NH$_3$) from 100/0 to 97/3). The product fractions were collected and the solvent was evaporated. Yield: 1.3 g of intermediate 92 (37%).

b) Preparation of Intermediate 93

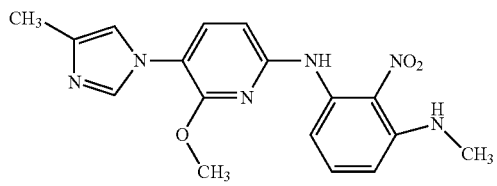

A mixture of intermediate 92 (354 mg, 1 mmol) and iron powder (223 mg, 4 mmol) in AcOH was stirred at 60° C. for 1 h. The mixture was cooled and filtered, and the filtrate was concentrated in vacuo. The residue was partitioned between DCM and an aq. K$_2$CO$_3$ solution. The organic layer was dried (MgSO$_4$), filtered and concentrated in vacuo. Yield: 324 mg of crude intermediate 93, which was used as such in the next reaction step.

Example A35

Preparation of Intermediate 94

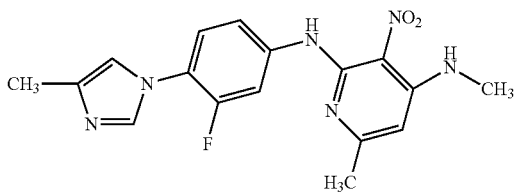

A mixture of 2-chloro-N-6-dimethyl-3-nitro-pyridin-4-amine (600 mg, 2.98 mmol) and intermediate 71 (1.14 g, 5.95 mmol) in DMA (12 ml) was heated under microwave conditions for 5 h at 140° C. followed by 90 min at 160° C. The r.m. was cooled to r.t. and poured into water. The resulting precipitate was filtered off, washed with water, and dried. Yield: 528 mg of intermediate 94 (50%).

Example A36 a) Preparation of Intermediate 95

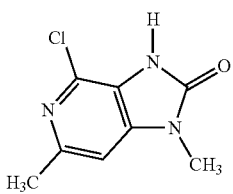

A mixture of 2-chloro-N-4,6-dimethyl-3,4-pyridinediamine, (2.99 g, 17.4 mmol) and urea (1.31 g, 21.8 mmol) in xylene (40 ml) was stirred at reflux overnight. The r.m. was cooled, and the resulting precipitate collected by filtration and washed with water. The solid was triturated with DIPE. Yield: 3.15 g of intermediate 95, which was used as such in the next reaction step.

b) Preparation of Intermediate 96

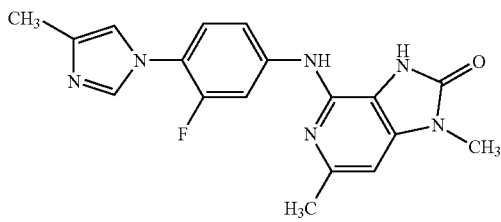 [SMILES: Cc1cn(-c2ccc(Nc3nc(C)cc4c3[nH]c(=O)n4C)cc2F)cn1]

Intermediate 71 (592 mg, 3.1 mmol), Pd$_2$(dba)$_3$ (334 mg, 0.36 mmol), X-Phos (347 mg, 0.73 mmol) and Cs$_2$CO$_3$ (3.56 g, 10.9 mmol) were added to a sol. of intermediate 95 (1 g, 1.7 mmol) in 2-methyl-2-propanol (35 ml) under a N$_2$ atmosphere. The r.m. was heated at 100° C. overnight. More Pd$_2$(dba)$_3$ (334 mg, 0.36 mmol), X-Phos (347 mg, 0.73 mmol) were added and the r.m. was again stirred at 100° C. overnight. Again, extra Pd$_2$(dba)$_3$ (174 mg, 0.18 mmol), X-Phos (167 mg, 0.37 mmol) were added and the r.m. was again stirred at 100° C. overnight. The mixture was cooled and partitioned between DCM and water. The organic layer was dried (MgSO$_4$), filtered and concentrated in vacuo. The residue was purified by flash column chromatography over silica gel (eluent: DCM/MeOH(NH$_3$) from 100/0 to 97/3). The product fractions were collected and the solvent was evaporated. Yield: 300 mg of intermediate 96 (50%).

c) Preparation of Intermediate 97

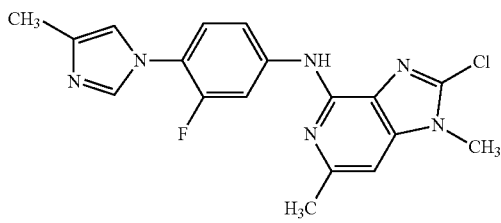 [SMILES: Cc1cn(-c2ccc(Nc3nc(C)cc4c3nc(Cl)n4C)cc2F)cn1]

POCl$_3$ (10 ml) was added intermediate 96 (1.03 g, 2.8 mmol) and the r.m. was heated at 115° C. for 24 h. The r.m. was concentrated in vacuo. The residue was neutralized with a sat. aq. NaHCO$_3$ sol., and extracted with EtOAc The organic layer was dried (MgSO$_4$), filtered and concentrated in vacuo. Yield: 635 mg of crude intermediate 97 which was used as such in the next reaction step.

Example A37 a) Preparation of Intermediate 98

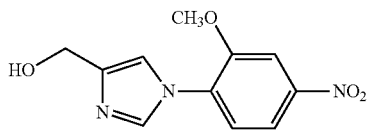

A mixture of 1-fluoro-2-methoxy-4-nitrobenzene (2.45 g, 14.3 mmol), 4-hydroxymethyl-1H-imidazole (1.54 g, 15.7 mmol) and K$_2$CO$_3$ (3.95 g, 28.6 mmol) in DMF (20 ml) was stirred at 100° C. for 16 h. The mixture was concentrated in vacuo, and the residue was partitioned between EtOAc and water. Undissolved material was collected by filtration and dissolved in a mixture of THF and CH$_3$CN. The combined organic layers were dried (MgSO$_4$), filtered and the solvent was evaporated. The residue was triturated in DIPE/2-propanol, filtered off and dried. Yield: 1.2 g of intermediate 98 which was used as such in the next reaction step.

b) Preparation of Intermediate 99

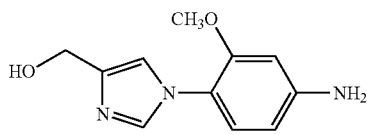

MeOH (100 ml) was added to Pd/C 10% (0.5 g) under N$_2$ atmosphere. Subsequently, a 0.4% thiophene sol. in DIPE (2 ml) and intermediate 98 (1.2 g, 3.4 mmol) were added. The r.m. was stirred at 25° C. under H$_2$ atmosphere until 3 eq of H$_2$ was absorbed. The catalyst was filtered off over diatomaceous earth. The filtrate was evaporated. Yield: 0.56 g of intermediate 99, which was used as such in the next reaction step.

Example A38 a) Preparation of Intermediate 100

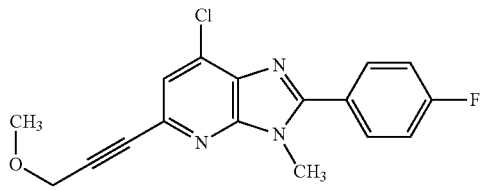 [SMILES: COCC#Cc1cc(Cl)c2nc(-c3ccc(F)cc3)n(C)c2n1]

A mixture of intermediate 61 (500 mg, 1.29 mmol), 3-methoxy-propyne (99 mg, 1.4 mmol), PdCl$_2$(PPh$_3$)$_2$ (36 mg, 0.05 mmol) and CuI (9 mg, 0.049 mmol) in Et$_3$N (6 ml) was stirred at 50° C. for 20 h under a N$_2$ atmosphere. The mixture was concentrated in vacuo, and the residue was partitioned between DCM and water. The organic layer was dried (MgSO$_4$), filtered, and concentrated in vacuo. The residue was purified by column chromatography over silicagel (eluent: DCM/MeOH 99/1). The product fractions were collected and the solvent was evaporated in vacuo. Yield: 440 mg of intermediate 100 (quantitative).

b) Preparation of Intermediate 41

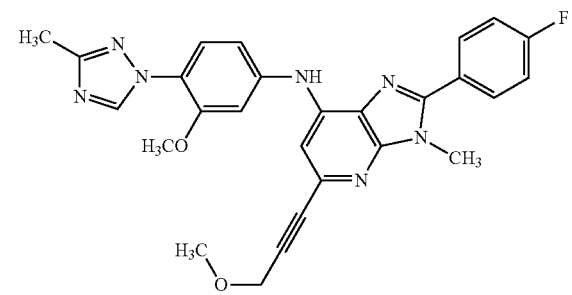 [SMILES: COCC#Cc1cc(Nc2ccc(-n3cnc(C)n3)c(OC)c2)c2nc(-c3ccc(F)cc3)n(C)c2n1]

Intermediate 5 (62 mg, 0.3 mmol), Pd$_2$(dba)$_3$ (28 mg, 0.03 mmol), X-phos (28 mg, 0.06 mmol) and Cs$_2$CO$_3$ (300 mg, 0.91 mmol) were added to a solution of intermediate 100 (100 mg, 0.3 mmol) in 2-methyl-2-propanol (15 ml) under a N$_2$ atmosphere. The r.m. was heated at 100° C. for 20 h. Then, the r.m. was cooled, water was added and the mixture was extracted with DCM. The combined organic layers were dried (MgSO$_4$), filtered and the solvent was evaporated. The residue was purified by flash chromatography over silicagel (eluent: DCM/MeOH(NH₃) from 100/0 to 99/1). The product fractions were collected and the solvent was evaporated in vacuo. Yield: 140 mg of intermediate 41 (93%).

B. Preparation of the Compounds

Example B1

Preparation of Compound 1

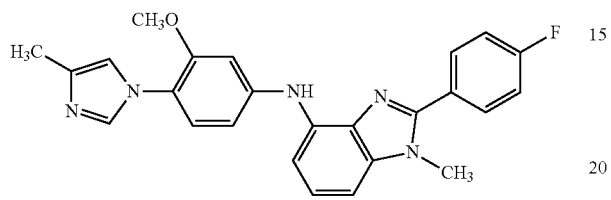

2-Methyl-2-propanol, sodium salt (0.299 g, 3.1 mmol), BINAP (97 mg, 0.16 mmol), Pd(OAc)₂ (23 mg, 0.1 mmol) and intermediate 24 (332 mg, 1.24 mmol) were added to a sol. of 1-(4-bromo-2-methoxyphenyl)-4-methyl-1H-imidazole (250 mg, 1.04 mmol) in toluene (10 ml) and the mixture was purged with N₂ for 5 min. The r.m. was stirred and heated at 100° C. overnight under a N₂ atmosphere. Then, the r.m. was cooled to r.t., water was added, and the mixture was extracted with DCM. The combined organic layers were dried (MgSO₄), filtered and concentrated in vacuo. The residue was purified by flash column chromatography over silica gel (eluent: DCM/MeOH(NH₃) from 100/0 to 97/3). The product fractions were collected and the solvent was evaporated. The residue was triturated with DIPE. The solid was collected and dried in vacuo. Yield: 0.28 g of compound 1 (63%).

Example B2

Preparation of Compound 2

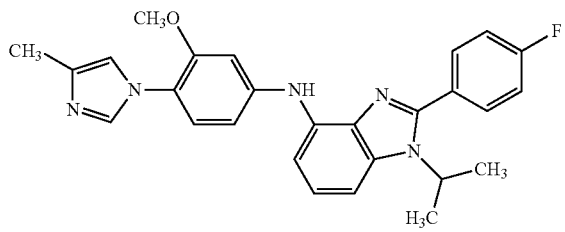

Pd₂(dba)₃ (14 mg, 0.015 mmol) and X-Phos (34 mg, 0.06 mmol) were added to a N₂ purged mixture of 1-(4-bromo-2-methoxyphenyl)-4-methyl-1H-imidazole (51 mg, 0.19 mmol), intermediate 26 (40 mg, 0.15 mmol), and Cs₂CO₃ (97 mg, 0.3 mmol) in toluene (5 ml). The r.m. was heated at 100° C. overnight under a N₂ atmosphere. Then, the solvent was evaporated and the residue was partitioned between water and DCM. The combined organic layers were dried (MgSO₄), filtered and concentrated in vacuo. The residue was purified by RP preparative HPLC [RP Shandon Hyperprep® C18 BDS (8 μm, 250 g, I.D. 5 cm); mobile phase: a gradient of (0.25% NH₄HCO₃ sol. in water)/MeOH/CH₃CN]. The product fractions were collected and worked up. Yield: 30 mg of compound 2 (44%).

Example B3

Preparation of Compound 3

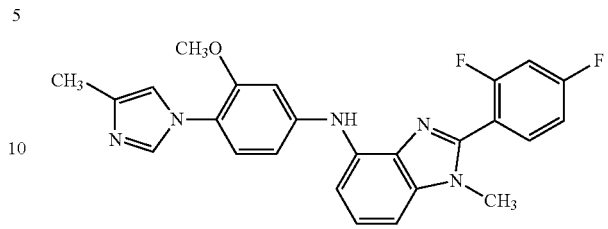

2-Methyl-2-propanol, sodium salt (207 mg, 2.15 mmol), BINAP (25 mg, 0.04 mmol), Pd(OAc)₂ (6 mg, 0.027 mmol) and 1-(4-bromo-2-methoxyphenyl)-4-methyl-1H-imidazole (215 mg, 0.81 mmol) were added to a sol. of intermediate 52 (139 mg, 0.54 mmol) in toluene (10 ml), and the mixture was purged with N₂. The r.m. was stirred and heated at 150° C. for 1 h under microwave irradiation. Then, the r.m. was cooled to r.t., water was added, and the mixture was extracted with DCM. The combined organic layers were dried (MgSO₄), filtered and concentrated in vacuo. The residue was purified by RP preparative HPLC [RP Shandon Hyperprep® C18 BDS (8 μm, 250 g, I.D. 5 cm); mobile phase: a gradient of (0.25% NH₄HCO₃ sol. in water)/MeOH/CH₃CN]. The product fractions were collected and worked up. Yield: 67 mg of compound 3 (28%).

Example B4

Preparation of Compound 4

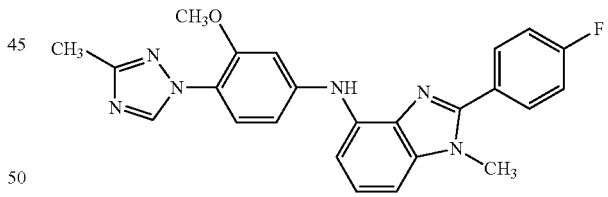

Intermediate 5 (340 mg, 1.66 mmol), Pd₂(dba)₃ (152 mg, 0.166 mmol), X-Phos (173 mg, 0.366 mmol) and Cs₂CO₃ (1.63 g, 5 mmol) were added to a sol. of intermediate 12 (508 mg, 1.66 mmol) in 2-methyl-2-propanol (25 ml) under a N₂ atmosphere. The r.m. was heated at 110° C. for 2 h. Then, the r.m. was cooled to r.t., water was added and the mixture was extracted with DCM. The combined organic layers were dried (MgSO₄), filtered and the solvent was evaporated. The residue was purified by RP preparative HPLC [RP Shandon Hyperprep® C18 BDS (8 μm, 250 g, I.D. 5 cm); mobile phase: a gradient of (0.25% NH₄HCO₃ sol. in water)/MeOH/CH₃CN]. The product fractions were collected and worked up. The residue was triturated with DIPE. The solid was collected and dried in vacuo. Yield: 0.31 g of compound 4 (44%).

Example B5

Preparation of Compound 5

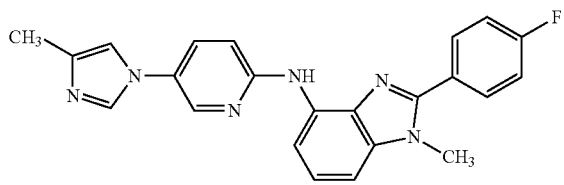 [SMILES: Cc1cn(-c2ccc(Nc3cccc4c3nc(-c3ccc(F)cc3)n4C)nc2)cn1]

Intermediate 30 (155 mg, 0.89 mmol), Pd$_2$(dba)$_3$ (71 mg, 0.077 mmol), X-Phos (81 mg, 0.17 mmol) and Cs$_2$CO$_3$ (757 mg, 2.32 mmol) were added to a sol. of intermediate 12 (236 mg, 0.77 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH(NH$_3$) from 100/0 to 98/2). The product fractions were collected and the solvent was evaporated. The residue was partitioned between an aq. NH$_4$OH sol. and DCM. The combined organic layers were dried (MgSO$_4$), filtered and the solvent was evaporated. Yield: 0.05 g of compound 5 (16%).

Example B6

Preparation of Compound 6

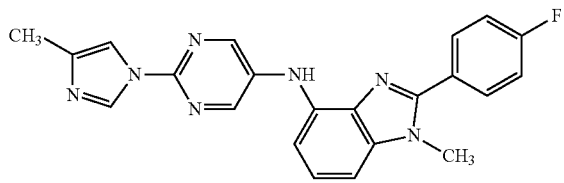 [SMILES: Cc1cn(-c2ncc(Nc3cccc4c3nc(-c3ccc(F)cc3)n4C)cn2)cn1]

Intermediate 29 (70 mg, 0.4 mmol), Pd$_2$(dba)$_3$ (50 mg, 0.055 mmol), X-Phos (58 mg, 0.12 mmol) and Cs$_2$CO$_3$ (537 mg, 1.65 mmol) were added to a sol. of intermediate 12 (168 mg, 0.55 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH(NH$_3$) from 100/0 to 98/2). Yield: 0.075 g of compound 6 (34%).

Example B7

Preparation of Compound 7

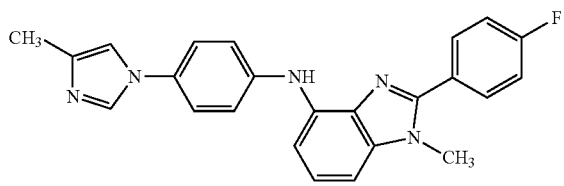

1-(4-aminophenyl)-4-methyl-1H-imidazole (130 mg, 0.75 mmol), Pd$_2$(dba)$_3$ (60 mg, 0.065 mmol), X-Phos (69 mg, 0.144 mmol) and Cs$_2$CO$_3$ (641 mg, 1.97 mmol) were added to a sol. of intermediate 12 (200 mg, 0.65 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH (NH$_3$) from 100/0 to 98/2). The product fractions were collected and concentrated in vacuo. The residue was purified further by RP preparative SFC [RP Shandon Hyperprep® C18 BDS (8 μm, 250 g, I.D. 5 cm); mobile phase: 35% MeOH (with 0.2% isopropylamine), 65% CO$_2$. The product fractions were collected and worked up. Yield: 0.052 g of compound 7 (20%).

Example B8

Preparation of Compound 8

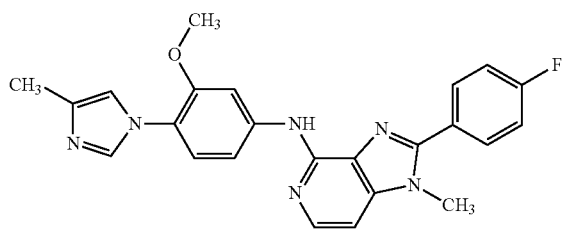 [SMILES: COc1cc(Nc2nccc3c2nc(-c2ccc(F)cc2)n3C)ccc1-n1cnc(C)c1]

Intermediate 2a (93 mg, 0.457 mmol), Pd$_2$(dba)$_3$ (42 mg, 0.046 mmol), X-Phos (58 mg, 0.1 mmol) and Cs$_2$CO$_3$ (456 mg, 1.4 mmol) were added to a sol. of intermediate 35 (140 mg, 0.457 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH from 100/0 to 99/1). The residue was treated with DIPE and a drop CH$_3$CN to provide a solid. Yield: 0.063 g of compound 8 (32%).

Example B9 a1) Preparation of Compound 212

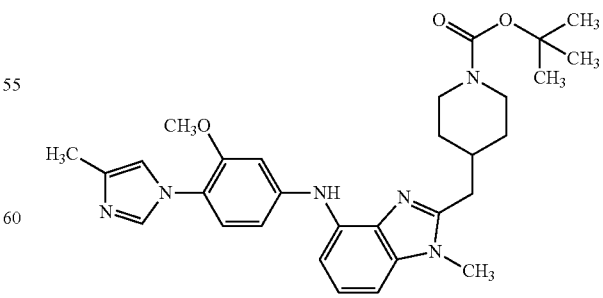

Intermediate 2a (2.01 g, 6.17 mmol), Pd$_2$(dba)$_3$ (188 mg, 0.206 mmol), dicyclohexyl[2',4',6'-tris(1-methylethyl)[1,1'-biphenyl]-2-yl]phosphine (216 mg, 0.453 mmol) and $Cs_2CO_3$ (1.63 g, 5 mmol) were added to a sol. of intermediate 40 (840 mg, 1.83 mmol) in 2-methyl-2-propanol (40 ml) under a $N_2$ atmosphere. The r.m. was heated for 20 h at 110° C. Then, the r.m. was cooled to r.t., water was added and the mixture was extracted with DCM. The combined organic layers were dried ($MgSO_4$), filtered and the solvent was evaporated. The residue was purified by flash column chromatography over silica gel (eluent: DCM/MeOH($NH_3$) from 100/0 to 96/4). The product fractions were collected and the solvent was evaporated. Yield: 0.685 g of compound 212 (70%).

a2) Preparation of Compound 9

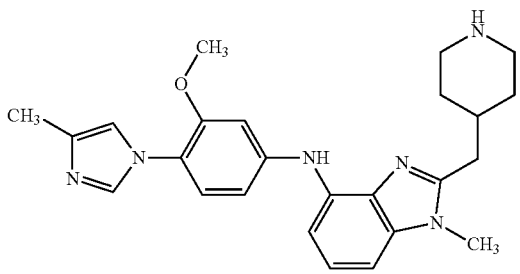 [SMILES: COc1cc(Nc2cccc3c2nc(CC2CCNCC2)n3C)ccc1-n1cnc(C)c1]

Compound 212 (660 mg, 1.24 mmol) was added to a mixture of DCM (5 ml) and TFA (5 ml). The r.m. was stirred at r.t. for 6 h. The r.m. was concentrated in vacuo, and the residue was partitioned between DCM and a sat. aq. $NaHCO_3$ sol. The organic layer was dried ($MgSO_4$), filtered and concentrated in vacuo. Yield 430 mg of compound 9 (80%), which was used as such in the following steps. 80 mg was purified further by RP preparative HPLC [RP Shandon Hyperprep® C18 BDS (10 μm, 250 g, I.D. 5 cm); mobile phase: a gradient of (0.25% $NH_4HCO_3$ sol. in water)/MeOH/$CH_3CN$]. The product fractions were collected and worked up to yield: 47 mg of pure compound 9.

b) Preparation of Compound 10

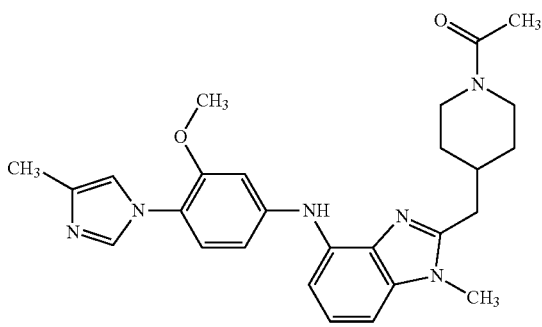 [SMILES: COc1cc(Nc2cccc3c2nc(CC2CCN(C(C)=O)CC2)n3C)ccc1-n1cnc(C)c1]

To a sol. of compound 9 (65 mg, 0.15 mmol) in DCM (5 ml) was added acetic acid anhydride (16 mg, 0.15 mmol). The r.m. was stirred at r.t. for 30 min. The r.m. was treated with water (1 ml) and then dried by filtration over an Isolute® HM-N filter. The organic layer was evaporated. The residue was purified by RP preparative HPLC [RP Shandon Hyperprep® C18 BDS (10 μm, 250 g, I.D. 5 cm); mobile phase: a gradient of (0.25% $NH_4HCO_3$ sol. in water)/MeOH/$CH_3CN$]. The product fractions were collected and worked up. Yield 41 mg of compound 10 (58%).

c) Preparation of Compound 11

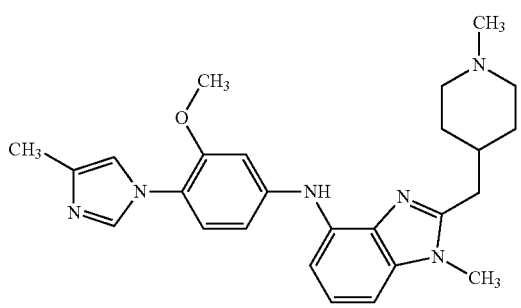 [SMILES: COc1cc(Nc2cccc3c2nc(CC2CCN(C)CC2)n3C)ccc1-n1cnc(C)c1]

A mixture of compound 9 (70 mg, 0.163 mmol), a formaldehyde sol. in water (37 weight %, 0.054 ml, 0.65 mmol), in DCE (1.5 ml) and MeOH (1.5 ml) was cooled to 0° C. Sodium triacetoxyborohydride (69 mg, 0.325 mmol) was added to this mixture, and the r.m. was stirred at r.t. for 16 h. Then, the r.m. was partitioned between DCM and water. The organic layer was dried ($MgSO_4$), filtered and concentrated in vacuo.

The residue was purified by RP preparative HPLC [RP Shandon Hyperprep® C18 BDS (10 μm, 250 g, I.D. 5 cm); mobile phase: a gradient of (0.25% $NH_4HCO_3$ sol. in water)/MeOH]. The product fractions were collected and worked up. Yield 8 mg of compound 11 (10%).

Example B10

Preparation of Compound 12

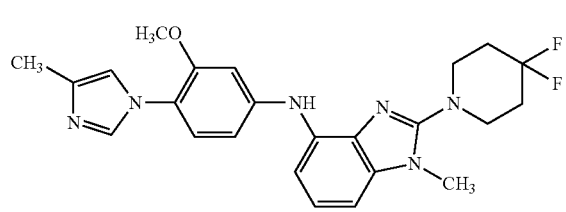 [SMILES: COc1cc(Nc2cccc3c2nc(N2CCC(F)(F)CC2)n3C)ccc1-n1cnc(C)c1]

Intermediate 2a (123 mg, 0.61 mmol), $Pd_2(dba)_3$ (56 mg, 0.061 mmol), X-Phos (63 mg, 0.13 mmol) and $Cs_2CO_3$ (592 mg, 1.82 mmol) were added to a sol. of intermediate 15 (200 mg, 0.61 mmol) in 2-methyl-2-propanol (15 ml) under a $N_2$ atmosphere. The r.m. was heated at 110° C. for 6 h. Then, the r.m. was cooled to r.t., water was added and the mixture was extracted with EtOAc. The combined organic layers were dried ($MgSO_4$), filtered and concentrated in vacuo. The residue was purified by RP preparative HPLC [RP Shandon Hyperprep® C18 BDS (8 μm, 250 g, I.D. 5 cm); mobile phase: a gradient of (0.25% $NH_4HCO_3$ sol. in water)/MeOH/$CH_3CN$]. The product fractions were collected and worked up. Yield 90 mg of compound 12 (33%).

Example B11

Preparation of Compound 13

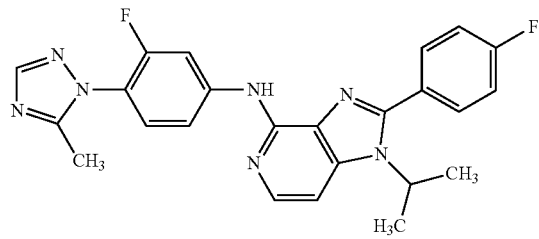 [SMILES: Cc1ncnn1-c1ccc(Nc2nccc3c2nc(-c2ccc(F)cc2)n3C(C)C)cc1F]

Cs₂CO₃ (472 mg, 1.45 mmol), X-Phos (46 mg, 0.097 mmol) and Pd₂(dba)₃ (44 mg, 0.048 mmol), were added to a sol. of intermediate 37 (140 mg, 0.483 mmol) and intermediate 9 (93 mg, 0.483 mmol) in 2-methyl-2-propanol (5 ml) under a N₂ atmosphere. The r.m. was heated at 100° C. for 16 h. Then, the r.m. was cooled to r.t., water was added and the mixture was extracted with DCM. The combined organic layers were dried (MgSO₄), filtered and concentrated in vacuo. The residue was purified by RP preparative HPLC [RP Vydac DenaliC18 (10 µm, 250 g, I.D. 5 cm); mobile phase: a gradient of (0.25% NH₄HCO₃ sol. in water)/MeOH]. The product fractions were collected and worked up. Yield 51 mg of compound 13 (24%).

Example B12

Preparation of Compound 14

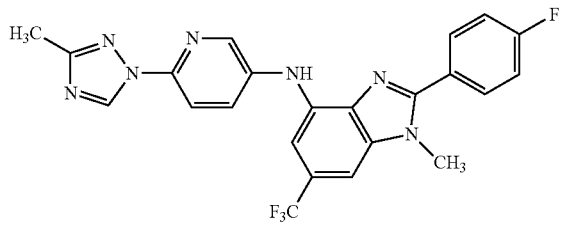 [SMILES: Cc1ncn(-c2ccc(Nc3cc(C(F)(F)F)cc4c3nc(-c3ccc(F)cc3)n4C)cn2)n1]

Intermediate 31 (113 mg, 0.643 mmol), Cs₂CO₃ (629 mg, 1.93 mmol), X-Phos (61 mg, 0.129 mmol) and Pd₂(dba)₃ (59 mg, 0.064 mmol), were added to a sol. of intermediate 39 (240 mg, 0.643 mmol) in 2-methyl-2-propanol (10 ml) under a N₂ atmosphere. The r.m. was heated at 110° C. for 16 h. Then, the r.m. was cooled to r.t., water was added and the mixture was extracted with DCM. The combined organic layers were dried (MgSO₄), filtered and concentrated in vacuo. The residue was purified by flash column chromatography over silica gel (eluent: DCM/MeOH from 100/0 to 98/2). The residue was treated with DIPE to provide a solid. Yield: 0.2 g of compound 14 (66%).

Example B13

Preparation of Compound 15

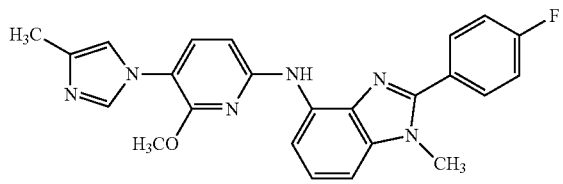 [SMILES: COc1nc(Nc2cccc3c2nc(-c2ccc(F)cc2)n3C)ccc1-n1cnc(C)c1]

Intermediate 45 (232 mg, 0.819 mmol), Cs₂CO₃ (801 mg, 2.46 mmol), X-Phos (86 mg, 0.18 mmol) and Pd₂(dba)₃ (75 mg, 0.082 mmol), were added to a sol. of intermediate 12 (250 mg, 0.819 mmol) in 2-methyl-2-propanol (15 ml) under a N₂ atmosphere. The r.m. was heated at 110° C. for 6 h. Then, the r.m. was cooled to r.t., water was added and the mixture was extracted with DCM. The combined organic layers were dried (MgSO₄), filtered and concentrated in vacuo. The residue was purified by RP preparative HPLC [RP Shandon Hyperprep® C18 BDS (8 µm, 250 g, I.D. 5 cm); mobile phase: a gradient of (0.25% NH₄HCO₃ sol. in water)/CH₃CN]. The product fractions were collected and worked up. Yield 45 mg of compound 15 (13%).

Example B14

Preparation of Compound 16

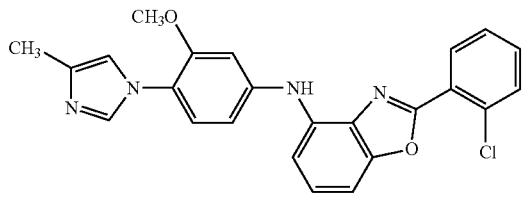

Intermediate 2a (0.178 g, 0.875 mmol), Pd₂(dba)₃ (0.053 g, 0.058 mmol), X-Phos (0.061 g, 0.128 mmol) and Cs₂CO₃ (0.570 g, 1.75 mmol) were added to a sol. of intermediate 47 (0.18 g, 0.583 mmol) in 2-Methyl-2-propanol (5 ml) and the r.m. was heated at 110° C. overnight. Then H₂O was added and the product was extracted with DCM The organic phase was dried (MgSO4) and evaporated off. The residue was purified by preparative HPLC [RP Shandon Hyperprep® C18 BDS (8 µm, 250 g, I.D. 5 cm); mobile phase: (0.5% NH₄Ac sol. in water+10% CH₃CN, MeOH]. The product fractions were collected and worked up. Yield: 0.072 g of compound 16 (28.6%).

Example B15

Preparation of Compound 17

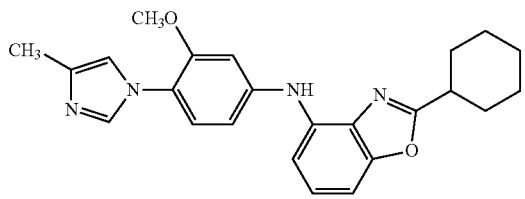

Intermediate 2a (0.123 g, 0.607 mmol), Pd₂(dba)₃ (0.028 g, 0.030 mmol), X-Phos (0.032 g, 0.067 mmol) and Cs₂CO₃ (0.296 g, 0.91 mmol) were added to a sol. of intermediate 49 (0.085 g, 0.303 mmol) in 2-methyl-2-propanol (5 ml) and the r.m. was heated at 110° C. for 20 h. Then H₂O was added and the product was extracted with DCM The organic phase was dried (MgSO4) and evaporated off. The residue was purified by preparative HPLC [RP Shandon Hyperprep® C18 BDS (8 µm, 250 g, I.D. 5 cm); mobile phase: (0.25% NH₄CO₃ sol. in water, MeOH). The product fractions were collected and worked up. Yield: 0.015 g of compound 17 (12%).

Example B16

Preparation of Compound 18

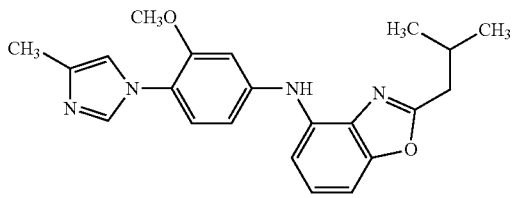

Intermediate 2a (0.160 g, 0.787 mmol), Pd$_2$(dba)$_3$ (0.036 g, 0.039 mmol), X-Phos (0.041 g, 0.086 mmol) and Cs$_2$CO$_3$ (0.384 g, 1.18 mmol) were added to a sol. of intermediate 51 (0.1 g, 0.394 mmol) in 2-Methyl-2-propanol (5 ml) and the r.m. was heated at 110° C. for 20 h. Then H$_2$O was added and the product was extracted with DCM The organic phase was dried (MgSO4) and evaporated off. The residue was purified by flash column chromatography (eluent: DCM/MeOH (NH$_3$) from 100/0 to 98/2). The product fractions were collected and concentrated in vacuo. Yield: 0.110 g of compound 18 (71%).

Example B17 a) Preparation of Compound 46

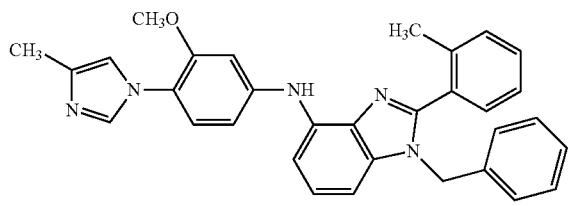

Intermediate 2a (0.244 g, 1.2 mmol), Pd$_2$(dba)$_3$ (0.092 g, 0.1 mmol), BINAP (0.093 g, 0.15 mmol) and Cs$_2$CO$_3$ (0.977 g, 3 mmol) were added to a sol. of intermediate 54 (0.377 g, 1 mmol) in DMF (15 ml) and the r.m. was heated at 150° C. for 5 h under microwave irradiation. The r.m. was cooled to r.t. and the solvent was removed under reduced pressure. The residue was partitioned between DCM and water. The organic phase was dried (MgSO4) and concentrated in vacuo. The residue was purified by preparative HPLC [RP Shandon Hyperprep® C18 BDS (8 μm, 250 g, I.D. 5 cm); mobile phase: (0.25% NH$_4$CO$_3$ sol. in water, MeOH/CH$_3$CN). The product fractions were collected and worked up. Yield: 0.155 g of compound 46 (31%).

b) Preparation of Compound 45

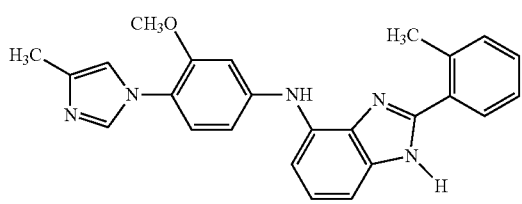

MeOH (50 ml) was added to Pd/C 10% (20 mg) under N$_2$ atmosphere. Subsequently, compound 46 (143 mg, 0.286 mmol) was added. The r.m. was stirred at 25° C. under H$_2$ atmosphere until 1 eq of H$_2$ was absorbed. The catalyst was filtered off over diatomaceous earth and the filtrate was evaporated. The residue was purified by flash column chromatography over silica gel (eluent: DCM/MeOH(NH$_3$) from 100/0 to 95/5). The product fractions were collected and evaporated. The residue was treated with DIPE/2-propanol to provide a solid. This was purified further by RP preparative HPLC [RP Shandon Hyperprep® C18 BDS (8 μm, 250 g, I.D. 5 cm); mobile phase: a gradient of (0.25% NH$_4$HCO$_3$ sol. in water)/MeOH/CH$_3$CN]. The product fractions were collected and worked up. Yield: 41 mg of compound 45 (35%).

Example B18

Preparation of Compound 106

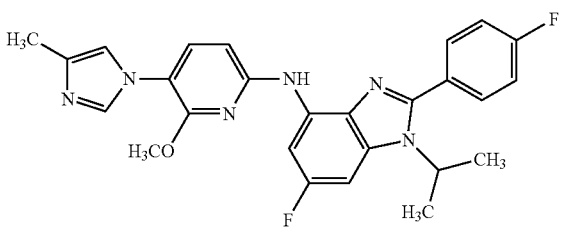 [SMILES: COc1nc(Nc2cc(F)cc3c2nc(-c2ccc(F)cc2)n3C(C)C)ccc1-n1cnc(C)c1]

Intermediate 45 (81 mg, 0.40 mmol), Cs$_2$CO$_3$ (390 mg, 1.2 mmol), X-Phos (46 mg, 0.096 mmol) and Pd$_2$(dba)$_3$ (30 mg, 0.032 mmol), were added to a sol. of intermediate 56 (140 mg, 0.40 mmol) in 2-methyl-2-propanol (10 ml) under a N$_2$ atmosphere. The r.m. was heated at 100° C. for 3 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH(NH$_3$) from 100/0 to 96/4). The product fractions were collected and concentrated in vacuo. The residue was suspended in DIPE. The solid was filtered off, washed with DIPE and dried. Yield 120 mg of compound 106 (63%).

Example B19

Preparation of Compound 107

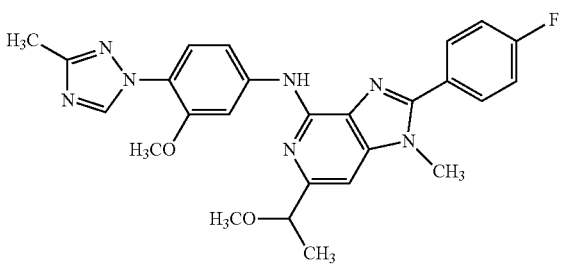 [SMILES: COc1cc(Nc2nc(C(C)OC)cc3c2nc(-c2ccc(F)cc2)n3C)ccc1-n1cnc(C)n1]

Intermediate 5 (118 mg, 0.58 mmol), Cs$_2$CO$_3$ (709 mg, 2.18 mmol), X-Phos (69 mg, 0.145 mmol) and Pd$_2$(dba)$_3$ (66 mg, 0.073 mmol), were added to a sol. of intermediate 56 (200 mg, 0.66 mmol) in 2-methyl-2-propanol (8 ml) under a N$_2$ atmosphere. The r.m. was heated at 100° C. for 16 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH(NH$_3$) from 100/0 to 97/3). The product fractions were collected and concentrated in vacuo. Yield 186 mg of compound 107 (60%).

Example B20 a) Preparation of Compound 108

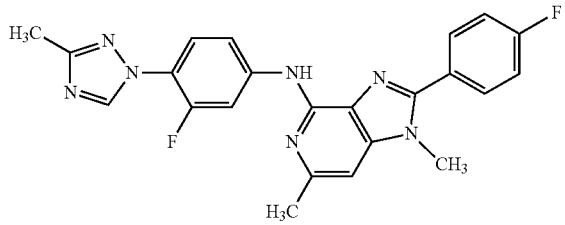 [SMILES: Cc1cc2c(nc(-c3ccc(F)cc3)n2C)c(Nc2ccc(-n3cnc(C)n3)c(F)c2)n1]

Intermediate 71 (1.2 g, 6.3 mmol), Cs$_2$CO$_3$ (7.22 g, 22.2 mmol), X-Phos (704 mg, 1.48 mmol) and Pd$_2$(dba)$_3$ (677 mg, 0.74 mmol), were added to a sol. of intermediate 65 (2.32 g, 7.39 mmol) in 2-methyl-2-propanol (50 ml) under a N$_2$ atmosphere. The r.m. was heated at 100° C. for 16 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH(NH$_3$) from 100/0 to 97/3). The product fractions were collected and concentrated in vacuo. Yield 1.96 g of compound 108 (62%).

b) Preparation of Compound 108, Alternative Procedure

Intermediate 71 (6.24 g, 32.6 mmol) and methanesulfonic acid (10.5 g, 109 mmol) were added to a solution of intermediate 65 (10 g, 36.3 mmol) in 2-propanol (88 ml). The r.m. was heated at 90° C. for 36 h. Then, the r.m. was cooled slowly to r.t., and the resulting precipitate was collected by filtration. The solid was partitioned between DCM and a sat. aq. NaHCO$_3$ sol. The organic layer was dried (MgSO$_4$), filtered and concentrated in vacuo. Yield 11.2 g of compound 108 (85%).

Example B21 a) Preparation of Compound 109

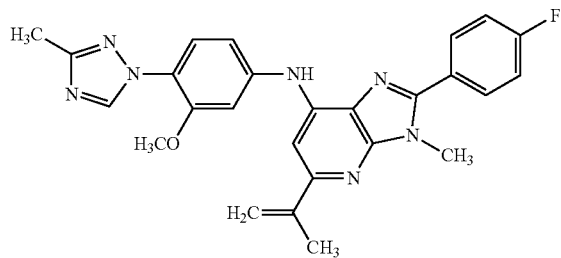 [SMILES: C=C(C)c1cc(Nc2ccc(-n3cnc(C)n3)c(OC)c2)c2nc(-c3ccc(F)cc3)n(C)c2n1]

Intermediate 5 (195 mg, 0.96 mmol), Cs$_2$CO$_3$ (1.1 g, 3.38 mmol), X-Phos (107 mg, 0.23 mmol) and Pd$_2$(dba)$_3$ (103 mg, 0.11 mmol), were added to a sol. of intermediate 62 (340 mg, 1.13 mmol) in 2-methyl-2-propanol (15 ml) under a N$_2$ atmosphere. The r.m. was heated at 100° C. for 16 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH(NH$_3$) from 100/0 to 97/3). The product fractions were collected and concentrated in vacuo. Yield 310 mg of compound 109 (59%).

b) Preparation of Compound 110

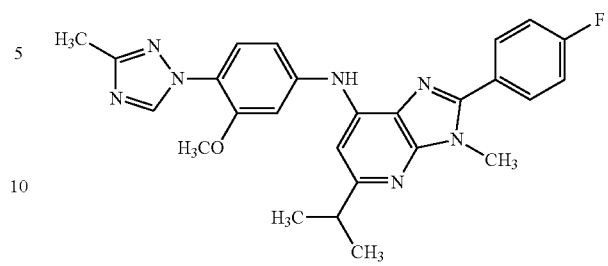

MeOH (40 ml) was added to Pt/C 5% (100 mg) under N$_2$ atmosphere. Subsequently, compound 109 (310 mg, 0.66 mmol) was added. The r.m. was stirred at 25° C. under H$_2$ atmosphere until 1 eq of H$_2$ was absorbed. The catalyst was filtered off over diatomaceous earth and the filtrate was concentrated in vacuo. The residue was purified by flash column chromatography (eluent: DCM/MeOH(NH$_3$) from 100/0 to 97/3). The product fractions were collected and concentrated in vacuo. The residue was triturated with diethylether. Yield: 250 mg of compound 110.

Example B22

Preparation of Compound 111

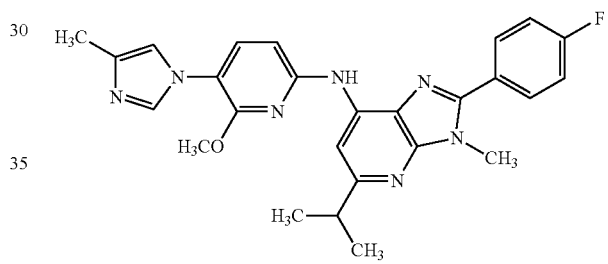

Intermediate 45 (118 mg, 0.58 mmol), Cs$_2$CO$_3$ (709 mg, 2.18 mmol), X-Phos (69 mg, 0.145 mmol) and Pd$_2$(dba)$_3$ (66 mg, 0.073 mmol), were added to a sol. of intermediate 63 (200 mg, 0.66 mmol) in 2-methyl-2-propanol (8 ml) under a N$_2$ atmosphere. The r.m. was heated at 100° C. for 16 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH(NH$_3$) from 100/0 to 97/3). The product fractions were collected and concentrated in vacuo. Yield 166 mg of compound III (53%).

Example B23

Preparation of Compound 112

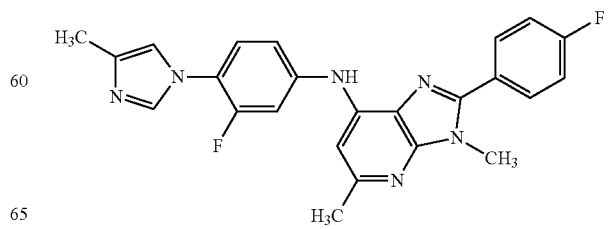

Intermediate 71 (187 mg, 0.98 mmol), Cs₂CO₃ (957 mg, 2.94 mmol), X-Phos (93 mg, 0.196 mmol) and Pd₂(dba)₃ (89 mg, 0.098 mmol), were added to a sol. of intermediate 64 (270 mg, 0.98 mmol) in 2-methyl-2-propanol (10 ml) under a N₂ atmosphere. The r.m. was heated at 100° C. for 20 h. Then, the r.m. was cooled to r.t., water was added and the mixture was extracted with DCM. The combined organic layers were dried (MgSO₄), filtered and concentrated in vacuo. The residue was purified by flash column chromatography (eluent: DCM/MeOH(NH₃) from 100/0 to 99/1). The product fractions were collected and concentrated in vacuo. The residue was triturated with DIPE/CH₃CN. Yield 37 mg of compound 112 (9%).

Example B24

Preparation of Compound 113

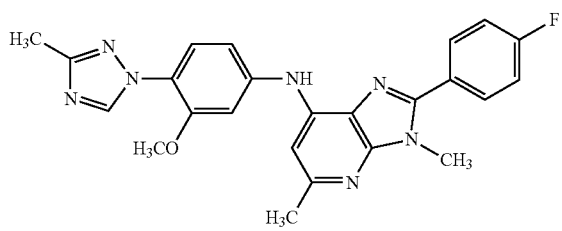 [SMILES: COc1cc(Nc2cc(C)nc3c2nc(-c2ccc(F)cc2)n3C)ccc1-n1cnc(C)n1]

Intermediate 5 (55 mg, 0.27 mmol), Cs₂CO₃ (284 mg, 0.87 mmol), X-Phos (28 mg, 0.058 mmol) and Pd₂(dba)₃ (26 mg, 0.029 mmol), were added to a sol. of intermediate 64 (80 mg, 0.29 mmol) in 2-methyl-2-propanol (10 ml) under a N₂ atmosphere. The r.m. was heated at 100° C. for 20 h. Then, the r.m. was cooled to r.t., water was added and the mixture was extracted with DCM. The combined organic layers were dried (MgSO₄), filtered and evaporated. The residue was purified by preparative HPLC [RP Vydac Denali C18 (10 um, 250 g, I.D. 5 cm); mobile phase: (0.25% NH₄CO₃ sol. in water, MeOH/CH₃CN). The product fractions were collected and worked up. The residue was triturated with DIPE. Yield: 27 mg of compound 113 (21%).

Example B25

Preparation of Compound 114

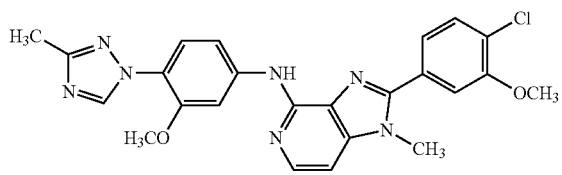 [SMILES: COc1cc(-c2nc3c(Nc4ccc(-n5cnc(C)n5)c(OC)c4)nccc3n2C)ccc1Cl]

Intermediate 5 (139 mg, 0.68 mmol), Cs₂CO₃ (635 mg, 1.95 mmol), X-Phos (68 mg, 0.143 mmol) and Pd₂(dba)₃ (59 mg, 0.065 mmol), were added to a sol. of intermediate 73 (200 mg, 0.65 mmol) in 2-methyl-2-propanol (10 ml) under a N₂ atmosphere. The r.m. was heated at 75° C. for 16 h. Then, the r.m. was cooled to r.t., water was added and the mixture was extracted with DCM. The combined organic layers were dried (MgSO₄), filtered and concentrated in vacuo. The residue was purified by flash column chromatography (eluent: DCM/MeOH(NH₃) from 100/0 to 99/1). The product fractions were collected and concentrated in vacuo. The residue was triturated with DIPE. Yield 70 mg of compound 114 (22%).

Example B26

Preparation of Compound 174

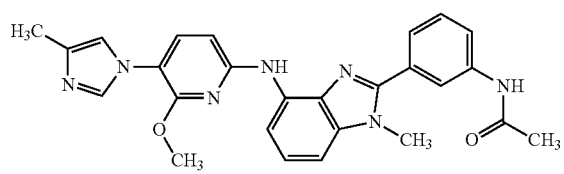 [SMILES: COc1nc(Nc2cccc3c2nc(-c2cccc(NC(C)=O)c2)n3C)ccc1-n1cnc(C)c1]

3-Acetamidophenylboronic acid (134 mg, 0.75 mmol) and Pd(PPh₃)₄ (115 mg, 0.1 mmol) were added to a mixture of intermediate 91 (184 mg, 0.5 mmol) and K₂CO₃ (207 mg, 1.5 mmol) in dioxane (10 ml) and DMF (2.5 ml). The r.m. was stirred and heated in a closed vessel at 140° C. for 20 h. The r.m. was cooled and concentrated in vacuo. The residue was dissolved in a minimal amount of DCM, and then filtered over diatomaceous earth. The organic layer was evaporated. The residue was purified by RP preparative HPLC [RP Vydac Denali C18 (10 μm, 250 g, I.D. 5 cm); mobile phase: a gradient of (0.25% NH₄HCO₃ sol. in water)/MeOH]. The product fractions were collected and worked up. Yield 158 mg of compound 174 (64%).

Example B27

Preparation of Compound 184

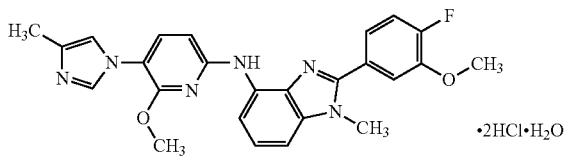

4-Fluoro-3-methoxyphenylboronic acid (127 mg, 0.75 mmol) and Pd(PPh₃)₄ (115 mg, 0.1 mmol) were added to a mixture of intermediate 91 (184 mg, 0.5 mmol) and K₂CO₃ (207 mg, 1.5 mmol) in dioxane (10 ml) and DMF (2.5 ml). The r.m. was stirred and heated in a closed vessel at 140° C. for 20 h. The r.m. was cooled and concentrated in vacuo. The residue was dissolved in a minimal amount of DCM, and then filtered over diatomaceous earth. The organic layer was evaporated. The residue was purified by RP preparative HPLC [RP Vydac Denali C18 (10 μm, 250 g, I.D. 5 cm); mobile phase: a gradient of (0.25% NH₄HCO₃ sol. in water)/MeOH]. The product fractions were collected and worked up. The residue was dissolved in hot 2-propanol and treated with a 6 N HCl sol. in 2-propanol. The resulting precipitate was collected by filtration and dried. Yield: 168 mg of compound 184 (61%) as HCl salt (.2HCl.H₂O).

Example B28

Preparation of Compound 133

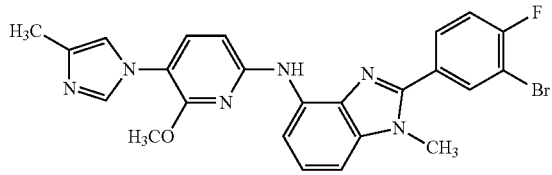 [SMILES: COc1nc(Nc2cccc3c2nc(-c2ccc(F)c(Br)c2)n3C)ccc1-n1cnc(C)c1]

Na$_2$S$_2$O$_5$ (0.4 g, 2.11 mmol) and 3-bromo-4-fluoro-benzaldehyde (243 mg, 1.2 mmol) were added to a sol. of intermediate 93 (324 mg, 1 mmol) in DMA (10 ml). The r.m. was stirred overnight at 80° C. Then, the r.m. was cooled to r.t. and poured into water. The mixture was extracted with DCM. The combined organic layers were dried (MgSO$_4$), filtered and concentrated in vacuo. The residue was purified by flash column chromatography (eluent: DCM/MeOH(NH$_3$) from 100/0 to 96/4). The product fractions were collected and concentrated in vacuo. The residue was triturated with DIPE. Yield: 110 mg of compound 133 (22%).

Example B29

Preparation of Compound 141

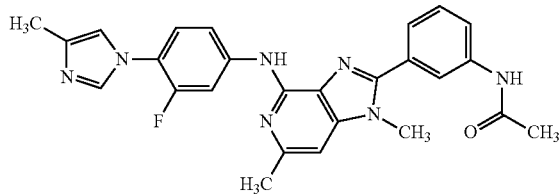 [SMILES: CC(=O)Nc1cccc(-c2nc3c(Nc4ccc(-n5cnc(C)c5)c(F)c4)nc(C)cc3n2C)c1]

3-Acetamidophenylboronic acid (46 mg, 0.26 mmol), K$_2$CO$_3$ (89 mg, 0.64 mmol) and Pd(PPh$_3$)$_4$ (37 mg, 0.032 mmol) were added to a sol. of intermediate 97 (80 mg, 0.21 mmol) in dioxane (3.2 ml) and DMF (0.8 ml). The r.m. was stirred and heated at 150° C. for 20 min under microwave irradiation. Extra 3-acetamidophenyl-boronic acid (23 mg), Pd(PPh$_3$)$_4$ (19 mg), and DMF (0.5 ml) were added, and the r.m. was stirred and heated at 150° C. for 20 min under microwave irradiation. The mixture was cooled to r.t. and partitioned between H$_2$O and EtOAc. The organic layers were separated, dried (MgSO$_4$), filtered and concentrated in vacuo. The residue was purified by flash column chromatography (eluent: DCM/MeOH(NH$_3$) from 100/0 to 95/5). The product fractions were collected and concentrated. Yield: 50 mg of compound 141 (50%).

Example B30

Preparation of Compound 154

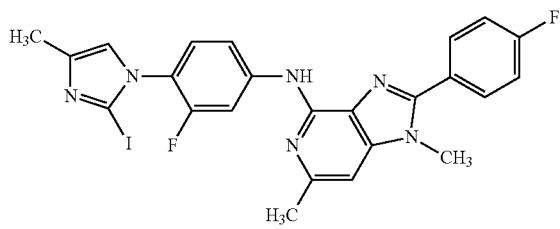 [SMILES: Cc1cc2c(nc(-c3ccc(F)cc3)n2C)c(Nc2ccc(-n3cc(C)nc3I)c(F)c2)n1]

A 2 M sol. of lithium diisopropylamide in THF (1.6 ml, 3.2 mmol) was added at −40° C. to a solution of compound 108 (460 mg, 1.07 mmol) in THF (35 ml). The r.m. was stirred at −40° C. for 1 h., and subsequently I$_2$ (271 mg, 1.07 mmol) in THF (5 ml) was added. The r.m. was allowed to warm to r.t., and was then partitioned between DCM and water. The organic layer was separated, dried (MgSO$_4$), filtered and concentrated in vacuo. The reaction was repeated using 100 mg of compound 108. The crude residues obtained from both reactions were combined and purified by flash column chromatography (eluent: DCM/MeOH(NH$_3$) from 100/0 to 95/5). The product fractions were collected and concentrated in vacuo. Yield: 52 mg of compound 154 (7%).

Example B31

Preparation of Compound 119

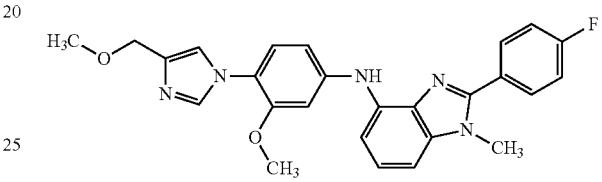

SOCl$_2$ (62 mg, 0.52 mmol) was added to a sol. of compound 118 (prepared according to example B4 from intermediate 99 and intermediate 12) (80 mg, 0.17 mmol) in DCM (5 ml). The r.m. was stirred at r.t. for 1 h and then MeOH (10 ml) was added. The r.m. was stirred at r.t. overnight and then DCM (100 ml) was added. The mixture was first washed with a sat. aq. NaHCO$_3$ sol., and then with water. The organic layer was dried (MgSO$_4$), filtered and the solvent was evaporated. The residue was purified by preparative HPLC [RP Vydac Denali C18 (10 μm, 250 g, I.D. 5 cm); mobile phase: (0.25% NH$_4$CO$_3$ sol. in water, MeOH). The product fractions were collected and worked up. Yield: 26 mg of compound 119 (33%).

Example B32

Preparation of Compound 208

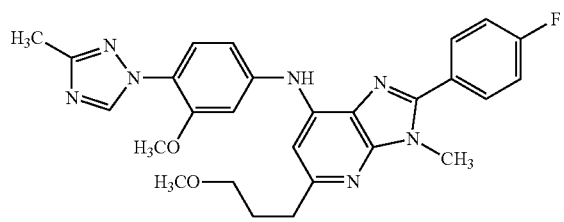 [SMILES: COCCCc1cc(Nc2ccc(-n3cnc(C)n3)c(OC)c2)c2nc(-c3ccc(F)cc3)n(C)c2n1]

A mixture of intermediate 41 (140 mg, 0.28 mmol), and Raney nickel (20 mg), in THF (40 ml) was stirred at r.t. under H$_2$ (atmospheric pressure). After uptake of H$_2$ (2 eq), the catalyst was filtered off over diatomaceous earth. The solvent was evaporated and the residue was partitioned between DCM and water. The organic layer was dried (MgSO$_4$), filtered and concentrated in vacuo. The residue was purified by preparative HPLC [RP Vydac Denali C18 (10 μm, 250 g, I.D. 5 cm); mobile phase: (0.25% NH$_4$CO$_3$ sol. in water, MeOH)]. The product fractions were collected, concentrated in vacuo, and the residue was purified further by preparative HPLC [RP Vydac Denali C18 (10 μm, 250 g, I.D. 5 cm); mobile phase: (0.25% NH₄CO₃ sol. in water, CH₃CN)].

The product fractions were collected and concentrated under reduced pressure. Yield: 14 mg of compound 208 (10%).

Example B33

Preparation of Compound 187

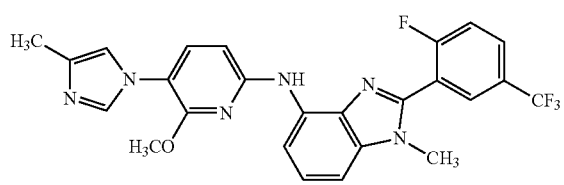 [SMILES: COc1nc(Nc2cccc3c2nc(-c2cc(C(F)(F)F)ccc2F)n3C)ccc1-n1cnc(C)c1]

2-Fluoro-5-trifluoromethyl-benzaldehyde (189 mg, 0.98 mmol) and Na₂S₂O₄ (427 mg, 2.46 mmol) were added to a sol. of intermediate 92 (290 mg, 0.82 mmol) in EtOH (15 ml). The r.m. was heated under microwave conditions at 160° C. for 45 min. The r.m. was cooled to r.t. and filtered over diatomaceous earth, eluting with EtOAc. The filtrate was concentrated in vacuo. The residue was partitioned between DCM and water. The organic phase was separated, dried (MgSO₄), filtered and the solvent was evaporated in vacuo. The residue was purified by flash column chromatography over silica gel (eluent: DCM/MeOH(NH₃) 100/0 to 97/3). The product fractions were collected and the solvent was evaporated. The residue was dissolved in 2-propanol and DIPE and treated with a 6N HCl sol. in 2-propanol. The resulting precipitate was collected by filtration and dried. Yield: 86 mg of compound 187 (18%) as HCl salt (.2HCl.H₂O).

Compounds 1 to 212 in tables 1a, 1b, 1c and 1d were prepared by analogy to one of the above Examples. In case no salt form is indicated, the compound was obtained as a free base. 'Co. No.' means compound number. 'Pr.' refers to the Example number according to which protocol the compound was synthesized. B1* means that the compound was synthesized according to the protocol as described in B1, but that an intermediate of formula (II-a) was reacted with an intermediate of formula (III-a) instead of an intermediate of formula (II-b) with (III-b) as was exemplified in B1.

TABLE 1a

| Co. No. | Pr. | $R^1$ | X | $A^1$ | $R^3$ | Z | $R^4$ | salt form |
|---|---|---|---|---|---|---|---|---|
| 19 | B4 | CH₃ | CH | COCH₃ | CH₃ | NCH₃ | H | |
| 20 | B4 | CH₃ | N | CH | CH₃ | NCH(CH₃)₂ | H | |
| 21 | B4 | CH₃ | N | COCH₃ | CH₃ | NCH(CH₃)₂ | H | |
| 22 | B4 | CH₃ | CH | COCH₃ | CH₃ | N-CH₂-Ph (N-methyl) | H | |
| 23 | B4 | CH₃ | N | CH | CH₃ | N-CH₂-Ph (N-methyl) | H | |
| 24 | B4 | CH₃ | N | CF | propyl | NCH₃ | H | |
| 25 | B1* | CH₃ | CH | COCH₃ | CH(CH₃)₂ | NCH₃ | H | •2 HCl |
| 26 | B4 | CH₃ | N | CH | CH(CH₃)₂ | N-CH(CH₃)₂ (N-methyl) | H | |

TABLE 1a-continued

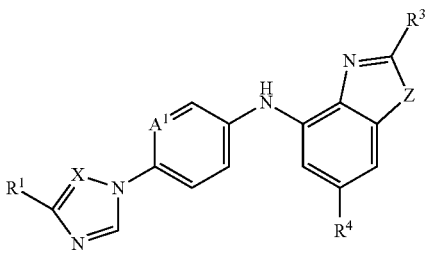

| Co. No. | Pr. | R¹ | X | A¹ | R³ | Z | R⁴ | salt form |
|---|---|---|---|---|---|---|---|---|
| 27 | B4 | CH₃ | N | CH | -CH(CH₃)CH₂CH₃ (isobutyl) | -N(CH₃)CH₂CH₂OCH₃ | H | •2 HCl |
| 18 | B16 | CH₃ | CH | COCH₃ | isobutyl | O | H | |
| 28 | B4 | CH₃ | N | COCH₃ | isobutyl | O | H | |
| 29 | B1* | CH₃ | CH | COCH₃ | neopentyl (C(CH₃)₃CH₂-) | NCH₃ | H | |
| 30 | B4 | CH₃ | CH | COCH₃ | neopentyl | O | H | |
| 31 | Br | CH₃ | CH | COCH₃ | -OCH(CH₃)₂ | NCH₃ | H | |
| 32 | B1* | CH₃ | CH | COCH₃ | -CH₂CH₂CH₂OCH₃ | NCH₃ | H | |
| 33 | B4 | CH₃ | CH | COCH₃ | -SCH₂CH(CH₃)₂ | NCH₃ | H | |
| 34 | B4 | CH₃ | CH | COCH₃ | -CH₂CH₂CF₃ | NCH₃ | H | |
| 35 | B1* | CH₃ | CH | COCH₃ | -CH₂CH₂CF₃ | NCH₂CH₃ | H | |
| 36 | B1* | CH₃ | CH | COCH₃ | -CH₂-cyclopropyl | NCH₂CH₃ | H | |
| 37 | B4 | CH₃ | CH | COCH₃ | cyclopentyl | O | H | |

TABLE 1a-continued

| Co. No. | Pr. | R¹ | X | A¹ | R³ | Z | R⁴ | salt form |
|---|---|---|---|---|---|---|---|---|
| 17 | B15 | CH₃ | CH | COCH₃ | cyclohexyl | O | H | |
| 38 | B1 | CH₃ | CH | COCH₃ | cyclohexyl | NCH₃ | H | |
| 39 | B4 | CH₃ | CH | COCH₃ | piperidin-1-yl | NCH₃ | H | |
| 9 | B9.a2 | CH₃ | CH | COCH₃ | piperidin-4-ylmethyl (NH) | NCH₃ | H | |
| 11 | B9.c | CH₃ | CH | COCH₃ | (1-methylpiperidin-4-yl)methyl | NCH₃ | H | |
| 10 | B9.b | CH₃ | CH | COCH₃ | (1-acetylpiperidin-4-yl)methyl | NCH₃ | H | |
| 40 | B4 | CH₃ | CH | COCH₃ | 1-methylpiperidin-4-yl | O | H | |
| 41 | B4 | CH₃ | CH | COCH₃ | 1-acetylpiperidin-4-yl | O | H | |
| 42 | B4 | CH₃ | CH | COCH₃ | 1-(tert-butoxycarbonyl)piperidin-4-yl | O | H | |

TABLE 1a-continued
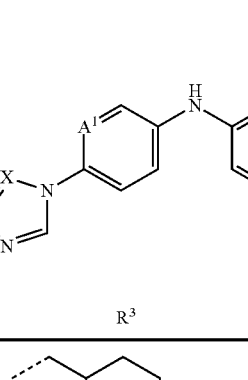
| Co. No. | Pr. | R¹ | X | A¹ | R³ | Z | R⁴ | salt form |
|---|---|---|---|---|---|---|---|---|
| 212 | B9.a1 | CH₃ | CH | COCH₃ | 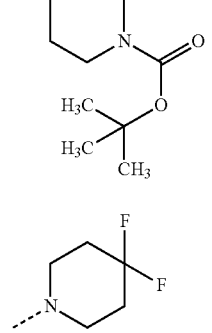 | NCH₃ | H | |
| 12 | B10 | CH₃ | CH | COCH₃ | 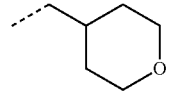 | NCH₃ | H | |
| 43 | B17.a | CH₃ | CH | COCH₃ | 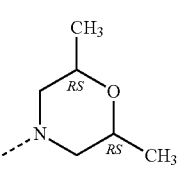 | NCH₃ | H | •2 HCl |
| 44 | B1 | CH₃ | CH | COCH₃ | 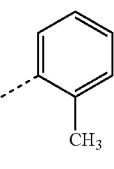 | NCH₃ | H | |
| 45 | B17.b | CH₃ | CH | COCH₃ | 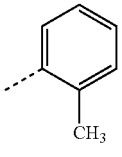 | NH | H | |
| 46 | B17.a | CH₃ | CH | COCH₃ | 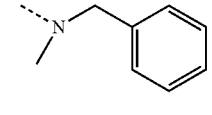 | 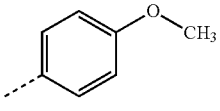 | H | |
| 47 | B1 | CH₃ | CH | COCH₃ | 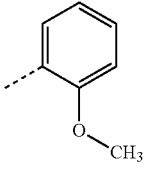 | NCH₃ | H | |
| 48 | B4 | CH₃ | CH | COCH₃ |  | O | H | |

TABLE 1a-continued
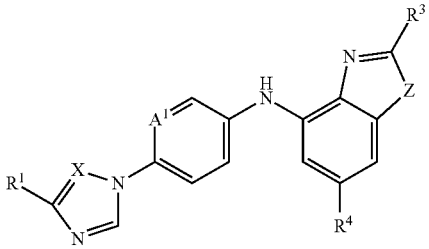
| Co. No. | Pr. | R¹ | X | A¹ | R³ | Z | R⁴ | salt form |
|---|---|---|---|---|---|---|---|---|
| 49 | B1* | CH₃ | CH | COCH₃ | H₃C-O-C₆H₄- (3-methoxyphenyl) | NCH₃ | H | |
| 50 | B4 | CH₃ | N | CH | H₃C-O-C₆H₄- (3-methoxyphenyl) | NCH₃ | H | |
| 51 | B4 | CH₃ | N | CH | H₃C-O-C₆H₄- (3-methoxyphenyl) | NCH(CH₃)₂ | H | |
| 52 | B4 | CH₃ | N | COCH₃ | H₃C-O-C₆H₄- (3-methoxyphenyl) | NCH₃ | H | |
| 53 | B4 | CH₃ | N | COCH₃ | H₃C-O-C₆H₄- (3-methoxyphenyl) | NCH(CH₃)₂ | H | |
| 54 | B4 | CH₃ | CH | COCH₃ | H₃C-O-C₆H₄- (3-methoxyphenyl) | N(CH₂)₂OCH₃ | H | •2 HCl |
| 55 | B4 | CH₃ | N | CH | H₃C-O-C₆H₄- (3-methoxyphenyl) | NCH₃ | H | |

TABLE 1a-continued
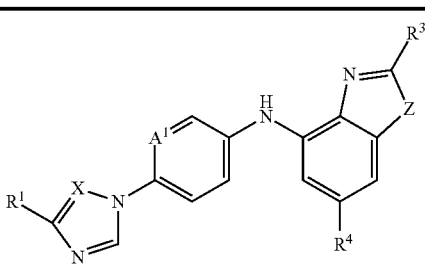
| Co. No. | Pr. | R$^1$ | X | A$^1$ | R$^3$ | Z | R$^4$ | salt form |
|---|---|---|---|---|---|---|---|---|
| 56 | B4 | CH$_3$ | N | COCH$_3$ | 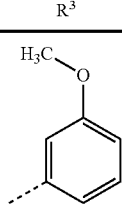 | NCH$_3$ | H | |
| 57 | B4 | CH$_3$ | N | CF | 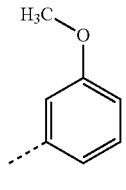 | NCH$_3$ | H | |
| 58 | B4 | CH$_3$ | N | COCH$_3$ | 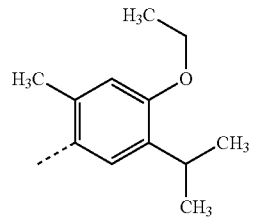 | NCH$_3$ | H | |
| 59 | B4 | CH$_3$ | N | COCH$_3$ | 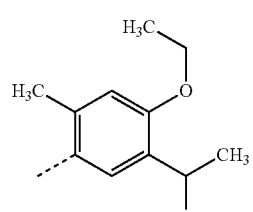 | O | H | |
| 60 | B4 | CH$_3$ | CH | COCH$_3$ | 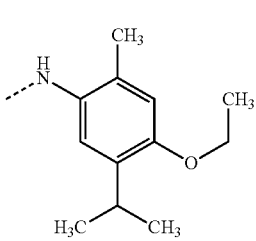 | NCH$_3$ | H | |
| 61 | B4 | CH$_3$ | CH | COCH$_3$ | 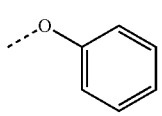 | NCH$_3$ | H | |
| 62 | B17.b | CH$_3$ | CH | COCH$_3$ | 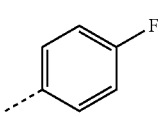 | NH | H | |

TABLE 1a-continued
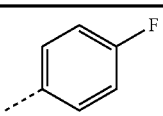
| Co. No. | Pr. | R¹ | X | A¹ | R³ | Z | R⁴ | salt form |
|---|---|---|---|---|---|---|---|---|
| 63 | B17.a | H | CH | COCH₃ | 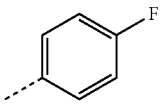 4-F-phenyl | NCH₃ | H | |
| 64 | B4 | H | N | COCH₃ | 4-F-phenyl | NCH₃ | H | |
| 65 | B4 | H | N | CF | 4-F-phenyl | NCH₃ | H | |
| 7 | B7 | CH₃ | CH | CH | 4-F-phenyl | NCH₃ | H | |
| 66 | B1 | CH₃ | CH | COCH₃ | 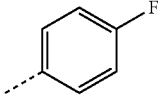 2-F-phenyl | NCH₃ | H | |
| 1 | B1 | CH₃ | CH | COCH₃ | 4-F-phenyl | NCH₃ | H | |
| 67 | B4 | CH₃ | CH | CF | 4-F-phenyl | NCH₃ | H | |
| 68 | B12 | CH₃ | CH | N | 4-F-phenyl | NCH₃ | H | |
| 69 | B4 | CH₃ | N | CH | 4-F-phenyl | NCH₃ | CF₃ | |
| 4 | B4 | CH₃ | N | COCH₃ | 4-F-phenyl | NCH₃ | H | |
| 70 | B4 | CH₃ | N | N | 4-F-phenyl | NCH₃ | H | |

TABLE 1a-continued

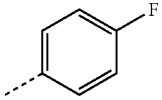

| Co. No. | Pr. | R¹ | X | A¹ | R³ | Z | R⁴ | salt form |
|---|---|---|---|---|---|---|---|---|
| 14 | B12 | CH₃ | N | N | 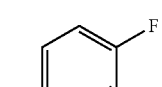 4-F-phenyl | NCH₃ | CF₃ | |
| 71 | B1* | Br | CH | COCH₃ | 4-F-phenyl | NCH₃ | H | |
| 72 | B1* | CN | CH | COCH₃ | 4-F-phenyl | NCH₃ | H | |
| 2 | B2 | CH₃ | CH | COCH₃ | 4-F-phenyl | NCH(CH₃)₂ | H | |
| 73 | B4 | CH₃ | N | CH | 4-F-phenyl | NCH(CH₃)₂ | H | •2 HCl |
| 74 | B4 | CH₃ | N | CF | 4-F-phenyl | NCH(CH₃)₂ | H | •2 HCl |
| 75 | B4 | CH₃ | N | COCH₃ | 4-F-phenyl | NCH(CH₃)₂ | H | •2 HCl |
| 76 | B12 | CH₃ | N | N | 4-F-phenyl | NCH(CH₃)₂ | H | |
| 77 | B4 | CH₃ | N | CH | 4-F-phenyl | NC(CH₃)₃ | H | |
| 78 | B4 | CH₃ | N | COCH₃ | 4-F-phenyl | NC(CH₃)₃ | H | •2 HCl |
| 79 | B1 | CH₃ | CH | COCH₃ | 4-F-phenyl | N(CH₃)CH₂-phenyl | H | |

TABLE 1a-continued
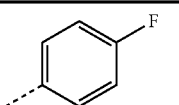
| Co. No. | Pr. | R¹ | X | A¹ | R³ | Z | R⁴ | salt form |
|---|---|---|---|---|---|---|---|---|
| 80 | B4 | CH₃ | CH | COCH₃ | 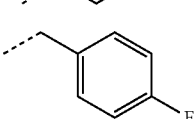 | O | H | |
| 81 | B17.a | CH₃ | CH | COCH₃ | 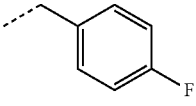 | NCH₃ | H | •2 HCl |
| 82 | B4 | CH₃ | CH | COCH₃ | 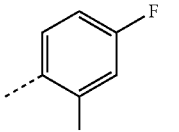 | O | H | |
| 3 | B3 | CH₃ | CH | COCH₃ | 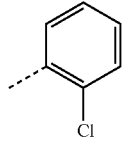 | NCH₃ | H | |
| 16 | B14 | CH₃ | CH | COCH₃ | 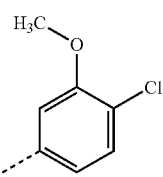 | O | H | |
| 83 | B1* | H | N | CF | 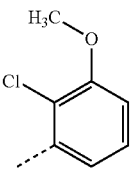 | NCH₃ | H | |
| 84 | B4 | CH₃ | N | COCH₃ | 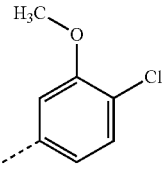 | NCH₃ | H | |
| 85 | B1* | CH₃ | N | COCH₃ | 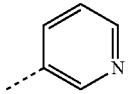 | NCH₃ | H | |
| 86 | B4 | CH₃ | CH | COCH₃ |  | O | H | |

TABLE 1a-continued

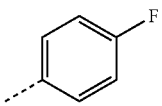

| Co. No. | Pr. | R¹ | X | A¹ | R³ | Z | R⁴ | salt form |
|---|---|---|---|---|---|---|---|---|
| 103 | B4 | CH₃ | N | CH | 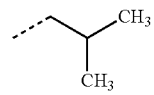 4-F-phenyl | NCH₃ | H | |
| 105 | B4 | CH₃ | N | COCH₃ | 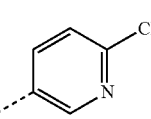 isopropyl (CH(CH₃)₂) | NCH₂CF₃ | H | |
| 117 | B4 | CH₃ | CH | COCH₃ | 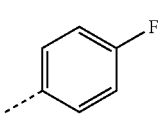 2-CF₃-pyridyl | NCH(CH₃)₂ | H | •2HCl •3H₂O |
| 118 | B4 | CH₂OH | CH | COCH₃ | 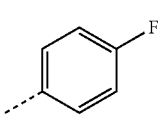 4-F-phenyl | NCH₃ | H | |
| 119 | B31 | CH₂OCH₃ | CH | COCH₃ | 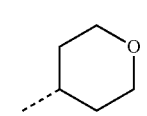 4-F-phenyl | NCH₃ | H | |
| 120 | B4 | CH₃ | N | COCH₃ | 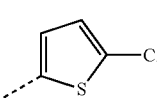 tetrahydropyran-4-yl | NCH(CH₃)₂ | H | •2HCl |
| 121 | B4 | CH₃ | N | COCH₃ | 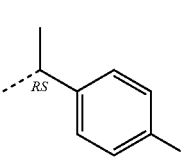 5-Cl-thiophen-2-yl | NCH(CH₃)₂ | H | |
| 122 | B4 | CH₃ | N | COCH₃ | 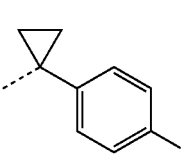 1-(4-Cl-phenyl)ethyl RS | NCH₃ | H | •2HCl |
| 123 | B4 | CH₃ | N | COCH₃ | 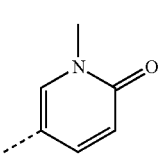 1-(4-Cl-phenyl)cyclopropyl | NCH₃ | H | •2HCl |
| 124 | B18 | CH₃ | CH | CF | N-methyl-2-pyridone-5-yl | NCH₃ | H | |

TABLE 1a-continued
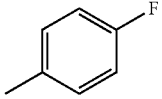
| Co. No. | Pr. | R¹ | X | A¹ | R³ | Z | R⁴ | salt form |
|---|---|---|---|---|---|---|---|---|
| 125 | B1* | CH₃ | CH | CF | 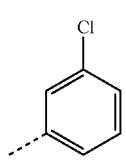 4-F-phenyl | NCH(CH₃)₂ | F | |
| 126 | B4 | CH₃ | N | COCH₃ | 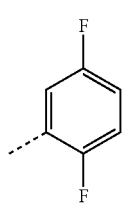 3-Cl-phenyl | NCH(CH₃)₂ | H | •2HCl |
| 127 | B4 | CH₃ | N | COCH₃ | 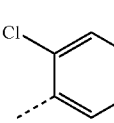 2,5-diF-phenyl | NCH₂CH₃ | F | |
| 128 | B4 | CH₃ | N | COCH₃ | 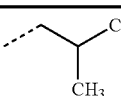 2-Cl-phenyl | NCH₃ | F | |
TABLE 1b
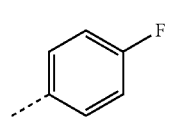
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 87 | B13 | CH₃ | N | H | CH | N | CH | CH | CH | O | isopropyl | H |
| 88 | B4 | H | N | CH₃ | CH | CH | CH | CH | CH | NCH(CH₃)₂ | 4-F-phenyl | H |
| 5 | B5 | CH₃ | CH | H | CH | N | CH | CH | CH | NCH₃ | 4-F-phenyl | H |

TABLE 1b-continued

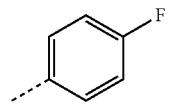

| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 89 | B13 | CH₃ | N | H | CH | N | CH | CH | CH | NCH(CH₃)₂ | 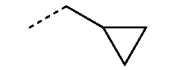 4-F-phenyl | H |
| 101 | B11 | H | N | CH₃ | COCH₃ | CH | CH | CH | N | NCH₃ | 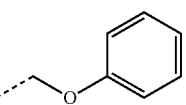 CH₂-cyclopropyl | H |
| 99 | B4 | H | N | CH₃ | COCH₃ | CH | CH | CH | CH | NCH₃ | 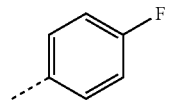 CH₂-O-phenyl | H |
| 90 | B8 | CH₃ | CH | H | COCH₃ | CH | CH | CH | N | NH | 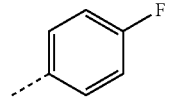 4-F-phenyl | H |
| 91 | B8 | H | N | CH₃ | COCH₃ | CH | CH | CH | CH | NCH₃ | 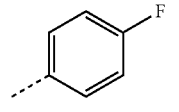 4-F-phenyl | H |
| 8 | B8 | CH₃ | CH | H | COCH₃ | CH | CH | CH | N | NCH₃ | 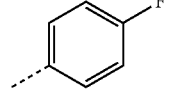 4-F-phenyl | H |
| 92 | B11 | CH₃ | N | H | COCH₃ | CH | CH | CH | N | NCH₃ | 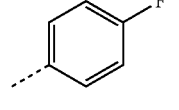 4-F-phenyl | H |
| 115 | B18 | CH₃ | CH | H | COCH₃ | N | CH | CH | CH | NCH₃ | 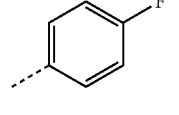 4-F-phenyl | F |
| 116 | B18 | CH₃ | CH | H | COCH₃ | N | CH | CH | CH | NCH(CH₃)₂ | 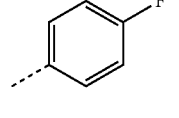 4-F-phenyl | H |
| 106 | B18 | CH₃ | CH | H | COCH₃ | N | CH | CH | CH | NCH(CH₃)₂ | 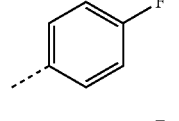 4-F-phenyl | F |
| 93 | B13 | CH₃ | CH | H | COCH₃ | CH | CH | N | CH | NCH₃ | 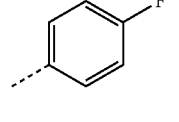 4-F-phenyl | H |
| 94 | B1* | CH₃ | CH | H | COCH₃ | CH | N | CH | CH | NCH₃ | 4-F-phenyl | H |

TABLE 1b-continued

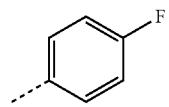

| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 15 | B13 | CH₃ | CH | H | COCH₃ | N | CH | CH | CH | NCH₃ | 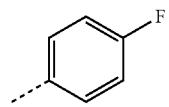 4-F-phenyl | H |
| 210 | B13 | CH₃ | CH | H | COCH₃ | N | CH | CH | CH | NCH₃ | 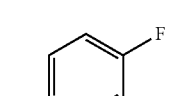 4-F-phenyl | H |
| 107 | B19 | CH₃ | N | H | COCH₃ | CH | CH | CH | N | NCH₃ | 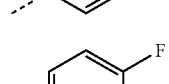 4-F-phenyl | CH(CH₃)₂ |
| 98 | B11 | CH₃ | N | H | COCH₃ | CH | CH | CH | N | NCH₃ | 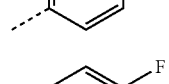 2,4-diF-phenyl | H |
| 96 | B4 | H | N | CH₃ | COCH₃ | CH | CH | CH | CH | NCH₃ | 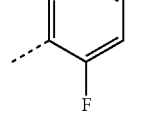 3-Cl-phenyl | H |
| 114 | B25 | CH₃ | N | H | COCH₃ | CH | CH | CH | N | NCH₃ |  4-Cl-3-OCH₃-phenyl | H |
| 108 | B20 | CH₃ | CH | H | CF | CH | CH | CH | N | NCH₃ | 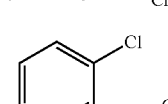 4-F-phenyl | CH₃ |
| 211 | B20 | CH₃ | CH | H | CF | CH | CH | CH | N | NCH₃ | 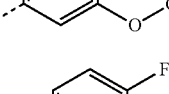 4-F-phenyl | CH₃ |
| 209 | B20 | CH₃ | CH | H | CF | CH | CH | CH | N | NCH₃ | 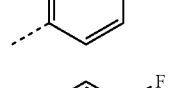 4-F-phenyl | CH₃ |
| 97 | B11 | H | N | CH₃ | CF | CH | CH | CH | N | NCH₃ | 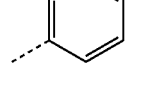 4-F-phenyl | H |
| 102 | B4 | CH₃ | N | H | CF | CH | CF | CH | CH | NCH₃ | 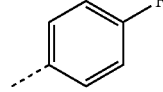 4-F-phenyl | H |

TABLE 1b-continued

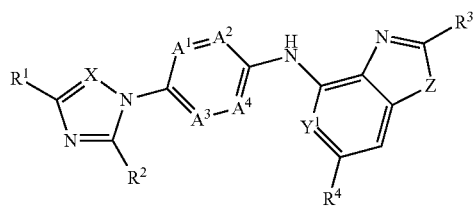

| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 100 | B11 | H | N | CH₃ | CF | CH | CH | CH | N | NCH₃ | 4-F-phenyl | CH₃ |
| 13 | B11 | H | N | CH₃ | CF | CH | CH | CH | N | NCH(CH₃)₂ | 4-F-phenyl | H |
| 104 | B11 | CH₃ | CH | H | CF | CH | CH | CH | N | NCH₃ | 2,4-diF-phenyl | H |
| 6 | B6 | CH₃ | CH | H | N | CH | N | CH | CH | NCH₃ | 4-F-phenyl | H |
| 95 | B4 | CH₃ | CH | H | N | N | CH | CH | CH | NCH₃ | 4-F-phenyl | H |
| 129 | B24 | CH₃ | N | H | CH | CF | CH | CH | N | NCH₃ | 2,4-diF-phenyl | H |
| 130 | B23 | CH₃ | N | H | COCH₃ | CH | CH | CH | N | NCH₃ | 2-CF₃-phenyl | H |
| 131 | B18 | CH₃ | CH | H | COCH₃ | N | CH | CH | CH | NCH(CH₃)₂ | 4-Cl-3-OCH₃-phenyl | H |
| 132 | B26 | CH₃ | CH | H | COCH₃ | N | CH | CH | CH | NCH₃ | 3-F-5-CF₃-phenyl | H |

TABLE 1b-continued
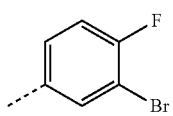
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 133 | B28 | CH₃ | CH | H | COCH₃ | N | CH | CH | CH | | NCH₃ | 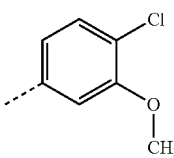 | H |
| 134 | B1* | CH₃ | CH | H | COCH₃ | N | CH | CH | CH | | NCH₃ | 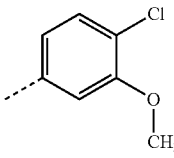 | H |
| 135 | B20.b | CH₃ | N | H | COCH₃ | CH | CH | CH | N | | NCH₃ | 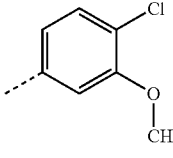 | CH₃ |
| 136 | B20.b | CH₃ | CH | H | CF | CH | CH | CH | N | | NCH₃ | 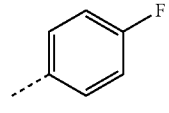 | CH₃ |
| 137 | B23 | CH₃ | CH | H | CF | CH | CH | CH | N | | NCH₃ | 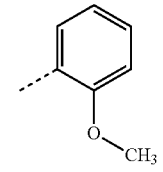 | H |
| 138 | B29 | CH₃ | CH | H | CF | CH | CH | CH | N | | NCH₃ | 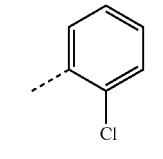 | CH₃ |
| 139 | B20.a | CH₃ | CH | H | CF | CH | CH | CH | N | | NCH₃ | 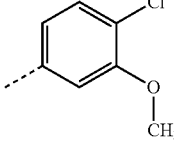 | CH₃ |
| 140 | B18 | CH₃ | CH | H | COCH₃ | N | CH | CH | CH | | NCH₃ |  | F |

TABLE 1b-continued
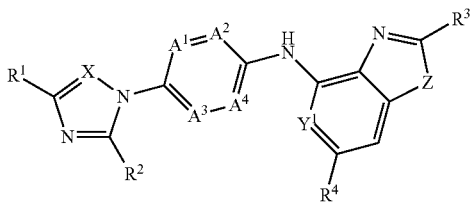
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 141 | B29 | CH₃ | CH | H | CF | CH | CH | CH | N | NCH₃ | 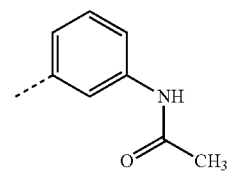 | CH₃ |
| 142 | B29 | CH₃ | CH | H | CF | CH | CH | CH | N | NCH₃ | 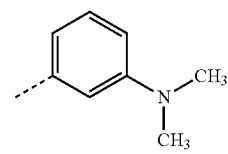 | CH₃ |
| 143 | B29 | CH₃ | CH | H | CF | CH | CH | CH | N | NCH₃ | 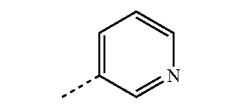 | CH₃ |
| 144 | B29 | CH₃ | CH | H | CF | CH | CH | CH | N | NCH₃ | 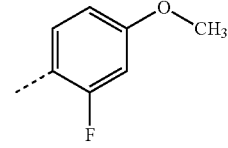 | CH₃ |
| 145 | B23 | CH₃ | N | H | COCH₃ | CH | CH | CH | N | NCH₃ | 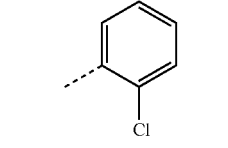 | H |
| 146 | B18 | CH₃ | CH | H | COCH₃ | N | CH | CH | CH | NCH₃ | 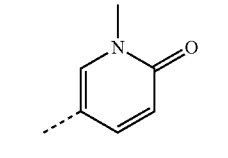 | H |
| 147 | B19 | CH₃ | N | H | COCH₃ | CH | CH | CH | N | NCH₃ | 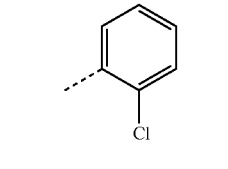 | CH₃ |
| 148 | B24 | CH₃ | N | CH₃ | COCH₃ | CH | CH | CH | N | NCH₃ | 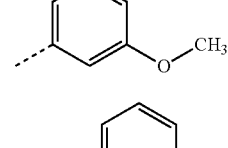 | H |
| 149 | B19 | CH₃ | CH | H | COCH₃ | N | CH | CH | N | NCH₃ | 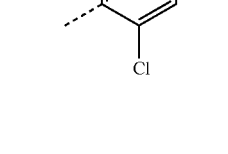 | CH₃ |

TABLE 1b-continued

| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 150 | B19 | CH₃ | CH | H | COCH₃ | N | CH | CH | N | NCH₃ | 4-F-phenyl | CH₃ |
| 151 | B4 | CH₃ | CH | H | COCH₃ | N | CH | CH | CH | NCH₃ | 2-Cl-phenyl | F |
| 152 | B14 | CH₃ | CH | H | COCH₃ | N | CH | CH | CH | O | 3-OCH₃-phenyl | H |
| 153 | B29 | CH₃ | CH | H | CF | CH | CH | CH | N | NCH₃ | 3-OCH₂CH₃-phenyl | CH₃ |
| 154 | B30 | CH₃ | CH | I | CF | CH | CH | CH | N | NCH₃ | 4-F-phenyl | CH₃ |
| 155 | B33 | CH₃ | CH | H | CF | CH | CH | CH | N | NCH₃ | 3-Br-4-F-phenyl | CH₃ |
| 156 | B23 | CH₃ | N | H | COCH₃ | CH | CH | CH | N | NCH₃ | 4-F-phenyl | Cl |
| 157 | B24 | CH₃ | N | CH₃ | COCH₃ | CH | CH | CH | N | NCH(CH₃)₂ | 3-OCH₃-phenyl | H |
| 159 | B23 | CH₃ | CH | H | COCH₃ | N | CH | CH | N | NCH₃ | 4-F-phenyl | CH(CH₃)₂ |
| 160 | B18 | CH₃ | CH | H | COCH₃ | N | CH | CH | CH | NCH₃ | 4-F-phenyl | OCH₃ |

TABLE 1b-continued
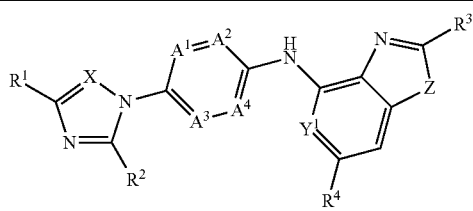
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 161 | B18 | CH₃ | N | H | COCH₃ | N | CH | CH | CH | NCH₃ | 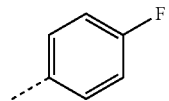 | H |
| 162 | B18 | CH₃ | N | H | COCH₃ | N | CH | CH | CH | NCH(CH₃)₂ | 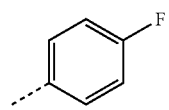 | H |
| 163 | B24 | CH₃ | N | H | COCH₃ | CH | CH | CH | N | NCH₃ | 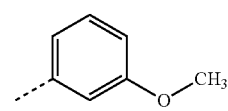 | CH₃ |
| 164 | B19 | CH₃ | N | H | COCH₃ | CH | CH | CH | N | NCH₃ | 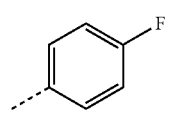 | CH₃ |
| 165 | B27 | CH₃ | CH | H | COCH₃ | N | CH | CH | CH | NCH₃ | 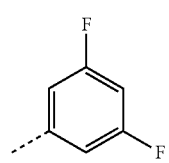 | H |
| 166 | B23 | CH₃ | N | CH₃ | COCH₃ | CH | CH | CH | N | NCH(CH₃)₂ | 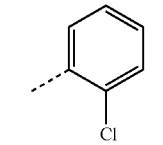 | H |
| 167 | B27 | CH₃ | CH | H | COCH₃ | N | CH | CH | CH | NCH₃ | 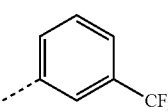 | H |
| 168 | B27 | CH₃ | CH | H | COCH₃ | N | CH | CH | CH | NCH₃ | 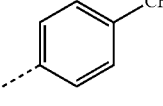 | H |
| 169 | B33 | CH₃ | CH | H | COCH₃ | N | CH | CH | CH | NCH₃ | 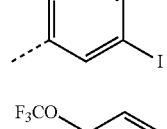 | H |
| 170 | B27 | CH₃ | CH | H | COCH₃ | N | CH | CH | CH | NCH₃ | 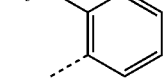 | H |

TABLE 1b-continued
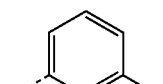
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 171 | B27 | CH₃ | CH | H | COCH₃ | N | CH | CH | CH | NCH₃ | 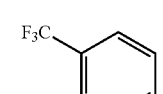 | H |
| 172 | B27 | CH₃ | CH | H | COCH₃ | N | CH | CH | CH | NCH₃ | 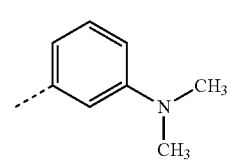 | H |
| 173 | B26 | CH₃ | CH | H | COCH₃ | N | CH | CH | CH | NCH₃ | 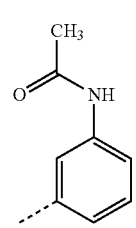 | H |
| 174 | B26 | CH₃ | CH | H | COCH₃ | N | CH | CH | CH | NCH₃ | 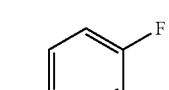 | H |
| 175 | B26 | CH₃ | CH | H | COCH₃ | N | CH | CH | CH | NCH₃ | 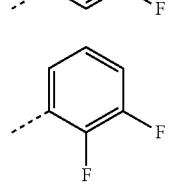 | H |
| 176 | B27 | CH₃ | CH | H | COCH₃ | N | CH | CH | CH | NCH₃ | 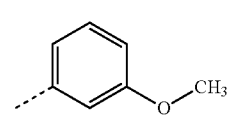 | H |
| 177 | B27 | CH₃ | CH | H | COCH₃ | N | CH | CH | CH | NCH₃ | 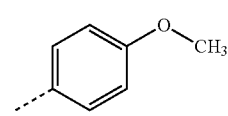 | H |
| 178 | B27 | CH₃ | CH | H | COCH₃ | N | CH | CH | CH | NCH₃ | 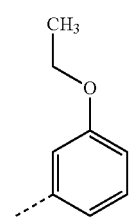 | H |
| 179 | B27 | CH₃ | CH | H | COCH₃ | N | CH | CH | CH | NCH₃ |  | H |

TABLE 1b-continued
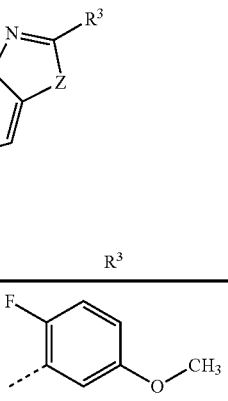
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 180 | B27 | CH₃ | CH | H | COCH₃ | N | CH | CH | CH | NCH₃ | 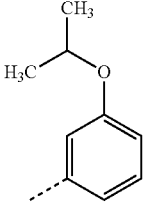 | H |
| 181 | B27 | CH₃ | CH | H | COCH₃ | N | CH | CH | CH | NCH₃ | 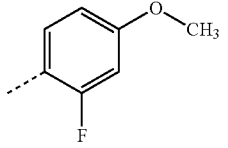 | H |
| 182 | B27 | CH₃ | CH | H | COCH₃ | N | CH | CH | CH | NCH₃ | 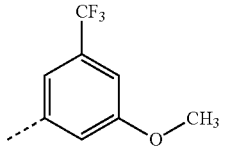 | H |
| 183 | B27 | CH₃ | CH | H | COCH₃ | N | CH | CH | CH | NCH₃ | 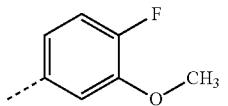 | H |
| 184 | B27 | CH₃ | CH | H | COCH₃ | N | CH | CH | CH | NCH₃ | 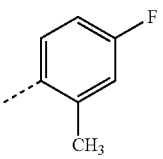 | H |
| 185 | B27 | CH₃ | CH | H | COCH₃ | N | CH | CH | CH | NCH₃ | 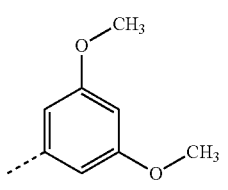 | H |
| 186 | B27 | CH₃ | CH | H | COCH₃ | N | CH | CH | CH | NCH₃ | 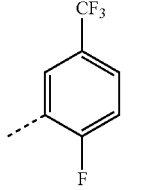 | H |
| 187 | B33 | CH₃ | CH | H | COCH₃ | N | CH | CH | CH | NCH₃ |  | H |

TABLE 1b-continued
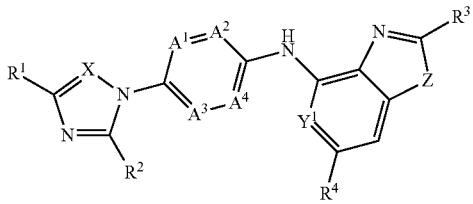
| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 188 | B26 | CH₃ | CH | H | COCH₃ | N | CH | CH | CH | NCH₃ | 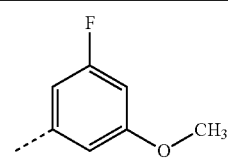 | H |
| 189 | B26 | CH₃ | CH | H | COCH₃ | N | CH | CH | CH | NCH₃ | 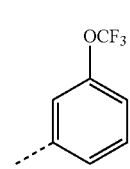 | H |
| 190 | B27 | CH₃ | CH | H | COCH₃ | N | CH | CH | CH | NCH₃ | 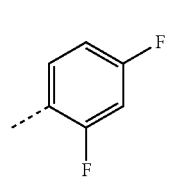 | H |
| 191 | B26 | CH₃ | CH | H | COCH₃ | N | CH | CH | CH | NCH₃ | 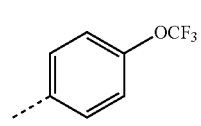 | H |
| 192 | B26 | CH₃ | CH | H | COCH₃ | N | CH | CH | CH | NCH₃ | 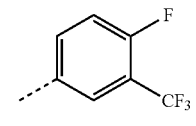 | H |
| 193 | B26 | CH₃ | CH | H | COCH₃ | N | CH | CH | CH | NCH₃ | 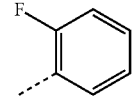 | H |
| 194 | B26 | CH₃ | CH | H | COCH₃ | N | CH | CH | CH | NCH₃ | 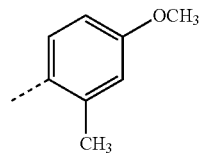 | H |
| 195 | B26 | CH₃ | CH | H | COCH₃ | N | CH | CH | CH | NCH₃ | 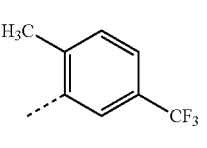 | H |
| 196 | B26 | CH₃ | CH | H | COCH₃ | N | CH | CH | CH | NCH₃ | 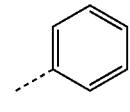 | H |

TABLE 1b-continued

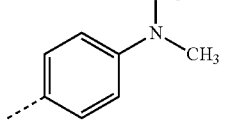

| Co. No. | Pr. | R¹ | X | R² | A¹ | A² | A³ | A⁴ | Y¹ | Z | R³ | R⁴ |
|---|---|---|---|---|---|---|---|---|---|---|---|---|
| 197 | B26 | CH₃ | CH | H | COCH₃ | N | CH | CH | CH | NCH₃ | 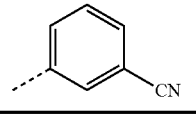 | H |
| 198 | B26 | CH₃ | CH | H | COCH₃ | N | CH | CH | CH | NCH₃ | 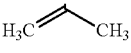 | H |

Compounds 165, 167, 168, 170-172, 176-187 and 190 were obtained as HCl salt forms (.2HCl.H₂O). Compound 166 was obtained as a HCl salt form (.1.5HCl.1.4H₂O). Compounds 210 and 211 were obtained as a HCl salt form (.2HCl). Compound 209 was obtained as a mesylate (.2CH₃SO₃H). All other compounds in Table 1b were obtained as free bases.

TABLE 1c

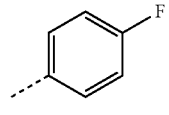

(all compounds in table 1c were obtained as free bases)

| Co. No. | Pr. | R¹ | X | A¹ | A² | R⁴ | Y³ | Z | R³ |
|---|---|---|---|---|---|---|---|---|---|
| 109 | B21 | CH₃ | N | COCH₃ | CH | 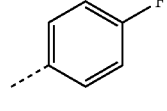 | N | NCH₃ | 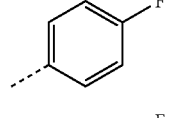 |
| 110 | B21 | CH₃ | N | COCH₃ | CH | CH(CH₃)₂ | N | NCH₃ | 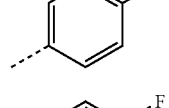 |
| 111 | B22 | CH₃ | CH | COCH₃ | N | CH(CH₃)₂ | N | NCH₃ | 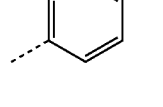 |
| 112 | B23 | CH₃ | CH | CF | CH | CH₃ | N | NCH₃ | |
| 113 | B24 | CH₃ | N | COCH₃ | CH | CH₃ | N | NCH₃ | |

TABLE 1c-continued

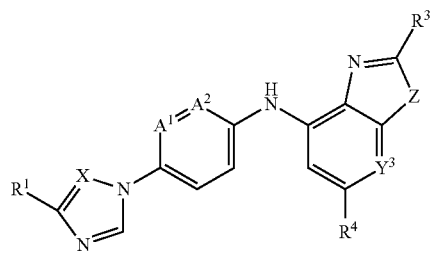

(all compounds in table 1c were obtained as free bases)

| Co. No. | Pr. | R¹ | X | A¹ | A² | R⁴ | Y³ | Z | R³ |
|---|---|---|---|---|---|---|---|---|---|
| 199 | B23 | CH₃ | N | COCH₃ | CH | cyclopropyl | N | NCH₃ | 4-F-phenyl |
| 200 | B23 | CH₃ | N | COCH₃ | CH | H | N | NCH₃ | 4-F-phenyl |
| 201 | B22 | CH₃ | CH | COCH₃ | N | H | N | NCH₃ | 4-F-phenyl |
| 202 | B23 | CH₃ | CH | COCH₃ | N | OCH₃ | N | NCH₃ | 4-F-phenyl |
| 203 | B22 | CH₃ | CH | COCH₃ | N | CH₃ | N | NCH₃ | 4-F-phenyl |
| 204 | B23 | CH₃ | CH | CF | CH | OCH₃ | N | NCH₃ | 4-F-phenyl |
| 205 | B23 | CH₃ | CH | CF | CH | H | N | NCH₃ | 4-F-phenyl |
| 206 | B23 | CH₃ | CH | CF | CH | CH(CH₃)₂ | N | NCH₃ | 4-F-phenyl |
| 207 | B23 | CH₃ | CH | CF | CH | cyclopropyl | N | NCH₃ | 4-F-phenyl |
| 208 | B32 | CH₃ | N | COCH₃ | CH | (CH₂)₃OCH₃ | N | NCH₃ | 4-F-phenyl |

TABLE 1d

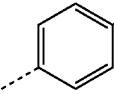

| Co. No. | Pr. | R¹ | X | A¹ | A² | Y² | Z | R³ |
|---|---|---|---|---|---|---|---|---|
| 158 | B19 | CH₃ | N | COCH₃ | CH | N | NCH₃ | (4-F-phenyl) |

Analytical Part
LCMS
General Procedure A

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure B

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure C

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 sec using a dwell time of 0.1 sec. The capillary needle voltage was 3 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM NH₄OAc in H₂O/CH₃CN 95/5; mobile phase B: CH₃CN) were used to run a gradient condition from 95% A and 5 B to 5% A and 95 B in 1.3 minutes and hold for 0.3 minutes (min). An injection volume of 0.5 μl was used. Cone voltage was 10 V for positive ionization mode and 20 V for negative ionization mode.

LCMS Method 2

In addition to general procedure A: Reversed phase UPLC was carried out on a BEH C18 column (1.7 μm, 2.1×50 mm; Waters Acquity) with a flow rate of 0.8 ml/min. Two mobile phases (mobile phase A: 0.1% formic acid in H₂O/MeOH 95/5; mobile phase B: MeOH) were used to run a gradient condition from 95% A and 5% B to 5% A and 95 B in 1.3 min and hold for 0.2 min. An injection volume of 0.5 μl was used. Cone voltage was 10 V for positive and 20 V for negative ionization mode.

LCMS Method 3

In addition to general procedure B: Reversed phase HPLC was carried out on a YMC-Pack ODS-AQ C18 column (4.6×50 mm) with a flow rate of 2.6 ml/min. A gradient run was used from 95% water and 5% CH₃CN to 95% CH₃CN in 4.80 min and was hold for 1.20 min. Mass spectra were acquired by scanning from 100 to 1400. Injection volume was 10 μl. Column temperature was 35° C.

LCMS Method 4

In addition to general procedure C: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM NH₄OAc+5% CH₃CN; mobile phase B: CH₃CN; mobile phase C: MeOH) were employed to run a gradient condition from 100% A to 50% B and 50% C in 6.5 min, to 100% B in 0.5 min and hold these conditions for 1 min and reequilibrate with 100% A for 1.5 min. An injection volume of 10 μl was used. Cone voltage was 10 V for positive ionization mode and 20 V for negative ionization mode.

LCMS Method 5

In addition to general procedure C: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% MeOH+30% H₂O; mobile phase B: 0.1% formic acid in H₂O/MeOH 95/5) were employed to run a gradient condition from 100% B to 5% B+95% A in 9 min and hold these conditions for 3 min. An injection volume of 10 μl was used. Cone voltage was 10 V for positive ionization mode and 20 V for negative ionization mode.

LCMS Method 6

In addition to general procedure C: Reversed phase HPLC was carried out on an Xterra MS C18 column (3.5 μm, 4.6×100 mm) with a flow rate of 1.6 ml/min. Three mobile phases (mobile phase A: 95% 25 mM NH₄OAc+5% CH₃CN; mobile phase B: CH₃CN; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. An injection volume of 10 was used. Cone voltage was 10 V for positive ionization mode and 20 V for negative ionization mode.

LCMS Method 7

In addition to general procedure A: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM NH₄OAc in H₂O/CH₃CN 95/5; mobile phase B: CH₃CN) were used to run a gradient condition from 95% A and 5% B to 5% A and 95% B in 1.3 min and hold for 0.3 min. An injection volume of 0.5 μl was used. Cone voltage was 30 V for positive ionization mode and 30 V for negative ionization mode.

LCMS Method 8

In addition to general procedure C: Reversed phase HPLC was carried out on an Xterra MS C18 column (3.5 μm, 4.6× 100 mm) with a flow rate of 1.6 ml/min. Three mobile phases (mobile phase A: 95% 25 mM $NH_4OAc$+5% $CH_3CN$; mobile phase B: $CH_3CN$; mobile phase C: MeOH) were employed to run a gradient condition from 100% A to 1% A, 49% B and 50% C in 6.5 min, to 1% A, 99% B in 0.5 min and keep these conditions for 1 min. An injection volume of 10 μl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./minute. Maximum temperature was 400° C. Values are peak values.

The results of the analytical measurements are shown in table 2.

TABLE 2

Retention time ($R_t$) in min., [M + H]$^+$ peak (protonated molecule), LCMS method and m.p. (melting point in ° C.).

| Co. No. | $R_t$ | [M + H]$^+$ | LCMS Method | m.p. (° C.) |
|---|---|---|---|---|
| 1 | 1.05 | 428 | 1 | 130.9 |
| 2 | 1.15 | 456 | 1 | n.d. |
| 3 | 1.05 | 446 | 2 | n.d. |
| 4 | 1.02 | 429 | 1 | 185.2 |
| 5 | 0.99 | 399 | 1 | n.d. |
| 6 | 0.99 | 400 | 1 | 201.7 |
| 7 | 1.05 | 398 | 1 | n.d. |
| 8 | 1.01 | 429 | 1 | n.d. |
| 9 | 0.74 | 431 | 1 | n.d. |
| 10 | 0.86 | 473 | 1 | n.d. |
| 11 | 0.62 | 445 | 2 | n.d. |
| 12 | 0.92 | 453 | 2 | 81.2 |
| 13 | 1.13 | 446 | 1 | n.d. |
| 14 | 1.17 | 468 | 1 | n.d. |
| 15 | 1.10 | 429 | 1 | n.d. |
| 16 | 1.22 | 431 | 1 | n.d. |
| 17 | 7.19 | 403 | 6 | n.d. |
| 18 | 1.16 | 377 | 1 | n.d. |
| 19 | 0.57 | 348 | 2 | n.d. |
| 20 | 0.98 | 346 | 2 | n.d. |
| 21 | 0.93 | 377 | 1 | n.d. |
| 22 | 1.06 | 424 | 1 | n.d. |
| 23 | 1.01 | 395 | 1 | 148.2 |
| 24 | 1.04 | 379 | 1 | n.d. |
| 25 | 1.04 | 390 | 1 | n.d. |
| 26 | 1.23 | 403 | 1 | 82.1 |
| 27 | 1.03 | 405 | 1 | n.d. |
| 28 | 1.17 | 378 | 1 | 88.6 |
| 29 | 1.61 | 390 | 3 | n.d. |
| 30 | 1.19 | 377 | 1 | n.d. |
| 31 | 1.09 | 392 | 1 | n.d. |
| 32 | 1.47 | 406 | 3 | n.d. |
| 33 | 1.21 | 422 | 1 | n.d. |
| 34 | 1.02 | 430 | 1 | n.d. |
| 35 | 2.09 | 444 | 3 | n.d. |
| 36 | 1.65 | 402 | 3 | n.d. |
| 37 | 7.51 | 389 | 5 | n.d. |
| 38 | 1.13 | 416 | 1 | 166.8 |
| 39 | 1.11 | 417 | 1 | n.d. |
| 40 | 0.80 | 418 | 1 | n.d. |
| 41 | 0.89 | 446 | 1 | n.d. |
| 42 | 1.20 | 504 | 1 | n.d. |
| 43 | 0.92 | 432 | 1 | n.d. |
| 44 | 0.88 | 447 | 2 | n.d. |
| 45 | 0.96 | 410 | 1 | n.d. |
| 46 | 1.23 | 500 | 1 | n.d. |
| 47 | 0.92 | 440 | 2 | n.d. |
| 48 | 1.16 | 427 | 1 | n.d. |
| 49 | 2.15 | 440 | 3 | n.d. |
| 50 | 2.50 | 411 | 3 | n.d. |
| 51 | 2.98 | 439 | 3 | n.d. |
| 52 | 2.54 | 441 | 3 | n.d. |
| 53 | 3.06 | 469 | 3 | n.d. |
| 54 | 1.07 | 484 | 1 | n.d. |
| 55 | 3.29 | 429 | 3 | n.d. |
| 56 | 3.34 | 459 | 3 | n.d. |
| 57 | 3.39 | 447 | 3 | n.d. |
| 58 | 1.01 | 511 | 1 | n.d. |
| 59 | 1.13 | 498 | 1 | n.d. |
| 60 | 0.93 | 525 | 1 | 203.7 |
| 61 | 1.09 | 426 | 1 | n.d. |
| 62 | 6.23 | 414 | 5 | n.d. |
| 64 | 0.99 | 415 | 1 | n.d. |
| 65 | 1.22 | 403 | 2 | 215.8 |
| 66 | 1.06 | 428 | 1 | n.d. |
| 67 | 1.07 | 416 | 1 | n.d. |
| 68 | 0.98 | 399 | 2 | n.d. |
| 69 | 1.14 | 467 | 1 | 110.6 |
| 70 | 1.01 | 400 | 1 | 230.9 |
| 71 | 1.15 | 492 | 1 | 131.3 |
| 72 | 5.56 | 439 | 4 | n.d. |
| 73 | 1.14 | 427 | 1 | n.d. |
| 74 | 1.17 | 445 | 1 | n.d. |
| 75 | 1.14 | 457 | 1 | n.d. |
| 76 | 1.11 | 428 | 1 | n.d. |
| 77 | 1.17 | 441 | 1 | n.d. |
| 78 | 1.17 | 471 | 1 | n.d. |
| 79 | 1.20 | 504 | 1 | n.d. |
| 80 | 1.20 | 415 | 1 | n.d. |
| 81 | 1.06 | 442 | 1 | n.d. |
| 82 | 1.15 | 429 | 1 | n.d. |
| 83 | 3.13 | 449 | 3 | n.d. |
| 84 | 2.97 | 475 | 3 | n.d. |
| 85 | 3.16 | 475 | 3 | n.d. |
| 86 | 0.97 | 398 | 1 | n.d. |
| 87 | 1.09 | 349 | 1 | n.d. |
| 88 | 1.11 | 427 | 1 | 197.2 |
| 89 | 1.09 | 428 | 1 | 221.3 |
| 90 | 5.23 | 415 | 5 | n.d. |
| 91 | 0.97 | 429 | 1 | n.d. |
| 92 | 1.00 | 430 | 1 | 239.3 |
| 93 | 1.00 | 429 | 1 | n.d. |
| 94 | 5.98 | 429 | 6 | n.d. |
| 95 | 5.18 | 400 | 4 | n.d. |
| 96 | 3.11 | 445 | 3 | n.d. |
| 97 | 0.97 | 418 | 1 | 270.8 |
| 98 | 0.98 | 448 | 1 | 233.2 |
| 99 | 1.00 | 441 | 1 | 173.2 |
| 100 | 1.08 | 432 | 1 | 258.7 |
| 101 | 0.83 | 390 | 7 | 171.1 |
| 102 | 0.99 | 435 | 7 | n.d. |
| 103 | 0.99 | 399 | 7 | n.d. |
| 104 | 1.07 | 435 | 7 | 211.5 |
| 105 | 3.35 | 459 | 3 | n.d. |
| 106 | 1.24 | 475 | 7 | n.d. |
| 107 | 1.19 | 472 | 7 | 224.9 |
| 108 | 1.12 | 431 | 7 | 259.2 |
| 109 | 1.17 | 470 | 7 | n.d. |
| 110 | 1.14 | 472 | 7 | n.d. |
| 111 | 1.21 | 472 | 7 | 172.3 |
| 112 | 1.00 | 431 | 7 | n.d. |
| 113 | 0.94 | 444 | 7 | n.d. |
| 114 | 1.03 | 476 | 7 | 186.8 |
| 115 | 1.13 | 447 | 7 | n.d. |
| 116 | 1.44 | 457 | 2 | n.d. |
| 117 | 1.16 | 507 | 7 | n.d. |
| 118 | 0.94 | 444 | 7 | 0.94 |
| 119 | 1.03 | 458 | 7 | n.d. |
| 120 | 0.97 | 447 | 7 | n.d. |
| 121 | 1.53 | 479 | 2 | n.d. |
| 122 | 1.17 | 473 | 7 | n.d. |
| 123 | 1.18 | 485 | 7 | n.d. |
| 124 | 0.82 | 429 | 7 | 239.3 |

TABLE 2-continued

Retention time ($R_t$) in min., $[M + H]^+$ peak (protonated molecule), LCMS method and m.p. (melting point in °C.).

| Co. No. | $R_t$ | $[M + H]^+$ | LCMS Method | m.p. (°C.) |
|---|---|---|---|---|
| 125 | 1.27 | 462 | 7 | 234.6 |
| 126 | 1.21 | 473 | 7 | n.d. |
| 127 | 1.13 | 479 | 7 | 175.2 |
| 128 | 1.10 | 463 | 7 | n.d. |
| 129 | 1.01 | 436 | 7 | 240.2 |
| 130 | 1.00 | 480 | 7 | 211.5 |
| 131 | 1.31 | 503 | 7 | 224.7 |
| 132 | 1.23 | 497 | 7 | 203.0 |
| 133 | 1.20 | 507 | 7 | n.d. |
| 134 | 1.18 | 475 | 7 | n.d. |
| 135 | 1.13 | 490 | 7 | 217.1 |
| 136 | 1.19 | 477 | 7 | 230.0 |
| 138 | 1.12 | 443 | 7 | n.d. |
| 139 | 1.16 | 447 | 7 | 187.0 |
| 140 | 1.22 | 493 | 7 | 225.9 |
| 141 | 0.97 | 470 | 7 | 257.2 |
| 142 | 1.21 | 456 | 7 | 211.8 |
| 143 | 0.92 | 414 | 7 | 233.4 |
| 144 | 1.15 | 461 | 7 | 252.5 |
| 145 | 0.99 | 446 | 7 | 193.7 |
| 146 | 0.83 | 442 | 7 | 253.5 |
| 147 | 1.08 | 460 | 7 | 185.3 |
| 148 | 0.96 | 442 | 7 | 202.9 |
| 149 | 1.16 | 460 | 7 | 233.0 |
| 150 | 1.12 | 444 | 7 | 216.5 |
| 151 | 1.17 | 463 | 7 | n.d. |
| 152 | 1.27 | 428 | 7 | 155.7 |
| 153 | 1.21 | 457 | 7 | 178.3 |
| 154 | 1.22 | 557 | 7 | n.d. |
| 155 | 1.23 | 509 | 7 | n.d. |
| 156 | 1.10 | 464 | 7 | 257.6 |
| 157 | 6.08 | 470 | 6 | n.d. |
| 158 | 0.81 | 430 | 7 | 221.6 |
| 159 | 1.26 | 459 | 7 | 226.9 |
| 160 | 1.10 | 459 | 7 | 180.7 |
| 161 | 6.14 | 430 | 6 | 233.2 |
| 162 | 6.47 | 458 | 6 | 180.0 |
| 163 | 1.11 | 456 | 2 | 250.2 |
| 164 | 1.05 | 444 | 7 | 254.8 |
| 165 | 1.15 | 447 | 7 | n.d. |
| 166 | 1.11 | 474 | 7 | n.d. |
| 167 | 1.20 | 479 | 7 | n.d. |
| 168 | 1.20 | 479 | 7 | n.d. |
| 169 | 1.22 | 555 | 7 | n.d. |
| 170 | 1.18 | 495 | 7 | n.d. |
| 171 | 1.12 | 429 | 7 | n.d. |
| 172 | 1.13 | 479 | 7 | n.d. |
| 173 | 6.66 | 454 | 6 | n.d. |
| 174 | 5.68 | 468 | 8 | n.d. |
| 175 | 1.08 | 447 | 2 | 166.7 |
| 176 | 6.30 | 447 | 8 | n.d. |
| 177 | 6.31 | 441 | 8 | n.d. |
| 178 | 6.29 | 441 | 8 | n.d. |
| 179 | 6.52 | 455 | 8 | n.d. |
| 180 | 6.32 | 459 | 8 | n.d. |
| 181 | 6.77 | 447 | 6 | n.d. |
| 182 | 1.10 | 459 | 2 | n.d. |
| 183 | 6.70 | 509 | 4 | n.d. |
| 184 | 6.29 | 459 | 4 | n.d. |
| 185 | 6.37 | 443 | 4 | n.d. |
| 186 | 6.42 | 471 | 4 | n.d. |
| 187 | 1.22 | 497 | 7 | n.d. |
| 188 | 1.00 | 459 | 2 | 184.4 |
| 189 | 1.25 | 495 | 7 | n.d. |
| 190 | 1.13 | 447 | 7 | n.d. |
| 191 | 1.24 | 495 | 7 | 167.1 |
| 192 | 1.22 | 497 | 7 | n.d. |
| 193 | 1.12 | 429 | 7 | n.d. |
| 194 | 1.15 | 455 | 7 | n.d. |
| 195 | 1.24 | 493 | 7 | n.d. |
| 196 | 1.11 | 411 | 7 | 181.7 |
| 197 | 1.17 | 454 | 7 | n.d. |
| 198 | 1.06 | 436 | 7 | n.d. |
| 199 | 1.13 | 470 | 7 | n.d. |
| 200 | 0.91 | 430 | 7 | n.d. |
| 201 | 0.98 | 430 | 7 | 252.1 |
| 202 | 6.70 | 460 | 6 | 234.4 |
| 203 | 1.04 | 444 | 7 | 149.8 |
| 204 | 1.14 | 447 | 7 | 185.4 |
| 205 | 0.94 | 417 | 7 | n.d. |
| 206 | 1.20 | 459 | 7 | 101.5 |
| 207 | 1.18 | 457 | 7 | n.d. |
| 208 | 0.99 | 502 | 7 | n.d. |
| 209 | 1.13 | 431 | 7 | 196.9 |
| 211 | 1.13 | 431 | 7 | 266.2 |
| 212 | 6.51 | 531 | 6 | n.d. |

(n.d. means not determined)

For Co. No. 137, the $[M - H]^-$ peak was detected: Rt 5.98; $[M - H]^-$ 415; LCMS Method 5; Melting Point: 225.6° C.

$^1$H NMR

For a number of compounds, $^1$H NMR spectra were recorded on a Bruker DPX-360, on a Bruker DPX-400 or on a Bruker Avance 600 spectrometer with standard pulse sequences, operating at 360 MHz, 400 MHz and 600 MHz respectively, using CHLOROFORM-d (deuterated chloroform, $CDCl_3$) or DMSO-$d_6$ (deuterated DMSO, dimethyl-d6 sulfoxide) as solvents. Chemical shifts (δ) are reported in parts per million (ppm) relative to tetramethylsilane (TMS), which was used as internal standard.

Co. No. 1: (360 MHz, DMSO-$d_6$) δ ppm 2.14 (s, 3 H), 3.74 (s, 3 H), 3.86 (s, 3 H), 6.93 (dd, J=8.5, 2.2 Hz, 1 H), 7.01 (s, 1 H), 7.12-7.23 (m, 5 H), 7.43 (t, 6 J=8.8 Hz, 2 H), 7.63 (d, J=1.3 Hz, 1 H), 7.92 (dd, J=8.6, 5.5 Hz, 2 H), 8.46 (s, 1 H).

Co. No. 2: (360 MHz, DMSO-$d_6$) δ ppm 1.59 (d, J=6.9 Hz, 6 H), 2.14 (s, 3 H), 3.74 (s, 3 H), 4.58-4.71 (m, J=6.9, 6.9, 6.9, 6.9 Hz, 1 H), 6.95 (dd, J=8.5, 2.26 Hz, 1 H), 7.01 (s, 1 H), 7.12-7.20 (m, 4 H), 7.29-7.37 (m, 1 H), 7.43 (t, J=8.8 Hz, 2 H), 7.63 (d, J=1.3 Hz, 1 H), 7.73 (dd, J=8.5, 5.5 Hz, 2 H), 8.41 (s, 1 H).

Co. No. 3: (360 MHz, DMSO-$d_6$) δ ppm 2.14 (s, 3 H), 3.70 (s, 3 H), 3.73 (s, 3 H), 6.93 (dd, J=8.5, 2.3 Hz, 1 H), 7.01 (s, 1 H), 7.12 (d, J=2.3 Hz, 1 H), 7.15-6 7.26 (m, 4 H), 7.35 (td, J=8.5, 2.6 Hz, 1 H), 7.56 (td, J=9.9, 2.5 Hz, 1 H), 7.63 (d, J=1.3 Hz, 1 H), 7.76-7.83 (m, 1 H), 8.50 (s, 1 H).

Co. No. 4: (360 MHz, DMSO-$d_6$) δ ppm 2.32 (s, 3 H), 3.78 (s, 3 H), 3.86 (s, 3 H), 6.95 (dd, J=8.7, 2.2 Hz, 1 H), 7.13 (d, J=2.2 Hz, 1 H), 7.17-7.25 (m, 3 H), 6 7.38 (d, J=8.6 Hz, 1 H), 7.43 (t, J=8.8 Hz, 2 H), 7.92 (dd, J=8.6, 5.5 Hz, 2 H), 8.55 (s, 1 H), 8.61 (s, 1H).

Co. No. 5: (360 MHz, $CDCl_3$) δ ppm 2.31 (s, 3 H), 3.86 (s, 3 H), 6.93 (s, 1 H), 6.99-7.06 (m, 2 H), 7.26 (t, 2 H), 7.34 (t, J=8.2 Hz, 1 H), 7.53 (dd, J=8.8, 2.7 Hz, 1 H), 7.66 (s, 1 H), 7.76 (dd, J=8.5, 5.3 Hz, 2 H), 7.92 (s, 1 H), 8.24 (d, J=8.0 Hz, 1 H), 8.36 (d, J=2.7 Hz, 1 H).

Co. No. 6: (600 MHz, $CDCl_3$) δ ppm 2.30 (d, J=1.1 Hz, 3 H), 3.86 (s, 3 H), 6.93 (br. s, 1 H), 7.03 (dd, J=8.1, 0.8 Hz, 1 H), 7.07 (dd, J=8.1, 0.8 Hz, 1 H), 7.24-7.28 (m, 3 H), 7.53-7.56 (m, J=1.1, 1.1, 1.1, 1.1 Hz, 1 H), 7.75 (dd, J=8.7, 5.3 Hz, 2 H), 8.45 (d, J=1.3 Hz, 1 H), 8.67 (s, 2 H).

Co. No. 7: (600 MHz, $CDCl_3$) δ ppm 2.30 (d, J=1.1 Hz, 3 H), 3.84 (s, 3 H), 6.94 (dd, J=8.0, 0.9 Hz, 1 H), 6.95-6.96 (m, J=1.2, 1.2, 1.2, 1.2 Hz, 1 H), 7.10 (br. s, 1 H), 7.19 (dd, J=8.0, 0.9 Hz, 1 H), 7.22-7.26 (m, 3 H), 7.28 (d, J=8.7 Hz, 2 H), 7.36 (d, J=8.7 Hz, 2 H), 7.69 (d, J=1.4 Hz, 1 H), 7.74 (dd, J=8.7, 5.3 Hz, 2 H).

Co. No. 8: (400 MHz, DMSO-d$_6$) δ ppm 2.15 (d, J=1.0 Hz, 3 H), 3.81 (s, 3 H), 3.86 (s, 3 H), 7.04 (s, 1 H), 7.17 (d, J=5.8 Hz, 1 H), 7.23 (d, J=8.6 Hz, 1 H), 6 7.45 (t, J=8.8 Hz, 2 H), 7.66 (s, 1 H), 7.91 (dd, J=8.6, 2.2 Hz, 1 H), 7.96 (dd, J=8.7, 5.5 Hz, 2 H), 8.00-8.02 (m, 2 H), 9.23 (s, 1 H).

Co. No. 15: (400 MHz, CDCl$_3$) δ ppm 2.29 (d, J=1.01 Hz, 3 H) 3.83 (s, 3 H) 4.06 (s, 3H) 6.57 (d, J=8.31 Hz, 1 H) 6.86 (t, J=1.01 Hz, 1 H) 7.02 (dd, J=8.06, 0.76 Hz, 1 H) 7.24 (t, J=8.81 Hz, 2 H) 7.31 (t, J=8.06 Hz, 1 H) 7.39 (d, J=8.06 Hz, 1 H) 7.62 (d, J=1.26 Hz, 1 H) 7.74 (dd, J=8.81, 5.29 Hz, 2 H) 7.94 (s, 1 H) 8.16 (d, J=7.81 Hz, 1 H).

Co. No. 16: (360 MHz, CDCl$_3$) δ ppm 2.31 (s, 3 H), 3.83 (s, 3 H), 6.89 (s, 1 H), 6.91 (s, 1 H), 6.93-6.98 (m, 2 H), 7.16 (dd, J=7.3, 1.5 Hz, 1 H), 7.20 (d, J=9.1 Hz, 1 H), 7.24-7.33 (m, 2 H), 7.41-7.50 (m, 2 H), 7.59 (dd, J=7.4, 1.9 Hz, 1 H), 7.64 (s, 1 H), 8.14 (dd, J=7.2, 2.3 Hz, 1 H).

Co. No. 17: (360 MHz, CDCl$_3$) δ ppm 1.27-1.50 (m, 3 H), 1.65-1.77 (m, 3 H), 1.84-1.93 (m, 2 H), 2.11-2.20 (m, 2 H), 2.30 (s, 3 H), 2.96 (tt, J=11.4, 3.6 Hz, 1 H), 3.81 (s, 3 H), 6.72 (s, 1 H), 6.85-6.91 (m, 3 H), 7.02-7.08 (m, 1 H), 7.14-7.22 (m, 3 H), 7.63 (s, 1 H).

Co. No. 18: (360 MHz, CDCl$_3$) δ ppm 1.05 (d, J=6.7 Hz, 6 H), 2.23-2.36 (m, 1 H), 2.30 (s, 3 H), 2.81 (d, J=7.2 Hz, 2 H), 3.81 (s, 3 H), 6.72 (s, 1 H), 6.86-6.91 (m, 3 H), 7.03-7.09 (m, 1 H), 7.16 (d, J=9.1 Hz, 1 H), 7.19-7.24 (m, 2 H), 7.62 (d, J=1.3 Hz, 1H).

Co. No. 25: (360 MHz, DMSO-d$_6$) δ ppm 1.02 (d, J=7.0 Hz, 6 H), 2.27-2.43 (m, 4 H), 3.09 (d, J=7.3 Hz, 2 H), 3.82 (s, 3 H), 3.98 (s, 3 H), 6.94 (dd, J=8.6, 2.2 Hz, 1 H), 7.08 (d, J=2.2 Hz, 1 H), 7.39-7.55 (m, 4 H), 7.66 (s, 1 H), 9.31 (d, J=1.5 Hz, 1 H), 9.53 (br. s, 1 H).

Co. No. 37: (360 MHz, CDCl$_3$) δ ppm 1.68-1.80 (m, 2 H), 1.81-1.93 (m, 2 H), 1.98-2.10 (m, 2 H), 2.12-2.22 (m, 2 H), 2.30 (s, 3 H), 3.33-3.43 (m, J=8.1, 8.1, 8.1, 8.1 Hz, 1H), 3.81 (s, 3 H), 6.70 (s, 1 H), 6.85-6.90 (m, 3 H), 7.01-7.07 (m, 1 H), 7.14-7.22 (m, 3H), 7.63 (d, J=1.3 Hz, 1 H).

Co. No. 38: (360 MHz, CDCl$_3$) δ ppm 1.32-1.51 (m, 3 H), 1.73-1.87 (m, 3 H), 1.88-2.04 (m, 4 H), 2.30 (s, 3 H), 2.86 (tt, J=11.8, 3.4 Hz, 1 H), 3.75 (s, 3 H), 3.81 (s, 3 H), 6.84-6.90 (m, 2 H), 6.91-6.96 (m, 2 H), 7.04 (s, 1 H), 7.12-7.18 (m, 3 H), 7.62 (s, 1 H).

Co. No. 40: (360 MHz, CDCl$_3$) δ ppm 2.06-2.26 (m, 4 H), 2.30 (s, 3 H), 2.36 (s, 3 H), 2.89-3.04 (m, 3 H), 3.64 (br. s, 2 H), 3.79 (s, 3 H), 6.75 (s, 1 H), 6.84-6.91 (m, 3 H), 7.02-7.09 (m, 1 H), 7.17 (d, J=8.8 Hz, 1 H), 7.19-7.23 (m, 2 H), 7.65 (s, 1 H).

Co. No. 41: (360 MHz, CDCl$_3$) δ ppm 1.85-2.03 (m, 2 H), 2.15 (s, 3 H), 2.16-2.25 (m, 2 H), 2.30 (s, 3 H), 2.95 (ddd, J=13.7, 11.1, 3.1 Hz, 1 H), 3.22 (tt, J=10.7, 4.0 Hz, 1 H), 3.30 (ddd, J=13.8, 11.1, 2.8 Hz, 1 H), 3.82 (s, 3 H), 3.92 (dt, J=13.8, 4.2 Hz, 1 H), 4.56 (dt, J=13.5, 4.2 Hz, 1 H), 6.74 (s, 1 H), 6.86-6.91 (m, 3 H), 7.02-7.08 (m, 1 H), 7.17 (d, J=9.0 Hz, 1 H), 7.20-7.25 (m, 2 H), 7.63 (d, J=1.3 Hz, 1 H).

Co. No. 42: (360 MHz, CDCl$_3$) δ ppm 1.48 (s, 9 H), 1.84-1.97 (m, 2 H), 2.08-2.18 (m, 2 H), 2.30 (s, 3 H), 2.99 (t, J=12.0 Hz, 2 H), 3.13 (tt, J=11.0, 3.9 Hz, 1 H), 3.82 (s, 3H), 4.16 (br. s, 2 H), 6.71 (s, 1 H), 6.86-6.91 (m, 3 H), 7.02-7.07 (m, 1 H), 7.16-7.23 (m, 3 H), 7.63 (d, J=1.3 Hz, 1 H).

Co. No. 44: (600 MHz, DMSO-d$_6$) δ ppm 1.15 (d, J=6.2 Hz, 6 H), 2.14 (d, J=1.0 Hz, 3H), 2.61 (dd, J=12.3, 10.4 Hz, 2 H), 3.44 (d, J=12.0 Hz, 2 H), 3.62 (s, 36 H), 3.73 (s, 3H), 3.81-3.87 (m, 2 H), 6.82 (dd, J=8.5, 2.3 Hz, 1 H), 6.96 (dd, J=6.5, 2.4 Hz, 1 H), 6.98 (t, J=1.2 Hz, 1 H), 7.01-7.06 (m, 3 H), 7.13 (d, J=8.5 Hz, 1 H), 7.60 (d, J=1.3 Hz, 1 H), 7.99 (s, 1 H).

Co. No. 47: (360 MHz, DMSO-d$_6$) δ ppm 2.14 (s, 3 H), 3.74 (s, 3 H), 3.85 (s, 3 H), 3.85 (s, 3 H), 6.92 (dd, J=8.5, 2.3 Hz, 1 H), 7.01 (s, 1 H), 7.11-7.21 (m, 76 H), 7.63 (d, J=1.3 Hz, 1 H), 7.81 (d, J=8.6 Hz, 2 H), 8.42 (s, 1 H).

Co. No. 48: (360 MHz, CDCl$_3$) δ ppm 2.31 (s, 3 H), 3.81 (s, 3 H), 4.02 (s, 3 H), 6.88 (s, 1 H), 6.91-6.94 (m, 2 H), 7.09-7.19 (m, 5 H), 7.23-7.29 (m, 2 H), 7.49-7.55 (m, 1H), 7.63 (s, 1 H), 8.12 (dd, J=7.7, 1.8 Hz, 1 H).

Co. No. 54: (360 MHz, DMSO-d$_6$) δ ppm 2.35 (s, 3 H) 3.15 (s, 3 H) 3.78 (t, J=4.76 Hz, 2 H) 3.83 (s, 3 H) 3.89 (s, 3 H) 4.62 (t, J=4.76 Hz, 2 H) 7.01 (dd, J=8.78, 2.20 Hz, 1 H) 7.16 (d, J=2.20 Hz, 1 H) 7.30 (dd, J=8.05, 1.83 Hz, 1 H) 7.41-7.57 (m, 5 H) 7.58-7.65 (m, 2 H) 7.66 (s, 1 H) 9.31 (d, J=1.46 Hz, 1 H) 9.44 (br. s, 1 H) 15.01 (br. s, 1 H).

Co. No. 62: (360 MHz, DMSO-d$_6$) δ ppm 2.14 (s, 3 H), 3.75 (s, 3 H), 6.93 (dd, J=8.5, 2.3 Hz, 1 H), 7.02 (s, 1 H), 7.06-7.20 (m, 5 H), 7.42 (t, J=8.7 Hz, 2 H), 6 7.64 (s, 1 H), 8.23 (dd, J=8.5, 5.4 Hz, 2 H), 8.38 (s, 1 H), 12.93 (s, 1 H).

Co. No. 63: (400 MHz, CDCl$_3$) δ ppm 3.81 (s, 3 H) 3.85 (s, 3 H) 6.92-7.01 (m, 3 H) 7.13-7.21 (m, 4 H) 7.21-7.30 (m, 4 H) 7.69-7.79 (m, 3 H).

Co. No. 66: (360 MHz, DMSO-d$_6$) δ ppm 2.14 (s, 3 H), 3.70 (d, J=1.6 Hz, 3 H), 3.74 (s, 3 H), 6.93 (dd, J=8.5, 2.3 Hz, 1 H), 7.01 (s, 1 H), 7.12 (d, J=2.2 Hz, 16 H), 7.15-7.20 (m, 3 H), 7.24 (t, J=7.7 Hz, 1 H), 7.41-7.51 (m, 2 H), 7.63 (d, J=1.3 Hz, 1 H), 7.63-7.69 (m, 1 H), 7.70-7.75 (m, 1 H), 8.50 (s, 1 H).

Co. No. 67: (400 MHz, CDCl$_3$) δ ppm 2.31 (s, 3 H), 3.85 (s, 3 H), 6.92 (s, 1 H), 6.99-7.03 (m, 1 H), 7.06 (dd, J=8.7, 2.5 Hz, 1 H), 7.15 (s, 1 H), 7.18-7.30 (m, 6 H), 7.65 (s, 1 H), 7.74 (dd, J=8.5, 5.3 Hz, 2 H).

Co. No. 70: (400 MHz, DMSO-d$_6$) δ ppm 2.37 (s, 3 H), 3.86 (s, 3 H), 7.10 (dd, J=6.2, 2.5 Hz, 1 H), 7.19-7.26 (m, 2 H), 7.42 (t, J=8.8 Hz, 2 H), 7.67 (d, J=8.86 Hz, 1 H), 7.81 (dd, J=8.8, 2.8 Hz, 1 H), 7.91 (dd, J=8.6, 5.6 Hz, 2 H), 8.41 (d, J=2.7 Hz, 1 H), 8.74 (s, 1 H), 9.06 (s, 1 H).

Co. No. 71: (360 MHz, DMSO-d$_6$) δ ppm 3.75 (s, 3 H), 3.86 (s, 3 H), 6.93 (dd, J=8.8, 2.2 Hz, 1 H), 7.13 (d, J=2.2 Hz, 1 H), 7.16-7.25 (m, 4 H), 7.44 (t, J=8.86 Hz, 2 H), 7.50 (d, J=1.1 Hz, 1 H), 7.78 (d, J=1.1 Hz, 1 H), 7.92 (dd, J=8.5, 5.5 Hz, 2 H), 8.55 (s, 1 H).

Co. No. 74: (360 MHz, DMSO-d$_6$) δ ppm 1.67 (d, J=6.9 Hz, 6 H), 2.35 (s, 3 H), 4.67-4.80 (m, J=6.9, 6.9, 6.9, 6.9 Hz, 1 H), 7.13 (dd, J=8.7, 2.5 Hz, 1 H), 7.18 6 (dd, J=12.8, 2.6 Hz, 1 H), 7.42-7.52 (m, 2 H), 7.55-7.62 (m, 3 H), 7.75 (d, J=7.8 Hz, 1 H), 7.91 (dd, J=8.5, 5.3 Hz, 2 H), 8.76 (d, J=2.0 Hz, 1 H), 9.32 (br. s, 1 H).

Co. No. 75: (360 MHz, DMSO-d$_6$) δ ppm 1.69 (d, J=6.95 Hz, 6 H) 2.37 (s, 3 H) 3.84 (s, 3 H) 4.77 (spt, J=6.95 Hz, 1 H) 6.96 (dd, J=8.42, 2.20 Hz, 1 H) 7.08 (d, J=2.20 Hz, 1 H) 7.47-7.55 (m, 3 H) 7.62 (t, J=8.78 Hz, 2 H) 7.67-7.73 (m, 1 H) 7.96 (dd, J=8.78, 5.12 Hz, 2 H) 8.91 (s, 1 H) 9.40 (br. s, 1 H).

Co. No. 79: (360 MHz, CDCl$_3$) δ ppm 2.31 (s, 3 H), 3.82 (s, 3 H), 5.41 (s, 2 H), 6.80 (d, J=7.9 Hz, 1 H), 6.88 (s, 1 H), 6.94-6.99 (m, 2 H), 7.09-7.20 (m, 7 H), 7.25 (d, J=8.1 Hz, 1 H), 7.30-7.38 (m, 3 H), 7.61-7.68 (m, 3 H).

Co. No. 80: (400 MHz, DMSO-d$_6$) δ ppm 2.15 (d, J=1.0 Hz, 3 H), 3.76 (s, 3 H), 6.90 (dd, J=8.5, 2.3 Hz, 1 H), 7.03 (s, 1 H), 7.10 (d, J=2.3 Hz, 1 H), 7.22 (d, 6 J=8.5 Hz, 1H), 7.25-7.34 (m, 3 H), 7.47 (t, J=8.8 Hz, 2 H), 7.65 (d, J=1.3 Hz, 1 H), 8.25 (dd, J=8.8, 5.4 Hz, 2 H), 8.74 (s, 1 H).

Co. No. 82: (360 MHz, CDCl$_3$) δ ppm 2.30 (s, 3 H), 3.80 (s, 3 H), 4.25 (s, 2 H), 6.74 (s, 1 H), 6.85-6.89 (m, 3 H), 7.01-7.08 (m, 3 H), 7.16 (d, J=9.0 Hz, 1 H), 7.19-7.22 (m, 2 H), 7.35 (dd, J=8.4, 5.3 Hz, 2 H), 7.62 (d, J=1.1 Hz, 1 H).

Co. No. 86: (360 MHz, CDCl$_3$) δ ppm 2.31 (s, J=1.0 Hz, 3 H), 3.84 (s, 3 H), 6.87 (s, 1H), 6.88-6.91 (m, 1 H), 6.93-6.97 (m, 2 H), 7.16 (dd, J=7.4, 1.5 Hz, 1 H), 7.21 (d, J=9.0 Hz, 1 H), 7.25-7.32 (m, 2 H), 7.49 (ddd, J=8.0, 4.9, 0.9 Hz, 1 H), 7.65

(d, J=1.3 Hz, 1 H), 8.50 (dt, J=8.0, 1.9 Hz, 1 H), 8.77 (dd, J=4.9, 1.7 Hz, 1 H), 9.48 (dd, J=2.2, 0.9 Hz, 1 H).

Co. No. 92: (360 MHz, DMSO-$d_6$) δ ppm 2.34 (s, 3 H) 3.85 (s, 3 H) 3.87 (s, 3 H) 7.20 (d, J=5.85 Hz, 1 H) 7.38-7.53 (m, 3 H) 7.92-8.00 (m, 3 H) 8.03 (d, J=5.85 Hz, 1 H) 8.06 (d, J=2.20 Hz, 1 H) 8.65 (s, 1 H) 9.34 (s, 1 H).

Co. No. 104: (360 MHz, DMSO-$d_6$) δ ppm 2.17 (s, 3 H) 3.72 (s, 3 H) 7.18 (s, 1 H) 7.24 (d, J=5.85 Hz, 1 H) 7.37 (td, J=8.60, 2.20 Hz, 1 H) 7.46 (t, J=8.97 Hz, 1 H) 7.59 (td, J=9.15, 2.20 Hz, 1 H) 7.78-7.89 (m, 2 H) 7.95 (dd, J=9.15, 1.83 Hz, 1 H) 8.06 (d, J=5.85 Hz, 1 H) 8.39 (dd, J=14.27, 2.20 Hz, 1 H) 9.69 (s, 1 H).

Co. No. 106: (360 MHz, CDCl$_3$) δ ppm 1.63 (d, J=7.0 Hz, 6 H), 2.30 (s, 3 H), 4.10 (s, 3 H), 4.70 (spt, J=7.0 Hz, 1 H), 6.53 (d, J=8.1 Hz, 1 H), 6.88 (s, 1 H), 6.90 (dd, J=9.1, 2.2 Hz, 1 H), 7.26 (t, J=8.6 Hz, 2 H), 7.43 (d, J=8.1 Hz, 1 H), 7.55-7.68 (m, 3 H), 7.96 (s, 1 H), 8.12 (dd, J=12.8, 2.2 Hz, 1 H).

Co. No. 107: (360 MHz, CHLOROFORM-d) δ ppm 1.42 (d, J=7.0 Hz, 6 H), 2.49 (s, 3H), 3.12 (spt, J=7.0 Hz, 1 H), 3.82 (s, 3 H), 4.00 (s, 3 H), 6.74 (s, 1 H), 7.16 (dd, J=8.8, 1.8 Hz, 1 H), 7.22-7.31 (m, 2 H), 7.58 (d, J=8.8 Hz, 1 H), 7.74 (dd, J=8.1, 5.9 Hz, 2H), 7.78 (s, 1 H), 8.51 (s, 1 H), 8.58 (s, 1 H).

Co. No. 108: (600 MHz, CDCl$_3$) δ ppm 2.31 (d, J=1.0 Hz, 3 H), 2.65 (s, 3 H), 3.81 (s, 3 H), 6.77 (d, J=0.8 Hz, 1 H), 6.92-6.95 (m, 1 H), 7.24-7.30 (m, 3 H), 7.44 (d, J=8.7, 2.4 Hz, 1 H), 7.67 (t, J=1.4 Hz, 1 H), 7.74 (dd, J=8.8, 5.2 Hz, 2 H), 7.80 (s, 1 H), 8.35 (dd, J=13.5, 2.4 Hz, 1 H).

Co. No. 110: (360 MHz, CDCl$_3$) δ ppm 1.34 (d, J=6.95 Hz, 6 H) 2.50 (s, 3 H) 3.10 (spt, J=6.95 Hz, 1 H) 3.91 (s, 3 H) 3.93 (s, 3 H) 6.98-7.08 (m, 3 H) 7.25 (t, J=8.42 Hz, 2 H) 7.33 (s, 1 H) 7.70 (d, J=8.05 Hz, 1 H) 7.78 (dd, J=8.42, 5.31 Hz, 2 H) 8.54 (s, 1H).

Co. No. 111: (360 MHz, CDCl$_3$) δ ppm 1.39 (d, J=7.0 Hz, 6 H), 2.31 (s, 3 H), 3.17 (spt, J=6.9 Hz, 1 H), 3.94 (s, 3 H), 4.14 (s, 3 H), 6.60 (d, J=8.1 Hz, 1 H), 6.90 (s, 1 H), 7.20-7.32 (m, 2 H), 7.48 (d, J=8.1 Hz, 1 H), 7.67 (s, 1 H), 7.79 (dd, J=8.1, 5.5 Hz, 2H), 8.05 (s, 1 H), 8.21 (s, 1 H).

Co. No. 112: (360 MHz, DMSO-$d_6$) δ ppm 2.17 (s, 3 H), 2.51 (s, 3 H), 3.85 (s, 3 H), 6.95 (s, 1 H), 7.20 (s, 1 H), 7.33 (dd, J=8.8, 2.2 Hz, 1 H), 7.37-7.47 (m, 3 H), 7.52 (t, J=8.8 Hz, 1 H), 7.84 (s, 1 H), 7.96 (dd, J=8.8, 5.5 Hz, 2 H), 9.36 (s, 1 H).

Co. No. 113: (360 MHz, CDCl$_3$) δ ppm 2.50 (s, 3 H) 2.60 (s, 3 H) 3.91 (s, 3 H) 3.92 (s, 3 H) 6.93 (s, 1 H) 6.97 (d, J=2.20 Hz, 1 H) 7.08 (dd, J=8.42, 2.20 Hz, 1 H) 7.26 (t, J=8.60 Hz, 2 H) 7.35 (s, 1 H) 7.70 (d, J=8.42 Hz, 1 H) 7.78 (dd, J=8.78, 5.49 Hz, 2 H) 8.55 (s, 1 H).

Co. No. 114: (360 MHz, DMSO-$d_6$) δ ppm 2.33 (s, 3 H), 3.85 (s, 3 H), 3.89 (s, 3 H), 3.97 (s, 3 H), 7.21 (d, J=5.9 Hz, 1 H), 7.45 (d, J=8.8 Hz, 1 H), 7.48 (dd, J=8.1, 1.8 Hz, 1 H), 7.62 (d, J=1.8 Hz, 1 H), 7.67 (d, J=8.1 Hz, 1 H), 7.99 (dd, J=8.8, 2.2 Hz, 1 H), 8.03 (d, J=5.9 Hz, 1 H), 8.05 (d, J=2.2 Hz, 1 H), 8.66 (s, 1 H), 9.40 (s, 1 H).

Co. No. 115: (360 MHz, CDCl$_3$) δ ppm 2.30 (s, 3 H), 3.81 (s, 3 H), 4.10 (s, 3 H), 6.54 (d, J=8.1 Hz, 1 H), 6.70 (dd, J=8.4, 2.2 Hz, 1 H), 6.89 (s, 1 H), 7.21-7.32 (m, 2 H), 7.44 (d, J=8.1 Hz, 1 H), 7.65 (s, 1 H), 7.74 (dd, J=8.2, 5.3 Hz, 2 H), 7.94 (s, 1 H), 8.15 (dd, J=12.8, 2.2 Hz, 1 H).

Co. No. 116: (360 MHz, CDCl$_3$) δ ppm 1.67 (d, J=7.0 Hz, 6 H), 2.30 (s, 3 H), 4.06 (s, 3 H), 4.73 (spt, J=7.0 Hz, 1 H), 6.57 (d, J=8.1 Hz, 1 H), 6.87 (s, 1 H), 7.21-7.30 (m, 4H), 7.40 (d, J=8.1 Hz, 1 H), 7.57-7.68 (m, 3 H), 7.89 (s, 1 H), 8.14 (dd, J=6.9, 1.8 Hz, 1 H).

Co. No. 118: (360 MHz, DMSO-$d_6$) δ ppm 3.75 (s, 3 H) 3.86 (s, 3 H) 4.39 (s, J=5.49 Hz, 2 H) 4.91 (t, J=5.49 Hz, 1 H) 6.94 (dd, J=8.42, 2.20 Hz, 1 H) 7.09-7.26 (m, 6 H) 7.44 (t, J=8.78 Hz, 2 H) 7.69 (s, 1 H) 7.92 (dd, J=8.78, 5.49 Hz, 2 H) 8.47 (s, 1 H).

Co. No. 131: (360 MHz, DMSO-$d_6$) δ ppm 1.60 (d, J=6.95 Hz, 6 H) 2.14 (s, 3 H) 3.94 (s, 3 H) 3.96 (s, 3 H) 4.69 (spt, J=6.95 Hz, 1 H) 6.95 (d, J=8.42 Hz, 1 H) 7.07 (t, J=1.10 Hz, 1 H) 7.18-7.29 (m, 2 H) 7.38 (d, J=8.05 Hz, 1 H) 7.41 (d, J=1.83 Hz, 1 H) 7.60 (d, J=8.42 Hz, 1 H) 7.65 (d, J=8.05 Hz, 1 H) 7.70 (d, J=1.10 Hz, 1 H) 8.21 (d, J=8.05 Hz, 1 H) 9.17 (s, 1 H).

Co. No. 132: (360 MHz, DMSO-$d_6$) δ ppm 2.15 (s, 3 H) 3.94 (s, 3 H) 3.97 (s, 3 H) 6.97 (d, J=8.42 Hz, 1 H) 7.08 (s, 1 H) 7.24 (d, J=8.05 Hz, 1 H) 7.31 (t, J=7.87 Hz, 1 H) 7.62 (d, J=8.42 Hz, 1 H) 7.71 (d, J=1.10 Hz, 1 H) 7.94 (dt, J=8.42, 1.83 Hz, 1 H) 8.09-8.17 (m, 2 H) 8.28 (d, J=8.05 Hz, 1 H) 9.24 (s, 1 H).

Co. No. 133: (360 MHz, DMSO-$d_6$) δ ppm 2.15 (s, 3 H) 3.88 (s, 3 H) 3.97 (s, 3 H) 6.96 (d, J=8.42 Hz, 1 H) 7.08 (s, 1 H) 7.20 (d, J=7.68 Hz, 1 H) 7.28 (t, J=8.05, 7.68 Hz, 1H) 7.56-7.67 (m, 2 H) 7.71 (s, 1 H) 7.96 (ddd, J=8.42, 4.76, 2.20 Hz, 1 H) 8.19-8.30 (m, 2 H) 9.20 (s, 1 H).

Co. No. 135: (360 MHz, CDCl$_3$) δ ppm 2.49 (s, 3 H) 2.63 (s, 3 H) 3.83 (s, 3 H) 3.98 (s, 3 H) 4.02 (s, 3 H) 6.74 (s, 1 H) 7.14-7.24 (m, 2 H) 7.39 (s, 1 H) 7.54 (d, J=8.05 Hz, 1H) 7.59 (d, J=8.78 Hz, 1 H) 7.73 (s, 1 H) 8.47 (d, J=1.46 Hz, 1 H) 8.51 (s, 1 H).

Co. No. 136: (360 MHz, CDCl$_3$) δ ppm 2.31 (s, 3 H) 2.65 (s, 3 H) 3.83 (s, 3 H) 4.02 (s, 3 H) 6.76 (s, 1 H) 6.93 (s, 1 H) 7.20 (dd, J=8.23, 1.65 Hz, 1 H) 7.26 (t, J=9.15, 7.68 Hz, 1 H) 7.38 (d, J=1.83 Hz, 1 H) 7.46 (dd, J=8.78, 2.20 Hz, 1 H) 7.54 (d, J=8.05 Hz, 1 H) 7.67 (s, 1 H) 7.79 (s, 1 H) 8.34 (dd, J=13.72, 2.38 Hz, 1 H).

Co. No. 142: (360 MHz, CDCl$_3$) δ ppm 2.31 (s, 3 H) 2.64 (s, 3 H) 3.05 (s, 6 H) 3.81 (s, 3 H) 6.76 (s, 1 H) 6.89 (dd, J=8.42, 2.56 Hz, 1 H) 6.93 (s, 1 H) 6.96 (d, J=7.32 Hz, 1H) 7.05 (s, 1 H) 7.25 (t, J=8.42 Hz, 1 H) 7.39 (t, J=7.87 Hz, 1 H) 7.46 (dd, J=8.78, 1.83 Hz, 1 H) 7.66 (s, 1 H) 7.82 (s, 1 H) 8.34 (dd, J=13.90, 2.20 Hz, 1 H).

Co. No. 150: (360 MHz, CDCl$_3$) δ ppm 2.30 (s, 3 H) 2.65 (s, 3 H) 3.81 (s, 3 H) 3.95 (s, 3 H) 6.79 (s, 1 H) 6.90 (s, 1 H) 7.27 (t, J=8.42 Hz, 2 H) 7.55 (d, J=8.05 Hz, 1 H) 7.66 (s, 1 H) 7.76 (dd, J=8.42, 5.12 Hz, 2 H) 8.27 (s, 1 H) 8.45 (d, J=8.42 Hz, 1 H).

Co. No. 160: (360 MHz, CDCl$_3$) δ ppm 2.30 (s, 3 H) 3.80 (s, 3 H) 3.92 (s, 3 H) 4.09 (s, 3 H) 6.48 (d, J=1.46 Hz, 1 H) 6.57 (d, J=8.42 Hz, 1 H) 6.88 (s, 1 H) 7.24 (t, J=8.78 Hz, 2 H) 7.41 (d, J=8.42 Hz, 1 H) 7.64 (s, 1 H) 7.73 (dd, J=8.78, 5.49 Hz, 2 H) 7.88 (s, 1H) 7.96 (d, J=1.46 Hz, 1 H).

Co. No. 161: (360 MHz, DMSO-$d_6$) δ ppm 2.33 (s, 3 H) 3.86 (s, 3 H) 3.99 (s, 3 H) 6.96 (d, J=8.42 Hz, 1 H) 7.22 (d, 1 H) 7.27 (t, J=8.05 Hz, 1 H) 7.44 (t, J=8.78 Hz, 2 H) 7.77 (d, J=8.42 Hz, 1 H) 7.94 (dd, J=8.78, 5.49 Hz, 2 H) 8.20 (d, J=7.68 Hz, 1 H) 8.68 (s, 1H) 9.30 (s, 1 H).

Co. No. 162: (360 MHz, DMSO-$d_6$) δ ppm 1.60 (d, J=6.95 Hz, 6 H) 2.33 (s, 3 H) 3.99 (s, 3 H) 4.64 (spt, J=6.95 Hz, 1 H) 6.96 (d, J=8.42 Hz, 1 H) 7.23 (t, J=8.23 Hz, 1 H) 7.34-7.50 (m, 3 H) 7.67-7.80 (m, 3 H) 8.19 (d, J=7.68 Hz, 1 H) 8.68 (s, 1 H) 9.27 (s, 1H).

Co. No. 164: (360 MHz, CDCl$_3$) δ ppm 2.49 (s, 3 H) 2.63 (s, 3 H) 3.81 (s, 3 H) 3.98 (s, 3 H) 6.74 (s, 1 H) 7.20 (dd, J=8.78, 2.20 Hz, 1 H) 7.26 (t, J=8.78 Hz, 2 H) 7.59 (d, J=8.42 Hz, 1 H) 7.69-7.79 (m, 3 H) 8.44 (d, J=2.20 Hz, 1 H) 8.51 (s, 1 H).

Co. No. 165: (360 MHz, DMSO-$d_6$) δ ppm 2.35 (s, 3 H) 3.97 (s, 3 H) 3.99 (s, 3 H) 7.00 (d, J=8.42 Hz, 1 H) 7.24-7.49 (m, 2 H) 7.53-7.77 (m, 4 H) 7.85 (d, J=8.78 Hz, 1 H) 8.32 (dd, J=6.95, 2.20 Hz, 1 H) 9.33 (d, J=1.46 Hz, 1 H) 9.82 (br. s, 1 H) 14.91 (br. s, 1H).

Co. No. 167: (360 MHz, DMSO-$d_6$) δ ppm 2.35 (s, 3 H) 4.00 (s, 6 H) 7.01 (d, J=8.42 Hz, 1 H) 7.47-7.57 (m, 2 H) 7.71

(s, 1 H) 7.89 (d, J=8.42 Hz, 1 H) 7.95 (t, J=7.68 Hz, 1 H) 8.10 (d, J=8.05 Hz, 1 H) 8.30 (d, J=8.05 Hz, 1 H) 8.36 (s, 1 H) 8.44 (dd, J=6.22, 2.20 Hz, 1 H) 9.34 (d, J=1.46 Hz, 1 H) 10.18 (br. s, 1 H) 15.04 (br. s, 1 H).

Co. No. 170: (360 MHz, DMSO-$d_6$) δ ppm 2.35 (s, 3 H) 3.77 (s, 3 H) 3.98 (s, 3 H) 6.99 (d, J=8.42 Hz, 1 H) 7.23-7.38 (m, 1 H) 7.41-7.51 (m, 1 H) 7.60-8.01 (m, 6 H) 8.35 (dd, J=7.32, 1.46 Hz, 1 H) 9.34 (d, J=1.46 Hz, 1 H) 9.97 (br. s, 1 H) 15.02 (br. s, 1 H).

Co. No. 184: (360 MHz, DMSO-$d_6$) δ ppm 2.36 (s, 3 H) 4.01 (s, 3 H) 4.02 (s, 3 H) 4.05 (s, 3 H) 7.04 (d, J=8.42 Hz, 1 H) 7.52-7.66 (m, 4 H) 7.72 (s, 1 H) 7.86 (d, J=8.05 Hz, 1H) 7.92 (d, J=8.42 Hz, 1 H) 8.56 (d, J=6.22 Hz, 1 H) 9.36 (d, J=1.46 Hz, 1 H) 10.49 (br. s, 1 H) 15.13 (br. s, 1 H).

Co. No. 186: (360 MHz, DMSO-$d_6$) δ ppm 2.35 (d, J=0.73 Hz, 3 H) 3.89 (s, 6 H) 4.00 (s, 3 H) 4.04 (s, 3 H) 6.88 (t, J=1.83 Hz, 1 H) 7.03 (d, J=8.42 Hz, 1 H) 7.17 (d, J=1.83 Hz, 2 H) 7.56 (br. s, 2 H) 7.72 (t, J=0.73 Hz, 1 H) 7.91 (d, J=8.42 Hz, 1 H) 8.52 (br. s, 1 H) 9.35 (d, J=1.83 Hz, 1 H) 10.46 (br. s, 1 H) 15.01 (br. s, 1 H).

Co. No. 201: (360 MHz, CDCl$_3$) δ ppm 2.31 (s, 3 H) 3.96 (s, 3 H) 4.11 (s, 3 H) 6.63 (d, J=8.05 Hz, 1 H) 6.90 (t, J=1.10 Hz, 1 H) 7.28 (t, J=8.60 Hz, 2 H) 7.50 (d, J=8.05 Hz, 1H) 7.67 (d, J=1.10 Hz, 1 H) 7.81 (dd, J=8.96, 5.31 Hz, 2 H) 8.10 (s, 1 H) 8.22 (d, J=5.85 Hz, 1 H) 8.32 (d, J=5.85 Hz, 1 H).

Co. No. 202: (360 MHz, CDCl$_3$) δ ppm 2.30 (s, 3 H) 3.88 (s, 3 H) 4.02 (s, 3 H) 4.11 (s, 3 H) 6.61 (d, J=8.05 Hz, 1 H) 6.89 (t, J=1.10 Hz, 1 H) 7.25 (t, J=8.42 Hz, 2 H) 7.48 (d, J=8.05 Hz, 1 H) 7.63-7.69 (m, 2 H) 7.77 (dd, J=8.78, 5.49 Hz, 2 H) 7.96 (s, 1 H).

Co. No. 203: (360 MHz, CDCl$_3$) δ ppm 2.31 (d, J=0.73 Hz, 3 H) 2.67 (s, 3 H) 3.93 (s, 3 H) 4.12 (s, 3 H) 6.62 (d, J=8.05 Hz, 1 H) 6.90 (t, J=1.10 Hz, 1 H) 7.26 (t, J=8.78 Hz, 2 H) 7.49 (d, J=8.05 Hz, 1 H) 7.67 (d, J=1.10 Hz, 1 H) 7.79 (dd, J=8.78, 5.12 Hz, 2 H) 8.02 (s, 1 H) 8.14 (s, 1 H).

Co. No. 207: (360 MHz, CDCl$_3$) δ ppm 0.95-1.03 (m, 2 H) 1.06-1.12 (m, 2 H) 2.01-2.13 (m, 1 H) 2.32 (s, 3 H) 3.87 (s, 3 H) 6.94-6.98 (m, 2 H) 7.15 (dd, J=8.78, 2.20 Hz, 1 H) 7.19-7.29 (m, 3 H) 7.30-7.38 (m, 2 H) 7.70 (t, J=1.46 Hz, 1 H) 7.77 (dd, J=8.78, 5.12 Hz, 2 H).

Co. No. 209: (360 MHz, CDCl$_3$) δ ppm 2.48 (s, 3 H) 2.69 (s, 3 H) 2.89 (s, 6 H) 3.98 (s, 3 H) 7.04 (s, 1 H) 7.14 (s, 1 H) 7.21-7.34 (m, 5 H) 7.43 (t, J=8.60 Hz, 1 H) 7.71 (dd, J=8.42, 5.12 Hz, 2 H) 9.04 (s, 1 H) 11.34 (s, 1 H).

Co. No. 210: (360 MHz, DMSO-$d_6$) δ ppm 2.35 (s, 3 H) 3.97 (s, 3 H) 3.98 (s, 3 H) 7.00 (d, J=8.78 Hz, 1 H) 7.50 (br. s, 2 H) 7.58 (t, J=8.78 Hz, 2 H) 7.71 (s, 1 H) 7.88 (d, J=8.42 Hz, 1 H) 8.05 (dd, J=8.23, 5.67 Hz, 2 H) 8.40 (br. s, 1 H) 9.33 (d, J=1.46 Hz, 1H) 10.19 (br. s, 1 H) 14.89 (br. s, 1 H).

Co. No. 211: (360 MHz, DMSO-$d_6$) δ ppm 2.38 (s, 3 H) 2.59 (s, 3 H) 3.89 (s, 3 H) 7.33 (br. s, 1 H) 7.49 (t, J=8.78 Hz, 2 H) 7.73 (t, J=8.42 Hz, 1 H) 7.80-7.90 (m, 2 H) 7.96 (dd, J=8.78, 5.49 Hz, 2 H) 8.25 (br. s, 1 H) 9.49 (s, 1 H) 10.48 (br. s, 1 H).

Pharmacology

A) Screening of the Compounds of the Invention for γ-secretase-modulating Activity A1) Method 1

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67. Briefly, cells were plated in a 96-well plate at about $10^5$ cells/ml one day prior to addition of compounds. Compounds were added to the cells in Ultraculture (Lonza, BE12-725F) supplemented with 1% glutamine (Invitrogen, 25030-024) for 18 hours. The media was assayed by two sandwich ELISAs, for Aβ42 and Aβtotal. Toxicity of the compounds was assayed by WST-1 cell proliferation reagent (Roche, 1 644 807) according to the manufacturer's protocol.

To quantify the amount of Aβ42 in the cell supernatant, commercially available Enzyme-Linked-Immunosorbent-Assay (ELISA) kits were used (Innotest® β-Amyloid$_{(1-42)}$, Innogenetics N.V., Ghent, Belgium). The Aβ42 ELISA was performed essentially according to the manufacturer's protocol. Briefly, the standards (dilutions of synthetic Aβ1-42) were prepared in polypropylene Eppendorf with final concentrations of 8000 down to 3.9 pg/ml (1/2 dilution step). Samples, standards and blanks (100 μl) were added to the anti-Aβ42-coated plate supplied with the kit (the capture antibody selectively recognizes the C-terminal end of the antigen). The plate was allowed to incubate 3 h at 25° C. in order to allow formation of the antibody-amyloid complex. Following this incubation and subsequent wash steps a selective anti-Aβ-antibody conjugate (biotinylated 3D6) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of 3,3',5,5'-tetramethylbenzidine (TMB)/peroxide mixture, resulting in the conversion of the substrate into a coloured product. This reaction was stopped by the addition of sulfuric acid (0.9 N) and the colour intensity was measured by means of photometry with an ELISA-reader with a 450 nm filter.

To quantify the amount of Aβtotal in the cell supernatant, samples and standards were added to a 6E10-coated plate. The plate was allowed to incubate overnight at 4° C. in order to allow formation of the antibody-amyloid complex. Following this incubation and subsequent wash steps a selective anti-Aβ-antibody conjugate (biotinylated 4G8) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of Quanta Blu fluorogenic peroxidase substrate according to the manufacturer's instructions (Pierce Corp., Rockford, Ill.).

To obtain the values reported in Table 3a, the sigmoidal dose response curves were analysed by computerised curve-fitting, with percent of inhibition plotted against compound concentration. A 4-parameter equation (model 205) in XLfit was used to determine the IC$_{50}$. The top and the bottom of the curve were fixed to 100 and 0, respectively, and the hill slope was fixed to 1. The IC$_{50}$ represents the concentration of a compound that is required for inhibiting a biological effect by 50% (Here, it is the concentration where Aβ peptide level is reduced by 50%).

The IC$_{50}$ values are shown in Table 3a:

| Co. No. | IC$_{50}$ Aβ42 (μM) | IC$_{50}$ Aβtotal (μM) |
|---|---|---|
| 1 | 0.022 | >1 |
| 2 | 0.012 | >1 |
| 3 | 0.013 | >1 |
| 4 | 0.023 | >3 |
| 5 | 0.031 | >3 |
| 6 | 0.029 | >1 |

-continued

| Co. No. | IC$_{50}$ Aβ42 (μM) | IC$_{50}$ Aβtotal (μM) |
|---|---|---|
| 7 | 0.022 | >1 |
| 8 | 0.022 | >3 |
| 9 | 0.600 | >3 |
| 10 | 0.751 | >30 |
| 11 | 1.590 | 12.05 |
| 12 | 0.084 | >3 |
| 13 | 0.603 | >10 |
| 14 | 0.132 | >10 |
| 15 | 0.006 | >3 |
| 16 | 0.267 | >10 |
| 17 | 0.178 | >3 |
| 18 | 0.101 | >5 |
| 19 | 1.660 | >10 |
| 20 | >3 | >3 |
| 21 | 0.905 | >33 |
| 22 | <0.11 | >3 |
| 23 | 1.912 | >10 |
| 24 | 0.505 | 18.00 |
| 25 | 0.019 | >3 |
| 26 | 0.517 | >10 |
| 27 | 1.250 | >10 |
| 28 | 1.350 | >3 |
| 29 | 1.090 | >10 |
| 30 | 0.790 | >3 |
| 31 | 0.550 | 29.70 |
| 32 | 0.216 | >10 |
| 33 | <0.11 | >3 |
| 34 | 0.051 | >1 |
| 35 | 0.024 | >1 |
| 36 | 0.031 | >3 |
| 37 | 0.266 | >10 |
| 38 | 0.104 | >3 |
| 39 | 0.069 | >3 |
| 40 | 1.950 | >3 |
| 41 | >3 | >3 |
| 42 | 1.100 | >3 |
| 43 | 0.123 | >1 |
| 44 | 0.135 | >5 |
| 45 | 0.015 | >1 |
| 46 | 0.010 | >1 |
| 47 | 0.016 | >1 |
| 48 | 0.427 | >10 |
| 49 | 0.020 | >1 |
| 50 | 0.101 | >10 |
| 51 | 0.053 | >3 |
| 52 | 0.020 | >3 |
| 53 | 0.022 | >1 |
| 54 | 0.020 | >1 |
| 56 | 0.032 | >3 |
| 57 | 0.028 | >10 |
| 58 | 0.068 | >3 |
| 59 | 7.300 | 26.40 |
| 60 | 0.014 | >1 |
| 61 | 0.063 | >3 |
| 62 | 0.114 | >1 |
| 63 | 0.023 | >1 |
| 64 | 0.048 | >3 |
| 65 | 0.089 | >3 |
| 66 | 0.027 | >3 |
| 67 | 0.012 | >3 |
| 68 | 0.027 | >1 |
| 69 | 0.106 | n.d. |
| 70 | 0.050 | >3 |
| 71 | 0.028 | >1 |
| 72 | 0.720 | >3 |
| 73 | 0.096 | >3 |
| 74 | 0.065 | >3 |
| 75 | 0.019 | >3 |
| 76 | 0.048 | >3 |
| 77 | 0.190 | >3 |
| 78 | <0.11 | >3 |
| 79 | 0.024 | >10 |
| 80 | 1.850 | >30 |
| 81 | 0.021 | >1 |
| 82 | 0.147 | >3 |
| 83 | 0.047 | >3 |
| 84 | 0.141 | >3 |
| 85 | 0.010 | >1 |
| 86 | >3 | >3 |
| 87 | >3 | >3 |
| 88 | 0.058 | >3 |
| 89 | 0.326 | >3 |
| 90 | 0.039 | >1 |
| 91 | 0.036 | >3 |
| 92 | 0.129 | >10 |
| 93 | 0.415 | >3 |
| 94 | 0.012 | >1 |
| 95 | 0.331 | >10 |
| 96 | 0.031 | >1 |
| 97 | 0.435 | >3 |
| 98 | 0.357 | >3 |
| 99 | 0.436 | >3 |
| 100 | 0.653 | >3 |
| 101 | >3 | n.d. |
| 102 | 0.839 | >3 |
| 103 | 0.087 | n.d. |
| 104 | 0.050 | >3 |
| 105 | 0.129 | 2.8 |
| 108 | 0.016 | >3 |
| 110 | 0.004 | >3 |
| 114 | 0.010 | >3 |
| 115 | 0.002 | >10 |

To obtain the values reported in Table 3b, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the IC$_{50}$. The values reported in Table 3b are averaged IC$_{50}$ values.

The IC$_{50}$ values are shown in Table 3b:

| Co. No. | IC50 Aβ42 (μM) | IC50 Aβtotal (μM) |
|---|---|---|
| 1 | 0.021 | 13.5 |
| 2 | 0.012 | >1 |
| 3 | 0.013 | >3 |
| 4 | 0.022 | >3 |
| 5 | 0.030 | >3 |
| 6 | 0.028 | >3 |
| 7 | 0.023 | >3 |
| 8 | 0.022 | >3 |
| 9 | 0.603 | >3 |
| 10 | 0.575 | 29.5 |
| 11 | 1.259 | 16.6 |
| 12 | 0.076 | >3 |
| 13 | 0.603 | >10 |
| 14 | 0.132 | >10 |
| 15 | 0.008 | >3 |
| 16 | 0.257 | >10 |
| 17 | 0.174 | >3 |
| 18 | 0.102 | >10 |
| 19 | 1.660 | >10 |
| 20 | >3 | >3 |
| 21 | 0.891 | 45.7 |
| 22 | <0.110 | >3 |
| 23 | 1.862 | >10 |
| 24 | 0.380 | 17.8 |
| 25 | 0.019 | >3 |
| 26 | 0.708 | >10 |
| 27 | 1.122 | 17.4 |
| 28 | 1.349 | >3 |
| 29 | 0.437 | >10 |

| Co. No. | IC50 Aβ42 (μM) | IC50 Aβtotal (μM) |
|---|---|---|
| 30 | 0.794 | >3 |
| 31 | 0.501 | >30 |
| 32 | 0.209 | >10 |
| 33 | <0.110 | >3 |
| 34 | 0.043 | >1 |
| 35 | 0.022 | >10 |
| 36 | 0.028 | >3 |
| 37 | 0.275 | >10 |
| 38 | 0.126 | >3 |
| 39 | 0.087 | >5 |
| 40 | 1.950 | >3 |
| 41 | >3 | >3 |
| 42 | 1.100 | >3 |
| 43 | 0.120 | >5 |
| 44 | 0.135 | >5 |
| 45 | 0.013 | >3 |
| 46 | 0.010 | >3 |
| 47 | 0.013 | >3 |
| 48 | 0.398 | >10 |
| 49 | 0.028 | >3 |
| 50 | 0.081 | >10 |
| 51 | 0.058 | >3 |
| 52 | 0.019 | >3 |
| 53 | 0.019 | >3 |
| 54 | 0.025 | >3 |
| 55 | 0.513 | >10 |
| 56 | 0.032 | >3 |
| 57 | 0.028 | >10 |
| 58 | 0.065 | >3 |
| 59 | 7.762 | >30 |
| 60 | 0.014 | >3 |
| 61 | 0.059 | >3 |
| 62 | 0.195 | >3 |
| 63 | 0.022 | >3 |
| 64 | 0.049 | >3 |
| 65 | 0.081 | >3 |
| 66 | 0.024 | >3 |
| 67 | 0.008 | >3 |
| 68 | 0.026 | >1 |
| 69 | 0.117 | n.d. |
| 70 | 0.037 | >3 |
| 71 | 0.028 | >3 |
| 72 | 0.724 | >3 |
| 73 | 0.089 | >3 |
| 74 | 0.059 | >3 |
| 75 | 0.019 | >3 |
| 76 | 0.046 | >10 |
| 77 | 0.191 | >3 |
| 78 | <0.110 | >3 |
| 79 | 0.023 | >10 |
| 80 | 1.738 | >10 |
| 81 | 0.021 | >1 |
| 82 | 0.141 | >3 |
| 83 | 0.045 | >3 |
| 84 | 0.141 | >3 |
| 85 | 0.010 | >3 |
| 86 | >3 | >3 |
| 87 | >3 | n.d. |
| 88 | 0.072 | >3 |
| 89 | 0.324 | >3 |
| 90 | 0.039 | >5 |
| 91 | 0.033 | >3 |
| 92 | 0.129 | >10 |
| 93 | 0.398 | >3 |
| 94 | 0.011 | >3 |
| 95 | 0.331 | >10 |
| 96 | 0.024 | >3 |
| 97 | 0.398 | >10 |
| 98 | 0.331 | >10 |
| 99 | 0.427 | >10 |
| 100 | 0.661 | >10 |
| 101 | >3 | n.d. |
| 102 | 0.871 | >3 |
| 103 | 0.089 | n.d. |
| 104 | 0.044 | >3 |
| 105 | 0.129 | 2.5 |
| 108 | 0.016 | >3 |
| 109 | 0.032 | >3 |
| 110 | 0.018 | 1.17 |
| 114 | 0.054 | >3 |
| 116 | 0.010 | n.d. |
| 117 | 0.033 | >3 |
| 118 | 0.069 | >3 |
| 120 | >3 | n.d. |
| 121 | 0.020 | >3 |
| 127 | 0.056 | >3 |
| 128 | 0.011 | >3 |
| 129 | >3 | n.d. |
| 130 | 0.069 | >3 |
| 137 | 0.050 | >3 |
| 145 | 0.209 | >3 |
| 148 | 0.039 | >3 |
| 149 | 0.316 | >10 |
| 150 | 0.437 | 6.92 |
| 151 | 0.005 | >3 |
| 156 | 0.058 | >3 |
| 157 | 0.062 | >3 |
| 163 | 0.048 | >3 |
| 164 | 0.032 | >3 |
| 207 | 0.054 | >3 |
| 208 | 0.035 | >3 |

A2) Method 2

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 μg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3c, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

The IC50 values are shown in Table 3c:

| Co. No. | $IC_{50}$ Aβ42 (µM) | $IC_{50}$ Aβtotal (µM) |
|---|---|---|
| 1 | 0.016 | 0.59 |
| 2 | 0.009 | 9.33 |
| 4 | 0.027 | >10 |
| 8 | 0.017 | >10 |
| 9 | >3 | >3 |
| 15 | 0.006 | 7.94 |
| 20 | >3 | >3 |
| 22 | 0.151 | >10 |
| 23 | >3 | >3 |
| 33 | 0.245 | >10 |
| 35 | 0.060 | >10 |
| 36 | 0.078 | 7.41 |
| 40 | >3 | >3 |
| 41 | 7.59 | >10 |
| 49 | 0.013 | >10 |
| 51 | 0.079 | >10 |
| 55 | 0.059 | >10 |
| 59 | >3 | >3 |
| 61 | 0.141 | 8.51 |
| 66 | 0.021 | >10 |
| 67 | 0.036 | >10 |
| 68 | 0.035 | >10 |
| 69 | 0.417 | >10 |
| 73 | 0.288 | >10 |
| 75 | 0.045 | 7.76 |
| 76 | 0.072 | >10 |
| 78 | 0.100 | >10 |
| 86 | >10 | >10 |
| 87 | >10 | >10 |
| 89 | 0.575 | >10 |
| 92 | 0.178 | 4.27 |
| 101 | 5.888 | >10 |
| 102 | 1.290 | 8.13 |
| 103 | 0.102 | >10 |
| 106 | 0.004 | 6.17 |
| 107 | 0.032 | >10 |
| 108 | 0.018 | >10 |
| 110 | 0.020 | >10 |
| 111 | 0.004 | 4.79 |
| 112 | 0.019 | >10 |
| 113 | 0.035 | >10 |
| 114 | 0.021 | 3.89 |
| 115 | 0.002 | >10 |
| 116 | 0.004 | 6.61 |
| 117 | 0.028 | >10 |
| 119 | 0.065 | >10 |
| 120 | 9.772 | >10 |
| 121 | 0.034 | >10 |
| 122 | 0.372 | >10 |
| 123 | 0.145 | >10 |
| 124 | 3.890 | >10 |
| 125 | 0.026 | >10 |
| 126 | 0.019 | >10 |
| 129 | >10 | >10 |
| 130 | 0.129 | >10 |
| 131 | 0.005 | 8.13 |
| 132 | 0.005 | 4.57 |
| 133 | 0.009 | >10 |
| 134 | 0.005 | 6.92 |
| 135 | 0.010 | >10 |
| 136 | 0.009 | >10 |
| 137 | 0.021 | >10 |
| 138 | 0.126 | >10 |
| 139 | 0.035 | >10 |
| 140 | 0.004 | >10 |
| 141 | 0.079 | >10 |
| 142 | 0.015 | 9.33 |
| 143 | 0.550 | >10 |
| 144 | 0.145 | >10 |
| 146 | 0.347 | >10 |
| 147 | 0.044 | 7.94 |
| 148 | 0.066 | 2.88 |
| 149 | 0.195 | 9.77 |
| 150 | 0.145 | 4.90 |
| 151 | 0.011 | 4.90 |
| 152 | 0.234 | 8.13 |
| 153 | 0.012 | 6.46 |
| 154 | 0.019 | 0.56 |
| 155 | 0.008 | >10 |
| 157 | 0.079 | >10 |
| 158 | 0.166 | >10 |
| 159 | 0.021 | 5.13 |
| 160 | 0.005 | >10 |
| 161 | 0.007 | >10 |
| 162 | 0.005 | 5.62 |
| 163 | 0.029 | 4.27 |
| 164 | 0.046 | >10 |
| 165 | 0.006 | 3.72 |
| 166 | 0.151 | >10 |
| 167 | 0.007 | 5.25 |
| 168 | 0.008 | 7.76 |
| 169 | 0.005 | >10 |
| 170 | 0.036 | 9.12 |
| 171 | 0.027 | >10 |
| 172 | 0.023 | >10 |
| 173 | 0.020 | 7.94 |
| 174 | 0.038 | 9.55 |
| 175 | 0.021 | >10 |
| 176 | 0.023 | >10 |
| 177 | 0.020 | 8.91 |
| 178 | 0.023 | >10 |
| 179 | 0.011 | 7.94 |
| 180 | 0.018 | >10 |
| 181 | 0.009 | 8.13 |
| 182 | 0.039 | >10 |
| 183 | 0.010 | 9.12 |
| 184 | 0.013 | >10 |
| 185 | 0.025 | >10 |
| 186 | 0.012 | 8.32 |
| 187 | 0.036 | 7.24 |
| 188 | 0.014 | 8.32 |
| 189 | 0.017 | 8.32 |
| 190 | 0.026 | >10 |
| 191 | 0.018 | >10 |
| 192 | 0.013 | 8.91 |
| 193 | 0.039 | 7.08 |
| 194 | 0.022 | >10 |
| 195 | 0.025 | 6.46 |
| 196 | 0.019 | 8.51 |
| 197 | 0.035 | 8.23 |
| 198 | 0.048 | >10 |
| 199 | 0.013 | >10 |
| 200 | 0.040 | >10 |
| 201 | 0.004 | >10 |
| 202 | 0.005 | >10 |
| 203 | 0.004 | >10 |
| 204 | 0.014 | >10 |
| 205 | 0.063 | >10 |
| 206 | 0.015 | 6.76 |
| 207 | 0.025 | 10 |
| 208 | 0.091 | >10 |

B) Demonstration of in vivo Efficacy

B1) Method 1

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K.U. Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (Aβ) in the brain, eventually resulting in amyloid plaques within the subiculum, hippocampus and cortex. Animals treated with the Aβ42 lowering agent were examined and compared to those untreated or treated with vehicle and brain levels of soluble Aβ42 and total Aβ would be quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains were resuspended in 10 volumes of 0.4% DEA (diethylamine)/50 mM NaCl pH 10 (for non-transgenic animals) or 0.1% 3-[(3-cholamidopropyl)-dimethyl-ammonio]-1-propanesulfonate (CHAPS) in tris buffered saline (TBS) (for transgenic animals) containing protease inhibitors (Roche-11873580001 or 04693159001) per gram of tissue, e.g. for 0.158 g brain, add 1.58 ml of 0.4% DEA. All samples were sonicated for 30 seconds on ice at 20% power output (pulse mode). Homogenates were centrifuged at 221.300×g for 50 min. The resulting high speed supernatants were then transferred to fresh tubes and were optionally further purified before the next step. A portion of the supernatant was neutralized with 10% 0.5 M Tris-HCl and this was used to quantify Aβtotal.

The obtained supernatants were purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 ml per min, so the vacuum pressure was adjusted accordingly throughout the procedure. Columns were preconditioned with 1 ml of 100% MeOH, before equilibration with 1 ml of $H_2O$, Non-neutralized brain lysates were loaded onto the columns. The loaded samples were then washed twice with the first wash performed with 1 ml of 5% MeOH, and the second wash with 1 ml of 30% MeOH. Finally, the Aβ was eluted from the columns and into 100×30 mm glass tubes, with a solution of 90% MeOH with 2% $NH_4OH$. The eluate was then transferred into 1.5 ml tubes and concentrated in a speed-vac concentrator on high heat for about 1.5-2 h at 70° C. The concentrated Aβ was then resuspended in UltraCULTURE General Purpose Serum-Free Medium (Cambrex Corp., Walkersville, Md.) plus Protease Inhibitors added.

To quantify the amount of Aβ42 in the soluble fraction of the brain homogenates, commercially available Enzyme-Linked-Immunosorbent-Assay (ELISA) kits were used (e.g. Innotest® β-Amyloid$_{(1-42)}$, Innogenetics N.V., Ghent, Belgium). The Aβ42 ELISA was performed using the plate provided with the kit only. Briefly, the standards (a dilution of synthetic Aβ1-42) were prepared in 1.5 ml Eppendorf tube in Ultraculture, with final concentrations ranging from 25000 to 1.5 pg/ml. Samples, standards and blanks (60 µl) were added to the anti-Aβ42-coated plate (the capture antibody selectively recognizes the C-terminal end of the antigen). The plate was allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) was added and incubated for a minimum of 1 h in order to allow formation of the antibody-Amyloid-antibody-complex. After incubation and appropriate wash steps, a Streptavidine-Peroxidase-Conjugate was added, followed 50 min later by an addition of Quanta Blu fluorogenic peroxidase substrate according to the manufacturer's instructions (Pierce Corp., Rockford, Ill.). A kinetic reading was performed every 5 min for 30 min (excitation 320 nm/emission 420 nm). To quantify the amount of Aβtotal in the soluble fraction of the brain homogenates, samples and standards were added to JRF/rAβ/2-coated plate. The plate was allowed to incubate overnight at 4° C. in order to allow formation of the antibody-amyloid complex. The ELISA was then performed as for Aβ42 detection.

In this model at least 20% Aβ42 lowering compared to untreated animals would be advantageous.

The results are shown in Table 4a:

| Co. No. | Aβ42 (% Ctrl) _Mean | Aβtotal (% Ctrl) _Mean |
|---|---|---|
| 1 | 57 | 100 |
| 3 | 46 | 87 |
| 4 | 64 | 92 |
| 5 | 62 | 94 |
| 6 | 66 | 91 |
| 7 | 58 | 89 |
| 8 | 46 | 91 |
| 15 | 31 | 83 |
| 18 | 81 | 95 |
| 36 | 79 | 95 |
| 38 | 72 | 101 |
| 44 | 91 | 101 |
| 45 | 93 | 94 |
| 54 | 71 | 96 |

-continued

| Co. No. | Aβ42 (% Ctrl) _Mean | Aβtotal (% Ctrl) _Mean |
|---|---|---|
| 56 | 78 | 92 |
| 61 | 89 | 97 |
| 67 | 71 | 99 |
| 70 | 64 | 99 |
| 71 | 88 | 102 |
| 73 | 87 | 97 |
| 74 | 86 | 99 |
| 75 | 67 | 92 |
| 76 | 86 | 102 |
| 80 | 97 | 102 |
| 82 | 85 | 96 |
| 85 | 71 | 93 |
| 91 | 68 | 94 |
| 92 | 60 | 103 |
| 94 | 64 | 95 |
| 95 | 85 | 95 |
| 96 | 62 | 88 |
| 97 | 96 | 96 |
| 104 | 65 | 110 |
| 106 | 87 | 104 |
| 108 | 59 | 98 |
| 115 | 97 | 93 |
| 130 | 75 | 94 |
| 131 | 51 | 84 |
| 164 | 72 | 97 |

B2) Method 2

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320/emission 420).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model at least 20% Aβ42 lowering compared to untreated animals would be advantageous.

The results are shown in Table 4b:

| Co. No. | Aβ42 (% Ctrl) _Mean | Aβtotal (% Ctrl) _Mean |
|---|---|---|
| 15 | 39 | 82 |
| 110 | 78 | 106 |
| 136 | 77 | 104 |
| 142 | 73 | 98 |
| 160 | 84 | 78 |
| 162 | 79 | 97 |
| 165 | 44 | 85 |
| 167 | 46 | 84 |
| 174 | 90 | 104 |
| 184 | 31 | 88 |
| 186 | 38 | 88 |
| 187 | 75 | 96 |
| 189 | 48 | 95 |
| 202 | 82 | 102 |

C) Effect on the Notch-processing Activity of the γ-secretase-complex

Notch Cell-free Assay

The Notch transmembrane domain is cleaved by gamma secretase to release

Notch Intracellular C-terminal Domain (NICD). Notch is a signaling protein which plays a crucial role in developmental processes, and thus compounds are preferred which do not show an effect on the Notch-processing activity of the γ-secretase-complex.

To monitor the effect of compounds on NICD production, a recombinant Notch substrate (N99) was prepared. The Notch substrate, comprised of mouse Notch fragment (V1711-E1809), an N-terminal methionine and a C-terminal FLAG sequence (DYDDDDK), was expressed in E. coli and purified on a column containing an anti-FLAG M2 affinity matrix.

A typical Notch cell-free assay consisted of 0.3-0.5 μM Notch substrate, an enriched preparation of γ secretase and 1 μM of a test compound (compounds 8, 15, 92, 108, 114 and 130 of the present invention). Controls included a γ secretase inhibitor (GSI), such as (2S)—N-[2-(3,5-difluorophenyeacetyl]-L-alanyl-2-phenyl-glycine 1,1-dimethylethyl ester (DAPT) or (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide (Semagacestat), and DMSO, the final concentration of DMSO being 1%. Recombinant Notch substrate was pre-treated with 17 μM DTT (1,4-dithiothreitol) and 0.02% SDS (Sodium Dodecyl Sulfate) and heated at 65° C. for 10 min. The mixture of substrate, gamma secretase and compound/DMSO was incubated at 37° C. for 6 to 22 hours (h). 6 h incubation was sufficient to produce the maximal amount of NICD and the cleaved product remained stable for an additional 16 h. Reaction products were processed for SDS PAGE (Sodium Dodecyl Sulfate-Poly Acrylamide Gel Electrophoresis) and western blotting. Blots were probed with an anti-Flag M2 antibody, followed by LI-COR infrared secondary antibody, and analyzed with the Odyssey Infrared Imaging System (LI-COR® Biosciences).

In the cell-free Notch assay, no test compounds (compounds 8, 15, 92, 108, 114 and 130) inhibited the cleavage of C99 by gamma secretase, whereas the production of NICD was blocked by the control GSI (DAPT or Semagacestat). Thus it was demonstrated that compounds 8, 15, 92, 108, 114 and 130 did not show an effect on the Notch-processing activity of the γ-secretase-complex (production of NICD).

Notch Cell-based Assay

The Notch cell-based assay was based on the interaction of Notch and its ligand in a co-culture system and utilized the Dual-Glo Luciferase Assay System (Promega) to monitor NICD production. 2 stable cell lines, N2-CHO and DL-CHO, were established to express full-length mouse Notch2 and Delta respectively. Cells that expressed mouse Notch were also transfected with 2 plasmids, pTP1-Luc and pCMV-RLuc, to express firefly and Renilla luciferase. Expression of firefly luciferase was under the control of TP1 promoter that responded to NICD activation. The CMV promoter that drove the expression of Renilla luciferase did not respond to NICD activation and therefore was used to control for transfection efficiency and compound toxicity.

N2-CHO cells were seeded at $1 \times 10^5$/well in 24-well plates the day before transfection. On the second day, cells were double transfected with 3 μg/well pTP1-Luc (expressing firefly luciferase) and 0.3 ng/well pCMV-RLuc (expressing Renilla luciferase). After 6 h incubation, transfected N2-CHO cells were washed and DL-CHO cells ($2 \times 10^5$ cells/well) were added.

Compounds were pre-mixed with DL-CHO cell suspension in a five-point curve. Typically, compound treatment was performed in duplicate with a serial 1:10 dilution (3 μM-0.3 nM) in DMSO. The final concentration of DMSO in a given culture was 1%. Controls included non-transfected cells and transfected cells treated with a GSI or DMSO only. Luciferase assays were performed after 16 h co-culture and compound treatment.

The luciferase assay was carried out according to manufacture's instructions. Briefly, cells were washed with PBS (Phosphate Buffered Saline), lysed with Passive Lysis Buffer (Promega), and incubated at room temperature for 20 min. Lysates were mixed with Dual-Glo Luciferase Reagent and the firefly luciferase activity was measured by reading the luminescence signal in the EnVision 2101 Multilabel reader. Dual-Glo Stop & Glo Reagent was then added to each well and the Renilla luciferase signal was measured.

The results of the Notch cell-based assay were in agreement with those in the cell-free NICD assay. On the basis of luciferase assay readouts, the average $IC_{50}$ values of DAPT and Semagacestat from the Notch cell-based assay were 45 nM and 40 nM respectively, whereas compounds 15, 92, 108, 114 and 130 of the present invention were found to be non-inhibitory.

D. Composition Examples

"Active ingredient" as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound of formula (I)

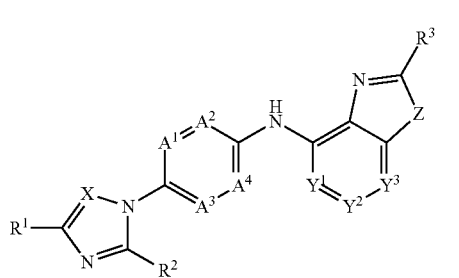

or a stereoisomeric form thereof, wherein
$R^1$ is hydrogen, cyano, $CF_3$, halo, or $C_{1-4}$alkyl optionally substituted with one or more substituents each independently selected from the group consisting of hydroxyl and $C_{1-4}$alkyloxy;
$R^2$ is hydrogen, $C_{1-4}$alkyl or halo;
X is $CR^5$ or N;
$R^5$ is hydrogen or halo;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH
$Y^2$ is $CR^4$;
$Y^3$ is CH;
$R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents;
$C_{1-6}$alkyl optionally substituted with one or more substituents each independently selected from the group consisting of piperidinyl, morpholinyl, pyrrolidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl substituted with one or more phenyl substituents optionally substituted with one or more halo substituents;
cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; NH—Ar; or 1,6-dihydro-1-methyl-6-oxo-3-pyridinyl;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is
phenyl optionally substituted with one or more substituents each independently selected from the group consisting of halo, $C_{1-4}$alkyloxy, cyano, $NR^7R^8$, morpholinyl, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl, $C_{1-4}$alkyloxy substituted with one or more halo substituents, and $C_{1-4}$alkyl substituted with one or more halo substituents;
each $R^7$ is selected independently from hydrogen or $C_{1-4}$alkyl;
each $R^8$ is selected independently from hydrogen, $C_{1-4}$alkyl or $C_{1-4}$alkylcarbonyl;
Z is $NR^9$;
$R^9$ is hydrogen, or $C_{1-6}$alkyl optionally substituted with one or more substituents each independently selected from the group consisting of halo, cyano, phenyl, cyclo$C_{3-7}$alkyl and $C_{1-4}$alkyloxy;
or a pharmaceutically acceptable addition salt thereof.
2. The compound according to claim 1 or a stereoisomeric form thereof, wherein
$R^1$ is hydrogen, $C_{1-4}$alkyl, cyano, $CF_3$, or halo;
$R^2$ is hydrogen or $C_{1-4}$alkyl;
X is $CR^5$ or N;
$R^5$ is hydrogen or halo;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH;
$Y^2$ is $CR^4$;
$Y^3$ is CH;
$R^4$ is hydrogen, halo, $C_{1-4}$alkyloxy, cyano, cyclo$C_{3-7}$alkyl, $C_{2-4}$alkenyl, or $C_{1-4}$alkyl optionally substituted with one or more substituents each independently selected from the group consisting of halo and $C_{1-4}$alkyloxy;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; or NH—Ar;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy, cyano, $NR^7R^8$, morpholinyl, $C_{1-4}$alkyl and $C_{1-4}$alkyl substituted with one or more halo substituents; or a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl and $C_{1-4}$alkyl substituted with one or more halo substituents;
each $R^7$ is selected independently from hydrogen or $C_{1-4}$alkyl;
each $R^8$ is selected independently from hydrogen or $C_{1-4}$alkyl;
Z is $NR^9$;

$R^9$ is hydrogen, or $C_{1-6}$alkyl optionally substituted with one or more substituents each independently selected from the group consisting of halo, phenyl and $C_{1-4}$alkyloxy;

or a pharmaceutically acceptable addition salt thereof.

3. The compound according to claim 1 or a stereoisomeric form thereof, wherein $R^1$ is hydrogen, $C_{1-4}$alkyl, cyano, $CF_3$, or halo;
$R^2$ is hydrogen or $C_{1-4}$alkyl;
X is $CR^5$ or N;
$R^5$ is hydrogen or halo;
$A^1$ is $CR^6$ or N;
$R^6$ is hydrogen, halo or $C_{1-4}$alkyloxy;
$A^2$, $A^3$ and $A^4$ each independently are CH, CF or N;
provided that no more than two of $A^1$, $A^2$, $A^3$ and $A^4$ are N;
$Y^1$ is CH;
$Y^2$ is $CR^4$;
$Y^3$ is CH;
$R^4$ is hydrogen, halo, $C_{1-4}$alkyloxy, cyano, or $C_{1-4}$alkyl optionally substituted with one or more halo substituents;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cyclo$C_{3-7}$alkyloxy and cyclo$C_{3-7}$alkyl; cyclo$C_{3-7}$alkyl; piperidinyl; morpholinyl; pyrrolidinyl; tetrahydropyranyl; O—Ar; $NR^7R^8$; $C_{1-6}$alkyloxy; $C_{1-6}$alkylthio; Ar; $CH_2$—O—Ar; S—Ar; $NCH_3$—Ar; or NH—Ar;
wherein each piperidinyl, morpholinyl and pyrrolidinyl may be substituted with one or more substituents each independently selected from the group consisting of $C_{1-4}$alkyl, $C_{2-6}$alkenyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy, cyano, $NR^7R^8$, morpholinyl, $C_{1-4}$alkyl and $C_{1-4}$alkyl substituted with one or more halo substituents; or a 5- or 6-membered heteroaryl selected from the group consisting of pyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl and pyrazinyl; wherein said 5- or 6-membered heteroaryl is optionally substituted with one or more substituents each independently selected from the group consisting of halo, $C_{1-4}$alkyloxy, cyano, $C_{1-4}$alkyl and $C_{1-4}$alkyl substituted with one or more halo substituents;
each $R^7$ is selected independently from hydrogen or $C_{1-4}$alkyl;
each $R^8$ is selected independently from hydrogen or $C_{1-4}$alkyl;
Z is $NR^9$;
$R^9$ is hydrogen, or $C_{1-6}$alkyl optionally substituted with one or more substituents each independently selected from the group consisting of halo, phenyl and $C_{1-4}$alkyloxy;

or a pharmaceutically acceptable addition salt thereof.

4. The compound according to claim 1 or a stereoisomeric form thereof, wherein $R_1$ is hydrogen, cyano, halo, or $C_{1-4}$alkyl optionally substituted with one or more hydroxyl radicals;
$R^5$ is hydrogen;
$Y^1$ is CH;
$Y^2$ is $CR^4$;
$Y^3$ is CH;
provided that only one of $Y_1$ and $Y^2$ may represent N;
$R^4$ is hydrogen, halo, $C_{1-4}$alkyloxy, cyclo$C_{3-7}$alkyl, $C_{2-4}$alkenyl, or
$C_{1-4}$alkyl optionally substituted with one or more substituents each independently selected from the group consisting of halo and $C_{1-4}$alkyloxy;
$R^3$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl and cyclo$C_{3-7}$alkyl;
cyclo$C_{3-7}$alkyl substituted with one or more phenyl substituents optionally substituted with one or more halo substituents; cyclo$C_{3-7}$alkyl; piperidinyl; morpholinyl; tetrahydropyranyl;
O—Ar; $C_{1-6}$alkyloxy; $C_{1-6}$alkylthio; Ar; $CH_2$—O—Ar; NH—Ar; or 1,6-dihydro-1-methyl-6-oxo-3-pyridinyl;
wherein each piperidinyl and morpholinyl may be substituted with one or more substituents each independently selected from the group consisting of $C_{1-4}$alkyl, $C_{1-4}$alkylcarbonyl, halo and $C_{1-4}$alkyloxycarbonyl;
wherein each Ar independently is phenyl optionally substituted with one or more substituents each independently selected from the group consisting of halo, $C_{1-4}$alkyloxy, cyano, $NR^7R^8$, $C_{1-4}$alkyl, $C_{1-4}$alkyloxy substituted with one or more halo substituents, and $C_{1-4}$alkyl substituted with one or more halo substituents; or
a 5- or 6-membered heteroaryl selected from the group consisting of pyridinyl and thiophenyl; wherein said 5- or 6-membered heteroaryl is optionally substituted with one or more substituents each independently selected from the group consisting of halo and $C_{1-4}$alkyl substituted with one or more halo substituents;
each $R^8$ is selected independently from $C_{1-4}$alkyl or $C_{1-4}$alkylcarbonyl or a pharmaceutically acceptable addition salt thereof.

5. The compound according to claim 1, or a stereoisomeric form thereof, wherein
$R^1$ is methyl;
$R^2$ is hydrogen;
or a pharmaceutically acceptable addition salt thereof.

6. The compound according to claim 1, or a stereoisomeric form thereof, wherein
$R^1$ is $C_{1-4}$alkyl;
$R^2$ is hydrogen;
X is CH or N;
$A^1$ is $CR^6$;
$R^6$ is hydrogen, methoxy or halo;
$A^2$ is CH or N;
$A^3$ and $A^4$ are CH;
$Y^1$ is CH; $Y^2$ is $CR^4$; $Y^3$ is CH;
$R^4$ is hydrogen, halo or $C_{1-4}$alkyl;
$R^3$ is phenyl optionally substituted with one or more substituents each independently selected from the group consisting of halo, $C_{1-4}$alkyloxy, $NR^7R^8$ and $C_{1-4}$alkyl substituted with one or more halo substituents;
$R^7$ is hydrogen;
$R^8$ is $C_{1-4}$alkylcarbonyl;
Z is $NR^9$;
$R^9$ is $C_{1-6}$alkyl;
or a pharmaceutically acceptable addition salt thereof.

7. The compound according to claim 1, or a stereoisomeric form thereof, wherein
$R^1$ is $C_{1-4}$alkyl;
$R^2$ is hydrogen;

X is CH;
A$^1$ is CR$^6$;
R$^6$ is F or methoxy;
A$^2$ is N or CH;
A$^3$ and A$^4$ are CH;
Y$^1$ is CH;
Y$^2$ is CR$^4$;
Y$^3$ is CH;
R$^4$ is hydrogen or methyl;
R$^3$ is phenyl optionally substituted with one or more substituents each independently selected from the group consisting of halo and methoxy;
Z is NR$^9$;
R$^9$ is C$_{1-6}$alkyl;
or a pharmaceutically acceptable addition salt thereof.

8. The compound according to claim 1, or a stereoisomeric form thereof, wherein
R$^1$ is C$_{1-4}$alkyl;
R$^2$ is hydrogen;
X is CH;
A$^1$ is COCH$_3$; A$^2$ is N; A$^3$ is CH; A$^4$ is CH;
Y$^1$, Y$^2$ and Y$^3$ are CH;
R$^3$ is phenyl optionally substituted with one or more halo substituents;
Z is NR$^9$;
R$^9$ is C$_{1-6}$alkyl;
or a pharmaceutically acceptable addition salt thereof.

9. The compound according to claim 1, wherein the compound is
N-[3-fluoro-4-(4-methyl-1H-imidazol-1-yl)phenyl]-2-(4-fluorophenyl)-1,6-dimethyl-1H-imidazo[4,5-c]pyridin-4-amine,
N-[3-fluoro-4-(4-methyl-1H-imidazol-1-yl)phenyl]-2-(4-fluorophenyl)-1,6-dimethyl-1H-imidazo[4,5-c]pyridin-4-amine.2CH$_3$SO$_3$H,
N-[3-fluoro-4-(4-methyl-1H-imidazol-1-yl)phenyl]-2-(4-fluorophenyl)-1,6-dimethyl-1H-imidazo[4,5-c]pyridin-4-amine.2HCl,
2-(4-fluorophenyl)-N-[6-methoxy-5-(4-methyl-1H-imidazol-1-yl)-2-pyridinyl]-1-methyl-1H-benzimidazol-4-amine,
2-(4-fluorophenyl)-N-[6-methoxy-5-(4-methyl-1H-imidazol-1-yl)-2-pyridinyl]-1-methyl-1H-benzimidazol-4-amine.2HCl,
2-(2,3-difluorophenyl)-N-[6-methoxy-5-(4-methyl-1H-imidazol-1-yl)-2-pyridinyl]-1-methyl-1H-benzimidazol-4-amine.2HCl.H$_2$O,
2-(2,3-difluorophenyl)-N-[6-methoxy-5-(4-methyl-1H-imidazol-1-yl)-2-pyridinyl]-1-methyl-1H-benzimidazol-4-amine,
2-(4-fluoro-3-methoxyphenyl)-N-[6-methoxy-5-(4-methyl-1H-imidazol-1-yl)-2-pyridinyl]-1-methyl-1H-benzimidazol-4-amine.2HCl.H$_2$O,
2-(4-fluoro-3-methoxyphenyl)-N-[6-methoxy-5-(4-methyl-1H-imidazol-1-yl)-2-pyridinyl]-1-methyl-1H-benzimidazol-4-amine,
2-(3,5-dimethoxyphenyl)-N-[6-methoxy-5-(4-methyl-1H-imidazol-1-yl)-2-pyridinyl]-1-methyl-1H-benzimidazol-4-amine.2HCl.H$_2$O, or
2-(3,5-dimethoxyphenyl)-N-[6-methoxy-5-(4-methyl-1H-imidazol-1-yl)-2-pyridinyl]-1-methyl-1H-benzimidazol-4-amine,
including any stereochemically isomeric form thereof or a pharmaceutically acceptable addition salt thereof.

10. The compound according to claim 1, wherein the compound is
2-(4-fluorophenyl)-N-[6-methoxy-5-(4-methyl-1H-imidazol-1-yl)-2-pyridinyl]-1-methyl-1H-benzimidazol-4-amine, or a pharmaceutically acceptable addition salt thereof.

11. A pharmaceutical composition comprising a pharmaceutically acceptable carrier and, as active ingredient, a therapeutically effective amount of a compound as defined in any one of claims 1 to 10.

12. A method for the treatment of a disease or condition selected from, traumatic brain injury, mild cognitive impairment, senility, dementia, dementia with Lewy bodies, cerebral amyloid angiopathy, multi-infarct dementia, Down's syndrome, dementia associated with Parkinson's disease and dementia associated with beta-amyloid, comprising administering to a subject a compound as defined in any one of claims 1 to 10.

\* \* \* \* \*